United States Patent
Carroll et al.

(10) Patent No.: US 8,501,794 B2
(45) Date of Patent: *Aug. 6, 2013

(54) COMPOUNDS AS CANNABINOID RECEPTOR LIGANDS

(75) Inventors: William A. Carroll, Evanston, IL (US); Michael J. Dart, Highland Park, IL (US); Teodozyj Kolasa, Lake Villa, IL (US); Tongmei Li, Lake Bluff, IL (US); Derek W. Nelson, Highland Park, IL (US); Meena V. Patel, Green Oaks, IL (US); Sridhar Peddi, Grayslake, IL (US); Arturo Perez-Medrano, Grayslake, IL (US); Xueqing Wang, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/612,504

(22) Filed: Nov. 4, 2009

(65) Prior Publication Data

US 2010/0234345 A1   Sep. 16, 2010

Related U.S. Application Data

(63) Continuation-in-part of application No. 12/100,731, filed on Apr. 10, 2008, now Pat. No. 7,872,033.

(60) Provisional application No. 60/923,951, filed on Apr. 17, 2007, provisional application No. 61/111,041, filed on Nov. 4, 2008.

(51) Int. Cl.
| | |
|---|---|
| *A61K 31/5377* | (2006.01) |
| *A61K 31/497* | (2006.01) |
| *A61K 31/454* | (2006.01) |
| *A61K 31/4439* | (2006.01) |
| *A61K 31/428* | (2006.01) |
| *A61K 31/427* | (2006.01) |
| *A61K 31/426* | (2006.01) |
| *A61K 31/425* | (2006.01) |
| *C07D 417/14* | (2006.01) |
| *C07D 417/12* | (2006.01) |
| *C07D 417/06* | (2006.01) |
| *C07D 275/03* | (2006.01) |
| *C07D 275/04* | (2006.01) |

(52) U.S. Cl.
USPC ...... 514/372; 514/373; 514/326; 514/255.05; 514/342; 514/228.8; 514/236.8; 514/365; 548/205; 548/206; 548/214; 546/209; 546/271.1; 544/133; 544/96; 544/405

(58) Field of Classification Search
USPC .......... 514/372, 373, 326, 255.05, 342, 514/228.8, 236.8, 365; 548/205, 206, 214; 546/209, 271.1; 544/133, 96, 405
See application file for complete search history.

(56) References Cited

U.S. PATENT DOCUMENTS

| | | | |
|---|---|---|---|
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| | | |
|---|---|---|
| EP | 1820504 A1 | 8/2007 |
| WO | WO9507271 A1 | 3/1995 |
| WO | WO9531448 A1 | 11/1995 |
| WO | WO9710223 A1 | 3/1997 |
| WO | WO0063207 A1 | 10/2000 |
| WO | WO0155139 A1 | 8/2001 |
| WO | WO0155140 A1 | 8/2001 |
| WO | WO2004110453 A1 | 12/2004 |
| WO | WO2005099353 A2 | 10/2005 |

(Continued)

OTHER PUBLICATIONS

Giron, D. J. Therm. Anal. Cal. 2001, 64, pp. 37-60.*

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The present application relates to isothiazolylidene containing compounds of Formula (I)

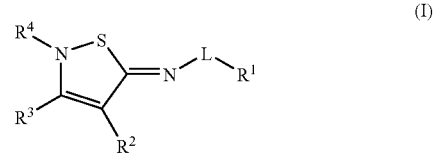

(I)

wherein $R^1$, $R^2$, $R^3$, $R^4$, and L are as defined in the specification, compositions comprising such compounds, and methods for treating conditions and disorders using such compounds and compositions.

7 Claims, No Drawings

FOREIGN PATENT DOCUMENTS

| | | | |
|---|---|---|---|
| WO | WO2005099353 A3 | 10/2005 | |
| WO | WO2006008754 A1 | 1/2006 | |
| WO | WO2006051704 A1 | 5/2006 | |
| WO | WO 2008130953 A2 | * 10/2008 | |
| WO | WO 2010054024 A2 | * 5/2010 | |

OTHER PUBLICATIONS

Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
CAPLUS Entry for International Application Publication No. WO 2008/130953, accessed Aug. 14, 2012 with structures relevant to claim 25 as filed Nov. 8, 2011.*
CAPLUS Entry for International Application Publication No. WO 2008/130953, accessed Aug. 14, 2012 with structures relevant to claim 35 as filed Nov. 8, 2011.*
Arevalo-Martin A. et al., "Therapeutic Action of Cannabinoids in a Murine Model of Multiple Sclerosis," Journal of Neuroscience, 2003, vol. 23 (7), pp. 2511-2516.
Benito C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, vol. 23 (35), pp. 11136-11141.
Berge S. M., et al., "Pharmaceutical Salts", J Pharmaceutical Sciences, 1977, vol. 66 (1), pp. 1-19.
Beylot M., et al., "In vivo studies of intrahepatic metabolic pathways," Diabetes Metabolism, 1997, 23 (3), 251-257.
Blagojevic N., et al., "Role of heavy water in Boron Neutron Capture Therapy," in Topics in Dosimetry & Treatment Planning for Neutron Capture Therapy, Advanced Medical Publishing, Madison, WI, 1994, 125-134.
Blake et al., "Studies with deuterated drugs," J. Pharm. Sci., 1975, 64 (3), 367-391.
Bouchard J. F et al., "Contribution of endocannabinoids in the endothelial protection afforded by ischemic preconditioning in the isolated rate heart," Life Sciences, 2003, vol. 72, pp. 1859-1870.
Boyle W. J. et al., "Osteoclast differentiation and activation," Nature, 2003, vol. 423, pp. 337-342.
Brennan T. J., et al., "Characterization of a rat model of incisional pain", Pain, 1996, vol. 64, pp. 493-501.
Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.
Buckley N. E. et al., "Immunomodulation by cannabinoids is absent in mice deficient for the cannabinoid CB receptor," European Journal of Pharmacology, 2000, vol. 396, pp. 141-149.
Carlisle S. J. et al., "Differential expression of the CB2 cannabinoid receptor by rodent macrophages and macrophage-like cells in relation to cell activation," International Immunopharmacology, 2002, vol. 2, pp. 69.
Carrier E. J. et al., "Endocannabinoids in Neuroimmunology and Stress," Current Drug Targets CNS & Neurological Disorders, 2005, vol. 4, pp. 657-665.
Casanova M. L. et al., "Inhibition of skin tumor growth and angiogenesis in vivo by activation of cannabinoid receptors," Journal of Clinical Investigation, 2003, vol. 111, pp. 43-50.
Chaplan S.R., et al., "Quantitative Assessment of Tactile Allodynia in the Rat Paw," Journal of Neuroscience Methods, 1994, vol. 53, pp. 55-63.
Cichewicz D. L. et al., "Synergistic interactions between cannabinoid and opioid analgesics," Life Sciences, 2004, vol. 74, pp. 1317-1324.
Clayton N., et al. , "CB1 and CB2 cannabinoid receptors are implicated in inflammatory pain," Pain, 2002, vol. 96, pp. 253-260.
Cotarca Livius, et al., "Bis (trichloromethyl) Carbonate in Organic Synthesis", Synthesis, 1996, 6, 553-576.

Cross L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Czajka D. M., "Effect of deuterium oxide on the reproductive potential of mice," Ann NY Acad Sci, 1960, vol. 84, pp. 770-779.
Czajka D.M., et al., "Physiological effects of deuterium on dogs," Am. J. Physiol., 1961, 201 (2), 357-362.
Dixon W.J., "Efficient Analysis of Experimental Observations," Annual Review of Pharmacology and Toxicology, 1980, vol. 20, pp. 441-462.
Eckert H. et al., "Triphosgene, a Crystalline Phosgene Substitute," Angew Chem Int Ed Engl, 1987, vol. 26 (9), pp. 894-895.
Filippo C. D. et al., "Cannabinoid CB2 receptor activation reduces mouse myocardial ischemia-reperfusion injury: involvement of cytokine/chemokines and PMN," Journal of Leukocyte Biology, 2004, vol. 75, pp. 453-459.
Foster, A.B., et al., "Deuterium Isotope Effects in the Metabolism of Drugs and Xenobiotics: Implications for Drug Design," Advances in Drug Research, 1985, 14, Academic Press, London, 2-36.
Galiégue et al., "Expression of central and peripheral cannabinoid receptors in human immune tissues and leukocyte subpopulations," European Journal of Biochemistry, 1995, vol. 232, pp. 54-61.
Goerdeler, et al., "Isothiazoles. VIII. Synthesis of sulfonylaminoisothiazoles and sulfonyliminioisothiazolines from sulfonyl isothiocyanates, Ueber isothiazole, VIII." Chemische Berichte, 1969, 102 (7), 2273-2284.
Greene T.W., et al., "Protection for the Amino group," Protective Groups in Organic Synthesis, 1999, Third Edition, pp. 494-653.
Grotenhermen F. et al., "IACM 2nd Conference on Cannabinoids in Medicine," Expert Opinion in Pharmacotherapy, 2003, vol. 4 (12), pp. 2367-2371.
Hamuro Yet al., "Solid-Phase Synthesis of Acyclic and Cyclic Amino Acid Derived Urea peptidomimetics Using Phoxime Resin," J Comb Chem, 1999, vol. 1, pp. 163-172.
Hanus L. et al., "HU-308: A specific agonist for CB 2, a peripheral cannabinoid receptor," Proceedings of the National Academy of Science, 1999, vol. 96, pp. 14228-14233.
Hohmann A. G. et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Hutchins SM et al., "A General Method for the Solid Phase Synthesis of Ureas," Tetrahedron Letters, 1994, vol. 35 (24), pp. 4055-4058.
Hutchins SM et al., "A Strategy for Urea Linked Diamine Libraries," Tetrahedron Letters, 1995, vol. 36 (15), pp. 2583-2586.
Ibrahim M. M. et al., "Activation of CB2 cannabinoid receptors by AM1241 inhibits experimental neuropathic pain: Pain inhibition by receptors not present in the CNS," Proceedings of the National Academy of Science, 2003, vol. 100 (18), pp. 10529-10533.
Ibrahim M. M. et al., "CB2 cannabinoid receptor activation produces antinociception by stimulating peripheral release of endogenous opioids," Proceedings of the National Academy of Science, 2005, vol. 102 (8), pp. 3093-3098.
Ihenetu K. et al., "Inhibition of interleukin-8 release in the human colonic epithelial cell line HT-29 by cannabinoids," European Journal of Pharmacology, 2003, vol. 458, pp. 207-215.
International Search Report for application No. PCT/US08/060400, Mailed on Oct. 17, 2008, 3 pages.
Joshi S. K., et al., "Comparison of Antinociceptive Actoins of Standard Analgesics in Attenuating Capsaicin and Nerve-Injury-Induced Mechanical Hypersensitivty," Neurosci, 2006, vol. 143, pp. 587-596.
Julien B et al., "Antifibrogenic Role of the Cannabinoid Receptor CB2 in the Liver," Gastroenterology, 2005, vol. 128, pp. 742-755.
Karsak M. et al., "Cannabinoid receptor type 2 gene is associated with human osteoporosis," Human Molecular Genetics, 2005, vol. 14 (22), pp. 3389-3396.
Kato et al., "Synthesis of Deuterated Mosapride Citrate," J. Labelled Comp. Radiopharmaceut, 1995, 36 (10), 927-932.
Katritzky AR et al., "A General Synthesis of Unsymmetrical Tetrasubstituted Ureas," J Org Chem, 1997, vol. 62, pp. 4155-4158.

Kim S.H., et al., "An Experimental Model for Peripheral Neuropathy Produced by Segmental Spinal Nerve Ligation in the Rat," Pain, 1992, vol. 50 (3), pp. 355-363.

Knolker HJ, "A Novel Method for the Synthesis of Isocyanates Under Mild Conditions," Angew Chem Int Ed Engl, 1995, 34/22, pp. 2497-2500.

Knolker HJ, "Synthesis of Symmetrical and Unsymmetrical Ureas by DMAP-Catalyzed Reaction of Alkyl- and Arylamines with Di-tert-butyldicarbonate," Synlett, 1996, pp. 502-504.

Kruijtzer, Jaw et al., "Approaches to the Synthesis of Ureapeptoid Peptidomimetics," Tetrahedron Letters, 1997, vol. 38 (30), pp. 5335-5338, Pergamon.

Kushner et al., "Pharmacological uses and perspectives of heavy water and deuterated compounds," Can J Physiol Pharmacol, 1999, vol. 77, pp. 79-88.

Lamothe M. et al., "A Simple One-Pot Preparation of N,N'-unsymmetrical ureas from N-Boc Protected Primary Anilines and Amines," Synlett, 1996, vol. 6, pp. 507-508.

Lemoucheux L. et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," J Org Chem, 2003, vol. 68 (19), pp. 7289-7297.

Lepicier P. et al., "Endocannabinoids protect the rat isolated heart against ischaemia," British Journal of Pharmacology, 2003, vol. 139, pp. 805-815.

Leung M. et al., "S,S-Dimethyl Dithiocarbonate: A Convenient Reagent for the Synthesis of Symmetrical and Unsymmetrical Ureas," J Org Chem, 1996, vol. 61, pp. 4175-4179.

Linn, et al., Journal of American Chemistry Society, 1963, 2032, vol. 85.

Lizondo J., et al., "Linezolid: Oxazolidinone antibacterial," Drugs of the Future, 1996, 21 (11), 1116-1123.

Lotersztajn S. et al., "Hepatic Fibrosis: Molecular Mechanisms and Drug Targets," Annual Review of Pharmacology and Toxicology, 2005, vol. 45, pp. 605-628.

Majer P. et al., "A Safe and Efficient Method for Preparation of N,-Unsymmetrically Disubstituted Ureas Utilizing Triphosgene," J Org Chem, 1994, vol. 59, pp. 1937-1938.

Malan T. P. et al., "CB2 cannabinoid receptor-mediated peripheral antinociception," Pain, 2001, vol. 93, pp. 239-245.

Mallesham B., et al., "Highly efficient CuI-catalyzed coupling of aryl bromides with oxazolidinones using Buchwald's protocol: a short route to linezolid and toloxatone," Org. Lett., 2003, 5 (7), 963-965.

Maresz K. et al., "Modulation of the cannabinoid CB2 receptor in microglial cells in response to inflammatory stimuli," Journal of Neurochemistry, 2005, vol. 95, pp. 437-445.

Mark A. Scialdone et al.,"Phosgenated p-Nitrophenyl(polystyrene)ketoxime or Phoxime Resin. A New Resin for the Solid-Phase Synthesis of Ureas via Thermolytic Cleavage of Oxime-Carbamates?," J. Org. Chem., 1998, vol. 63, pp. 4802-4807, American Chemical Society.

Mathison R. et al., "Effects of cannabinoid receptor-2 activation on accelerated gastrointestinal transit in lipopolysaccharide-treated rats," British Journal of Pharmacology, 2004, vol. 142, pp. 1247-1254.

McKallip R. J., et al., "Targeting CB2 cannabinoid receptors as a novel therapy to treat malignant lymphoblastic disease," Blood, 2002, vol. 15 (2), pp. 627-634.

Nackley A. G. et al., "Selective activation of cannabinoid CB2 receptors suppresses spinal fos protein expression and pain behavior in a rat model of inflammation," Neuroscience, 2003, vol. 119, pp. 747-757.

Ni X. et al., "Win 55212-2, a cannabinoid receptor agonist, attenuates leukocyte/endothelial interactions in an experimental autoimmune encephalomyelitis model," Multiple Sclerosis, 2004, vol. 10, pp. 158-164.

Nieuwenhuijzen JW, Conti PGM, "Solid and Solution Phase Combinatorial Synthesis of Ureas," Tetrahedron Letters, 1998, vol. 39, pp. 7811-7814, Pergamon.

Ozaki S., et al., "Recent advances in isocyanate chemistry", Chemical Reviews, 1972, 72 (5), 457-496.

Patel J. J. et al., "Inhibition of guinea-pig and human sensory nerve activity and the cough reflex in guinea-pigs by cannabinoid (CB2) receptor activation," British Journal of Pharmacology, 2003, vol. 140, pp. 261-268.

Pertwee R. G., "Cannabinoids and multiple sclerosis," Pharmacology & Therapeutics, 2002, vol. 95, pp. 165-174.

Prescott et al., "Lipid Vesicles as Carriers for Introducing Biologically Active Materials into Cells," Methods in Cell Biology, 1976, Academic Press, vol. 14 (33) pp. 33-71.

Quartilho A. et al., "Inhibition of Inflammatory Hyperalgesia by Activation of Peripheral CB2 Cannabinoid Receptors," Anesthesiology, 2003, vol. 99, pp. 955-960.

Ralston S. H., "Regulation of bone mass, bone loss and osteoclast activity by cannabinoid receptors," Nature Medicine, 2005, vol. 11, pp. 774-779.

Ramirez B. G. et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.

Rautio et al,"Prodrugs: design and clinical applications" Nature Reviews Drug Discovery, vol. 7, pp. 255-270, 2008.

Sanchez C. et al., "Inhibition of Glioma Growth in Vivo by Selective Activation of the CB2 Cannabinoid Receptor1," Cancer Research, 2001, vol. 61, pp. 5784-5789.

Smith, D.A. et al, "Do prodrugs deliver?" Current Opinion in Drug Discovery & Development, vol. 10 (5), pp. 550-559, 2007.

Steffens S. et al., "Low dose oral cannabinoid therapy reduces progression of atherosclerosis in mice," Nature, 2005, vol. 434, pp. 782-786.

Takeda K. et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.

Testa, B, "Prodrugs: bridging pharmacodynamic/pharmacokinetic gaps."Current Opinion in Chemical Biology, vol. 13 (3), pp. 338-344, 2009.

Thomson J. F., "Physiological effects of D2O in mammals," Ann. New York Acad. Sci., 1960, 84, 736-744.

Valenzano K. J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, vol. 48, pp. 658-672.

Wang et al, "Drug Delivery: Principles and Applications," John Wiley & Sons, Inc. Publication, pp. 136-137, 2005.

Warhurst A. C. et al., "Interferon gamma induces differential upregulation of alpha and beta chemokine secretion in colonic epithelial cell lines," Gut, 1998, vol. 42, pp. 208-213.

Wright K. et al., "Differential Expression of Cannabinoid Receptors in the Human Colon: Cannabinoids Promote Epithelial Wound Healing," Gastroenterology, 2005, vol. 129, pp. 437-453.

Yoshihara S. et al., "Cannabinoid Receptor Agonists Inhibit Sensory Nerve Activation in Guinea Pig Airways," American Journal of Respiratory and Critical Care Medicine, 2004, vol. 170, pp. 941-946.

Yoshihara S. et al., "Endogenous Cannabinoid Receptor Agonists Inhibit Neurogenic Inflammations in Guinea Pig Airways," Allergy and Immunology, 2005, vol. 138, pp. 80-87.

Yoshihara S. et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

* cited by examiner

COMPOUNDS AS CANNABINOID RECEPTOR LIGANDS

This application is a continuation in part of U.S. patent application Ser. No. 12/100,731 filed on Apr. 10, 2008 that seeks priority from a U.S. Provisional Application Ser. No. 60/923,951, filed on Apr. 17, 2007. Further this application is a Non-provisional application of U.S. Provisional Application Ser. No. 61/111,041, filed on Nov. 4, 2008. All of these applications are incorporated herein by reference, in their entirety.

TECHNICAL FIELD

The present application relates to isothiazolylidene containing compounds, compositions comprising such compounds, and methods for treating conditions and disorders using such compounds and compositions.

BACKGROUND (−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there may be no permanent nerve damage, "chronic" nociceptive pain results from some conditions when pain extends beyond six months. Examples of chronic nociceptive pain include osteoarthritis, rheumatoid arthritis, musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

Provided herein are compounds that are $CB_2$ receptor ligands and pharmaceutical compositions and methods for the treatment of disorders using these compounds and pharmaceutical compositions thereof.

Disclosed herein are compounds of formula (I)

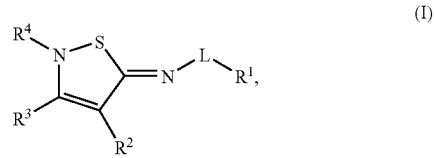

or pharmaceutically acceptable salts, solvates, prodrugs, or combinations thereof, wherein L is C=O, C=S, S(O)$_2$, or C=NCN;

$R^1$ is alkyl, alkenyl, alkynyl, —(CR$^a$R$^b$)$_m$—OH, —(CR$^a$R$^b$)$_m$—O(alkyl), —(CR$^a$R$^b$)$_m$—CN, haloalkyl, G$^1$, —NR$^{Z1}$R$^{Z5}$, or —OR$^{Z5}$;

$R^{Z5}$ is alkyl, haloalkyl, G$^{1a}$, —(CR$^a$R$^b$)$_m$-G$^{1a}$, —(CR$^a$R$^b$)$_n$—OR$^{Z1}$, —(CR$^a$R$^b$)$_n$—N(R$^{Z1}$)(R$^{Z1}$), —(CR$^a$R$^b$)$_m$—C(O)O(R$^{Z1}$), —(CR$^a$R$^b$)$_m$—C(O)R$^{Z1}$, —(CR$^a$R$^b$)$_m$—C(O)N(R$^{Z1}$)(R$^{Z1}$), —(CR$^a$R$^b$)$_m$—S(O)$_2$R$^{Z1}$, —(CR$^a$R$^b$)$_m$—S(O)$_2$N(R$^{Z1}$)(R$^{Z1}$), or —(CR$^a$R$^b$)$_m$—CN;

$R^2$ is alkyl, alkenyl, alkynyl, G$^1$, —C(R$^{Zb}$)=NO(R$^{Z1}$), —O(R$^{Za}$), —N(R$^{Z1}$)(R$^{Z2b}$), —(CR$^a$R$^b$)$_m$—N$_3$, —(CR$^a$R$^b$)$_m$—CN, haloalkyl, —(CR$^a$R$^b$)$_m$—O(R$^{Za}$), —(CR$^a$R$^b$)$_m$—S(R$^{Zb}$), —(CR$^a$R$^b$)$_m$—C(O)O(R$^{Zb}$), —(CR$^a$R$^b$)$_m$—C(O)N(R$^{Z1}$)(R$^{Z2a}$), —(CR$^a$R$^b$)$_m$—SO$_2$N(R$^{Z1}$)(R$^{Z2a}$), —(CR$^a$R$^b$)$_m$—C(O)(R$^{Zb}$), —(CR$^a$R$^b$)$_m$—SO$_2$(R$^{Zd}$), —SO$_2$(R$^{Zd}$), —(CR$^a$R$^b$)$_m$—C(R$^{Zb}$)=NO(R$^{Z1}$), —(CR$^a$R$^b$)$_m$—N(R$^{Z1}$)(R$^{Z2b}$), or —(CR$^a$R$^b$)$_m$-G$^1$;

$R^3$ is hydrogen, alkyl, halogen, —CN, -G$^2$, haloalkyl, or —(CR$^a$R$^b$)$_m$-G$^2$;

$R^4$ is alkyl, alkenyl, alkynyl, —(CR$^a$R$^b$)$_n$—CN, —(CR$^a$R$^b$)$_n$—OH, —(CR$^a$R$^b$)$_n$—O(alkyl), haloalkyl, G$^2$, or —(CR$^a$R$^b$)$_m$-G$^2$; or $R^2$ and $R^3$, or $R^3$ and $R^4$, together with the atoms to which they are attached, form a five-, six-, or seven-membered monocyclic ring containing zero or one additional double bond, zero or one additional heteroatom selected from O, S, N, and N(H), each said monocyclic ring is independently unsubstituted or substituted with 1, 2, 3, 4, or 5 substituents ($R^{21}$) selected from the group consisting of oxo, alkyl, alkenyl, alkynyl, halogen, —CN, —O($R^{1a}$), —C(O)OH, —C(O)O(alkyl), —C(O)($R^{1a}$), —N($R^{Z3}$)($R^{3a}$), —N($R^{3a}$)C(O)$R^{1a}$, —N($R^{3a}$)C(O)O($R^{1a}$), —N($R^{3a}$)C(O)N($R^{Z3}$)($R^{3a}$), —N($R^{3a}$)S(O)$_2$($R^{2a}$), —N($R^{3a}$)S(O)$_2$N($R^{Z3}$)($R^{3a}$), —SO$_2$($R^{2a}$), —C(O)N($R^{Z3}$)($R^{3a}$), —S(O)$_2$N($R^{Z3}$)($R^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O($R^{1a}$), and haloalkyl; two adjacent or non-adjacent atoms of each of said monocyclic ring are optionally linked by an alkylene bridge of one, two, three, or four carbon atoms; and two substituents ($R^{21}$) on the same carbon atom, together with said carbon atom, optionally form a 3-6 membered monocyclic ring containing 0, 1, or 2 heteroatoms selected from O, S, and N(H);

$R^{Za}$, at each occurrence, is independently hydrogen, alkyl, haloalkyl, —(CR$^c$R$^d$)$_p$—O(alkyl), G$^1$, —(CR$^c$R$^d$)$_q$—CN, or —(CR$^c$R$^d$)$_q$-G$^1$;

$R^{Zb}$, at each occurrence, is independently hydrogen, alkyl, haloalkyl, G$^1$, or —(CR$^c$R$^d$)$_q$-G$^1$;

$R^{Z1}$, at each occurrence, is independently hydrogen, alkyl, or haloalkyl;

$R^{Z2a}$, at each occurrence, is independently hydrogen, alkyl, haloalkyl, G$^1$, or —(CR$^c$R$^d$)$_q$-G$^1$, $R^{Z2b}$, at each occurrence, is independently hydrogen, alkyl, haloalkyl, G$^1$, —C(O)$R^{Zc}$, —C(O)O$R^{Zc}$, —C(O)N($R^{Z1}$)($R^{Zc}$), —S(O)$_2$$R^{Zd}$, —S(O)$_2$N($R^{Z1}$)($R^{Zc}$), or —(CR$^c$R$^d$)$_q$-G$^1$, $R^{Zc}$, at each occurrence, is independently hydrogen, alkyl, haloalkyl, G$^1$, or —(CR$^e$R$^f$)$_t$-G$^1$;

$R^{Zd}$, at each occurrence, is independently alkyl, haloalkyl, G$^1$, or —(CR$^e$R$^f$)$_t$-G$^1$;

G$^1$ and G$^{1a}$, at each occurrence, are each independently aryl, heteroaryl, cycloalkyl, cycloalkenyl, or heterocycle, wherein each G$^1$ and G$^{1a}$ is independently unsubstituted or substituted with 1, 2, 3, 4, or 5 substituents selected from the group consisting of alkyl, alkenyl, alkynyl, alkoxyalkenyl, hydroxyalkyl, halogen, —CN, oxo, -G$^2$, —NO$_2$, —C($R^{1a}$)=N—O($R^{1a}$), —OC(O)$R^{1a}$, —OC(O)N($R^{Z3}$)($R^{3a}$), —SR$^{1a}$, —S(O)$_2$R$^{2a}$, —S(O)$_2$N($R^{Z3}$)($R^{3a}$), —C(O)$R^{1a}$, —C(O)OR$^{1a}$, —C(O)N($R^{Z3}$)($R^{3a}$), -L$^1$-A$^1$, —N($R^{3a}$)C(O)$R^{1a}$, —N($R^{3a}$)S(O)$_2$R$^{2a}$, —N($R^{3a}$)C(O)O($R^{1a}$), —N($R^{3a}$)C(O)N($R^{Z3}$)($R^{3a}$), —(CR$^{1g}$R$^{1h}$)$_u$—NO$_2$, —(CR$^{1g}$R$^{1h}$)$_u$—OR$^{1a}$, —(CR$^{1g}$R$^{1h}$)$_u$—OC(O)R$^{1a}$, —(CR$^{1g}$R$^{1h}$)$_u$—OC(O)N($R^{Z3}$)($R^{3a}$), —(CR$^{1g}$R$^{1h}$)$_u$—SR$^{1a}$, —(CR$^{1g}$R$^{1h}$)$_u$—S(O)$_2$R$^{2a}$, —(CR$^{1g}$R$^{1h}$)$_u$—S(O)$_2$N($R^{Z3}$)($R^{3a}$), —(CR$^{1g}$R$^{1h}$)$_u$—C(O)$R^{1a}$, —(CR$^{1g}$R$^{1h}$)$_u$—C(O)OR$^{1a}$, —(CR$^{1g}$R$^{1h}$)$_u$—C(O)N($R^{Z3}$)($R^{3a}$), —(CR$^{1g}$R$^{1h}$)$_u$—N($R^{Z3}$)($R^{3a}$), —(CR$^{1g}$R$^{1h}$)$_u$—N($R^{3a}$)C(O)$R^{1a}$, —(CR$^{1g}$R$^{1h}$)$_u$—N($R^{3a}$)S(O)$_2$R$^{2a}$, —(CR$^{1g}$R$^{1h}$)$_u$—N($R^{3a}$)C(O)O($R^{1a}$), —(CR$^{1g}$R$^{1h}$)$_u$—N($R^{3a}$)C(O)N($R^{Z3}$)($R^{3a}$), —(CR$^{1g}$R$^{1h}$)$_u$-G$^2$, —(CR$^{1g}$R$^{1h}$)$_u$—CN, and haloalkyl;

A$^1$ is $R^{1a}$, —(CR$^{1g}$R$^{1h}$)$_u$-A$^2$, —N($R^{Z3}$)C(O)R$^{1a}$, —N($R^{Z3}$)C(O)OR$^{2a}$, —N($R^{Z3}$)($R^{1a}$), or —N=C($R^{Z3}$)($R^{1a}$);

A$^2$ is —C(O)$R^{1a}$, —S(O)$_2$R$^{2a}$, CON($R^{Z3}$)($R^{3a}$), CSN($R^{Z3}$)($R^{3a}$), —SO$_2$N($R^{Z3}$)($R^{3a}$), —CN, —C(=NOR$^{1a}$)$R^{1a}$, —N($R^{Z3}$)C(O)R$^{1a}$, —N($R^{3a}$)C(O)OR$^{2a}$, —N($R^{3a}$)S(O)$_2$R$^{2a}$, —N($R^{3a}$)C(O)N($R^{Z3}$)($R^{3a}$), —N($R^{3a}$)S(O)$_2$N($R^{Z3}$)($R^{3a}$), or -L$^2$-R$^{Z6}$;

R$^{Z6}$ is alkoxyalkyl, hydroxyalkyl, cyanoalkyl, haloalkoxyalkyl, G$^2$, or —(CR$^k$R$^x$)$_v$-G$^2$;

L$^1$ and L$^2$ are each independently O or N($R^{Z3}$);

R$^{1a}$ and R$^{3a}$, at each occurrence, are each independently hydrogen, alkyl, alkynyl, haloalkyl, alkoxy, alkoxyalkyl, hydroxyalkyl, cyanoalkyl, haloalkoxyalkyl, G$^2$, or —(CR$^k$R$^x$)$_v$-G$^2$;

R$^{2a}$, at each occurrence, is independently alkyl, haloalkyl, alkoxyalkyl, hydroxyalkyl, cyanoalkyl, haloalkoxyalkyl, G$^2$, or —(CR$^k$R$^x$)$_v$-G$^2$;

G$^2$, at each occurrence, is aryl, heteroaryl, cycloalkyl, cycloalkenyl, or heterocycle, wherein each G$^2$ is independently unsubstituted or substituted with 1, 2, 3, 4, or 5 substituents selected from the group consisting of —G$^3$, —(CR$^{2g}$R$^{2h}$)$_w$-G$^3$, alkyl, alkenyl, alkynyl, halogen, —CN, oxo, —NO$_2$, —OR$^{1b}$, —OC(O)R$^{1b}$, —OC(O)N($R^{Z4}$)($R^{3b}$), —SR$^{1b}$, —S(O)$_2$R$^{2b}$, —S(O)$_2$N($R^{Z4}$)($R^{3b}$), —C(O)R$^{1b}$, —C(O)OR$^{1b}$, —C(O)N($R^{Z4}$)($R^{3b}$), —N($R^{Z4}$)($R^{3b}$), —N($R^{Z4}$)C(O)R$^{1b}$, —N($R^{Z4}$)C(O)OR$^{1b}$, —N($R^{Z4}$)C(O)N($R^{Z4}$)($R^{3b}$), —(CR$^{2g}$R$^{2h}$)$_w$—NO$_2$, —(CR$^{2g}$R$^{2h}$)$_w$—OR$^{1b}$, —(CR$^{2g}$R$^{2h}$)$_w$—OC(O)R$^{1b}$, —(CR$^{2g}$R$^{2h}$)$_w$—OC(O)N($R^{Z4}$)($R^{3b}$), —(CR$^{2g}$R$^{2h}$)$_w$—SR$^{1b}$, —(CR$^{2g}$R$^{2h}$)$_w$S(O)$_2$R$^{2b}$, —(CR$^{2g}$R$^{2h}$)$_w$—S(O)$_2$N($R^{Z4}$)($R^{3b}$), —(CR$^{2g}$R$^{2h}$)$_w$—C(O)R$^{1b}$, —(CR$^{2g}$R$^{2h}$)$_w$—C(O)OR$^{1b}$, —(CR$^{2g}$R$^{2h}$)$_w$—C(O)N($R^{Z4}$)($R^{3b}$), —(CR$^{2g}$R$^{2h}$)$_w$—N($R^{Z4}$)($R^{3b}$), —(CR$^{2g}$R$^{2h}$)$_w$—N($R^{Z4}$)C(O)R$^{1b}$, —(CR$^{2g}$R$^{2h}$)$_w$—N($R^{Z4}$)C(O)O($R^{1b}$), —(CR$^{2g}$R$^{2h}$)$_w$—N($R^{Z4}$)C(O)N($R^{Z4}$)($R^{3b}$), —(CR$^{2g}$R$^{2h}$)$_w$—CN, and haloalkyl;

G$^3$, at each occurrence, is independently monocyclic heterocycle, monocyclic heteroaryl, or monocyclic cycloalkyl; wherein each occurrence of G$^3$ is independently unsubstituted or substituted with 1, 2, 3, or 4 substituents selected from the group consisting of —N($R^{Z4}$)($R^{3b}$), alkyl, haloalkyl, alkoxy, haloalkoxy, halo, oxo, CN, and OH;

m, q, t, u, v, and w, at each occurrence, are each independently 1, 2, 3, 4, or 5;

n and p, at each occurrence, are each independently 2, 3, 4, or 5;

R$^{1b}$ and R$^{3b}$, at each occurrence, are each independently hydrogen, alkyl, haloalkyl, monocyclic cycloalkyl, or —(CR$^{2g}$R$^{2h}$)$_w$-monocyclic cycloalkyl;

R$^{2b}$, at each occurrence, is independently alkyl, haloalkyl, monocyclic cycloalkyl, or —(CR$^{2g}$R$^{2h}$)$_w$-monocyclic cycloalkyl;

R$^a$, R$^c$, R$^d$, R$^e$, R$^f$, R$^{1g}$, R$^{2g}$, R$^{2h}$, R$^k$, and R$^x$, at each occurrence, are each independently hydrogen, halogen, alkyl, or haloalkyl;

R$^{1h}$, at each occurrence, is independently hydrogen, halogen, alkyl, haloalkyl, —OR$^{1b}$, —N($R^{Z4}$)($R^{3b}$), —N($R^{Z4}$)C(O)R$^{1b}$, —N($R^{Z4}$)C(O)O($R^{1b}$), or —N($R^{Z4}$)S(O)$_2$R$^{1b}$;

each occurrence of R$^b$ is independently hydrogen, halogen, alkyl, haloalky, or OH;

R$^{Z3}$ and R$^{Z4}$, at each occurrence, are each independently hydrogen, alkyl, or haloalkyl; and the monocyclic cycloalkyl, as a substituent or as part of a substituent as represented by R$^{1b}$, R$^{2b}$, and R$^{3b}$, is unsubstituted or substituted with 1, 2, 3, 4, 5, or 6 substituents selected from the group consisting of alkyl, halogen, haloalkyl, hydroxy, oxo, and alkoxy;

with the proviso that the compound is other than 4-methyl-N-[(3Z)-1-phenyl-1,4,5,6-tetrahydro-3H-cyclopenta[c]isothiazol-3-ylidene]benzenesulfonamide; N-[(3Z)-1-cyclohexyl-4,5,6,7-tetrahydro-2,1-b enzisothiazol-3(1H)-ylidene]-4-methylbenzenesulfonamide; 4-methyl-N-[(3Z)-1-phenyl-4,5,6,7-tetrahydro-2,1-benzisothiazol-3(1H)-ylidene]benzenesulfonamide; and ethyl (5Z)-2,4-diphenylisothiazol-5(2H)-ylidenecarbamate.

Another aspect relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s). Such compositions can be administered in accordance with methods described herein, typically as part of a therapeutic regimen for treatment or prevention of conditions and disorders related to cannabinoid (CB) receptor subtype $CB_2$. More particularly, the methods are useful for treating conditions related to pain such as, but not limited to, chronic pain, neuropathic pain, nociceptive pain, osteoarthritic pain, inflammatory pain, cancer pain, lower back pain, post operative pain, and eye pain; inflammatory disorders, immune disorders, neurological disorders, cancers of the immune system, respiratory disorders, obesity, diabetes, cardiovascular disorders, or for providing neuroprotection.

Further, provided herein are uses of the present compounds or pharmaceutically acceptable salts, solvates, or salts of solvates thereof, in the manufacture of medicaments for the treatment of the disease or conditions described above, alone or in combination with one or more pharmaceutically acceptable carrier(s), particularly for the treatment of pain such as, but not limited to, chronic pain, neuropathic pain, nociceptive pain, osteoarthritic pain, inflammatory pain, cancer pain, lower back pain, post operative pain, and eye pain, or combinations thereof.

The compounds, compositions comprising the compounds, and methods for treating or preventing conditions and disorders by administering the compounds or compositions thereof, are further described herein.

These and other objectives are described in the following paragraphs. These objectives should not be deemed to narrow the scope of the invention.

DETAILED DESCRIPTION

Compounds of Formula (I) are disclosed,

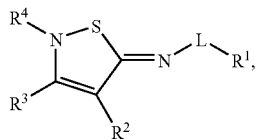

(I)

wherein $R^1$, $R^2$, $R^3$, $R^4$, and L are as defined above in the Summary and below in the Detailed Description. Compositions comprising such compounds and methods for treating conditions and disorders using such compounds and compositions are also disclosed.

In various embodiments, the present compounds may have one or more variable that occurs more than one time in any substituent or in the compounds or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

a. Definition of Terms

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl(allyl), 2-methyl-2-propenyl, 3-butenyl, but-1-enyl, 4-pentenyl, 5-hexenyl, 2-heptenyl, 2-methyl-1-heptenyl, and 3-decenyl.

The term "alkoxy," as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl (1-methylpropyl), iso-butyl, tert-butyl, n-pentyl, 1,1-dimethylpropyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl (ethynyl), 1-propynyl, 2-propynyl, 3-butynyl, 2-pentynyl, and 1-butynyl.

The term "aryl" as used herein, means phenyl or a bicyclic aryl. The bicyclic aryl is naphthyl (including naphth-1-yl), or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups can be unsubstituted or substituted.

The term "cyano" as used herein, refers to a —CN group.

The term "cyanoalkyl" as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The term "$C_{3-6}$ cycloalkyl" as used herein, means a monocyclic cycloalkyl containing three to six carbon atoms, zero heteroatoms and zero double bonds. Examples of $C_{3-6}$ cycloalkyl include cyclopropyl, cyclobutyl, cyclopentyl, and cyclohexyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic cycloalkyls include, but are not limited to, bicyclo[3.1.1]heptyl, bicyclo[2.2.1]heptyl, bicyclo[2.2.2]octyl (including bicyclo[2.2.2]oct-1-yl), bicyclo[3.2.2]nonyl, bicyclo[3.3.1]nonyl, and bicyclo[4.2.1]nonyl. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of between one and four carbon atoms of the bicyclic cycloalkyl ring. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). Spirocyclic cycloalkyl is exemplified by a monocyclic cycloalkyl ring wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, tricyclic, and spirocyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkoxyalkyl" as used herein, means a haloalkoxy group, as defined herein, appended to the parent molecular moiety through an alkyl group, as defined herein. Representative examples of haloalkoxyalkyl include, but are not limited to, chloromethoxymethyl and trifluoromethoxymethyl.

The term "haloalkyl" as used herein, means an alkyl group, as defined herein, in which one, two, three, four, five or six hydrogen atoms are replaced by halogen. The term "$C_{1-6}$ haloalkyl" as used herein, means a $C_{1-6}$ alkyl group, as defined herein, in which one, two, three, four, five or six hydrogen atoms are replaced by halogen. Representative examples of haloalkyl include, but are not limited to, chloromethyl, fluoromethyl, 2-fluoroethyl, 1,1-difluoroethyl, 2,2-difluoroethyl, 2,2,2-trichloroethyl, 2,2,2-trifluoroethyl, 2,2,2-trifluoro-1,1-dimethylethyl, 2-fluoro-1,1-dimethylethyl, trifluoromethyl, difluoromethyl, 4-fluoro-4-methylpentyl, 4,4-difluoropentyl, 4-fluorobutyl, 3-fluoro-3-methylbutyl, 4,4,4-trifluorobutyl, pentafluoroethyl, and 2-chloro-3-fluoropentyl.

The term "heterocycle" or "heterocyclic" as used herein, means a monocyclic, a bicyclic, a tricyclic, or a spirocyclic ring system, containing at least one heteroatom. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven-membered ring contains zero, one, two, or three double bonds and one, two, or three heteroatoms selected from the group consisting of O, N, and S. Representative examples of monocyclic heterocycles include, but are not limited to, azetidinyl (including azetidin-1-yl), azepanyl, aziridinyl, diazepanyl, dihydro-oxazolyl (e.g. 4,5-dihydro-1,3-oxazol-2-yl), 1,3-dioxanyl (including 1,3-dioxan-2-yl), 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl (including morpholin-4-yl), 4,5-dihydroisoxazolyl (including 4,5-dihydroisoxazol-5-yl), dihydro-oxazinyl (e.g. 5,6-dihydro-4H-1,3-oxazin-2-yl), oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl (including pyrrolidin-3-yl, pyrrolidin-2-yl, pyrrolidin-1-yl), tetrahydrofuranyl (including tetrahydrofuran-2-yl), tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, oxabicyclo[2.2.1]heptyl (including oxabicyclo[2.2.1]hept-2-yl), and 2,3-dihydro-1H-indolyl. Spirocyclic heterocycle means a monocyclic heterocycle wherein two of the substituents on the same carbon atom form a 4-, 5-, or 6-membered monocyclic cycloalkyl, wherein the cycloalkyl is optionally substituted with 1, 2, 3, 4, or 5 alkyl groups. One example of a spiroheterocycle is 5-oxaspiro[3,4]octane. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge consisting of one, two, three, or four carbon atoms.

Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane such as 1-azatricyclo[3.3.1.1$^{3,7}$]decane, and oxa-adamantane such as 2-oxatricyclo[3.3.1.1$^{3,7}$]decane. The monocyclic, bicyclic, tricyclic, and spirocyclic heterocycles are connected to the parent molecular moiety through any carbon atom or any nitrogen atom contained within the rings, and can be unsubstituted or substituted. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl (including furan-2-yl), imidazolyl, isoxazolyl, isothiazolyl, oxadiazolyl, 1,3-oxazolyl, pyridinyl (including pyridin-2-yl, pyridin-3-yl, pyridin-4-yl), pyridazinyl, pyrimidinyl, pyrazinyl, pyrazolyl, pyrrolyl, tetrazolyl, thiadiazolyl, 1,3-thiazolyl (including 1,3-thiazol-4-yl, 1,3-thiazol-2-yl), thienyl (including thien-2-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl (including quinolin-8-yl), thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any carbon atom or any nitrogen atom contained within the ring systems. The nitrogen and sulfur heteroatoms of the heteroaryl rings may optionally be oxidized, and are contemplated within the scope of the invention.

The term "heteroatom" as used herein, means a nitrogen, oxygen, or sulfur atom.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 2-hydroxypropyl, 3-hydroxypropyl, 2,3-dihydroxypentyl, 2-hydroxy-2-methylpropyl, 1-hydroxy-1-methylethyl, and 2-ethyl-4-hydroxyheptyl.

The term "hydroxy" as used herein, means an —OH group.
The term "oxo" as used herein, means a =O group.

b. Compounds

Compounds of Formula (I) is as described above.

Particular values of variable groups in compounds of Formula (I) are as follows. Such values may be used where appropriate with any of the other values, definitions, claims or embodiments defined hereinbefore or hereinafter.

As described generally in the Summary section for compounds of Formula (I), $R^2$ is alkyl, alkenyl, alkynyl, $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl, —(CR$^a$R$^b$)$_m$—O($R^{Za}$), —(CR$^a$R$^b$)$_m$—S($R^{Zb}$), —(CR$^a$R$^b$)$_m$—C(O)O($R^{Zb}$), —(CR$^a$R$^b$)$_m$—C(O)N($R^{Z1}$)($R^{Z2a}$), —(CR$^a$R$^b$)$_m$—SO$_2$N($R^{Z1}$)($R^{Z2a}$), —(CR$^a$R$^b$)$_m$—C(O)($R^{Zb}$), —(CR$^a$R$^b$)$_m$—SO$_2$ (e), —SO$_2$ (e), —(CR$^a$R$^b$)$_m$—C($R^{Zb}$))=NO($R^{Z1}$), —(CR$^a$R$^b$)$_m$—N($R^{Z1}$)($R^{Z2b}$), or —(CR$^a$R$^b$)$_m$-$G^1$, wherein $G^1$, $R^a$, $R^b$, m, $R^{Za}$, $R^{Zb}$, $R^{Zd}$, $R^{Z1}$, $R^{Z2a}$, and $R^{Z2b}$ are as described in the Summary and in embodiments herein.

In certain embodiments of compounds of Formula (I), $R^2$ is alkyl (e.g., methyl, ethyl, n-propyl, isobutyl, n-butyl, n-pentyl, and the like), alkenyl (for example, allyl, vinyl, but-1-enyl, and the like), alkynyl, $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —(CR$^a$R$^b$)$_m$—O($R^{Za}$), —(CR$^a$R$^b$)$_m$—C(O)O($R^{Zb}$), —(CR$^a$R$^b$)$_m$—C(O)($R^{Zb}$), —(CR$^a$R$^b$)$_m$—C($R^{Zb}$)=NO($R^{Z1}$), —(CR$^a$R$^b$)$_m$—N($R^{Z1}$)($R^{Z2b}$), or —(CR$^a$R$^b$)$_m$-$G^1$, wherein $G^1$, $R^a$, $R^b$, m, $R^{Za}$, $R^{Zb}$, $R^{Z1}$, and $R^{Z2b}$ are as described in the Summary and in embodiments herein. For example, in certain embodiments, m is 1, 2, 3, or 4. In other embodiments, m is 1, 2, or 3. In yet other embodiments, m is 1 or 2.

In certain embodiments of compounds of Formula (I), $R^2$ is alkyl (e.g., methyl, ethyl, n-propyl, isobutyl, n-butyl, n-pentyl, and the like), alkenyl (for example, allyl, vinyl, but-1-enyl, and the like), alkynyl, —(CR$^a$R$^b$)$_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —(CR$^a$R$^b$)$_m$—O($R^{Za}$), or —(CR$^a$R$^b$)$_m$-$G^1$, wherein $G^1$, $R^a$, $R^b$, m, and $R^{Za}$, are as described in the Summary and in embodiments herein. For example, in certain embodiments, m is 1, 2, 3, or 4. In other embodiments, m is 1, 2, or 3. In yet other embodiments, m is 1 or 2.

In certain embodiments of compounds of Formula (I), $R^2$ is alkyl (e.g., methyl, ethyl, n-propyl, isobutyl, n-butyl, n-pentyl, and the like), alkenyl (for example, allyl, vinyl, but-1-enyl, and the like), alkynyl, or $C_{1-6}$ haloalkyl (e.g., 4-fluoro-4-methylpentyl, 4,4-difluoropentyl, 3-fluoro-3-methylbutyl, 4,4,4-trifluorobutyl, 4-fluorobutyl).

In certain embodiments, $R^2$ is $G^1$ wherein $G^1$ is as described in the Summary. Examples of $G^1$ include, but are not limited to, cycloalkyl (e.g. monocyclic cycloalkyl such as, but not limited to, cyclopropyl) and heterocycle (e.g. monocyclic heterocycle such as, but not limited to, tetrahydropyranyl), each of which is optionally substituted as described generally in the Summary section. Examples of the optional substituents, when present, include, but are not limited to, alkyl (e.g. methyl, ethyl), oxo, and haloalkyl.

In certain embodiments, $R^2$ is —(CR$^a$R$^b$)$_m$-$G^1$ wherein m, $G^1$, $R^a$, m, and $R^b$ are as described in the Summary. Examples of $G^1$ include, but are not limited to, aryl (e.g. phenyl), cycloalkyl (e.g. cyclopropyl, cyclobutyl, cyclopentyl, cyclohexyl), heterocycle (e.g. 4,5-dihydroisoxazolyl, morpholinyl, 1,3-dioxanyl, 1,3-dioxolanyl, tetrahydrofuranyl), heteroaryl (e.g. furanyl, 1,3-thiazolyl, thienyl), each of which is optionally substituted as described generally in the Summary section. Examples of the optional substituents, when present, include, but are not limited to, alkyl (e.g. methyl, ethyl), haloalkyl, and oxo. $R^a$ and $R^b$ are as described generally in the Summary section. Examples of $R^a$ include, but are not limited to, hydrogen and $C_{1-6}$ alkyl (e.g. methyl, ethyl, isopropyl). Examples of $R^b$ include, but are not limited to, hydrogen, $C_{1-6}$ alkyl (e.g. methyl, ethyl, isopropyl), and OH.

In certain embodiments, $R^2$ is —C($R^{Zb}$)=NO($R^{Z1}$), —(CR$^a$R$^b$)$_m$—N$_3$, —(CR$^a$R$^b$)$_m$—CN, —(CR$^a$R$^b$)$_m$—C(O)

O($R^{Zb}$), $(CR^aR^b)_m$—C(O)($R^{Zb}$), or -$(C^aR^b)_m$—C($R^{Zb}$)=NO($R^{Z1}$), wherein $R^a$, $R^b$, $R^{Z1}$, $R^{Zb}$ and m, are as described in the Summary. Each occurrence of $R^a$, $R^b$, $R^{Zb}$, and $R^{Z1}$ are, for example, independently, hydrogen or $C_{1-6}$ alkyl (e.g. methyl, ethyl, isopropyl).

In certain embodiments, $R^2$ is —O($R^{Za}$) or —N($R^{Z1}$)($R^{Z2b}$) wherein $R^{Za}$, $R^{Z1}$, and $R^{Z2b}$ are as set forth in the Summary. Examples of $R^{Za}$ include, but are not limited to, hydrogen, alkyl (e.g. $C_{1-6}$ alkyl such as, but not limited to, methyl, ethyl, 1-methylpropyl, isopropyl), haloalkyl (e.g., 4-flourobutyl), —$(CR^cR^d)_q$—CN and —$(CR^cR^d)_q$-$G^1$ wherein $R^c$, $R^d$, q, $G^1$ are as set forth in the Summary. $G^1$, for example, is optionally substituted phenyl or optionally substituted pyrrolidinyl. Each occurrence of $R^c$ and $R^d$, are each independently hydrogen or $C_{1-6}$ alkyl (e.g. methyl, ethyl, isopropyl). q is 1 or 2. In certain embodiments, q is 1. $R^{Z1}$, for example, is hydrogen or $C_{1-3}$ alkyl (e.g. methyl). $R^{Z2b}$, for example, is —C(O)O($R^{Zc}$) wherein $R^{Zc}$ is as described in the Summary. $R^{Za}$, for example, is $C_{1-6}$ alkyl (e.g. tert-butyl).

In certain embodiments, $R^2$ is —$(CR^aR^b)_m$—O($R^{Za}$) or —$(CR^aR^b)_m$—N($R^{Z1}$)($R^{Z2b}$) wherein m, $R^a$, $R^b$, $R^{Za}$, $R^{Z1}$, and $R^{Z2b}$ are as described in the Summary and in embodiments herein. In certain embodiments, $R^{Za}$ is hydrogen, alkyl (e.g. $C_{1-6}$ alkyl such as, but not limited to, methyl, ethyl, 1-methylpropyl, isopropyl), haloalkyl (e.g. $C_{1-6}$ haloalkyl such as, but not limited to, 2,2,2-trifluoroethyl, 2-fluoroethyl, 2,2-difluoroethyl), or —$(CR^cR^d)_q$-$G^1$ wherein q, $R^c$, $R^d$, and $G^1$ are as described in the Summary and in embodiments herein. $G^1$, for example, is optionally substituted heterocycle (e.g. monocyclic heterocycle such as, but not limited to, tetrahydrofuran) or optionally substituted phenyl. In certain embodiments, each occurrence of $R^a$, $R^c$, and $R^d$, are, for example, independently, hydrogen or $C_{1-6}$ alkyl (e.g. methyl, ethyl, isopropyl). $R^b$, at each occurrence is, for example, independently, hydrogen, $C_{1-6}$ alkyl (e.g. methyl, ethyl, isopropyl), or OH. q is 1 or 2. In certain embodiments, q is 1. $R^{Z1}$ and $R^{Z2b}$ are, for example, independently hydrogen or $C_{1-6}$ alkyl (e.g. methyl, ethyl, isopropyl).

As described generally above in the Summary, $R^3$ is hydrogen, alkyl, halogen, —CN, -$G^2$, haloalkyl, or —$(CR^aR^b)_m$-$G^2$. In certain embodiments, $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups). In certain embodiments, $R^3$ is hydrogen or $C_{1-6}$ alkyl (e.g. methyl).

As generally described in the Summary, $R^4$ is alkyl, alkenyl, alkynyl, —$(CR^aR^b)_n$—CN, —$(CR^aR^b)_n$—OH, —$(CR^aR^b)_n$—O(alkyl), haloalkyl, $G^2$, or —$(CR^aR^b)_m$-$G^2$. In certain embodiments, $R^4$ is alkyl (e.g. $C_{1-6}$ alkyl such as, but not limited to, methyl, tert-butyl, 1,1-dimethylpropyl), haloalkyl (e.g. 2-fluoro-1,1-dimethylethyl, 2,2,2-trifluoro-1,1-dimethylethyl), or $G^2$ (e.g. optionally substituted $C_{3-6}$ cycloalkyl such as, but not limited to, optionally substituted cyclopropyl or optionally substituted cyclobutyl, or optionally substituted monocyclic heterocycle such as, but not limited to, optionally substituted oxetanyl or optionally substituted tetrahydrofuranyl). In certain embodiments, $G^2$ is cyclopropyl or cyclobutyl, each of which is optionally substituted with one or two $C_{1-3}$ alkyl (e.g. methyl).

In each of the embodiments described for $R^2$, m, if present, is as described in the Summary. For example, in certain embodiments, m is 1, 2, 3, or 4. In other embodiments, m is 1, 2, or 3. In yet other embodiments, m is 1 or 2.

As generally described in the Summary, L is C=O, C=S, S(O)$_2$, or C=NCN.

In certain embodiments, L is C=O.

In certain embodiments, L is C=S.
In certain embodiments, L is S(O)$_2$.
In certain embodiments, L is C=NCN.

As described generally in the Summary, $R^1$ is alkyl, alkenyl, alkynyl, —$(CR^aR^b)_m$—OH, —$(CR^aR^b)_m$—O(alkyl), —$(CR^aR^b)_m$—CN, haloalkyl, $G^1$, —$NR^{Z1}R^{Z5}$, or —$OR^{Z5}$.

In certain embodiments, $R^1$ is $G^1$, —$NR^{Z1}R^{Z5}$, or —$OR^{Z5}$ wherein $G^1$, $R^{Z1}$, and $R^{Z5}$ are as set forth in the Summary and in embodiments herein.

In certain embodiments, $R^1$ is —$OR^{Z5}$ wherein $R^{Z5}$ is as disclosed in the Summary. For example, $R^{Z5}$ is alkyl (e.g. neopentyl), haloalkyl (e.g. 2,2,2-trichloroethyl), or $G^{1a}$, and $G^{1a}$ is as set forth in the Summary. For example, $G^{1a}$ is optionally substituted cycloalkyl such as, but not limited to, optionally substituted adamantyl.

In certain embodiments, $R^1$ is —$NR^{Z1}R^{Z5}$ wherein $R^{Z1}$ and $R^{Z5}$ are as set forth in the Summary. For example, $R^{Z5}$ is $G^{1a}$ or —$(CR^aR^b)_m$—C(O)N($R^{Z1}$)($R^{Z1}$) wherein $G^{1a}$, $R^a$, $R^b$, m, and $R^{Z1}$ are as set forth in the Summary. For example, each occurrence of $R^a$ and $R^b$ are each independently hydrogen or alkyl (e.g. methyl, ethyl, tert-butyl). $R^{Z1}$, at each occurrence, is independently hydrogen or alkyl (e.g. methyl, ethyl, tert-butyl). m, for example, is 1 or 2. $G^{1a}$, for example, is optionally substituted cycloalkyl such as, but not limited to, optionally substituted cyclohexyl. Non limiting examples of the optional substituents of $G^{1a}$ are alkyl, haloalkyl, and oxo.

In certain embodiments, $R^1$ is $G^1$ wherein $G^1$ is as described generally in the Summary. In yet other embodiments, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and in embodiments herein below.

In certain embodiments, $R^1$ is $G^1$, wherein $G^1$ is phenyl or naphthyl, each of which is optionally substituted as described generally in the Summary and embodiments herein below.

In certain embodiments, $R^1$ is $G^1$, wherein $G^1$ is heteroaryl, optionally substituted as described in the Summary and embodiments herein below. In certain embodiments, $R^1$ is optionally substituted quinolin-8-yl.

In certain embodiments, $R^1$ is $G^1$, wherein $G^1$ is cycloalkyl (e.g., e.g., cyclopropyl, cyclobutyl, cyclopentyl, cyclohexyl, bicyclo[2.2.2]octyl, adamantyl, noradamantyl), each of which is optionally substituted as described in the Summary and embodiments herein below.

In certain embodiments, $R^1$ is $G^1$, wherein $G^1$ is heterocycle, optionally substituted as described in the Summary. In certain embodiments, $R^1$ is pyrrolidinyl, dihydropyranyl, oxa-adamantyl, or oxabicyclo[2.2.1]heptyl, each of which is optionally substituted as described in the Summary and in embodiments herein below.

In certain embodiments, examples of the optional substituents of $G^1$ when $R^1$ is $G^1$ include, but are not limited to:
(a). alkyl (e.g. methyl, ethyl, isopropyl),
(b). alkynyl (e.g. ethynyl),
(c). halogen (e.g. F, Cl, I),
(d). —CN,
(e). oxo;
(f). —C($R^{1a}$)=N—O($R^{1a}$) wherein $R^{1a}$ is as disclosed in the Summary. For example, each occurrence of $R^{1a}$ is independently hydrogen or $C_{1-6}$ alkyl (e.g. methyl);
(g). $L^1$-$A^1$, wherein $L^1$ and $A^1$ are as disclosed in the Summary. For example, $L^1$ is O and $A^1$ is $R^{1a}$, N($R^{Z3}$)($R^{1a}$), or —$(CR^{1g}R^{1h})_u$-$A^2$, wherein $R^{1a}$; $R^{Z3}$; $R^{1g}$; $R^{1h}$, u, and $A^2$ are as disclosed in the Summary and embodiments herein. For example, when $L^1$ is O and $A^1$ is $N(R_{Z3})(R^{1a})$, non-limiting examples include those wherein $R^{Z3}$ is hydrogen and $R^{1a}$ is alkyl (e.g. tert-butyl, isopropyl). For compounds where $L^1$ is O and $A^1$ is $R^{1a}$ then $R^{1a}$, for example, is hydrogen, alkyl (e.g. $C_{1-6}$ alkyl such as, but not limited to, methyl, ethyl), haloalkyl (e.g. 2,2,2-trifluoroethyl, 2-fluoroethyl, trifluoromethyl), hydroxyalkyl (e.g. 2-hydroxy-2-methylpropyl), or —$(CR^kR^x)_v$-G2; wherein $R^k$, $R^x$, v, and $G^2$ are as disclosed in the Summary. For example, $R^k$, $R^x$ are, for example, are each independently hydrogen or $C_{1-3}$ alkyl (e.g. methyl). v, for example, is 1. $G^2$, for example, is optionally substituted heterocycle (e.g. optionally substituted monocyclic heterocycle such as, but not limited to, pyrrolidinyl, oxazolidinyl, piperidinyl), or optionally substituted heteroaryl (e.g. optionally substituted monocyclic heteroaryl such as, but not limited to, pyridinyl, pyrazinyl). Examples of the optional substituents of $G^2$ include, but are not limited to, $C_{1-6}$ alkyl (e.g. methyl), oxo, halogen, and haloalkyl. For those where $A^1$ is —$(CR^{1g}R^{1h})_u$-$A^2$, then $A^2$, for example, is $CON(R^{Z3})(R^{3a})$ or CN, wherein $R^{Z3}$ and $R^{3a}$ are as disclosed in the Summary. $R^{1g}$ and $R^{1h}$ are, for example, hydrogen. u, for example, is 1. $R^{Z3}$ and $R^{3a}$ for $CON(R^{Z3})(R^{3a})$ include, but are not limited to, hydrogen and $C_{1-6}$ alkyl (e.g., methyl). Other examples of compounds include, but are not limited to, those wherein the substituent of $R^1$ is $L^1$-$A^1$ wherein $L^1$ is $N(R^{Z3})$, and $A^1$ is as disclosed in the Summary. Other examples of compounds include, but are not limited to, those wherein the substituent of $R^1$ is $L^1$-$A^1$ wherein $L^1$ is $N(R^{Z3})$ and $A^1$ is $R^{1a}$ wherein $R^{Z3}$ and $R^{1a}$ are as disclosed as the Summary. For example, $R^{Z3}$ and $R^{1a}$ are each independently hydrogen or $C_{1-6}$ alkyl (e.g., methyl);

(h). —$S(O)_2R^{2a}$ wherein $R^{2a}$ is as disclosed in the Summary. For example, $R^{2a}$ is $C_{1-6}$ alkyl (e.g., methyl), (i). —$C(O)R^{1a}$ wherein $R^{1a}$ is as disclosed in the Summary. For example, $R^{1a}$ is hydrogen, $C_{1-6}$ alkyl (e.g. methyl, ethyl), or $G^2$ wherein $G^2$ is as disclosed in the Summary. For example, $G^2$ is optionally substituted phenyl or optionally substituted heterocycle (e.g. optionally substituted azetidinyl, pyrrolidinyl). Examples of the optional substituents of $G^2$ include, but are not limited to, alkyl (e.g. methyl), halogen (e.g. F, Cl), —$OR^{1b}$ (e.g. $R^{1b}$ is hydrogen or $C_{1-3}$ alkyl), and haloalkyl (e.g. trifluoromethyl);

(j). —$C(O)OR^{1a}$ wherein $R^{1a}$ is as disclosed in the Summary. For example, $R^{1a}$ is hydrogen or $C_{1-6}$ alkyl (e.g. methyl, ethyl, tert-butyl), (k). —$C(O)N(R^{Z3})(R^{3a})$ wherein $R^{Z3}$ and $R^{3a}$ are as disclosed in the Summary. For example, $R^{Z3}$ is hydrogen or $C_{1-6}$ alkyl (e.g., methyl). $R^{3a}$, for example, is hydrogen, $C_{1-6}$ alkyl (e.g., methyl, ethyl, n-propyl, isopropyl), alkynyl (e.g. prop-2-ynyl), alkoxy (e.g. methoxy), haloalkyl (e.g. 2,2,2-trifluoroethyl), hydroxyalkyl (e.g. 2-hydroxyethyl, 3-hydroxypropyl), alkoxyalkyl (e.g. 2-methoxyethyl), $G^2$, or —$(CR^kR^x)_v$-$G^2$; wherein $R^k$, $R^x$, v, and $G^2$ are as disclosed in the Summary. For example, $R^k$, $R^x$ are, for example, are each independently hydrogen or $C_{1-3}$ alkyl (e.g. methyl). v, for example, is 1. $G^2$, for example, is phenyl, heteroaryl (e.g. monocyclic heteroaryl such as, but not limited to, pyridinyl), cycloalkyl (e.g. monocyclic cycloalkyl such as, but not limited to, cyclopropyl, cyclobutyl) or heterocycle (e.g. monocyclic heterocycle such as, but not limited to, tetrahydrofuranyl, pyrrolidinyl); each of which is optionally substituted as described in the Summary, for example, optionally substituted with substituents independently selected from the group consisting of alkyl, halogen, and haloalkyl;

(l). —$N(R^{3a})C(O)R^{1a}$ wherein $R^{3a}$ and $R^{1a}$ are as disclosed in the Summary. For example, $R^{3a}$ is hydrogen or $C_{1-6}$ alkyl (e.g., methyl), and $R^{1a}$ is hydrogen, $C_{1-6}$ alkyl (e.g., methyl), or $G^2$ wherein $G^2$ is as disclosed in the Summary. For example, $G^2$ is phenyl or heterocycle (e.g. monocyclic heterocycle such as, but not limited to, azetidinyl, pyrrolidinyl, morpholinyl), each of which is optionally substituted as described in the Summary and herein. Examples of the optional substituent of $G^2$ include, but are not limited to, alkyl, halogen, haloalkyl, and OH;

(m). haloalkyl (e.g. difluoromethyl, 1,1-difluoroethyl, fluoromethyl, trifluoromethyl);

(n). $N(R^{3a})C(O)O(R^{1a})$ wherein $R^{3a}$ and $R^{1a}$ are as disclosed in the Summary. For example, $R^{3a}$ is hydrogen, and $R^{1a}$ is $C_{1-6}$ alkyl (e.g., methyl, ethyl, tert-butyl);

(o). $N(R^{3a})C(O)N(R^{Z3})(R^{3a})$ wherein $R^{3a}$ and $R^{Z3}$ are as disclosed in the Summary. For example, $R^{Z3}$ is hydrogen or $C_{1-6}$ alkyl (e.g., methyl), and $R^{3a}$ is hydrogen, $C_{1-6}$ alkyl (e.g., methyl), hydroxyalkyl (e.g. 2-hydroxyethyl, 2-hydroxypropyl, 3-hydroxypropyl), or $G^2$ wherein $G^2$ is as disclosed in the Summary, for example, $G^2$ is optionally substituted phenyl; and (p). $G^2$; wherein $G^2$ is as disclosed in the Summary. For example, $G^2$ is phenyl, heterocycle (e.g. dihydro-1,3-oxazolyl, dihydro-1,3-oxazinyl), or heteroaryl (e.g. pyridinyl), each of which is optionally substituted as described in the Summary. Examples of the optional substituents of $G^2$ include, but are not limited to, $C_{1-6}$ alkyl (e.g. methyl), halogen (e.g. F, Cl), haloalkyl (e.g. trifluoromethyl), and CN.

It is appreciated that the present application contemplates compounds of Formula (I) with combinations of the above embodiments, including particular, more particular and preferred embodiments.

Accordingly, one aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is alkyl (e.g., methyl, ethyl, n-propyl, isobutyl, n-butyl, n-pentyl, and the like), alkenyl (for example, allyl, vinyl, but-1-enyl, and the like), alkynyl, $G^1$, —$C(R^{Zb})$=$NO(R^{Z1})$, —$O(R^{Za})$, —$N(R^{Z1})(R^{Z2b})$, —$(CR^aR^b)_m$—$N_3$, —$(CR^aR^b)_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —$(CR^aR^b)_m$—$O(R^{Za})$, —$(CR^aR^b)_m$—$C(O)O(R^{Zb})$, —$(CR^aR^b)_m$—$C(O)(R^{Zb})$, —$(CR^aR^b)_m$—$C(R^{Zb})$=NO$(R^{Z1})$, —$(CR^aR^b)_m$—$N(R^{Z1})(R^{Z2b})$, or —$(CR^aR^b)_m$-$G^1$, wherein $G^1$, $R^{Zb}$, $R^{Z1}$, $R^{Za}$, $R^{Z2b}$, $R^a$, $R^b$, and m are as described generally in the Summary and the Detailed Description sections. For example, in certain embodiments, m is 1, 2, 3, or 4. In other embodiments, m is 1, 2, or 3. In yet other embodiments, m is 1 or 2. In certain embodiments, $R^3$ is hydrogen or $C_{1-6}$ alkyl (e.g. methyl).

Another aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is alkyl (e.g., methyl, ethyl, n-propyl, isobutyl, n-butyl, n-pentyl, and the like), alkenyl (for example, allyl, vinyl, but-1-enyl, and the like), alkynyl, —$(CR^aR^b)_m$—CN, haloalkyl (e.g., 4-fluoro-4-methylpentyl, 4,4-difluoropentyl, 3-fluoro-3-methylbutyl, 4,4,4-trifluorobutyl, 4-fluorobutyl), —$(CR^aR^b)_m$—$O(R^{Za})$, or —$(CR^aR^b)_m$-$G^1$, wherein $G^1$, $R^a$, $R^b$, m, and $R^{Za}$, are as described in the Summary and the Detailed Description sections. For example, in certain embodiments, m is 1, 2, 3, or 4.

In other embodiments, m is 1, 2, or 3. In yet other embodiments, m is 1 or 2. In certain embodiments, $R^3$ is hydrogen or $C_{1-6}$ alkyl (e.g. methyl).

Another aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is alkyl (e.g., methyl, ethyl, isobutyl, n-butyl, n-pentyl, and the like), alkenyl (for example, allyl, vinyl, but-1-enyl, and the like) or $C_{1-6}$ haloalkyl (e.g., 4-fluoro-4-methylpentyl, 4,4-difluoropentyl, 3-fluoro-3-methylbutyl, 4,4,4-trifluorobutyl, 4-fluorobutyl). In certain embodiments, $R^3$ is hydrogen or $C_{1-6}$ alkyl (e.g. methyl).

Yet another aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is $G^1$ wherein $G^1$ is as described in the Summary and the Detailed Description sections. Examples of $G^1$ include, but are not limited to, cycloalkyl (e.g. monocyclic cycloalkyl such as, but not limited to, cyclopropyl) and heterocycle (e.g. monocyclic heterocycle such as, but not limited to, tetrahydropyranyl), each of which is optionally substituted as described generally in the Summary section. Examples of the optional substituents, when present, include, but are not limited to, alkyl (e.g. methyl, ethyl), oxo, and haloalkyl. In certain embodiments, $R^3$ is hydrogen or $C_{1-6}$ alkyl (e.g. methyl).

Still another aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is —$(CR^aR^b)_m$-$G^1$ wherein $G^1$, $R^a$, m, and $R^b$ are as described in the Summary and the Detailed Description sections. Examples of $G^1$ include, but are not limited to, aryl (e.g. phenyl), cycloalkyl (e.g. cyclopropyl, cyclobutyl, cyclopentyl, cyclohexyl), heterocycle (e.g. 4,5-dihydroisoxazolyl, morpholinyl, 1,3-dioxanyl, 1,3-dioxolanyl, tetrahydrofuranyl), heteroaryl (e.g. furanyl, 1,3-thiazolyl, thienyl), each of which is optionally substituted as described generally in the Summary section. Examples of the optional substituents, when present, include, but are not limited to, alkyl (e.g. methyl, ethyl), haloalkyl, and oxo. $R^a$ and $R^b$ are as described generally in the Summary section. Examples of $R^a$ include, but are not limited to, hydrogen and $C_{1-6}$ alkyl (e.g. methyl, ethyl, isopropyl). Examples of $R^b$ include, but are not limited to, hydrogen, $C_{1-6}$ alkyl (e.g. methyl, ethyl, isopropyl), and OH. In certain embodiments, $R^3$ is hydrogen or $C_{1-6}$ alkyl (e.g. methyl). In certain embodiments, m is 1 or 2.

A further aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is —$C(R^{Zb})$=$NO(R^{Z1})$, —$(CR^aR^b)_m$—$N_3$, —$(CR^aR^b)_m$—CN, —$(CR^aR^b)_m$—C(O)O($R^{Zb}$), $(CR^aR^b)_m$ C(O) ($R^{Zb}$), or —$(CR^aR^b)_m$—$C(R^{Zb})$=$NO(R^{Z1})$, wherein $R^{Zb}$, $R^a$, $R^b$, $R^{Z1}$, and m are as described in the Summary. Each occurrence of $R^{Zb}$, $R^a$, $R^b$, and $R^{Z1}$ are, for example, independently, hydrogen or $C_{1-6}$ alkyl (e.g. methyl, ethyl, isopropyl). In certain embodiments, $R^3$ is hydrogen or $C_{1-6}$ alkyl (e.g. methyl).

A still further aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is —$O(R^{Za})$ or —$N(R^{Z1})(R^{Z2b})$ wherein $R^{Za}$, $R^{Z1}$, and $R^{Z2b}$ are as set forth in the Summary and the Detailed Description section. Examples of $R^{Za}$ include, but are not limited to, hydrogen, alkyl (e.g. $C_{1-6}$ alkyl such as, but not limited to, methyl, ethyl, 1-methylpropyl, isopropyl), haloalkyl (e.g., 4-fluorobutyl), —$(CR^cR^d)_q$—CN, and —$(CR^cR^d)_q$-$G^1$ wherein $R^c$, $R^d$, q, and $G^1$ are as set forth in the Summary and the Detailed Description sections. $G^1$, for example, is optionally substituted phenyl or optionally substituted pyrrolidinyl. Each occurrence of $R^c$ and $R^d$, are each independently hydrogen or $C_{1-6}$ alkyl (e.g. methyl, ethyl, isopropyl). q is 1 or 2. In certain embodiments, q is 1. $R^{Z1}$, for example, is hydrogen or $C_{1-3}$ alkyl (e.g. methyl). $R^{Z2b}$, for example, is —$C(O)O(R^{Zc})$ wherein $R^{Zc}$ is as described in the Summary. $R^{Zc}$, for example, is $C_{1-6}$ alkyl (e.g. tert-butyl). In certain embodiments, $R^3$ is hydrogen or $C_{1-6}$ alkyl (e.g. methyl).

Still yet another aspect is directed to a group of compounds of Formula (I) wherein $R^3$ is hydrogen, $C_{1-6}$ alkyl (e.g. methyl), haloalkyl, or an optionally substituted cycloalkyl (e.g. optionally substituted monocyclic cycloalkyl such as, but not limited to, cyclopropyl optionally substituted with one or two $C_{1-3}$ alkyl groups); and $R^2$ is —$(CR^aR^b)_m$—$O(R^{Za})$ or —$(CR^aR^b)_m$—$N(R^{Z1})(R^{Z2b})$ wherein m, $R^a$, $R^{Za}$, $R^{Z1}$, and $R^{Z2b}$ are as described in the Summary and in embodiments herein. In certain embodiments, $R^{Za}$ is hydrogen, alkyl (e.g. $C_{1-6}$ alkyl such as, but not limited to, methyl, ethyl, 1-methylpropyl, isopropyl), haloalkyl (e.g. $C_{1-6}$ haloalkyl such as, but not limited to, 2,2,2-trifluoroethyl, 2-fluoroethyl, 2,2-difluoroethyl), or —$(CR^cR^d)_q$-$G^1$ wherein q, $R^c$, $R^d$, and $G^1$ are as described in the Summary and in the Detailed Description sections. $G^1$, for example, is optionally substituted heterocycle (e.g. monocyclic heterocycle such as, but not limited to, tetrahydrofuran) or optionally substituted phenyl. In certain embodiments, each occurrence of $R^a$, $R^c$, and $R^d$, are, for example, independently, hydrogen or $C_{1-6}$ alkyl (e.g. methyl, ethyl, isopropyl). $R^b$, at each occurrence is, for example, independently, hydrogen, $C_{1-6}$ alkyl (e.g. methyl, ethyl, isopropyl), or OH. q is 1 or 2. In certain embodiments, q is 1. $R^{Z1}$ and $R^{Z2b}$ are, for example, independently hydrogen or $C_{1-6}$ alkyl (e.g. methyl, ethyl, isopropyl). In certain embodiments, $R^3$ is hydrogen or $C_{1-6}$ alkyl (e.g. methyl). In certain embodiments, m is 1, 2, 3, or 4.

Still another group of compounds of Formula (I) include, but are not limited to, those wherein $R^2$ and $R^3$, together with the atoms to which they are attached, form a five-, six-, or seven-membered monocyclic ring containing zero or one additional double bond, zero or one additional heteroatom selected from O, S, N, and N(H), each said monocyclic ring is independently unsubstituted or substituted with 1, 2, 3, 4, or 5 substituents ($R^{21}$) selected from the group consisting of oxo, alkyl, alkenyl, alkynyl, halogen, —CN, —$O(R^{1a})$, —C(O)OH, —C(O)O(alkyl), —$C(O)(R^{1a})$, —$N(R^{Z3})(R^{3a})$, —$N(R^{3a})C(O)R^{1a}$, —$N(R^{3a})C(O)O(R^{1a})$, —$N(R^{3a})C(O)N(R^{Z3})(R^{3a})$, —$N(R^{3a})S(O)_2(R^{2a})$, —$N(R^{3a})S(O)_2N(R^{Z3})(R^{3a})$, —$SO_2(R^{2a})$, —$C(O)N(R^{Z3})(R^{3a})$, —$S(O)_2N(R^{Z3})(R^{3a})$, —$(CR^{1g}R^{1h})_u$-$G^2$, —$(CR^{1g}R^{1h})_u$—CN, —$(CR^{1g}R^{1h})_u$—$O(R^{1a})$, and haloalkyl, two adjacent or non-adjacent atoms of each said monocyclic ring are optionally linked by an alkylene bridge of one, two, three, or four carbon atoms; and two substituents ($R^{21}$) on the same carbon atom, together with said carbon atom, optionally form a 3-6 membered monocyclic ring containing 0, 1, or 2 heteroatoms selected from O, S, and N(H).

Yet another group of compounds of formula (I) include those wherein $R^2$ and $R^3$, together with the atoms to which they are attached, form a six-membered monocyclic ring containing zero additional double bond, zero or one N(H) in the ring, each said ring is independently unsubstituted or substituted with 1, 2, 3, 4, or 5 substituents ($R^{21}$) selected from the group consisting of oxo, alkyl, alkenyl, alkynyl, halogen, —CN, —O($R^{1a}$), —C(O)OH, —C(O)O(alkyl), —C(O)($R^{1a}$), —N($R^{Z3}$)($R^{3a}$), —N($R^{3a}$)C(O)$R^{1a}$, —N($R^{3a}$)C(O)O($R^{1a}$), —N($R^{3a}$)C(O)N($R^{Z3}$)($R^{3a}$), —N($R^{3a}$)S(O)$_2$($R^{2a}$), —N($R^{3a}$)S(O)$_2$N($R^{Z3}$)($R^{3a}$), —SO$_2$($R^{2a}$), —C(O)N($R^{Z3}$)($R^{3a}$), —S(O)$_2$N($R^{Z3}$)($R^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O($R^{1a}$), and haloalkyl; and two substituents ($R^{21}$) on the same carbon atom, together with said carbon atom, optionally form a 3-6 membered monocyclic ring containing 0, 1, or 2 heteroatoms selected from O, S, and N(H).

Yet other examples of a group of compounds of Formula (I) include, but are not limited to, those wherein $R^2$ and $R^3$, together with the atoms to which they are attached, form a six-membered monocyclic ring as described herein above, having formula (II)

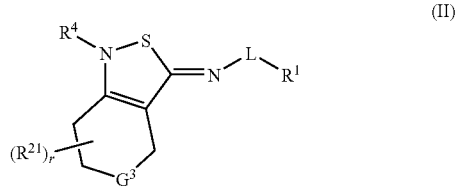

(II)

wherein $G^3$ is absent, CH$_2$, N(H), O, or S; $R^{21}$ is an optional substituent on any substitutable atoms of the ring containing $G^3$, and has values as described herein above, r is 0, 1, 2, 3, 4, or 5, and $R^1$, $R^4$, and L are as described generally the Summary and in embodiments above and herein. In certain embodiments, $G^3$ is N(H). In yet other embodiments $G^3$ is CH$_2$. Examples of $R^{21}$ include, but are not limited to, alkyl (e.g. $C_{1-6}$ alkyl such as, but not limited to, methyl, ethyl, isopropyl, n-butyl, n-propyl), haloalkyl (e.g. $C_{1-6}$ haloalkyl such as, but not limited to, trifluoromethyl), —C(O)O($C_{1-6}$ alkyl), —C(O)OH, and oxo; and two $R^{21}$ on the same carbon atoms, together with said carbon atom, optionally form a 3-6 membered monocyclic ring, optionally containing heteroatom(s) as described generally in the Summary. In certain embodiments, r is 0, 1, 2, or 3. In other embodiments, r is 0, 1, or 2.

Within each group of compounds of Formula (I) or (II) as described in the preceding paragraphs, $R^1$, $R^4$, L, and the optional substituents, when present, are as described generally in the Summary section and in embodiments described above and herein.

For example, for each group of compounds of Formula (I) or (II) as described herein above, examples of a subgroup include those wherein $R^1$ is $G^1$, —NR$^{Z1}$R$^{Z5}$, or —OR$^{Z5}$ wherein $G^1$, $R^{Z1}$ and $R^{Z5}$ are as set forth in the Summary and the Detailed Description sections.

Examples of another subgroup of compounds of Formula (I) or (II) include, but are not limited to, those wherein $R^1$ is —OR$^{Z5}$ and $R^{Z5}$ is as disclosed in the Summary and the Detailed Description sections. For example, $R^{Z5}$ is alkyl (e.g. neopentyl), haloalkyl (e.g. 2,2,2-trichloroethyl), or $G^{1a}$, and $G^{1a}$ is as set forth in the Summary and the Detailed Description sections. For example, $G^{1a}$ is optionally substituted cycloalkyl such as, but not limited to, optionally substituted adamantyl.

Other examples of a subgroup of compounds of Formula (I) or (II) include, but are not limited to, those wherein $R^1$ is —NR$^{Z1}$R$^{Z5}$, and $R^{Z1}$ and $R^{Z5}$ are as set forth in the Summary and the Detailed Description sections. For example, $R^{Z5}$ is $G^{1a}$ or —(CR$^a$R$^b$)$_m$—C(O)N(R$^{Z1}$)(R$^{Z1}$) wherein $G^{1a}$, $R^a$, $R^b$, m, and $R^{Z1}$ are as set forth in the Summary and the Detailed Description. For example, each occurrence of $R^a$ and $R^b$ are each independently hydrogen or alkyl (e.g. methyl, ethyl, isopropyl, tert-butyl). $R^{Z1}$, at each occurrence, is independently hydrogen or alkyl (e.g. methyl, ethyl, tert-butyl). m, for example, is 1 or 2. $G^{1a}$, for example, is optionally substituted cycloalkyl such as, but not limited to, optionally substituted cyclohexyl, as described in the Summary and the Detailed Description sections.

For each group of compounds of Formula (I) or (II) as described herein above, examples of a subgroup include those wherein $R^1$ is $G^1$, and $G^1$ is as described in the Summary and the Detailed Description sections. For example, $G^1$ is aryl (e.g., phenyl, naphthyl), heteroaryl (e.g. quinolin-8-yl), heterocycle (e.g. pyrrolidinyl, oxabicyclo[2.2.1]heptyl, dihydropyranyl), or cycloalkyl (e.g., cyclopropyl, cyclobutyl, cyclopentyl, cyclohexyl, bicyclo[2.2.2]octyl, adamantyl, noradamantyl), each of which is optionally substituted as described generally in the Summary and the Detailed Description sections.

Yet other examples of another subgroup of compounds of Formula (I) or (II) include those wherein $R^1$ is phenyl or naphthyl, each of which is optionally substituted as described generally in the Summary and the Detailed Description sections.

Yet other examples of a subgroup of compounds of Formula (I) or (II) include, but are not limited to, those wherein $R^1$ is heteroaryl (e.g. quinolin-8-yl), optionally substituted as described generally in the Summary and the Detailed Description sections.

Yet other examples of a subgroup of compounds of Formula (I) or (II) include, but are not limited to, those wherein $R^1$ is heterocycle (e.g. pyrrolidinyl, oxabicyclo[2.2.1]heptyl, oxa-adamantyl, dihydropyranyl), optionally substituted as described generally in the Summary and the Detailed Description sections.

Yet other examples of a subgroup of compounds of Formula (I) or (II) include, but are not limited to, those wherein $R^1$ is cycloalkyl (e.g., cyclopropyl, cyclobutyl, cyclopentyl, cyclohexyl, bicyclo[2.2.2]octyl, adamantyl, noradamantyl), optionally substituted as described generally in the Summary and the Detailed Description sections.

Within each group and subgroup of compounds of Formula (I)-(II) as described in the preceding paragraphs, L and $R^4$ are as described generally in the Summary section and in embodiments described above and herein.

For example, $R^4$ is alkyl (e.g. $C_{1-6}$ alkyl such as, but not limited to, methyl, tert-butyl, 1,1-dimethylpropyl), haloalkyl (e.g. 2-fluoro-1,1-dimethylethyl, 2,2,2-trifluoro-1,1-dimethylethyl), or $G^2$, wherein $G^2$ is as described in the Summary. For example, $G^2$ is optionally substituted $C_{3-6}$ cycloalkyl (e.g. optionally substituted cyclopropyl or optionally substituted cyclobutyl) or optionally substituted monocyclic heterocycle (e.g. optionally substituted oxetanyl or optionally substituted tetrahydrofuranyl). In certain embodiments, $G^2$ is cyclopropyl or cyclobutyl, each of which is optionally substituted with one or two $C_{1-3}$ alkyl (e.g. methyl).

Compounds included herein are also those in which $R^3$ is hydrogen or $C_{1-6}$ alkyl, $R^4$ is alkyl, haloalkyl, or $G^2$, and $G^2$ is as described in the Summary and the Detailed Description sections.

It is intended that the present application also includes those compounds wherein $R^3$ is hydrogen, $C_{1-6}$ alkyl, haloalkyl, or an optionally substituted cycloalkyl; $R^2$ is alkyl, alkenyl, alkynyl, $G^1$, —C($R^{Zb}$)=NO($R^{Z1}$), —O($R^{Za}$), —N($R^{Z1}$)($R^{Z2b}$), —(CR$^a$R$^b$)$_m$—N$_3$, —(CR$^a$R$^b$)$_m$—CN, haloalkyl, —(CR$^a$R$^b$)$_m$—O($R^{Za}$), —(CR$^a$R$^b$)$_m$—C(O)O($R^{Zb}$), —(CR$^a$R$^b$)$_m$—C(O)($R^{Zb}$), —(CR$^a$R$^b$)$_m$—C($R^{Zb}$)=NO($R^{Z1}$), —(CR$^a$R$^b$)$_m$—N($R^{Z1}$)($R^{Z2b}$), or —(CR$^a$R$^b$)$_m$-$G^1$; $R^1$ is $G^1$, —NR$^{Z1}$R$^{Z5}$, —OR$^{Z5}$; $R^4$ is alkyl (e.g. $C_{1-6}$ alkyl), haloalkyl, or $G^2$; $G^1$, $R^{Zb}$, $R^{Za}$, $R^{Z1}$, $R^{Z2b}$, $R^a$, $R^b$, m, $R^{Z5}$, and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

The present application also includes those compounds wherein $R^3$ is hydrogen, $C_{1-6}$ alkyl, haloalkyl, or an optionally substituted cycloalkyl; $R^2$ is alkyl, alkenyl, alkynyl, $G^1$, —C($R^{zb}$)=NO($R^{z1}$), —O($R^{Za}$), —N($R^{z1}$)($R^{z2b}$), —(CR$^a$R$^b$)$_m$—N$_3$, —(CR$^a$R$^b$)$_m$—CN, haloalkyl, —(CR$^a$R$^b$)$_m$—O($R^{Za}$), —(CR$^a$R$^b$)$_m$—C(O)O($R^{Zb}$), —(CR$^a$R$^b$)$_m$—C(O)($R^{Zb}$), —(CR$^a$R$^b$)$_m$—C($R^{Zb}$)=NO($R^{Z1}$), —(CR$^a$R$^b$)$_m$—N($R^{Z1}$)($R^{Z2b}$), or —(CR$^a$R$^b$)$_m$-$G^1$; $R^1$ is $G^1$; $R^4$ is alkyl (e.g. $C_{1-6}$ alkyl), haloalkyl, or $G^2$; and $G^1$, $R^{Zb}$, $R^{Za}$, $R^{Z1}$, $R^{Z2b}$, $R^a$, $R^b$, m, and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

Other compounds that are contemplated include those wherein $R^3$ is hydrogen or $C_{1-6}$ alkyl; $R^2$ is alkyl, alkenyl, alkynyl, —(CR$^a$R$^b$)$_m$—CN, haloalkyl, —(CR$^a$R$^b$)$_m$—O(R$^{Za}$) or —(CR$^a$R$^b$)$_m$-$G^1$; $R^4$ is alkyl (e.g. $C_{1-6}$ alkyl), haloalkyl, or $G^2$; $R^1$ is optionally substituted phenyl or optionally substituted naphthyl; $R^a$, $R^b$, m, $R^{Za}$, $G^1$, and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

Yet other compounds that are contemplated include those wherein $R^3$ is hydrogen or $C_{1-6}$ alkyl; $R^2$ is alkyl, alkenyl, alkynyl, —(CR$^a$R$^b$)$_m$—CN, haloalkyl, —(CR$^a$R$^b$)$_m$—O(R$^{Za}$) or —(CR$^a$R$^b$)$_m$-$G^1$; $R^4$ is alkyl (e.g. $C_{1-6}$ alkyl), haloalkyl, or $G^2$; $R^1$ is optionally substituted cycloalkyl; $R^a$, $R^b$, m, $R^{Za}$, $G^1$, and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

Still other compounds that are intended include those wherein $R^2$ and $R^3$, together with the carbon atoms to which they are attached, form a monocyclic ring as generally described in the Summary and in embodiments herein above, $R^1$ is $G^1$, —NR$^{Z1}$R$^{Z5}$, —OR$^{Z5}$; and $R^4$ is alkyl (e.g. $C_{1-6}$ alkyl), haloalkyl, or $G^2$, $R^{Z5}$, $R^{Z1}$; $G^1$, and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

Still other compounds that are intended include those wherein $R^2$ and $R^3$, together with the carbon atoms to which they are attached, form a monocyclic ring as generally described in the Summary and in embodiments herein above, $R^1$ is $G^1$; and $R^4$ is alkyl (e.g. $C_{1-6}$ alkyl), haloalkyl, or $G^2$; $G^1$ and $G^2$ are as described in the Summary and the Detailed Description sections, and any combination of L as described above. For example, L is C=O. In certain embodiments, L is C=S. In other embodiments, L is S(O)$_2$. In yet other embodiments, L is C=NCN.

Still other compounds that are intended include those wherein $R^2$ and $R^3$, together with the carbon atoms to which they are attached form a monocyclic ring as generally described in the Summary and in embodiments herein above, $R^1$ is optionally substituted phenyl or optionally substituted naphthyl; and $R^4$ is alkyl (e.g. $C_{1-6}$ alkyl), haloalkyl, or $G^2$; $G^2$ is as described in the Summary and the Detailed Description sections, and any combination of L as described above. For example, L is C=O. In certain embodiments, L is C=S. In other embodiments, L is S(O)$_2$. In yet other embodiments, L is C=NCN.

Still other compounds that are intended include those wherein $R^2$ and $R^3$, together with the carbon atoms to which they are attached, form a monocyclic ring as generally described in the Summary and in embodiments herein above, $R^1$ is optionally substituted cycloalkyl, and $R^4$ is alkyl (e.g. $C_{1-6}$ alkyl), haloalkyl, or $G^2$ (e.g. $C_{3-6}$ cycloalkyl); $G^2$ is as described in the Summary and the Detailed Description sections, and any combination of L as described above. For example, L is C=O. In certain embodiments, L is C=S. In other embodiments, L is S(O)$_2$. In yet other embodiments, L is C=NCN.

Exemplary compounds include, but are not limited to,
N-[5Z)-4-butyl-2-tert-butylisothiazol-5(2H)-ylidene]-5-chloro-2-methoxybenzamide;
N-[(5Z)-4-butyl-2-(1,1-dimethylpropyl)isothiazol-5(2H)-ylidene]-5-chloro-2-methoxybenzamide;
N-[(5Z)-4-butyl-2-cyclobutylisothiazol-5(2H)-ylidene]-5-chloro-2-methoxybenzamide;
N-[(5Z)-4-butyl-2,3-dimethylisothiazol-5(2H)-ylidene]hexahydro-2,5-methanopentalene-3a(1H)-carboxamide;
N-[(5Z)-4-butyl-2-(1-methylcyclobutyl)isothiazol-5(2H)-ylidene]-5-chloro-2-methoxybenzamide;
N-[(5Z)-4-allyl-2-tert-butylisothiazol-5(2H)-ylidene]-5-chloro-2-methoxybenzamide;
N-[(5Z)-2-tert-butyl-4-[(3-methyl-4,5-dihydroisoxazol-5-yl)methyl]isothiazol-5(2H)-ylidene]-5-chloro-2-methoxybenzamide;
N-[(5Z)-2-tert-butyl-4-(cyclopropylmethyl)isothiazol-5(2H)-ylidene]-5-chloro-2-methoxybenzamide;
N-[(3Z)-1-tert-butyl-5-propyl-4,5,6,7-tetrahydro-2,1-benzisothiazol-3(1H)-ylidene]-5-chloro-2-methoxybenzamide;
N-[(3Z)-1-tert-butyl-1,4,6,7-tetrahydro-3H-spiro[2,1-benzisothiazole-5,2'-[1,3]dioxolan]-3-ylidene]-5-chloro-2-methoxybenzamide;
N-[(5Z)-2-tert-butyl-4-(2-hydroxyethypisothiazol-5(2H)-ylidene]-5-chloro-2-methoxybenzamide;
N-[(5Z)-2-tert-butyl-4-(2-methoxyethyl)isothiazol-5(2H)-ylidene]-5-chloro-2-methoxybenzamide;
N-[(5Z)-2-tert-butyl-4-(2-morpholin-4-ylethyl)isothiazol-5(2H)-ylidene]-5-chloro-2-methoxybenzamide;
N-[(5Z)-2-tert-butyl-4-[2-(5,5-dimethyl-1,3-dioxan-2-yl)ethyl]isothiazol-5(2H)-ylidene]-5-chloro-2-methoxybenzamide;
N-[(5Z)-4-(2-azidoethyl)-2-tert-butylisothiazol-5(2H)-ylidene]-5-chloro-2-methoxybenzamide;
N-[(5Z)-2-tert-butyl-4-[3-(methoxyimino)propyl]isothiazol-5(2H)-ylidene]-5-chloro-2-methoxybenzamide;

N-[(5Z)-4-(2-aminoethyl)-2-tert-butylisothiazol-5(2H)-ylidene]-5-chloro-2-methoxybenzamide;
N-[(5Z)-2-tert-butyl-4-[2-(dimethylamino)ethyl]isothiazol-5(2H)-ylidene]-5-chloro-2-methoxybenzamide;
N-[(5Z)-2-tert-butyl-4-methylisothiazol-5(2H)-ylidene]-5-chloro-2-methoxybenzamide;
N-[(5Z)-2-tert-butyl-4-(3-hydroxybutyl)isothiazol-5(2H)-ylidene]-5-chloro-2-methoxybenzamide;
N-[(5Z)-2-tert-butyl-4-(2-cyanoethyl)isothiazol-5(2H)-ylidene]-5-chloro-2-methoxybenzamide;
N-[(5Z)-2-tert-butyl-4-(2,3-dihydroxypropyl)isothiazol-5(2H)-ylidene]-5-chloro-2-methoxybenzamide;
N-[(5Z)-2-tert-butyl-4-[(methoxyimino)methyl]isothiazol-5(2H)-ylidene]-5-chloro-2-methoxybenzamide;
N-[(5Z)-2-tert-butyl-4-(1,3-dioxolan-2-ylmethyl)isothiazol-5(2H)-ylidene]-5-chloro-2-methoxybenzamide;
N-[(5Z)-2-tert-butyl-4-(1-hydroxy-2-methylpropyl)isothiazol-5(2H)-ylidene]-5-chloro-2-methoxybenzamide;
N-[(5Z)-2-tert-butyl-4-(cyanomethyl)isothiazol-5(2H)-ylidene]-5-chloro-2-methoxybenzamide;
N-[(5Z)-4-[(1Z)-but-1-enyl]-2-tert-butylisothiazol-5(2H)-ylidene]-5-chloro-2-methoxybenzamide;
N-[(5Z)-4-butyl-2-tert-butylisothiazol-5(2H)-ylidene]-5-cyano-2-methoxybenzamide;
N-[(5Z)-2-tert-butyl-4-(2-ethylcyclopropyl)isothiazol-5(2H)-ylidene]-5-chloro-2-methoxybenzamide;
N-[(5Z)-2-tert-butyl-4-(hydroxymethyl)isothiazol-5(2H)-ylidene]-5-chloro-2-methoxybenzamide;
N-[(5Z)-2-tert-butyl-4-(methoxymethyl)isothiazol-5(2H)-ylidene]-5-chloro-2-methoxybenzamide;
N-[(5Z)-2-tert-butyl-4-(ethoxymethyl)isothiazol-5(2H)-ylidene]-5-chloro-2-methoxybenzamide;
N-[(5Z)-2-tert-butyl-4-(3-cyanopropyl)isothiazol-5(2H)-ylidene]-5-chloro-2-methoxybenzamide;
N-[(5Z)-2-tert-butyl-4-[hydroxy(phenyl)methyl]isothiazol-5(2H)-ylidene]-5-chloro-2-methoxybenzamide;
N-[(5Z)-4-(azidomethyl)-2-tert-butylisothiazol-5(2H)-ylidene]-5-chloro-2-methoxybenzamide;
N-[(5Z)-2-tert-butyl-4-(2-cyclobutyl-1-hydroxyethyp-isothiazol-5(2H)-ylidene]-5-chloro-2-methoxybenzamide;
N-[(5Z)-2-tert-butyl-4-[cyclobutyl(hydroxy)methyl]isothiazol-5(2H)-ylidene]-5-chloro-2-methoxybenzamide;
N-[(5Z)-4-benzyl-2-tert-butylisothiazol-5(2H)-ylidene]-5-chloro-2-methoxybenzamide;
N-[(5Z)-2-tert-butyl-4-(2-cyclobutylethyl)isothiazol-5(2H)-ylidene]-5-chloro-2-methoxybenzamide;
N-[(5Z)-2-tert-butyl-4-isobutylisothiazol-5(2H)-ylidene]-5-chloro-2-methoxybenzamide;
N-[(5Z)-2-tert-butyl-4-(cyclobutylmethyl)isothiazol-5(2H)-ylidene]-5-chloro-2-methoxybenzamide;
N-[(5Z)-2-tert-butyl-4-tetrahydro-2H-pyran-4-ylisothiazol-5(2H)-ylidene]-5-chloro-2-methoxybenzamide;
N-[(5Z)-2-tert-butyl-4-[hydroxy(1,3-thiazol-2-yl)methyl]isothiazol-5(2H)-ylidene]-5-chloro-2-methoxybenzamide;
N-[(5Z)-4-butyl-2-tert-butylisothiazol-5(2H)-ylidene]-2,5-dimethoxybenzamide;
N-[(5Z)-4-butyl-2-tert-butylisothiazol-5(2H)-ylidene]-5-fluoro-2-methoxybenzamide;
N-[(5Z)-4-butyl-2-tert-butylisothiazol-5(2H)-ylidene]-2-methoxy-5-methylbenzamide;
N-[(5Z)-2-tert-butyl-4-[hydroxy(thien-2-yl)methyl]isothiazol-5(2H)-ylidene]-5-chloro-2-methoxybenzamide;
methyl 4-{(5Z)-2-tert-butyl-5-[(5-chloro-2-methoxybenzoyl)imino]-2,5-dihydroisothiazol-4-yl}butanoate;
methyl 4-{(5Z)-2-tert-butyl-5-[(5-cyano-2-methoxybenzoyl)imino]-2,5-dihydroisothiazol-4-yl}butanoate;
N-[(5Z)-4-butyl-2-tert-butylisothiazol-5(2H)-ylidene]-5-chloro-2-fluorobenzamide;
N-[(5Z)-4-butyl-2-tert-butylisothiazol-5(2H)-ylidene]-5-chloro-2-(2,2,2-trifluoroethoxy)benzamide;
N-[(5Z)-4-butyl-2-tert-butylisothiazol-5(2H)-ylidene]-2-methoxy-5-(methylsulfonyl)benzamide;
N-[(5Z)-2-tert-butyl-4-[hydroxy(1,3-thiazol-4-yl)methyl]isothiazol-5(2H)-ylidene]-5-chloro-2-methoxybenzamide;
N-[(5Z)-2-tert-butyl-4-(2-furylmethyl)isothiazol-5(2H)-ylidene]-5-chloro-2-methoxybenzamide;
N-[(5Z)-2-tert-butyl-4-(2-furylmethyl)isothiazol-5(2H)-ylidene]-5-cyano-2-methoxybenzamide;
N-[(5Z)-2-tert-butyl-4-(1,3-thiazol-4-ylmethyl)isothiazol-5(2H)-ylidene]-5-chloro-2-methoxybenzamide;
N-[(5Z)-2-tert-butyl-4-(thien-2-ylmethyl)isothiazol-5(2H)-ylidene]-5-cyano-2-methoxybenzamide;
N-[(5Z)-2-tert-butyl-4-(thien-2-ylmethyl)isothiazol-5(2H)-ylidene]-5-chloro-2-methoxybenzamide;
5-amino-N-[(5Z)-4-butyl-2-tert-butylisothiazol-5(2H)-ylidene]-2-methoxybenzamide;
N-[(5Z)-4-butyl-2-tert-butylisothiazol-5(2H)-ylidene]-5-formyl-2-methoxybenzamide;
N-[(5Z)-4-butyl-2-tert-butylisothiazol-5(2H)-ylidene]-2-methoxy-5-[(methoxyimino)methyl]benzamide;
N-[(5Z)-4-butyl-2-tert-butylisothiazol-5(2H)-ylidene]-5-(formylamino)-2-methoxybenzamide;
N-[(5Z)-4-butyl-2-tert-butylisothiazol-5(2H)-ylidene]-5-[(hydroxyimino)methyl]-2-methoxybenzamide;
3-({[(5Z)-4-butyl-2-tert-butylisothiazol-5(2H)-ylidene]amino}carbonyl)-4-methoxybenzoic acid;
N-[(5Z)-4-butyl-2-tert-butylisothiazol-5(2H)-ylidene]-5-iodo-2-methoxybenzamide;
N-[(5Z)-4-butyl-2-tert-butylisothiazol-5(2H)-ylidene]-5-ethynyl-2-methoxybenzamide;
N-[(5Z)-4-butyl-2-tert-butylisothiazol-5(2H)-ylidene]-2-methoxy-5-(trifluoromethoxy)benzamide;
5-acetyl-N-[(5Z)-4-butyl-2-tert-butylisothiazol-5(2H)-ylidene]-2-methoxybenzamide;
N-[(5Z)-4-butyl-2-tert-butylisothiazol-5(2H)-ylidene]-5-(difluoromethyl)-2-methoxybenzamide;
N-[(5Z)-4-butyl-2-tert-butylisothiazol-5(2H)-ylidene]-5-(fluoromethyl)-2-methoxybenzamide;
N-[(5Z)-2-tert-butyl-4-(tetrahydrofuran-2-ylmethyl)isothiazol-5(2H)-ylidene]-5-chloro-2-methoxybenzamide;
N-[(5Z)-4-butyl-2-tert-butylisothiazol-5(2H)-ylidene]-5-[(1Z)-N-hydroxyethanimidoyl]-2-methoxybenzamide;
N-[(5Z)-4-butyl-2-tert-butylisothiazol-5(2H)-ylidene]-5-(1,1-difluoroethyl)-2-methoxybenzamide;
N-[(5Z)-2-tert-butyl-4-(2-furylmethyl)isothiazol-5(2H)-ylidene]-2-fluoro-3-(trifluoromethyl)benzamide;
N-[(5Z)-2-tert-butyl-4-(2-furylmethyl)isothiazol-5(2H)-ylidene]-2-methoxy-5-(trifluoromethyl)benzamide;
N-[(5Z)-2-tert-butyl-4-(isopropoxymethyl)isothiazol-5(2H)-ylidene]-5-chloro-2-methoxybenzamide;
N-[(5Z)-4-butyl-2-tert-butylisothiazol-5(2H)-ylidene]-2-fluoro-3-(trifluoromethyl)benzamide;
methyl 3-({[(5Z)-4-butyl-2-tert-butylisothiazol-5(2H)-ylidene]amino}carbonyl)-4-methoxybenzoate;
N-[(5Z)-2-tert-butyl-4-(4-oxopentyl)isothiazol-5(2H)-ylidene]-5-chloro-2-methoxybenzamide;
N-[(5Z)-2-tert-butyl-4-(4-oxopentyl)isothiazol-5(2H)-ylidene]-2-methoxy-5-(trifluoromethyl)benzamide;
N-[(5Z)-2-tert-butyl-4-(4-oxopentyl)isothiazol-5(2H)-ylidene]-2-fluoro-3-(trifluoromethyl)benzamide;
$N^3$-[(5Z)-4-butyl-2-tert-butylisothiazol-5(2H)-ylidene]-4-methoxyisophthalamide;

N-[(5Z)-2-tert-butyl-4-(4-hydroxy-4-methylpentyl) isothiazol-5(2H)-ylidene]-2-fluoro-3-(trifluoromethyl)benzamide;

N-[(5Z)-2-tert-butyl-4-(4-hydroxy-4-methylpentyl) isothiazol-5(2H)-ylidene]-5-chloro-2-methoxybenzamide;

N-[(5Z)-2-tert-butyl-4-(4-hydroxy-4-methylpentyl) isothiazol-5(2H)-ylidene]-2-methoxy-5-(trifluoromethyl) benzamide;

N-[(5Z)-4-butyl-2-tert-butylisothiazol-5(2H)-ylidene]-5-isopropyl-2-methoxybenzamide;

N-[(5Z)-2-tert-butyl-4-(4-fluoro-4-methylpentyl)isothiazol-5(2H)-ylidene]-5-chloro-2-methoxybenzamide;

N-[(5Z)-2-tert-butyl-4-(3-oxobutyl)isothiazol-5(2H)-ylidene]-5-chloro-2-methoxybenzamide;

N-[(5Z)-2-tert-butyl-4-[(2,2,2-trifluoroethoxy)methyl] isothiazol-5(2H)-ylidene]-5-chloro-2-methoxybenzamide;

N-[(5Z)-2-tert-butyl-4-(4,4-difluoropentyl)isothiazol-5 (2H)-ylidene]-5-chloro-2-methoxybenzamide;

N-[(5Z)-2-tert-butyl-4-(3-fluoro-3-methylbutyl)isothiazol-5(2H)-ylidene]-5-chloro-2-methoxybenzamide;

N-[(5Z)-2-tert-butyl-4-(4-fluoro-4-methylpentyl)isothiazol-5(2H)-ylidene]-2-methoxy-5-(trifluoromethyl)benzamide;

N-[(5Z)-2-tert-butyl-4-{[(2R)-tetrahydrofuran-2-ylmethoxy]methyl}isothiazol-5(2H)-ylidene]-5-chloro-2-methoxybenzamide;

N-[(5Z)-2-tert-butyl-4-[(2-fluoroethoxy)methyl]isothiazol-5(2H)-ylidene]-5-chloro-2-methoxybenzamide;

N-[(5Z)-2-tert-butyl-4-[(2,2-difluoroethoxy)methyl] isothiazol-5(2H)-ylidene]-5-chloro-2-methoxybenzamide;

methyl 3-({[(5Z)-4-butyl-2-tert-butylisothiazol-5(2H)-ylidene]amino}carbonyl)-2,2,3-trimethylcyclopentanecarboxylate;

methyl 3-({[(5Z)-4-butyl-2-tert-butylisothiazol-5(2H)-ylidene]amino}carbonyl)-1,2,2-trimethylcyclopentanecarboxylate;

N-[(5Z)-4-butyl-2-tert-butylisothiazol-5(2H)-ylidene]-1-phenylcyclohexanecarboxamide;

N-[(5Z)-4-butyl-2-tert-butylisothiazol-5(2H)-ylidene]-1-(2-chloro-4-fluorophenyl)cyclohexanecarboxamide;

3-({[(5Z)-4-butyl-2-tert-butylisothiazol-5(2H)-ylidene] amino}carbonyl)-2,2,3-trimethylcyclopentanecarboxylic acid;

N-[(5Z)-4-butyl-2-tert-butylisothiazol-5(2H)-ylidene]-3-oxocyclopentanecarboxamide;

N-[(5Z)-4-butyl-2-tert-butylisothiazol-5(2H)-ylidene]-1-phenylcyclopentanecarboxamide;

$N^1$-[(5Z)-4-butyl-2-tert-butylisothiazol-5(2H)-ylidene]-$N^3,N^3$,1,2,2-pentamethylcyclopentane-1,3-dicarboxamide;

$N^1$-[(5Z)-4-butyl-2-tert-butylisothiazol-5(2H)-ylidene]-$N^3$,1,2,2-tetramethylcyclopentane-1,3-dicarboxamide;

N-[(5Z)-4-butyl-2-tert-butylisothiazol-5(2H)-ylidene]-3-[(3,3-difluoroazetidin-1-yl)carbonyl]-1,2,2-trimethylcyclopentanecarboxamide;

(1S,4R)—N-[(5Z)-4-butyl-2-tert-butylisothiazol-5(2H)-ylidene]-4,7,7-trimethyl-3-oxo-2-oxabicyclo[2.2.1]heptane-1-carboxamide;

(1R,4S)—N-[(5Z)-4-butyl-2-tert-butylisothiazol-5(2H)-ylidene]-4,7,7-trimethyl-3-oxo-2-oxabicyclo[2.2.1]heptane-1-carboxamide;

ethyl 3-({[(5Z)-4-butyl-2-tert-butylisothiazol-5(2H)-ylidene]amino}carbonyl)pyrrolidine-1-carboxylate;

3-({[(5Z)-4-butyl-2-tert-butylisothiazol-5(2H)-ylidene] amino}carbonyl)-1,2,2-trimethylcyclopentanecarboxylic acid;

tert-butyl 3-({[(5Z)-4-butyl-2-tert-butylisothiazol-5(2H)-ylidene]amino}carbonyl)pyrrolidine-1-carboxylate;

N-[(5Z)-4-butyl-2-tert-butylisothiazol-5(2H)-ylidene]-1-(3-cyanopyridin-2-yl)pyrrolidine-3-carboxamide;

methyl 4-({[(5Z)-4-butyl-2-tert-butylisothiazol-5(2H)-ylidene]amino}carbonyl)bicyclo[2.2.2]octane-1-carboxylate;

N-[(5Z)-4-butyl-2-tert-butylisothiazol-5(2H)-ylidene]-5-oxo-1-phenylpyrrolidine-3-carboxamide;

N-[(5Z)-4-butyl-2-tert-butylisothiazol-5(2H)-ylidene]-5-chloro-N'-cyano-2-methoxybenzenecarboximidamide;

N-[(5Z)-4-butyl-2-tert-butylisothiazol-5(2H)-ylidene]-5-chloro-2-methoxybenzenecarbothioamide;

N-[(3Z)-1-tert-butyl-5-(trifluoromethyl)-4,5,6,7-tetrahydro-2,1-benzisothiazol-3(1H)-ylidene]-5-chloro-2-methoxybenzamide;

tert-butyl (3Z)-1-tert-butyl-3-[(5-chloro-2-methoxybenzoyl)imino]-1,4,6,7-tetrahydroisothiazolo[4,3-c]pyridine-5(3H)-carboxylate;

N-[(3Z)-1-tert-butyl-4,5,6,7-tetrahydroisothiazolo[4,3-c] pyridin-3(1H)-ylidene]-5-chloro-2-methoxybenzamide;

N-[(5Z)-4-butyl-2-tert-butylisothiazol-5(2H)-ylidene]-5-chloro-2-methoxybenzenesulfonamide;

N-[(5Z)-4-butyl-2-tert-butylisothiazol-5(2H)-ylidene] naphthalene-1-sulfonamide;

N-[(5Z)-4-butyl-2-tert-butylisothiazol-5(2H)-ylidene]-5-(dimethylamino)naphthalene-1-sulfonamide;

N-[(5Z)-4-butyl-2-tert-butylisothiazol-5(2H)-ylidene]cyclohexanesulfonamide;

N-[(5Z)-4-butyl-2-tert-butylisothiazol-5(2H)-ylidene] benzenesulfonamide;

N-[(5Z)-4-butyl-2-tert-butylisothiazol-5(2H)-ylidene] quinoline-8-sulfonamide;

N-[(5Z)-4-butyl-2-tert-butylisothiazol-5(2H)-ylidene]-2,2,3,3-tetramethylcyclopropanecarboxamide;

N-[(5Z)-4-butyl-2-tert-butylisothiazol-5(2H)-ylidene]-2,3-dichlorobenzenesulfonamide;

N-[(5Z)-4-butyl-2-tert-butylisothiazol-5(2H)-ylidene] adamantane-1-carboxamide;

N-[(5Z)-4-butyl-2-tert-butylisothiazol-5(2H)-ylidene]-N'-cyano-2-methoxy-5-(trifluoromethyl)benzenecarboximidamide;

N-[(5Z)-4-butyl-2-tert-butylisothiazol-5(2H)-ylidene]-2,2-dimethyl-4-oxo-3,4-dihydro-2H-pyran-6-carboxamide;

N-[(5Z)-4-butyl-2-tert-butylisothiazol-5(2H)-ylidene]-N'-cyano-2-ethoxy-5-(trifluoromethyl)benzenecarboximidamide;

N-[(5Z)-4-butyl-2-tert-butylisothiazol-5(2H)-ylidene]-2-methoxy-5-(trifluoromethyl)benzamide;

N-[(5Z)-2-tert-butyl-4-(3-cyanopropyl)isothiazol-5(2H)-ylidene]-5-chloro-N'-cyano-2-methoxybenzenecarboximidamide;

N-[(5Z)-4-butyl-2-tert-butylisothiazol-5(2H)-ylidene]-5-cyano-2-hydroxybenzamide;

N-[(5Z)-4-butyl-2-tert-butylisothiazol-5(2H)-ylidene]-5-cyano-2-(2,2,2-trifluoroethoxy)benzamide;

N-[(5Z)-2-tert-butyl-4-(3-cyanopropyl)isothiazol-5(2H)-ylidene]-5-cyano-2-(2,2,2-trifluoroethoxy)benzamide;

N-[(5Z)-2-tert-butyl-4-(3-cyanopropyl)isothiazol-5(2H)-ylidene]-5-cyano-2-hydroxybenzamide;

N-[(5Z)-2-tert-butyl-4-(3-cyanopropyl)isothiazol-5(2H)-ylidene]-5-chloro-2-(2,2,2-trifluoroethoxy)benzamide;

N-[(5Z)-2-tert-butyl-4-(3-cyanopropyl)isothiazol-5(2H)-ylidene]-2-methoxy-5-(trifluoromethyl)benzamide;

N-[(5Z)-4-butyl-2-tert-butylisothiazol-5(2H)-ylidene]-5-chloro-2-hydroxybenzamide;

N-[(5Z)-2-tert-butyl-4-(cyclopentylmethyl)isothiazol-5 (2H)-ylidene]-5-chloro-2-methoxybenzamide;

N-[(5Z)-2-tert-butyl-4-(3-cyano-3-methylbutyl)isothiazol-5(2H)-ylidene]-5-chloro-2-methoxybenzamide;

N-[(5Z)-2-tert-butyl-4-(4-cyanobutyl)isothiazol-5(2H)-ylidene]-5-chloro-2-methoxybenzamide;

N-[(5Z)-4-butyl-2-tert-butylisothiazol-5(2H)-ylidene]-5-chloro-2-(2-fluoroethoxy)benzamide;

2-(2-amino-2-oxoethoxy)-N-[(5Z)-4-butyl-2-tert-butylisothiazol-5(2H)-ylidene]-5-chlorobenzamide;

2-(2-amino-2-oxoethoxy)-N-[(5Z)-2-tert-butyl-4-(3-cyanopropyl)isothiazol-5(2H)-ylidene]-5-chlorobenzamide;

N-[(5Z)-2-tert-butyl-4-(4,4,4-trifluorobutyl)isothiazol-5(2H)-ylidene]-5-chloro-2-methoxybenzamide;

N-[(5Z)-2-tert-butyl-4-isobutylisothiazol-5(2H)-ylidene]-2-methoxy-5-(trifluoromethyl)benzamide;

N-[(5Z)-2-tert-butyl-4-isobutylisothiazol-5(2H)-ylidene]-5-chloro-2-(2-fluoroethoxy)benzamide;

N-[(5Z)-2-tert-butyl-4-isobutylisothiazol-5(2H)-ylidene]-5-cyano-2-methoxybenzamide;

N-[(5Z)-2-tert-butyl-4-isobutylisothiazol-5(2H)-ylidene]-2-ethoxy-5-(trifluoromethyl)benzamide;

N-[(5Z)-2-tert-butyl-4-pentylisothiazol-5(2H)-ylidene]-5-chloro-2-methoxybenzamide;

N-[(5Z)-2-tert-butyl-4-(4-fluorobutyl)isothiazol-5(2H)-ylidene]-5-chloro-2-methoxybenzamide;

N-[(5Z)-2-tert-butyl-4-(4-fluorobutyl)isothiazol-5(2H)-ylidene]-2-methoxy-5-(trifluoromethyl)benzamide;

N-[(5Z)-4-butyl-2-tert-butylisothiazol-5(2H)-ylidene]-5-chloro-2-[2-(dimethylamino)-2-oxoethoxy]benzamide;

N-[(5Z)-4-butyl-2-(2,2,2-trifluoro-1,1-dimethylethyl)isothiazol-5(2H)-ylidene]-5-chloro-2-methoxybenzamide;

N-[(5Z)-4-butyl-2-(2-fluoro-1,1-dimethylethyl)isothiazol-5(2H)-ylidene]-2-methoxy-5-(trifluoromethyl)benzamide;

N-[(5Z)-4-butyl-2-tert-butylisothiazol-5(2H)-ylidene]-5-chloro-2-(cyanomethoxy)benzamide;

N-[(5Z)-4-butyl-2-(2-fluoro-1,1-dimethylethyl)isothiazol-5(2H)-ylidene]-5-chloro-2-methoxybenzamide;

N-[(5Z)-4-(benzyloxy)-2-tert-butylisothiazol-5(2H)-ylidene]-5-chloro-2-methoxybenzamide;

N-[(5Z)-2-tert-butyl-4-hydroxyisothiazol-5(2H)-ylidene]-5-chloro-2-methoxybenzamide;

N-[(5Z)-2-tert-butyl-4-(1-methylethoxy)isothiazol-5(2H)-ylidene]-5-chloro-2-methoxybenzamide;

N-[(5Z)-2-tert-butyl-4-(1-methylpropoxy)isothiazol-5(2H)-ylidene]-5-chloro-2-methoxybenzamide;

N-[(5Z)-2-tert-butyl-4-(4-fluorobutoxy)isothiazol-5(2H)-ylidene]-5-chloro-2-methoxybenzamide;

N-[(5Z)-2-tert-butyl-4-(cyanomethoxy)isothiazol-5(2H)-ylidene]-5-chloro-2-methoxybenzamide;

N-[(5Z)-2-tert-butyl-4-{[(2S)-5-oxopyrrolidin-2-yl]methoxy}isothiazol-5(2H)-ylidene]-5-chloro-2-methoxybenzamide;

N-[(5Z)-2-tert-butyl-4-{[(2R)-5-oxopyrrolidin-2-yl]methoxy}isothiazol-5(2H)-ylidene]-5-chloro-2-methoxybenzamide;

tert-butyl [(5Z)-2-tert-butyl-5-{[(5-chloro-2-methoxyphenyl)carbonyl]imino}-3-methyl-2,5-dihydroisothiazol-4-yl]carbamate;

N-[(5Z)-2-tert-butyl-4-(1-hydroxyethyl)isothiazol-5(2H)-ylidene]-5-chloro-2-methoxybenzamide;

N-[(5Z)-2-tert-butyl-4-(1-ethoxyethyl)isothiazol-5(2H)-ylidene]-5-chloro-2-methoxybenzamide;

N-[(5Z)-2-tert-butyl-4-(1-methoxyethyl)isothiazol-5(2H)-ylidene]-5-chloro-2-methoxybenzamide;

N-[(5Z)-2-tert-butyl-4-[1-(2,2,2-trifluoro ethoxy)ethyl]isothiazol-5(2H)-ylidene]-5-chloro-2-methoxybenzamide;

N-[(5Z)-2-tert-butyl-4-vinylisothiazol-5(2H)-ylidene]-5-chloro-2-methoxybenzamide;

(1R,3S)-3-({[(5Z)-4-butyl-2-tert-butylisothiazol-5(2H)-ylidene]amino}carbonyl)-3-hydroxy-1,2,2-trimethylcyclopentanecarboxylic acid;

(1S,3R)-3-({[(5Z)-4-butyl-2-tert-butylisothiazol-5(2H)-ylidene]amino}carbonyl)-3-hydroxy-1,2,2-trimethylcyclopentanecarboxylic acid;

methyl (1R,3S)-3-({[(5Z)-4-butyl-2-tert-butylisothiazol-5(2H)-ylidene]amino}carbonyl)-1,2,2-trimethylcyclopentanecarboxylate;

(1R,3S)—$N^3$-[(5Z)-4-butyl-2-tert-butylisothiazol-5(2H)-ylidene]-1,2,2-trimethylcyclopentane-1,3-dicarboxamide;

(1S,3R)—N-[(5Z)-4-butyl-2-tert-butylisothiazol-5(2H)-ylidene]-1,2,2-trimethyl-3-(pyrrolidin-1-ylcarbonyl)cyclopentanecarboxamide;

(1S,3R)-3-({[(5Z)-4-butyl-2-tert-butylisothiazol-5(2H)-ylidene]amino}carbonyl)-2,2,3-trimethylcyclopentanecarboxylic acid;

(1R,3S)-3-({[(5Z)-4-butyl-2-tert-butylisothiazol-5(2H)-ylidene]amino}carbonyl)-2,2,3-trimethylcyclopentanecarboxylic acid;

ethyl (1S,3R)-3-({[(5Z)-4-butyl-2-tert-butylisothiazol-5(2H)-ylidene]amino}carbonyl)-2,2,3-trimethylcyclopentanecarboxylate;

ethyl (1R,3S)-3-({[(5Z)-4-butyl-2-tert-butylisothiazol-5(2H)-ylidene]amino}carbonyl)-2,2,3-trimethylcyclopentanecarboxylate;

methyl (1S,3R)-3-({[(5Z)-4-butyl-2-tert-butylisothiazol-5(2H)-ylidene]amino}carbonyl)-2,2,3-trimethylcyclopentanecarboxylate;

(1R,3S)-3-(azetidin-1-ylcarbonyl)-N-[(5Z)-4-butyl-2-tert-butylisothiazol-5(2H)-ylidene]-1,2,2-trimethylcyclopentanecarboxamide;

(1R,3S)—$N^1$-[(5Z)-4-butyl-2-tert-butylisothiazol-5(2H)-ylidene]-$N^3$,$N^3$,1,2,2-pentamethylcyclopentane-1,3-dicarboxamide;

(1R,3S)—N-[(5Z)-4-butyl-2-tert-butylisothiazol-5(2H)-ylidene]-3-[(3-hydroxyazetidin-1-yl)carbonyl]-1,2,2-trimethylcyclopentanecarboxamide;

(1R,3S)-3-({[(5Z)-4-butyl-2-tert-butylisothiazol-5(2H)-ylidene]amino}carbonyl)-1,2,2-trimethylcyclopentanecarboxylic acid;

(1R,3S)—$N^3$-[(5Z)-4-butyl-2-tert-butylisothiazol-5(2H)-ylidene]-$N^1$,1,2,2-tetramethylcyclopentane-1,3-dicarboxamide;

(1R,3S)—$N^3$-[(5Z)-4-butyl-2-tert-butylisothiazol-5(2H)-ylidene]-$N^1$,$N^1$,1,2,2-pentamethylcyclopentane-1,3-dicarboxamide;

(1R,3S)—$N^1$-[(5Z)-4-butyl-2-tert-butylisothiazol-5(2H)-ylidene]-$N^3$,1,2,2-tetramethylcyclopentane-1,3-dicarboxamide;

(1R,3S)—N-[(5Z)-4-butyl-2-tert-butylisothiazol-5(2H)-ylidene]-3-[(3,3-difluoroazetidin-1-yl)carbonyl]-1,2,2-trimethylcyclopentanecarboxamide;

methyl (1R,3S)-3-({[(5Z)-4-butyl-2-tert-butylisothiazol-5(2H)-ylidene]amino}carbonyl)-2,2,3-trimethylcyclopentanecarboxylate;

neopentyl (5Z)-4-butyl-2-tert-butylisothiazol-5(2H)-ylidenecarbamate;

2,2,2-trichloroethyl (5Z)-4-butyl-2-tert-butylisothiazol-5(2H)-ylidenecarbamate;

1-adamantyl (5Z)-4-butyl-2-tert-butylisothiazol-5(2H)-ylidenecarbamate;

$N^2$-({[(5Z)-4-butyl-2-tert-butylisothiazol-5(2H)-ylidene]amino}carbonyl)-$N^1$,3-dimethyl-L-valinamide;

N-[(5Z)-4-butyl-2-tert-butylisothiazol-5(2H)-ylidene]-N'-(4-methylcyclohexyl)urea;

N-[(5Z)-4-butyl-2-tert-butylisothiazol-5(2H)-ylidene]-2-{[(2S)-1-methylpyrrolidin-2-yl]methoxy}-5-(trifluoromethyl)benzamide;

N-[(5Z)-4-butyl-2-tert-butylisothiazol-5(2H)-ylidene]-N'-cyano-2-{[(2S)-1-methylpyrrolidin-2-yl]methoxy}-5-(trifluoromethyl)benzenecarboximidamide;

N-[(5Z)-4-butyl-2-tert-butylisothiazol-5(2H)-ylidene]-2-{[(2S)-5-oxopyrrolidin-2-yl]methoxy}-5-(trifluoromethyl)benzamide;

N-[(5Z)-4-butyl-2-tert-butylisothiazol-5(2H)-ylidene]-2-{[(4R)-2-oxo-1,3-oxazolidin-4-yl]methoxy}-5-(trifluoromethyl)benzamide;

N-[(5Z)-4-butyl-2-tert-butylisothiazol-5(2H)-ylidene]-2-[(1-methylpiperidin-2-yl)methoxy]-5-(trifluoromethyl)benzamide;

N-[(5Z)-2-tert-butyl-4-isobutylisothiazol-5(2H)-ylidene]-2-{[(2S)-1-methylpyrrolidin-2-yl]methoxy}-5-(trifluoromethyl)benzamide;

N-[(5Z)-4-butyl-2-tert-butylisothiazol-5(2H)-ylidene]-2-(pyrazin-2-ylmethoxy)-5-(trifluoromethyl)benzamide;

N-[(5Z)-2-tert-butyl-4-isobutylisothiazol-5(2H)-ylidene]-2-(pyrazin-2-ylmethoxy)-5-(trifluoromethyl)benzamide;

N-[(5Z)-2-tert-butyl-4-isobutylisothiazol-5(2H)-ylidene]-2-(pyridin-2-ylmethoxy)-5-(trifluoromethyl)benzamide;

(1R,3S)—$N^1$-[(5Z)-4-butyl-2-tert-butylisothiazol-5(2H)-ylidene]-$N^3$-ethyl-1,2,2-trimethylcyclopentane-1,3-dicarboxamide;

(1R,3S)—$N^1$-[(5Z)-4-butyl-2-tert-butylisothiazol-5(2H)-ylidene]-1,2,2-trimethyl-$N^3$-propylcyclopentane-1,3-dicarboxamide;

(1R,3S)—$N^1$-[(5Z)-4-butyl-2-tert-butylisothiazol-5(2H)-ylidene]-$N^3$-(2-hydroxyethyl)-1,2,2-trimethylcyclopentane-1,3-dicarboxamide;

methyl (1S,3R)-3-({[(5Z)-4-butyl-2-tert-butylisothiazol-5(2H)-ylidene]amino}carbonyl)-1,2,2-trimethylcyclopentanecarboxylate;

(1S,3R)-3-({[(5Z)-4-butyl-2-tert-butylisothiazol-5(2H)-ylidene]amino}carbonyl)-1,2,2-trimethylcyclopentanecarboxylic acid;

(1R,3S)—$N^1$-[(5Z)-4-butyl-2-tert-butylisothiazol-5(2H)-ylidene]-$N^3$-isopropyl-1,2,2-trimethylcyclopentane-1,3-dicarboxamide;

(1R,3S)—$N^1$-[(5Z)-4-butyl-2-tert-butylisothiazol-5(2H)-ylidene]-$N^3$-cyclobutyl-1,2,2-trimethylcyclopentane-1,3-dicarboxamide;

(1R,3S)—$N^1$-[(5Z)-4-butyl-2-tert-butylisothiazol-5(2H)-ylidene]-$N^3$-cyclopropyl-1,2,2-trimethylcyclopentane-1,3-dicarboxamide;

(1S,3R)—$N^3$-[(5Z)-4-butyl-2-tert-butylisothiazol-5(2H)-ylidene]-$N^1$,1,2,2-tetramethylcyclopentane-1,3-dicarboxamide;

(1S,3R)—$N^3$-[(5Z)-4-butyl-2-tert-butylisothiazol-5(2H)-ylidene]-$N^1$-ethyl-1,2,2-trimethylcyclopentane-1,3-dicarboxamide;

(1S,3R)—$N^3$-[(5Z)-4-butyl-2-tert-butylisothiazol-5(2H)-ylidene]-1,2,2-trimethyl-$N^1$-propylcyclopentane-1,3-dicarboxamide;

(1S,3R)—$N^3$-[(5Z)-4-butyl-2-tert-butylisothiazol-5(2H)-ylidene]-$N^1$-(2-hydroxyethyl)-1,2,2-trimethylcyclopentane-1,3-dicarboxamide;

(1R,3S)—$N^1$-[(5Z)-4-butyl-2-tert-butylisothiazol-5(2H)-ylidene]-$N^3$-(3-hydroxypropyl)-1,2,2-trimethylcyclopentane-1,3-dicarboxamide;

(1R,3S)—$N^1$-[(5Z)-4-butyl-2-tert-butylisothiazol-5(2H)-ylidene]-1,2,2-trimethyl-$N^3$-[(2R)-tetrahydrofuran-2-ylmethyl]cyclopentane-1,3-dicarboxamide;

methyl (1S,3R)-3-({[(5Z)-4-butyl-2-tert-butylisothiazol-5(2H)-ylidene]amino}carbonyl)-2,2,3-trimethylcyclopentylcarbamate;

ethyl (1S,3R)-3-({[(5Z)-4-butyl-2-tert-butylisothiazol-5(2H)-ylidene]amino}carbonyl)-2,2,3-trimethylcyclopentylcarbamate;

(1R,3S)—N-[(5Z)-4-butyl-2-tert-butylisothiazol-5(2H)-ylidene]-3-(4,5-dihydro-1,3-oxazol-2-yl)-1,2,2-trimethylcyclopentanecarboxamide;

(1S,3R)—$N^1$-[(5Z)-4-butyl-2-tert-butylisothiazol-5(2H)-ylidene]-$N^3$-1,2,2-tetramethylcyclopentane-1,3-dicarboxamide;

(1S,3R)—$N^1$-[(5Z)-4-butyl-2-tert-butylisothiazol-5(2H)-ylidene]-1,2,2-trimethyl-$N^3$-propylcyclopentane-1,3-dicarboxamide;

(1S,3R)—$N^1$-[(5Z)-4-butyl-2-tert-butylisothiazol-5(2H)-ylidene]-$N^3$-(2-methoxyethyl)-1,2,2-trimethylcyclopentane-1,3-dicarboxamide;

(1S,3R)—$N^1$-[(5Z)-4-butyl-2-tert-butylisothiazol-5(2H)-ylidene]-$N^3$-(3-hydroxypropyl)-1,2,2-trimethylcyclopentane-1,3-dicarboxamide;

(1S,3R)-3-(azetidin-1-ylcarbonyl)-N-[(5Z)-4-butyl-2-tert-butylisothiazol-5(2H)-ylidene]-1,2,2-trimethylcyclopentanecarboxamide;

(1S,3R)—$N^1$-[(5Z)-4-butyl-2-tert-butylisothiazol-5(2H)-ylidene]-$N^3$, $N^3$,1,2,2-pentamethylcyclopentane-1,3-dicarboxamide;

(1R,3S)—N-[(5Z)-4-butyl-2-tert-butylisothiazol-5(2H)-ylidene]-3-(4,5-dihydro-1,3-oxazol-2-yl)-2,2,3-trimethylcyclopentanecarboxamide;

(1S,3R)—$N^1$-[(5Z)-4-butyl-2-tert-butylisothiazol-5(2H)-ylidene]-$N^3$-cyclobutyl-1,2,2-trimethylcyclopentane-1,3-dicarboxamide;

(1R,3S)—$N^1$-[(5Z)-4-butyl-2-tert-butylisothiazol-5(2H)-ylidene]-1,2,2-trimethyl-$N^3$-[(2S)-tetrahydrofuran-2-ylmethyl]cyclopentane-1,3-dicarboxamide;

(1S,3R)—$N^3$-[(5Z)-4-butyl-2-tert-butylisothiazol-5(2H)-ylidene]-1,2,2-trimethyl-$N^1$-[(2S)-tetrahydrofuran-2-ylmethyl]cyclopentane-1,3-dicarboxamide;

(1S,3R)—$N^1$-[(5Z)-4-butyl-2-tert-butylisothiazol-5(2H)-ylidene]-$N^3$-(2-hydroxyethyl)-1,2,2-trimethylcyclopentane-1,3-dicarboxamide;

(1R,3S)—$N^3$-[(5Z)-4-butyl-2-tert-butylisothiazol-5(2H)-ylidene]-$N^1$-ethyl-1,2,2-trimethylcyclopentane-1,3-dicarboxamide;

(1R,3S)—$N^3$-[(5Z)-4-butyl-2-tert-butylisothiazol-5(2H)-ylidene]-$N^1$-(2-hydroxyethyl)-1,2,2-trimethylcyclopentane-1,3-dicarboxamide;

(1S,3R)—N-[(5Z)-4-butyl-2-tert-butylisothiazol-5(2H)-ylidene]-3-(4,5-dihydro-1,3-oxazol-2-yl)-1,2,2-trimethylcyclopentanecarboxamide;

(1S,3R)—N-[(5Z)-4-butyl-2-tert-butylisothiazol-5(2H)-ylidene]-3-(4,5-dihydro-1,3-oxazol-2-yl)-2,2,3-trimethylcyclopentanecarboxamide;

(1R,3S)—$N^3$-benzyl-$N^1$-[(5Z)-4-butyl-2-tert-butylisothiazol-5(2H)-ylidene]-1,2,2-trimethylcyclopentane-1,3-dicarboxamide;

(1R,3S)—$N^1$-[(5Z)-4-butyl-2-tert-butylisothiazol-5(2H)-ylidene]-1,2,2-trimethyl-$N^3$-(pyridin-2-ylmethyl)cyclopentane-1,3-dicarboxamide;

(1R,3S)—$N^1$-[(5Z)-4-butyl-2-tert-butylisothiazol-5(2H)-ylidene]-1,2,2-trimethyl-$N^3$-(pyridin-3-ylmethyl)cyclopentane-1,3-dicarboxamide;

(1R,3S)—N¹-[(5Z)-4-butyl-2-tert-butylisothiazol-5(2H)-ylidene]-1,2,2-trimethyl-N³-(pyridin-4-ylmethyl)cyclopentane-1,3-dicarboxamide;

(1R,3S)—N¹-[(5Z)-4-butyl-2-tert-butylisothiazol-5(2H)-ylidene]-1,2,2-trimethyl-N³-prop-2-ynylcyclopentane-1,3-dicarboxamide;

(1R,3S)—N¹-[(5Z)-4-butyl-2-tert-butylisothiazol-5(2H)-ylidene]-1,2,2-trimethyl-N³-(2,2,2-trifluoroethyl)cyclopentane-1,3-dicarboxamide;

(1S,3R)—N¹-[(5Z)-4-butyl-2-tert-butylisothiazol-5(2H)-ylidene]-1,2,2-trimethyl-N³-prop-2-ynylcyclopentane-1,3-dicarboxamide;

(1S,3R)—N¹-[(5Z)-4-butyl-2-tert-butylisothiazol-5(2H)-ylidene]-1,2,2-trimethyl-N³-(2,2,2-trifluoroethyl)cyclopentane-1,3-dicarboxamide;

(1R,3S)—N¹-[(5Z)-4-butyl-2-tert-butylisothiazol-5(2H)-ylidene]-N³-methoxy-N³,1,2,2-tetramethylcyclopentane-1,3-dicarboxamide;

(1S,3R)—N-[(5Z)-4-butyl-2-tert-butylisothiazol-5(2H)-ylidene]-3-(5,6-dihydro-4H-1,3-oxazin-2-yl)-1,2,2-trimethylcyclopentanecarboxamide;

(1R,3S)—N-[(5Z)-4-butyl-2-tert-butylisothiazol-5(2H)-ylidene]-3-(5,6-dihydro-4H-1,3-oxazin-2-yl)-1,2,2-trimethylcyclopentanecarboxamide;

N-[(1S,3R)-3-({[(5Z)-4-butyl-2-tert-butylisothiazol-5(2H)-ylidene]amino}carbonyl)-2,2,3-trimethylcyclopentyl]pyrrolidine-1-carboxamide;

(1R,3S)-3-[(aminocarbonyl)amino]-N-[(5Z)-4-butyl-2-tert-butylisothiazol-5(2H)-ylidene]-1,2,2-trimethylcyclopentanecarboxamide;

(1R,3S)-3-[(aminocarbonyl)amino]-N-[(5Z)-4-butyl-2-tert-butylisothiazol-5(2H)-ylidene]-2,2,3-trimethylcyclopentanecarboxamide;

(1R,3S)—N-[(5Z)-4-butyl-2-tert-butylisothiazol-5(2H)-ylidene]-2,2,3-trimethyl-3-{[(methylamino)carbonyl]amino}cyclopentanecarboxamide;

(1R,3S)—N-[(5Z)-4-butyl-2-tert-butylisothiazol-5(2H)-ylidene]-1,2,2-trimethyl-3-(morpholin-4-ylcarbonyl)cyclopentanecarboxamide;

(1R,3S)—N¹-[(5Z)-4-butyl-2-tert-butylisothiazol-5(2H)-ylidene]-1,2,2-trimethyl-N³-pyrrolidin-1-ylcyclopentane-1,3-dicarboxamide;

N-[(1S,3R)-3-({[(5Z)-4-butyl-2-tert-butylisothiazol-5(2H)-ylidene]amino}carbonyl)-2,2,3-trimethylcyclopentyl]morpholine-4-carboxamide;

N-[(1S,3R)-3-({[(5Z)-4-butyl-2-tert-butylisothiazol-5(2H)-ylidene]amino}carbonyl)-2,2,3-trimethylcyclopentyl]benzamide;

(1R,3S)—N-[(5Z)-4-butyl-2-tert-butylisothiazol-5(2H)-ylidene]-1,2,2-trimethyl-3-{[(methylamino)carbonyl]amino}cyclopentanecarboxamide;

(1S,3R)-3-[(aminocarbonyl)amino]-N-[(5Z)-4-butyl-2-tert-butylisothiazol-5(2H)-ylidene]-1,2,2-trimethylcyclopentanecarboxamide;

(1S,3R)—N-[(5Z)-4-butyl-2-tert-butylisothiazol-5(2H)-ylidene]-1,2,2-trimethyl-3-{[(methylamino)carbonyl]amino}cyclopentanecarboxamide;

N-[(1R,3S)-3-({[(5Z)-4-butyl-2-tert-butylisothiazol-5(2H)-ylidene]amino}carbonyl)-2,2,3-trimethylcyclopentyl]benzamide;

(1R,3S)-3-(acetylamino)-N-[(5Z)-4-butyl-2-tert-butylisothiazol-5(2H)-ylidene]-1,2,2-trimethylcyclopentanecarboxamide;

(1R,3S)—N-[(5Z)-4-butyl-2-tert-butylisothiazol-5(2H)-ylidene]-34 {[(2-hydroxyethyl)amino]carbonyl}amino)-1,2,2-trimethylcyclopentanecarboxamide;

(1R,3S)—N-[(5Z)-4-butyl-2-tert-butylisothiazol-5(2H)-ylidene]-3-[({[(2S)-2-hydroxypropyl]amino}carbonyl)amino]-1,2,2-trimethylcyclopentanecarboxamide;

(1R,3S)—N-[(5Z)-4-butyl-2-tert-butylisothiazol-5(2H)-ylidene]-3-[({[(2R)-2-hydroxypropyl]amino}carbonyl)amino]-1,2,2-trimethylcyclopentanecarboxamide;

N-[(1S,3R)-3-({[(5Z)-4-butyl-2-tert-butylisothiazol-5(2H)-ylidene]amino}carbonyl)-2,2,3-trimethylcyclopentyl]-3-hydroxyazetidine-1-carboxamide;

N-[(1S,3R)-3-({[(5Z)-4-butyl-2-tert-butylisothiazol-5(2H)-ylidene]amino}carbonyl)-2,2,3-trimethylcyclopentyl]-3,3-difluoroazetidine-1-carboxamide;

N-[(5Z)-4-butyl-2-tert-butylisothiazol-5(2H)-ylidene]-2-(2-hydroxy-2-methylpropoxy)-5-(trifluoromethyl)benzamide;

N-[(1S,3R)-3-({[(5Z)-4-butyl-2-tert-butylisothiazol-5(2H)-ylidene]amino}carbonyl)-2,2,3-trimethylcyclopentyl]azetidine-1-carboxamide;

(1R,3S)—N-[(5Z)-4-butyl-2-tert-butylisothiazol-5(2H)-ylidene]-1,2,2-trimethyl-3-({[methyl(phenyl)amino]carbonyl}amino)cyclopentanecarboxamide;

methyl 3-({[(5Z)-4-butyl-2-tert-butylisothiazol-5(2H)-ylidene]amino}carbonyl)adamantane-1-carboxylate;

3-({[(5Z)-4-butyl-2-tert-butylisothiazol-5(2H)-ylidene]amino}carbonyl)adamantane-1-carboxylic acid; and 2-[(tert-butylamino)oxy]-N-[(5Z)-4-butyl-2-tert-butylisothiazol-5(2H)-ylidene]-5-(trifluoromethyl)benzamide.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. Geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein may exhibit the phenomenon of tautomerism.

Thus, the formulae drawings within this specification can represent only one of the possible tautomeric or stereoisomeric forms. It is to be understood any tautomeric or stereoisomeric forms, and mixtures thereof are encompassed, and is not to be limited merely to any one tautomeric or stereoisomeric form utilized within the naming of the compounds or formulae drawings.

Compounds can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this application.

In another embodiment, the isotope-labeled compounds contain deuterium (2H), tritium (3H) or $^{14}$C isotopes. Isotope-labeled compounds can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds may be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10): 927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physico-chemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

c. General Synthesis

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds may be prepared by a variety of processes well known for the preparation of compounds of this class. For example, the compounds wherein the groups $L, L^1, A^1$, m, q, r, u, $G^1, G^2, R^a, R^b, R^c, R^d, R^{Z1}, R^{Z3}, R^{Z5}, R^{Z2b}, R^{Za}, R^{21}, R^1, R^{1a}, R^{1g}, R^{1h}, R^2, R^{2a}, R^3, R^{3a}$, and $R^4$ have the meanings as set forth in the summary section and in embodiments herein above unless otherwise noted, can be synthesized as shown in Schemes 1-14.

Abbreviations which have been used in the descriptions of the Schemes and the Examples that follow are: AIBN for azobisisobutyronitrile, DAST for (bis(methoxyethyl)amino sulfurtrifluoride; DMAP for 4-(dimethylamino)pyridine, DMF for N,N-dimethylformamide, DMSO for dimethyl sulfoxide, EDCI for 1-(3-dimethylaminopropyl)-3-ethylcarbodiimide hydrochloride, EtOH for ethanol, $Et_3N$ for triethylamine, $Et_2O$ for diethyl ether, $Et_2Zn$ for diethyl zinc, EtOAc for ethyl acetate, $CHCl_3$ for chloroform, $CH_2Cl_2$ for dichloromethane, HOBt for 1-hydroxybenzotriazole hydrate, KOtBu for potassium tert-butoxide, MeCN for acetonitrile, MeOH for methanol, NMP for N-methyl morpholine, $PdCl_2(PPh_3)_2$ for bis(triphenylphosphine)palladium(II) dichloride, $PdCl_2(dppf)$ for [1,1'-bis(diphenylphosphino)ferrocene]dichloropalladium(II), rt for room temperature, TBAF for is tetrabutyl ammonium fluoride, TMSI for iodotrimethylsilane, TFA for trifluoroacetic acid, and THF for tetrahydrofuran.

Compounds of general Formula (I) wherein L is C=O and $R^3$ is hydrogen can be prepared using general procedures as illustrated in Scheme 1.

Scheme 1

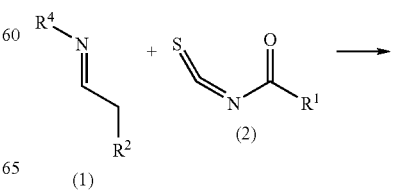

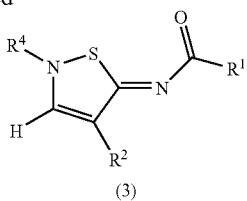

(3)

Isothiazolylidene compounds of structure (3) can be prepared by reacting a substituted imine of structure (1) with an isothiocyanate of structure (2) in a solvent such as but not limited to tetrahydrofuran, diethylether, acetonitrile, dichloromethane or chloroform, at a temperature from about 0° C. to about room temperature, for a period between about 1 and about 24 hours, followed by treatment with iodine or bromine, in a mixture of pyridine and methanol or ethanol, and subsequent treatment with sodium bicarbonate upon workup.

Isothiocyanates of structure (2) can be synthesized by treating acid halides of formula $R^1C(O)X^1$ wherein $X^1$ is halogen, with potassium thiocyanate in a solvent such as tetrahydrofuran, acetone, or mixture thereof, at ambient temperature. The acid halides can be obtained from the corresponding acids using general procedures known to one skilled in the art, for example, by treating with thionyl chloride in a suitable solvent such as toluene, at a temperature from about room temperature to about the reflux temperature of the solvent used.

Imines of structure (1) can be obtained from treatment of aldehydes of formula $R^2CH_2CHO$ with amines of formula $R^4NH_2$, optionally in the presence of an acid such as acetic acid, and optionally in the presence of a dehydrating agent such as magnesium sulfate, in a solvent such as dichloromethane. The reaction can be conducted at about room temperature to about 60° C.

Similarly, compounds of general formula (II) wherein L is C=O, and $G^3$ is absent, or selected from $CR^{101}R^{102}$, O, S, NC(O)O(alkyl) or N($R^{101}$), and $R^{101}$ and $R^{102}$ are each independently hydrogen, alkyl, or haloalkyl, can be prepared from imines of formula (4) (prepared from treating the corresponding ketones with amines of formula $R^4NH_2$) using general procedures described in Scheme 2 under conditions analogous to those in Scheme 1.

Scheme 2

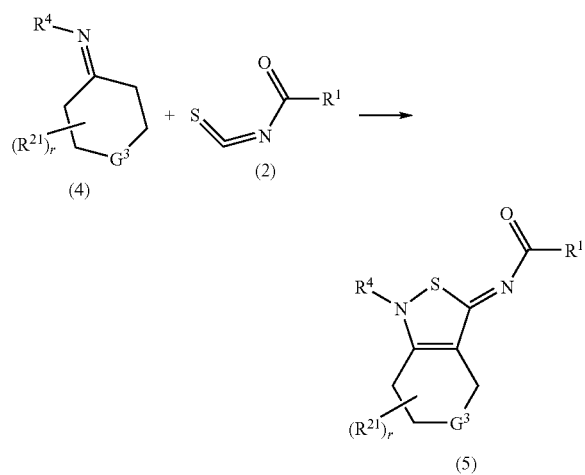

Compounds of general Formula (I) wherein L is C=O can be synthesized as shown in Scheme 3.

Scheme 3

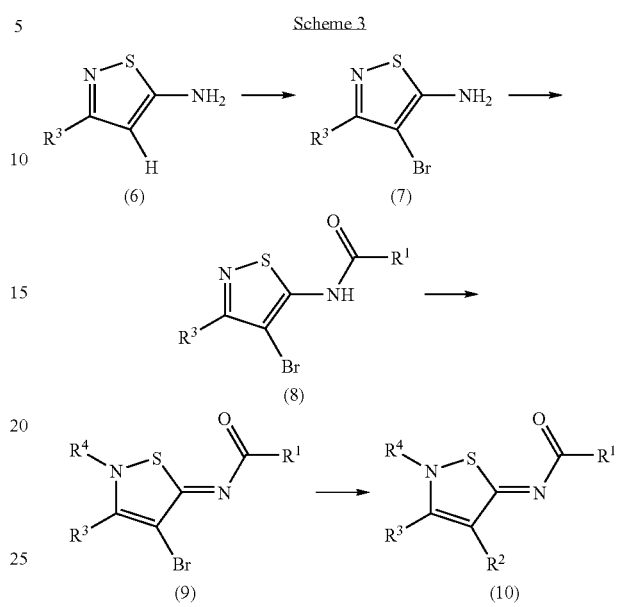

Aminoisothiazoles of structure (6) can be brominated with bromine in solvents such as benzene and/or acetic acid to provide compounds of formula (7). Acylation of compounds of structure (7) with acid halides of formula $R^1COX^1$, in the presence of a base such as triethylamine and in solvents such as tetrahydrofuran or dichloro methane afford compounds of structure (8). Alternatively, the transformation can be accomplished by treating compounds of structure (7) with acids of formula $R^1COOH$ in the presence of a coupling agent, a base and optionally a coupling auxiliary. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N', N'-tetramethyluronium hexafluorophosphate (HATU), and O-benzotriazol-1-yl-N,N,N',N'-tetramethyluronium tetrafluoroborate (TBTU). Examples of coupling auxiliarys include but are not limited to 1-hydroxy-7-oazabenzotriazole (HOAT) and 1-hydroxybenzotriazole hydrate (HOBT). Examples of suitable bases include, but are not limited to, an organic base such as N-methyl morpholine or diisopropylethylamine, or an inorganic base such as sodium bicarbonate. The coupling reaction can be carried out in a solvent such as chloroform, dichloromethane, tetrahydrofuran, N,N-dimethylformamide, or mixtures thereof, at a temperature from about 0° C. to about 50° C.

Alkylation of (8) with compounds of formula $R^4X^2$ wherein $X^2$ is halogen, triflate or tosylate, in the presence of a base such as potassium carbonate, sodium hydride, potassium hydroxide or potassium tert-butoxide, and in a solvent such as N,N-dimethylformamide, acetonitrile, tetrahydrofuran or acetone, provides compounds of structure (9). Organometallic coupling of (9) with a zinc reagent of formula $R^2ZnX^3$ wherein $X^3$ is Br or Cl, in the presence of a palladium catalyst such as bis(tri-tert-butylphosphine)palladium(0) affords compounds of structure (10). The conversion can be performed in a solvent such as dimethylacetamide with heating at a temperature from about 50° C. to about 120° C.

Compounds of general Formula (I) wherein L is C=S can be prepared from compounds of Formula (I) wherein L is C=O by treating with Lawesson's reagent, in a solvent such as toluene, at a temperature of about room temperature to about 80° C.

Compounds of general Formula (I) wherein L is C=NCN can be prepared using general procedure as outlined in Scheme 4

Scheme 4

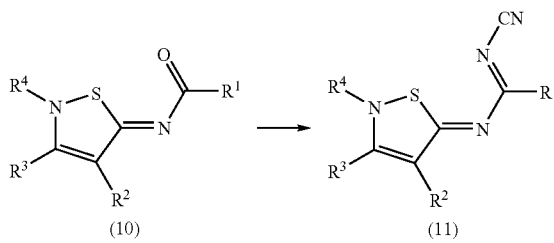

Compounds of structure (11) can be obtained from compounds of structure (10) by (a) treatment with Lawesson's reagent, in a solvent such as toluene, at a temperature of about room temperature to about 80° C., and (b) treatment of the product from step (a) with mercury (II) acetate and cyanamide.

Compounds of general formula (I) wherein $R^2$ is alkenyl or alkynyl can be functionalized to the corresponding cycloalkyl, heterocycle, heteroaryl, alcohols, acids and derivatives of acids, using procedures analogous to those known to one skilled in the art, for example, via [3+2] or [4+2] additions, ozonolysis, hydroboration, cyclopropanation, etc.

Scheme 5

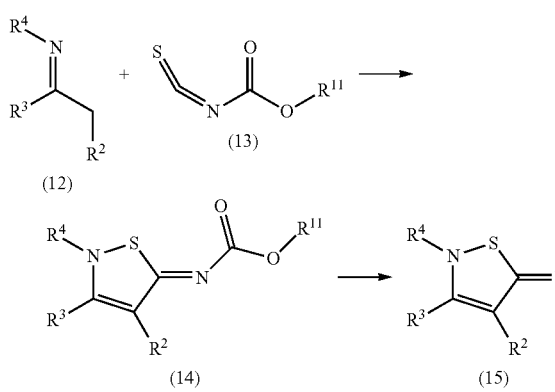

Compounds of formula (14) where $R^{11}$ is alkyl, allyl or benzyl can be prepared from compounds of formula (12) and (13) using the conditions described above in Scheme 1. Compounds of formula (14) where $R^{11}$ is alkyl (e.g. ethyl), can be converted to compounds of formula (15) by reaction with trimethylsilyliodide in a solvent such as dichloromethane or chloroform at temperatures from room temperature to about 70° C. Alternatively, compounds of formula (14) where $R^{11}$ is alkyl, for example ethyl, can be converted to compounds of formula (15) by hydrolysis with aqueous base such as sodium hydroxide or potassium hydroxide. When $R^{11}$ is tert-butyl, compounds of formula (14) can be converted to (15) by reaction with an acid such as trifluoroacetic acid or hydrochloric acid. When $R^{11}$ is benzyl, compounds of formula (14) can be converted to (15) by hydrogenation over a suitable transition metal catalyst like, for example, palladium on carbon.

Scheme 6

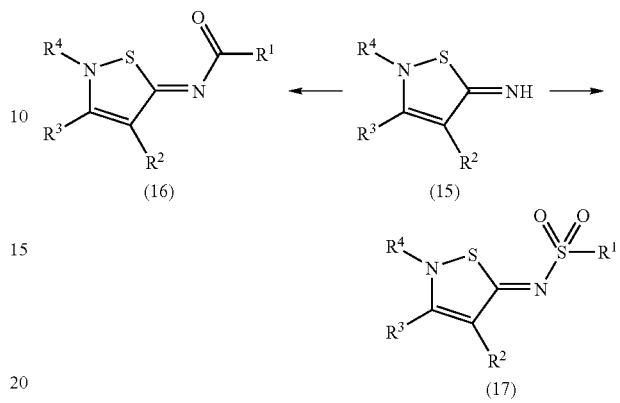

Compounds of formula (15) can be converted to compounds of formula (16) using the conditions described above for the conversion of compounds (7) to compounds (8). Compounds of formula (15) can be converted to compounds of formula (17) by reaction with a reagent $R^1SO_2Cl$ in the presence of a base such as, but not limited to, triethylamine or diethylisopropylamine and in a solvent such as, but not limited to, dichloromethane, tetrahydrofuran or dimethylformamide at room temperature to about 50° C.

Scheme 7

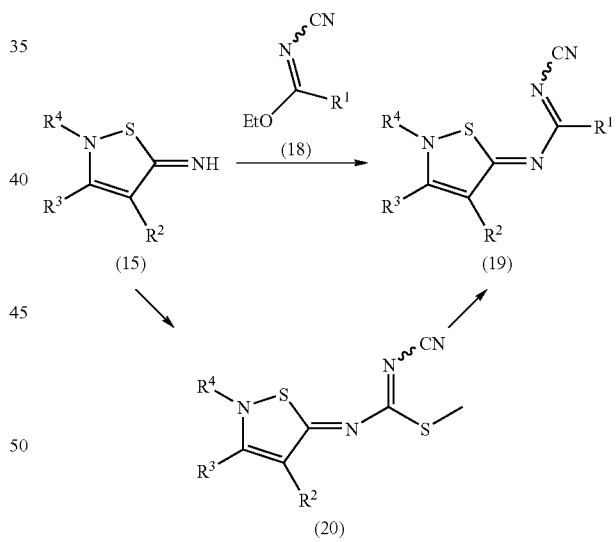

Compounds of formula (15) can be transformed to compounds of formula (19) by reaction with compounds of formula (18) in the presence of a base such as, but not limited to, triethylamine in solvents such as, but not limited to, ethanol, acetonitrile, tetrahydrofuran or toluene at temperatures from room temperature to about 100° C. Alternatively, compounds of formula (15) can be transformed to compounds of formula (19) through the intermediate compounds (20). Compounds of formula (15) can be converted to compounds of formula (20) by reaction with dimethylcyanocarbonimidodithioate in a solvent such as, but not limited to, THF, dioxane, acetonitrile, etc. in the presence of a base, like triethylamine, N-methylmorpholine, NaH, etc. at temperatures ranging from room temperature to about 50° C. for 8-24 hours. The intermediate (20) can be treated with a boronic acid (HO)$_2$B—R$^1$ in the presence of copper carboxylates (like commercially available copper acetate or copper 2-thiophenecarboxylate), a trialkylphosphite (e.g., triethylphosphite) and tris(dibenzylideneacetone)dipalladium(0) or other selected Pd(0) catalysts in dimethoxyethane (or other aprotic solvents) at 80-100° C. for 12-24 hours to give compounds of formula (19).

Scheme 8

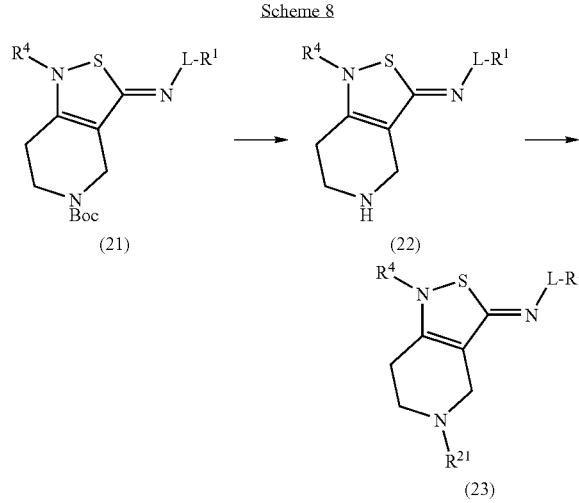

(21)  (22)  (23)

Compounds of formula (21) can be converted to compounds of formula (22) by reaction with an acid such as trifluoroacetic acid in a solvent such as dichloromethane or by reaction with hydrochloric acid. The compounds of formula (22) can be converted to compounds of formula (23) wherein R$^{21}$ is alkyl, alkenyl, alkynyl, —C(O)(R$^{1a}$), —SO$_2$(R$^{2a}$), —C(O)N(R$^{Z3}$)(R$^{3a}$), —S(O)$_2$N(R$^{Z3}$)(R$^{3a}$), —(CR$^{1g}$R$^{1h}$)$_u$-G$^2$, —(CR$^{1g}$R$^{1h}$)$_u$—CN, —(CR$^{1g}$R$^{1h}$)$_u$—O(R$^{1a}$), and haloalkyl by a variety of transformations well known to those skilled in the art. For example, the substituent R$^{21}$ may be appended via the well-known reductive amination method by reaction with an appropriate aldehyde or ketone reagent in the presence of a reducing agent such as sodium cyanoborohydride. Another well-known method to transform (22) to (23) is by alkylation with a suitable halide, tosylate, mesylate or triflate reagent. The types of R$^{21}$ groups that can be appended in this manner are alkyl, alkenyl, alkynyl, —(CR$^{1g}$R$^{1h}$)$_u$-G$^2$, —(CR$^{1g}$R$^{1h}$)$_u$—CN, —(CR$^{1g}$R$^{1h}$)$_u$—O(R$^{1a}$), and haloalkyl. Other R$^{21}$ groups such as —C(O)(R$^{1a}$), —SO$_2$(R$^{2a}$), —C(O)N(R$^{Z3}$)(R$^{3a}$) and —S(O)$_2$N(R$^{Z3}$)(R$^{3a}$) can be appended by reaction with appropriate acyl halides, sulfonyl halides, carbamoyl halides or isocyanates using conditions well-known to those skilled in the art.

Scheme 9

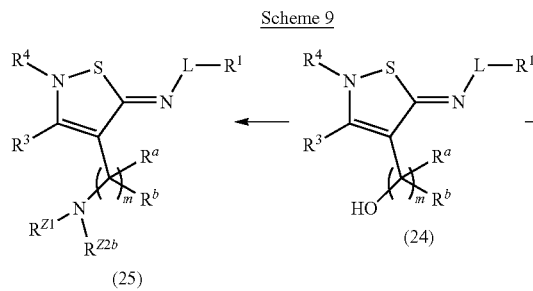

(25)  (24)

-continued

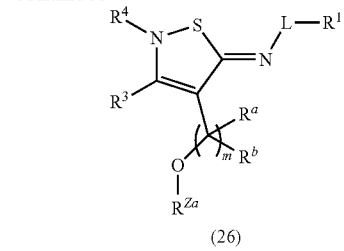

(26)

Compounds of formula (24) can be converted to compounds of formula (2S) by standard synthetic transformations well known to those skilled in the art. For example, (24) can be converted to amines of formula (2S) wherein R$^{Z2b}$ is hydrogen, alkyl, haloalkyl, G$^1$ or —(CR$^c$R$^d$)$_q$-G$^1$ by displacement of the corresponding halide, mesylate or tosylate derived from (24) with an appropriate amine R$^{Z1}$R$^{Z2b}$NH. Compounds (24) can be converted to primary amine compounds (2S) (R$^{Z1}$ and R$^{Z2b}$ are each hydrogen) through displacement of the corresponding halide, mesylate or tosylate with an azide reagent and then reduction of the latter using methods well-known to those skilled in the art. Compounds (2S) wherein R$^{Z1}$ and R$^{Z2b}$ are each hydrogen can be converted to compounds (2S) wherein R$^{Z1}$ or R$^{Z2b}$ are other than hydrogen by standard synthetic transformations involving reaction with carbonyl compounds (ie, reductive amination), alkyl halides, acyl halides, sulfonyl halides, isocyanates and the like.

Compounds of formula (24) can be converted to compounds of formula (26) by standard etherification methods well-known to those skilled in the art. For example, compounds (24) can be reacted with alkylating agents R$^{Za}$—X (X=halo, OMs, OTs, etc). Alternatively, compounds (26) can be prepared by displacement of the corresponding halide, mesylate or tosylate derived from (24) with an appropriate alcohol R$^{Za}$—OH.

Scheme 10

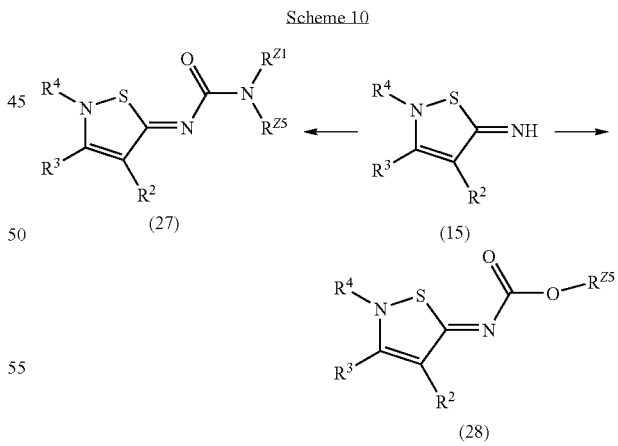

(27)  (15)

(28)

Reaction of compounds of formula (15) with isocyanates in a solvent such as, but not limited to, dichloromethane, toluene, dioxane, or dimethylformamide, at a temperature from about 25° C. to about 150° C. can provide compounds of formula (27) wherein R$^{Z1}$ is hydrogen. Alternatively, treatment of compounds of formula (15) with carbamylchlorides of formula ClCONR$^{Z1}$R$^{Z5}$ in a solvent such as, but not limited to, dichloromethane, toluene, dioxane, or dimethylformamide, at a temperature from about 25° C. to about 150° C. can provide compounds of formula (27) wherein $R^{Z1}$ is other than hydrogen.

Reaction of compounds of formula (15) with chloroformates or fluoroformates in a solvent such as, but not limited to, dichloromethane, tetrahydrofuran, or dimethylformamide, in the presence of a base such as, but not limited to, triethylamine, at a temperature from about 25° C. to about 50° C. can provide compounds of formula (28) wherein $R^{Z5}$ is as defined in formula (I).

Alternatively, compounds of formula (27) can be prepared using general procedures as shown in Scheme 11.

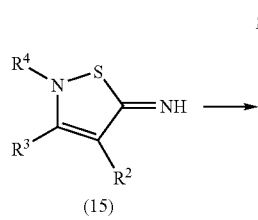

Reaction of compounds of formula (15) with 4-nitrophenylcarbonochloridate in a solvent such as, but not limited to, tetrahydrofuran or dichloromethane in the presence of a base such as, but not limited to, diisopropylethylamine or triethylamine, at about room temperature provides the intermediate (29). The intermediate (29) can be converted to (27) by reaction with amines of formula $HNR^{Z1}R^{Z5}$ in a solvent such as, but not limited to, tetrahydrofuran, acetonitrile, or dimethylformamide, at temperatures from about 25° C. to about 150° C. This reaction may be facilitated with microwave irradiation.

Many other methods for the preparation of ureas are known in the art and can be found, for example, in the following references: Chem. Rev., 1972, 72, 457-496; J. Org. Chem., 1994, 59, 1937-38; Synthesis, 1996, 553-76; Angew. Chem. Int. Ed. Engl., 1987, 26, 894-95; J. Org. Chem., 2003, 68, 7289-97; J. Org. Chem., 1997, 62, 4155-58; Tet. Lett., 1995, 36, 2583-86; Tet. Lett., 1994, 35, 4055-58; Tet. Lett., 1997, 38, 5335-38; Angew. Chem. Int. Ed. Engl., 1995, 34, 2497-2500; Synlett., 1996, 507-08; Synlett., 1996, 502-03; Tet. Lett., 1983, 24, 4569-72; Synthesis, 1989, 423-425; J. Org. Chem., 1996, 61, 4175-79; Tet. Lett., 1998, 39, 7811-14; J. Org. Chem., 1998, 63, 4802-07; and J. Comb. Chem., 1999, 1, 163-172.

Compounds of formulae (30) and (31) can be prepared using the methods in Scheme 12.

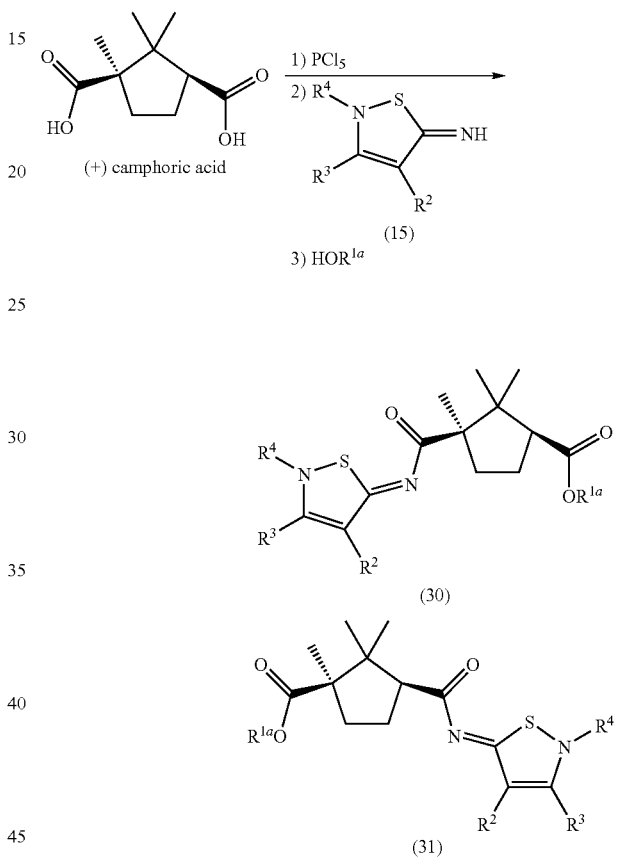

(+) Camphoric acid ((1R,3S)-1,2,2-trimethyl-1,3-cyclopentanedicarboxylic acid) can be reacted with phosphorus pentachloride in a solvent such as, but not limited to, hexane at a temperature from about room temperature to about 80° C. to provide an intermediate bis acid chloride, that can be reacted sequentially with compound (15), followed by an alcohol $HOR^{1a}$, in a solvent such as tetrahydrofuran, in the presence of a base such as triethylamine, to provide a mixture of (30) and (31). The mixture of (30) and (31) can be separated by silica gel chromatography. The foregoing sequence can also be conducted starting from (−) camphoric acid using the same conditions to provide analogous products with the opposite stereochemistries.

Compounds of formulae (32) and (33) can be prepared from (30) using the methods of Scheme 13.

Scheme 13

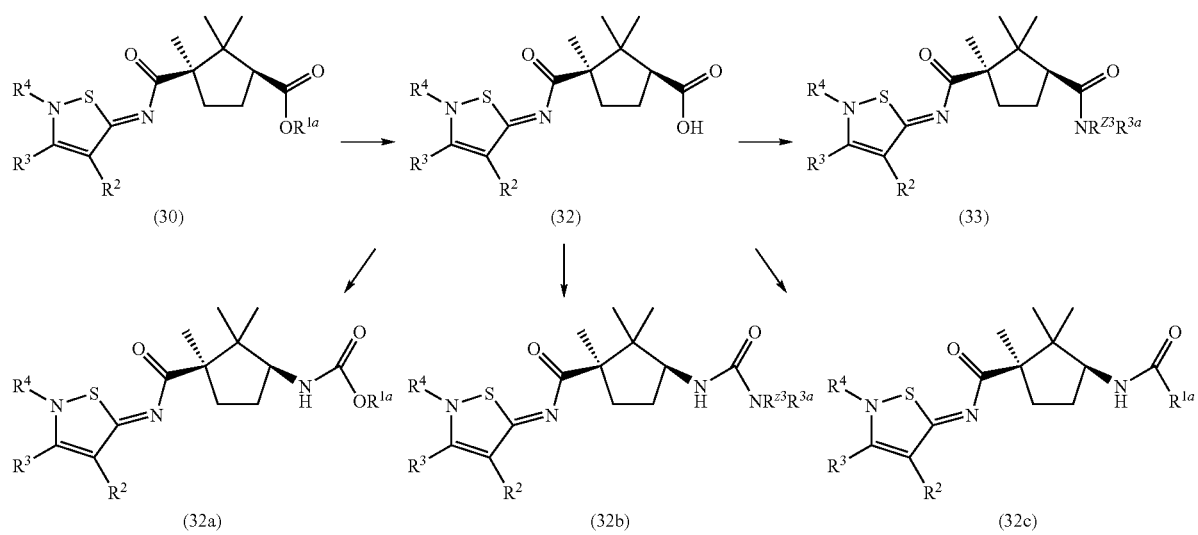

Compounds of formula (30), wherein $R^{1a}$ is alkyl, can be reacted with an alkali metal hydroxide (e.g., potassium hydroxide) in aqueous alcohol solvent (e.g., water-ethanol) at temperatures from about room temperature to about 80° C. to provide the carboxylic acid compounds (32). Compounds of formula (32) can be transformed to compounds of formula (33) by reaction with an amine $HNR^{Z3}R^{3a}$ (or salt thereof) in a solvent such as, but not limited to, tetrahydrofuran or dimethylformamide in the presence of a coupling reagent such as N-(3-dimethylaminopropyl)-n'-ethylcarbodiimide hydrochloride (EDC), 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine. Compounds of formula (33) wherein $R^{3a}$ is hydroxyalkylcan be converted to the corresponding oxazolines by reaction with para-toluenesulfonyl chloride, N,N-dimethylaminopyridine and triethylamine. Compounds of formula (32) can be reacted under Curtius-type rearrangement conditions, well known to those skilled in the art, to provide the corresponding amines, carbamates, ureas, or amides according to the choice of reaction conditions.

Compounds of formula (31), wherein $R^{1a}$ is alkyl, can also be reacted using the methods of Scheme 13 to generate the corresponding carboxylic acids and amides. The carboxylic acid and amide compounds so-derived from (31) can be further elaborated as described in the preceding paragraph to provide amines, carbamates, or oxazolines according to the compound and choice of reaction conditions.

Certain compounds of formula (I) where $R^1$ is $G^1$, $G^1$ is phenyl and said phenyl is -$L^1$-$A^{10}$, wherein $A^{10}$ is $A^1$ or a chemical derivative or precursor thereof, are represented by formula (35).

Scheme 14

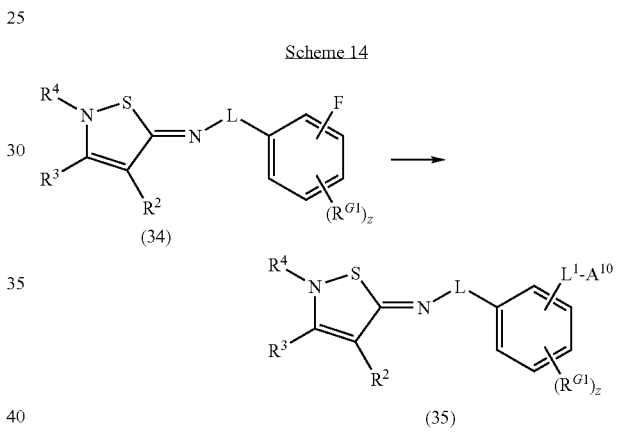

Compounds of formula (35), wherein L, $L^1$, $R^2$, $R^3$ and $R^4$ are as defined in formula (I); $A^{10}$ is $A^1$ or a chemical derivative or precursor thereof, $R^{G1}$ represents the optional substituents of $G^1$ as defined in formula (I), and z is 0, 1, 2, 3, or 4, can be prepared from compounds of formula (34) by reaction with either an alcohol HO-$A^{10}$ or an amine $HN(R^{Z3})(A^{10})$ in the presence or absence of a base such as, but not limited to, potassium tert-butoxide, sodium tert-butoxide, or triethylamine in a solvent such as, but not limited to, tetrahydrofuran or dimethylformamide at temperatures between about 0° C. and 150° C. The reaction with $HN(R^{Z3})(A^{10})$ may be facilitated with microwave irradition.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the convention manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

d. Examples

Example 1

N-[(5Z)-4-butyl-2-tert-butylisothiazol-5(2H)-ylidene]-5-chloro-2-methoxybenzamide Example 1A N-(tert-butyl)-N-hexylideneamine To t-butyl amine (5.25 mL, 50.0 mmol) and $MgSO_4$ (2 g) in $CH_2Cl_2$ (10 mL) at room temperature was added slowly hexanal (6.0 mL, 50 mmol) under $N_2$ at room temperature. The reaction became exothermic halfway through the addition so an ice bath was briefly used to control the reaction rate and avoid boiling off the solvent or amine. After the addition was complete, the reaction was stirred at room temperature for 2 h, filtered through celite under a stream of $N_2$ and washed with 20 mL dry $CH_2Cl_2$. The solvent was evaporated to give a pale yellow liquid. $^1$H NMR (300 MHz, $CDCl_3$) δ 0.87-0.91 (m, 3H), 1.17 (s, 9H), 1.25-1.35 (m, 4H), 1.45-1.55 (m, 2H), 2.23 (m, 2H), 7.59 (t, 1H).

Example 1B 5-chloro-2-methoxybenzoyl chloride

5-Chloro-2-methoxybenzoic acid (11.3 g, 60.56 mmol) and $SOCl_2$ (9 mL, 123.7 mmol) in toluene (20 mL) were heated gently while vigorous gas evolution occurred. After gas evolution had subsided, the reaction was heated to reflux for 1.5 h, cooled and stirred overnight at room temperature. The volatiles were evaporated in vacuo and the remaining material was treated with toluene and evaporated (2×) to remove excess $SOCl_2$ to provide a white solid that was taken directly on to the next step without purification. $^1$H NMR (300 MHz, $CDCl_3$) δ 3.92 (s, 3H), 6.95 (d, 1H), 7.53 (dd, 1H), 8.03 (d, 1H).

Example 1C 5-chloro-2-methoxybenzoyl isothiocyanate

The product of Example 1B (~60 mmol) and KSCN (5.83 g, 60 mmol) were mixed in anhydrous tetrahydrofuran (25 mL) and anhydrous acetone (40 mL) and stirred at room temperature for 2 hrs. The reaction was diluted with diethyl ether (100 mL), filtered through celite and solvents evaporated in vacuo to provide the title compound. $^1$H NMR (300 MHz, $CDCl_3$) δ 3.95 (s, 3H), 6.95 (d, 1H), 7.52 (dd, 1H), 7.84 (d, 1H).

Example 1D

N-[(5Z)-4-butyl-2-tert-butylisothiazol-5(2H)-ylidene]-5-chloro-2-methoxybenzamide To the product of Example 1A (1.90 g, 12.2 mmol) in tetrahydrofuran (10 mL) at room temperature under $N_2$ was added the product of Example 1C (2.30 g, 10.1 mmol). After 1 h at room temperature, the reaction was treated with $I_2$ (2.59 g, 10.2 mmol), methanol (30 mL) and pyridine (3 mL) and stirred for 1 hour. The reaction was then partitioned between saturated $NaHCO_3$/diethyl ether with continued stirring overnight. The reaction was diluted further with saturated $NaHCO_3$/diethyl ether, the layers separated and the aqueous phase extracted again with diethyl ether (2×). The organics were combined, dried ($MgSO_4$), filtered and solvent evaporated. Toluene/acetonitrile was added and evaporated 2× to remove excess pyridine and $H_2O$. The crude was flash chromatographed, eluting with diethyl ether:$CH_2Cl_2$:hexane (7:3:3) to provide 2.68 g of the desired product with impurities running above and below. This material was dissolved in a minimum of $CH_2Cl_2$, hexane added until slightly cloudy and allowed to sit for 4 hours. A white crystalline solid was collected and washed with cold 1:1 $CH_2Cl_2$:hexane to provide 962.78 mg of the title compound. The mother liquor was recrystallized from methanol to provide 555 mg additional title compound. The second mother liquor was concentrated to dryness, dissolved in a minimum of $CH_2Cl_2$ and flash chromatographed on silica gel, eluting with diethyl ether:$CH_2Cl_2$:hexane (7:1:3) to provide an additional 600 mg of the title compound. $^1$H NMR (300 MHz, $CDCl_3$) δ ppm 0.98 (t, 3H), 1.37-1.49 (m, 2H), 1.65 (s, 9H), 1.67-1.77 (m, 2H), 2.83 (t, 2H), 3.92 (s, 3H), 6.91 (d, 1H), 7.34 (dd, 1H), 7.95 (s, 1H), 8.11 (d, 1H). MS (DCI/NH$_4^+$) $^{m/z}$ 381 (M+H)$^+$. Anal. calcd for C$_{19}$H$_{25}$ClN$_2$O$_2$S: C, 59.91; H, 6.61; N, 7.35. Found: C, 59.88; H, 6.67; N, 7.42.

Example 2

N-[(5Z)-4-butyl-2-(1,1-dimethylpropyl)isothiazol-5(2H)-ylidene]-5-chloro-2-methoxybenzamide Hexanal (0.123 mL, 1.0 mmol) was added dropwise to t-amylamine (0.117 mL, 1.0 mmol) in diethyl ether (1 mL) with MgSO$_4$ (240 mg) at 0° C. The reaction was allowed to warm to room temperature with stirring over 1 h, cooled again to 0° C., treated with Example 1C (230 mg, 1 mmol), stirred 1.5 h at 0° C., then treated with I$_2$ (250 mg) and pyridine (0.17 mL) and the reaction allowed to warm to room temperature with stirring overnight. The reaction was quenched in saturated NaHCO$_3$ and extracted with diethyl ether (3×). The organics were dried (MgSO$_4$), filtered and solvent evaporated. Flash chromatography over silica gel (2×) eluting with 33% ethyl acetate/hexane and then 45% ethyl acetate/hexane provided 22 mg of the title compound. $^1$H NMR (300 MHz, CDCl$_3$) δ ppm 0.78 (t, 3H), 0.98 (t, 3H), 1.37-1.50 (m, 2H), 1.63 (s, 6H), 1.67-1.77 (m, 2H), 1.91 (q, 2H), 2.84 (t, 2H), 3.92 (s, 3H), 6.91 (d, 1H), 7.34 (dd, 1H), 7.90 (br s, 1H), 8.12 (d, 1H). MS (DCI/NH$_4^+$) m/z 395 (M+H)$^+$.

Example 3

N-[(5Z)-4-butyl-2-cyclobutylisothiazol-5(2H)-ylidene]-5-chloro-2-methoxybenzamide The title compound was prepared using the procedure as described in Example 2, substituting t-amylamine with cyclobutylamine. $^1$H NMR (300 MHz, CDCl$_3$) δ ppm 0.94 (t, 3H), 1.34-1.46 (m, 2H), 1.59-1.69 (m, 2H), 1.87-1.97 (m, 2H), 2.30-2.44 (m, 2H), 2.60 (br m, 2H), 2.65 (dt, 2H), 3.91 (s, 3H), 5.38 (br t, 1H), 6.89 (s, 1H), 6.91 (d, 1H), 7.33 (dd, 1H), 7.97 (d, 1H). LC/MS (APCI$^+$) m/z 379 (M+H)$^+$.

Example 4

N-[(5Z)-4-butyl-2,3-dimethylisothiazol-5(2H)-ylidene]hexahydro-2,5-methanopentalene-3a(1H)-carboxamide

Example 4A

Hexahydro-2,5-methanopentalene-3a(1H)-carbonyl chloride

3-Noradamantane carboxylic acid (4.99 g, 30.1 mmol) and SOCl$_2$ (5 mL, 69 mmol) in toluene (5 mL) were heated to 65° C. until vigorous evolution of gas commenced. The heating bath was removed for 5-10 minutes until gas evolution had moderated. Heating the reaction again at 65° C. was resumed for 2 hours. The reaction was cooled to room temperature, the volatiles removed in vacuo and toluene added and evaporated (2×) to remove excess SOCl$_2$. The crude acid chloride was used without further purification.

Example 4B

N-(4-bromo-3-methylisothiazol-5-yl)hexahydro-2,5-methanopentalene-3a(1H)-carboxamide To a solution of 4-bromo-3-methylisothiazol-5-amine (prepared as described in J. Chem. Soc. 1963, p 2032) (1.93 g, 10.1 mmol) in tetrahydrofuran (25 mL) with triethylamine (1.7 mL, 12.2 mmol) at 0° C. was added slowly a solution of Example 4A (1.9 g, 10.3 mmol) in tetrahydrofuran (15 mL). The reaction was allowed to warm to room temperature and stirred overnight. The reaction was evaporated to dryness, partitioned between H$_2$O/ethyl acetate and the aqueous extracted again (2×) with ethyl acetate. The organics were combined, dried (MgSO$_4$), filtered and solvent evaporated. Flash chromatography over silica gel eluting with 15% ethyl acetate/hexane provided 0.3 g of the title compound plus 1.8 g of diacylated compound. The latter was heated to reflux in methanol for 3 h, cooled, solvent evaporated and flash chromatographed over silica gel eluting with 20% ethyl acetate/hexane to provide an additional 0.99 g of the title compound. $^1$H NMR (300 MHz, CDCl$_3$) δ ppm 1.63-1.76 (m, 4H), 1.87-1.98 (m, 4H), 2.10-2.15 (m, 2H), 2.45 (s, 3H), 2.81 (t, 1H), 8.23 (br s, 1H).

Example 4C

N-[(5Z)-4-bromo-2,3-dimethylisothiazol-5(2H)-ylidene]hexahydro-2,5-methanopentalene-3a(1H)-carboxamide The product of Example 4B (1.29 g, 3.79 mmol), K$_2$CO$_3$ (0.85 g) and iodomethane (1.2 mL, 5 equiv.) in a mixture of acetonitrile (10 mL), tetrahydrofuran (10 mL) and CH$_2$Cl$_2$ (3 mL) were stirred overnight at room temperature, treated with additional iodomethane (1.2 mL), heated to 65° C. for 3 h then stirred overnight at room temperature. The reaction was evaporated in vacuo, partitioned between H$_2$O/CH$_2$Cl$_2$ and the aqueous extracted again (2×) with CH$_2$Cl$_2$. The organics were dried (MgSO$_4$), filtered and solvent evaporated. Flash chromatography over silica gel eluting with 35-40% EtOAc/hexane, followed by 100% ethyl acetate provided 0.77 g of the title compound. $^1$H NMR (300 MHz, CDCl$_3$) δ ppm 1.61-1.66 (m, 4H), 1.91 (m, 4H), 2.25-2.35 (m, 4H), 2.49 (s, 3H), 2.72 (t, 1H), 3.60 (s, 3H). MS (DCI/NH$_3$) m/z 355 (M+H)$^+$.

Example 4D

N-[(5Z)-4-butyl-2,3-dimethylisothiazol-5(2H)-ylidene]hexahydro-2,5-methanopentalene-3a(1H)-carboxamide A mixture of the product of Example 4C (44 mg, 0.12 mmol), bis(tri-tert-butylphosphine)palladium(0) (13 mg, 0.025 mmol) and 0.5 M n-butylzinc bromide/tetrahydrofuran (0.38 mL, 0.19 mmol) in dimethylacetamide (2 mL) was heated to 80-100° C. for 24 h, cooled, quenched in H$_2$O and extracted with diethyl ether (3×). The organics were filtered through celite to breakup slight emulsion and solvents evaporated. The crude was flash chromatographed over silica gel eluting with 15% ethyl acetate/hexane to 25% ethyl acetate/hexane to provide the title compound. $^1$H NMR (300 MHz, CDCl$_3$) δ ppm 0.94 (t, 3H), 1.28-1.40 (m, 2H), 1.51-1.64 (m, 6H), 1.82-1.92 (m, 4H), 2.28 (m, 4H), 2.32 (s, 3H), 2.67-2.77 (m, 3H), 3.53 (s, 3H). MS (DCI/NH$_4^+$) m/z 333 (M+H)$^+$.

Example 5

N-[(5Z)-4-butyl-2-(1-methylcyclobutyl)isothiazol-5(2H)-ylidene]-5-chloro-2-methoxybenzamide To a solution of 1-methylcyclobutylamine (454 mg, 5.33 mmol) in dry CH$_2$Cl$_2$ (1 mL) with MgSO$_4$ (250 mg) was added slowly hexanal (655 µL, 5.3 mmol). The reaction was stirred under N₂ for 1 h, filtered through a 0.45 µm PFTE filter, washed with 0.5 ml dry CH₂Cl₂, diluted with 2 mL tetrahydrofuran, and treated with Example 1C (703 mg, 3.09 mmol) with continued stirring. After 1 h, the reaction was treated with I₂ (750 mg), methanol (5 mL) and pyridine (1 mL) and continued stirring at room temperature for 1 h. The reaction was partitioned between saturated NaHCO₃/diethyl ether and stirred overnight. The layers were separated and the aqueous was extracted again with diethyl ether. The combined organic extracts were dried (MgSO₄), filtered and solvent evaporated. The crude was flash chromatographed on silica gel, eluting with diethyl ether:CH₂Cl₂:hexane (7:1:3) to provide 88.9 mg of the desired product with slight impurity. The product was chromatographed a second time using an Analogix® IT280™ instrument using an SF15-12 g column, gradient eluting with ethyl acetate:hexane (0:100 to 50:50) over 20 minutes to provide 75 mg of the title compound. $^1$H NMR (300 MHz, CDCl₃) δ ppm 0.98 (t, 3H), 1.39-1.49 (m, 2H), 1.70 (s, 3H), 1.71 (m, 2H), 1.95-2.06 (m, 2H), 2.29 (m, 2H), 2.69 (m, 2H), 2.83 (t, 2H), 3.91 (s, 3H), 6.91 (d, 1H), 7.33 (dd, 1H), 7.80 (s, 1H), 8.12 (d, 1H). MS (DCI/NH₃) m/z 393 (M+H)⁺.

Example 6

N-[(5Z)-4-allyl-2-tert-butylisothiazol-5(2H)-ylidene]-5-chloro-2-methoxybenzamide Example 6A 2-methyl-N-(pent-4-enylidene)propan-2-amine To t-butylamine (5.28 mL, 50 mmol) in CH₂Cl₂ (10 mL) with MgSO₄ (2.1 g) was added slowly at 0° C. under N₂ 4-pentenal (4.94 mL, 50 mmol). After the addition was complete the reaction was stirred at 0° C. for 15 min then allowed to warm to room temperature and stirred for 2 hours. The reaction was filtered through celite, washed with 20 mL dry CH₂Cl₂ and the solvent evaporated at ambient temperature to provide a clear light yellow liquid. $^1$H NMR (300 MHz, CDCl₃) δ ppm 1.17 (s, 9H), 2.2-2.4 (m, 4H), 4.95-5.1 (m, 2H), 5.83 (m, 1H), 7.61 (t, 1H).

Example 6B

N-[(5Z)-4-allyl-2-tert-butylisothiazol-5(2H)-ylidene]-5-chloro-2-methoxybenzamide The title compound was prepared using the procedure as described in Example 1D, substituting Example 6A for Example 1A. The product was purified by chromatography using an Analogix® IT280™ over a SF40-115 g column, gradient eluting with ethyl acetate:hexane (0:100 to 50:50 over 20 minutes, then 10 minutes at 50:50) to provide 1.1 g of material that contained some small impurities. The product was chromatographed a second time over silica gel, eluting with diethyl ether:CH₂Cl₂:hexane (7:2:3). The product obtained was crystallized from diethyl ether/hexane to provide the title compound. $^1$H NMR (300 MHz, CDCl₃) δ 1.65 (s, 9H), 3.62 (d, 2H), 3.92 (s, 3H), 5.16 (m, 2H), 6.0-6.15 (m, 1H) 6.92 (d, 1H), 7.34 (dd, 1H), 7.94 (s, 1H), 8.15 (d, 1H). MS (DCI/NH₃) m/z 365 (M+H)⁺.

Example 7

N-[(5Z)-2-tert-butyl-4-[3-methyl-4,5-dihydroisoxazol-5-yl)methyl]isothiazol-5(2H)-ylidene]-5-chloro-2-methoxybenzamide To a solution of acetaldoxime (95 µL, 2.43 mmol) in CHCl₃ (10 mL) under N₂ was added N-chlorosuccinimide (323 mg, 2.43 mmol) and pyridine (10 µL). After 2 hours at room temperature, Example 6B (150 mg) was added, followed by triethylamine (340 µL, 2.4 mmol) and the reaction continued to stir at room temperature for 21 hours. The reaction mixture was washed with water and partitioned. The aqueous layer was extracted again with CH₂Cl₂ and the combined organic extracts were dried (MgSO₄), filtered and solvent evaporated. The crude was chromatographed using the Analogix® IT280™ over a SF15-12 g column gradient eluting with ethyl acetate:hexane (0:100 to 100:0 over 25 minutes) to provide 128 mg of the title compound. $^1$H NMR (300 MHz, CDCl₃) δ ppm 1.66 (s, 9H), 1.89 (s, 3H), 2.85 (m, 1H), 3.0-3.23 (m, 3H), 3.92 (s, 3H), 4.95 (m, 1H), 6.93 (d, 1H), 7.35 (dd, 1H), 8.09 (d, 1H), 8.20 (s, 1H). MS (DCI/NH₃) m/z 422 (M+H)⁺.

Example 8

N-[(5Z)-2-tert-butyl-4-(cyclopropylmethyl)isothiazol-5(2H)-ylidene]-5-chloro-2-methoxybenzamide To a solution of dimethoxyethane (85 µL, 0.82 mmol) in dry CH₂Cl₂ (3 mL) under N₂ at −10° C. (EtOH/ice) was added dropwise a 1.0 M solution of Et₂Zn/heptane (0.82 mL). After the addition was complete, diiodomethane (0.13 mL, 1.6 mmol) was added dropwise and the reaction stirred 10 min at −10° C. The reaction was then treated with Example 6B (145 mg) in CH₂Cl₂ (1 mL) and allowed to warm to RT and stirred overnight (~16 h). The reaction was quenched in saturated NH₄Cl and extracted with a mix of EtOAc/Et₂O/CH₂Cl₂ and then again with Et₂O. The organics were dried (MgSO₄), filtered through celite and concentrated. The crude was chromatographed with the Analogix IT280™ gradient eluting with EtOAc:hexane (0:100 to 50:50) to provide 45 mg of the title compound. $^1$H NMR (300 MHz, CDCl₃) δ ppm 0.28 (m, 2H), 0.57 (m, 2H), 1.25 (m, 1H), 1.67 (3, 9H), 2.75 (d, 2H), 3.91 (s, 3H), 6.91 (d, 1H), 7.33 (dd, 1H), 8.09 (s, 1H), 8.10 (d, 1H). MS (DCI/NH₃) m/z 379 (M+H)⁺.

Example 9

N-[(3Z)-1-tert-butyl-5-propyl-4,5,6,7-tetrahydro-2,1-benzisothiazol-3(1H)-ylidene]-5-chloro-2-methoxybenzamide To a solution of tert-butylamine (366 mg, 5 mmol) in anhydrous hexane (20 mL) at 0° C. was added titanium(IV) chloride (133 mg, 0.5 mmol). After 5 min, the cooling bath was removed and 4-propylcyclohexanone (140 mg, 1 mmol) was added in one portion. The resulting mixture was stirred at ambient temperature for 2 h. Then, the precipitated solid was filtered and washed with anhydrous ethyl ether. The filtrate and washings were combined and concentrated under reduced pressure. The residue was dissolved in THF (20 mL) and treated with 5-chloro-2-methoxybenzoyl isothiocyanate (190 mg, 0.83 mmol) for 1 h at room temperature. Iodine (211 mg, 0.83 mmol) was added followed by addition of MeOH (10 mL) and pyridine (1 mL). The mixture was allowed to stir at room temperature for additional 2 h and then saturated sodium bicarbonate solution and ethyl ether were added. The mixture was stirred for 30 min, the ether layer was separated and the aqueous solution was extracted with ethyl ether. The ether extracts were combined, washed with brine, dried with anhydrous MgSO$_4$ and concentrated under reduced pressure. The residue was twice evaporated with toluene and acetonitrile and then purified by chromatography (hexane-EtOAc 1:1) to afford 70 mg of the title compound. $^1$H NMR (300 MHz, DMSO-d$_6$) δ ppm 0.85-1.02 (m, 3 H), 1.29-1.53 (m, 6 H), 1.68 (s, 9 H), 1.90-2.07 (m, 1 H), 2.19 (dd, J=15.9, 10.2 Hz, 1 H), 2.78-3.01 (m, 2 H), 3.09-3.26 (m, 1 H), 3.72-3.84 (m, 3 H), 7.11 (d, J=8.8 Hz, 1 H), 7.45 (dd, J=8.8, 3.1 Hz, 1 H), 7.68 (d, J=3.1 Hz, 1 H); MS (DCI/NH$_3$) m/z 421 (M+H)$^+$. Anal. calcd for C$_{22}$H$_{29}$ClN$_2$O$_2$S.0.1H$_2$O: C, 62.50; H, 6.96; N, 6.63. Found: C, 62.21; H, 6.99; N, 6.49.

Example 10

N-[(3Z)-1-tert-butyl-1,4,6,7-tetrahydro-3H-spiro[2,1-benzisothiazole-5,2'-[1,3]dioxolan]-3-ylidene]-5-chloro-2-methoxybenzamide The title compound was prepared according to the procedure of Example 9 by replacing 4-propylcyclohexanone with 1,4-dioxaspiro[4.5]decan-8-one. $^1$H NMR (300 MHz, DMSO-d$_6$) δ ppm 1.61-1.79 (m, 9 H), 1.94-2.08 (m, 2 H), 2.80-2.96 (m, 2 H), 3.13 (t, J=6.3 Hz, 2 H), 3.78 (s, 3 H), 3.90-4.06 (m, 4 H), 7.12 (d, J=9.1 Hz, 1 H), 7.46 (dd, J=8.7, 2.8 Hz, 1 H), 7.68-7.77 (m, 1 H); MS (DCI/NH$_3$) m/z 437 (M+H)$^+$.

Example 11

N-[(5Z)-2-tert-butyl-4-(2-methoxyethyl)isothiazol-5(2H)-ylidene]-5-chloro-2-methoxybenzamide Example 11A 4-(tert-butyldimethylsilyloxy)butanal To CH$_2$Cl$_2$ (150 mL) at −78° C. were added oxalyl chloride (6.83 g, 53.8 mmol) and dry DMSO (8.41 g, 108 mmol), dropwise. After 5 min, 4-(tert-butyldimethylsilyloxy)butan-1-ol (10 g, 48.9 mmol) in CH$_2$Cl$_2$ (5 mL) was added dropwise. The mixture was stirred for an additional 30 min at −78° C., and Et$_3$N (24.8 g, 245 mmol) was added. The mixture was then allowed to warm to room temperature over 30 min. After stirring for 3 hrs, 100 mL of water was added. The phases were separated, and the aqueous phase was extracted three times with 100 mL of diethyl ether. The combined organic phases were washed successively with 50 mL of aqueous 1% HCl, 50 mL of water, 50 mL of aqueous 5% NaHCO$_3$ and 50 mL of saturated aqueous NaCl. The organic layer was dried over MgSO$_4$, and the solvent was removed under reduced pressure, to provide the title compound.

Example 11B

N-(4-(tert-butyldimethylsilyloxy)butylidene)-2-methylpropan-2-amine

The title compound was prepared using the procedure as described in Example 1A substituting Example 11A for hexanal.

Example 11C

N-[(5Z)-2-tert-butyl-4-(2-{[tert-butyl(dimethyl)silyl]oxy}ethyl isothiazol-5(2H)-ylidene]-5-chloro-2-methoxybenzamide The title compound was prepared using the procedure as described in Example 1D substituting Example 11B for 1A. MS (DCI/NH$_4^+$) m/z 483 (M+H)$^+$.

Example 11D

N-[(5Z)-2-tert-butyl-4-(2-hydroxyethyl)isothiazol-5(2H)-ylidene]-5-chloro-2-methoxybenzamide The product from 11C (6.0 g, 12.4 mmol) in THF (10 mL) was treated with tetrabutylammonium fluoride (1M in THF) (14.9 mL, 14.9 mmol). The mixture was stirred at rt for 2 hrs. The reaction was diluted with H$_2$O, and the aqueous phase extracted with EtOAc (2×). The organics were combined, dried (MgSO$_4$), filtered and solvent evaporated. The residue was purified by column chromatography using an Analogix® Intelliflash280™(SiO$_2$, 0-50% Hexane in ethyl acetate) to afford 2.5 g (55%) of the title compound. $^1$H NMR (500 MHz, CDCl$_3$) δ ppm 1.68 (s, 9 H) 3.04 (t, J=5.19 Hz, 2 H) 3.93 (s, 3 H) 3.95 (t, J=4.88 Hz, 2 H) 6.92 (d, J=8.85 Hz, 1 H) 7.35 (dd, J=8.85, 2.75 Hz, 1 H) 7.97 (s, 1 H) 8.00 (d, J=2.75 Hz, 1 H); MS (DCI/NH$_4^+$) m/z 369 (M+H)$^+$.

Example 11E

N-[(5Z)-2-tert-butyl-4-(2-methoxyethyl)isothiazol-5(2H)-ylidene]-5-chloro-2-methoxybenzamide The product from 11D (70 mg, 0.19 mmol) in THF (5 mL) was treated with NaH (60%) (12 mg, 0.29 mmol) at rt. The mixture was stirred for 10 min, then to the mixture was added iodomethane (32.3 mg, 0.23 mmol). The reaction was stirred for an additional 30 min, quenched with H$_2$O, and extracted with EtOAc (2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 59 mg (81%) of the title compound. $^1$H NMR (500 MHz, CDCl$_3$) δ ppm 1.66 (s, 9 H) 3.10 (t, J=6.10 Hz, 2 H) 3.39 (s, 3 H) 3.72 (t, J=6.10 Hz, 2 H) 3.92 (s, 3 H) 6.92 (d, J=8.85 Hz, 1 H) 7.34 (dd, J=8.85, 2.75 Hz, 1 H) 8.09 (s, 1 H) 8.12 (d, J=2.75 Hz, 1 H); MS (DCI/NH$_4^+$) m/z 383 (M+H)$^+$.

Example 12

N-[(5Z)-2-tert-butyl-4-(2-morpholin-4-ylethyl)isothiazol-5(2H)-ylidene]-5-chloro-2-methoxybenzamide The product from 11D (100 mg, 0.27 mmol) in CH$_2$Cl$_2$ (10 mL) containing triethylamine (82 mg, 0.81 mmol) was treated with methanesulfonyl chloride (47 mg, 0.41 mmol) at 0° C. The mixture was stirred for 15 min at 0° C. and solvent removed. The residue was dissolved in THF (10 mL), treated with morpholine (118 mg, 1.36 mmol) and potassium carbonate (75 mg, 0.54 mmol) and refluxed for 12 hrs. Purification by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes afforded 62 mg (52%) of the title compound. $^1$H NMR (500 MHz, CDCl$_3$) δ ppm 1.66 (s, 9 H) 2.61-2.66 (m, 4 H) 2.75-2.80 (m, 2 H) 3.04 (t, J=7.93, 7.32 Hz, 2 H) 3.77 (t, J=4.58 Hz, 4 H) 3.92 (s, 3 H) 6.92 (d, J=8.85 Hz, 1 H) 7.35 (dd, J=8.85, 2.75 Hz, 1 H) 8.13 (s, 1 H) 8.15 (d, J=2.75 Hz, 1 H); MS (DCI/NH$_4^+$) m/z 438 (M+H)$^+$.

Example 13

N-[(5Z)-2-tert-butyl-4-[2-(5,5-dimethyl-1,3-dioxan-2-yl)ethyl]isothiazol-5(2H)-ylidene]-5-chloro-2-methoxybenzamide

Example 13A

N-(4-(5,5-dimethyl-1,3-dioxan-2-yl)butylidene)-2-methylpropan-2-amine

The title compound was prepared using the procedure as described in Example 1A substituting 4-(5,5-dimethyl-1,3-dioxan-2-yl)butanal for hexanal.

Example 13B

N-[(5Z)-2-tert-butyl-4-[2-(5,5-dimethyl-1,3-dioxan-2-yl)ethyl]isothiazol-5(2H)-ylidene]-5-chloro-2-methoxybenzamide The title compound was prepared using the procedure as described in Example 1D substituting Example 13A for 1A. $^1$H NMR (500 MHz, CDCl$_3$) δ ppm 0.73 (s, 3 H) 1.21 (s, 3 H) 1.64 (s, 9 H) 2.07-2.13 (m, 2 H) 2.95 (t, J=7.93 Hz, 2 H) 3.53 (dd, J=99.47, 11.29 Hz, 4 H) 3.92 (s, 3 H) 4.50 (t, J=5.19 Hz, 1 H) 6.91 (d, J=8.85 Hz, 1 H) 7.33 (dd, J=8.85, 2.75 Hz, 1 H) 7.98 (s, 1 H) 8.13 (d, J=2.75 Hz, 1 H); MS (DCI/NH$_4^+$) m/z 467 (M+H)$^+$.

Example 14

N-[(5Z)-4-(2-azidoethyl)-2-tert-butylisothiazol-5(2H)-ylidene]-5-chloro-2-methoxybenzamide The product from 11D (209 mg, 0.57 mmol) in CH$_2$Cl$_2$ (20 mL) containing triethylamine (172 mg, 1.7 mmol) was treated with methanesulfonyl chloride (97 mg, 0.85 mmol) at 0° C. The mixture was stirred for 20 min at 0° C., solvent removed, the residue dissolved in DMF (10 mL) and treated with sodium azide (184 mg, 2.83 mmol). The mixture was heated at 80° C. for 2 hrs, diluted with H$_2$O and extracted with EtOAc (2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 120 mg (54%) of the title compound. $^1$H NMR (500 MHz, CDCl$_3$) δppm 1.67 (s, 9 H) 3.10 (t, J=6.71 Hz, 2 H) 3.71 (t, J=6.41 Hz, 2 H) 3.93 (s, 3 H) 6.93 (d, J=8.85 Hz, 1 H) 7.36 (dd, J=8.85, 2.75 Hz, 1 H) 8.05 (s, 1 H) 8.11 (d, J=2.75 Hz, 1 H); MS (DCI/NH$_4^+$) m/z 394 (M+H)$^+$.

Example 15

N-[(5Z)-2-tert-butyl-4-[3-(methoxyimino)propyl]isothiazol-5(2H)-ylidene]-5-chloro-2-methoxybenzamide

Example 15A (Z)-N-(2-tert-butyl-4-(3-oxopropyl)isothiazol-5(2H)-ylidene)-5-chloro-2-methoxybenzamide Example 13B (620 mg, 1.33 mmol) in THF (2 mL) was treated with 2N HCl (10 mL, 20 mmol). The mixture was heated at 60° C. for 12 hrs, cooled to room temperature and extracted with isopropanol/CH$_2$Cl$_2$ (1:3)(2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 304 mg (60%) of the title compound. $^1$H NMR (500 MHz, CDCl$_3$) δ ppm 1.66 (s, 9 H) 3.02 (t, J=6.41 Hz, 2 H) 3.12 (t, J=6.71 Hz, 2 H) 3.92 (s, 3 H) 6.92 (d, J=8.85 Hz, 1 H) 7.35 (dd, J=8.85, 2.75 Hz, 1 H) 8.06 (s, 1 H) 8.09 (d, J=2.75 Hz, 1 H); MS (DCI/NH$_4^+$) m/z 381 (M+H)$^+$.

Example 15B

N-[(5Z)-2-tert-butyl-4-[3-(methoxyimino)propyl]isothiazol-5(2H)-ylidene]-5-chloro-2-methoxybenzamide The product from 15A (26 mg, 0.07 mmol) in EtOH (2 mL) was treated with O-methylhydroxylamine hydrochloride (12 mg, 0.14 mmol) and sodium acetate (6 mg, 0.07 mmol). The mixture was stirred at rt for 1 hr, solvent removed and purified by column chromatography using an Analogix® Intelliflash280™ (SiO$_2$, 0-50% Hexane in ethyl acetate) to afford 5.5 mg (19%) of the title compound. $^1$H NMR (500 MHz, CDCl$_3$) δ ppm 1.66 (s, 9 H) 2.64-2.71 (m, 2 H) 2.99-3.06 (m, 2 H) 3.82 (s, 3 H) 3.92 (s, 3 H) 6.93 (s, 1 H) 7.35 (dd, J=8.85, 2.75 Hz, 1 H) 7.46 (t, J=5.80 Hz, 1 H) 8.02 (s, 1 H) 8.10 (d, J=2.75 Hz, 1H); MS (DCI/NH$_4^+$) m/z 410 (M+H)$^+$.

Example 16

N-[(5Z)-2-tert-butyl-4-[2-(dimethylamino)ethyl]isothiazol-5(2H)-ylidene]-5-chloro-2-methoxybenzamide

Example 16A

N-[(5Z)-4-(2-aminoethyl)-2-tert-butylisothiazol-5(2H)-ylidene]-5-chloro-2-methoxybenzamide The product from Example 14 (70 mg, 0.18 mmol) in EtOH (10 mL) was treated with Pd/C (10 mg) under a hydrogen balloon for 3 hrs. The Pd/C was filtered off and washed with EtOH. The filtrate was concentrated to afford 60 mg (91%) of the title compound. $^1$H NMR (500 MHz, CDCl$_3$) δ ppm 1.68 (s, 9 H) 3.08 (dd, J=5.80, 4.88 Hz, 2 H) 3.27 (dd, J=5.19 Hz, 2 H) 3.92 (s, 3 H) 6.94 (d, J=8.85 Hz, 1 H) 7.37 (dd, J=8.85, 2.75 Hz, 1 H) 7.97 (d, J=2.75 Hz, 1 H) 8.03 (s, 1 H); MS (DCI/NH$_4^+$) m/z 368 (M+H)$^+$.

Example 16B

N-[(5Z)-2-tert-butyl-4-[2-(dimethylamino)ethyl]isothiazol-5(2H)-ylidene]-5-chloro-2-methoxybenzamide The product from Example 16A (60 mg, 0.16 mmol) in CH$_2$Cl$_2$ (10 mL) was treated with paraformaldehyde (60 mg) and sodium boroneacetate (44 mg, 0.16 mmol). The mixture was stirred at rt for 12 hrs. Diluted with H$_2$O, the mixture was extracted with CH$_2$Cl$_2$ (1×). The organics were combined, dried (MgSO$_4$), filtered and solvent evaporated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes to afford 13 mg (20%) of the title compound. $^1$H NMR (500 MHz, CDCl$_3$) δ ppm 1.66 (s, 9 H) 2.59 (s, 6 H) 3.03-3.10 (m, 2 H) 3.12-3.19 (m, 2 H) 3.93 (s, 3 H) 6.93 (d, J=8.85 Hz, 1 H) 7.36 (dd, J=8.85, 3.05 Hz, 1 H) 8.13 (d, J=2.75 Hz, 1 H) 8.17 (s, 1 H); MS (DCI/NH$_4^+$) m/z 396 (M+H)$^+$.

Example 17

N-[(5Z)-2-tert-butyl-4-methylisothiazol-5(2H)-ylidene]-5-chloro-2-methoxybenzamide

Example 17A 2-methyl-N-propylidenepropan-2-amine

The title compound was prepared using the procedure as described in Example 1A substituting propionaldehyde for hexanal.

Example 17B

N-[(5Z)-2-tert-butyl-4-methylisothiazol-5(2H)-ylidene]-5-chloro-2-methoxybenzamide The title compound was prepared using the procedure as described in Example 1D substituting Example 17A for Example 1A. $^1$H NMR (500 MHz, CDCl$_3$) δ ppm 2.39 (s, 3 H) 3.92 (s, 3 H) 6.92 (d, J=8.85 Hz, 1 H) 7.33 (dd, J=8.85, 2.75 Hz, 1 H) 7.97 (s, 1 H) 8.13 (d, J=2.75 Hz, 1 H); MS (DCI/NH$_4$) m/z 339 (M+H)$^+$.

Example 18

N-[(5Z)-2-tert-butyl-4-(3-hydroxybutyl)isothiazol-5(2H)-ylidene]-5-chloro-2-methoxybenzamide The product from Example 15A (125 mg, 0.33 mmol) in THF (20 mL) was treated with methylmagnesium bromide (3N) (220 µl, 0.66 mmol) at −40° C. The reaction mixture was allowed to warm to −15° C. for 2 hrs and quenched with NH$_4$Cl. The mixture was extracted with CH$_2$Cl$_2$ (2×). The organics were combined, dried (MgSO$_4$), filtered and solvent evaporated. The residue was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minutes to afford 29 mg (22%) of the title compound. $^1$H NMR (500 MHz, CDCl$_3$) δ ppm 1.14 (d, J=6.41 Hz, 3 H) 1.52-1.61 (m, 1 H) 1.67 (s, 9 H) 1.70-1.81 (m, 1 H) 2.72 (dt, J=14.34, 4.27 Hz, 1 H) 3.22-3.31 (m, 1 H) 3.53-3.62 (m, 1 H) 3.94 (s, 3 H) 6.92 (d, J=8.85 Hz, 1 H) 7.34 (dd, J=8.85, 2.75 Hz, 1 H) 7.99 (s, 1 H) 8.03 (d, J=2.75 Hz, 1 H); MS (DCI/NH$_4^+$) m/z 397 (M+H)$^+$.

Example 19

N-[(5Z)-2-tert-butyl-4-(2-cyanoethyl)isothiazol-5(2H)-ylidene]-5-chloro-2-methoxybenzamide The product from Example 15A (50 mg, 0.13 mmol) in NMP (1 mL) was treated with hydroxylamine hydrochloride (18 mg, 0.26 mmol). The mixture was heated at 100° C. in a microwave reactor (300 W, CEM Explorer®) for 15 min. The crude mixture was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minute to afford the title compound. $^1$H NMR (500 MHz, CDCl$_3$) δ ppm 1.68 (s, 9 H) 2.93 (t, J=6.71 Hz, 2 H) 3.14 (t, J=7.02 Hz, 2 H) 3.93 (s, 3 H) 6.94 (d, J=8.85 Hz, 1 H) 7.37 (dd, J=8.85, 3.05 Hz, 1 H) 8.07 (d, J=2.75 Hz, 1 H) 8.11 (s, 1 H); MS (DCI/NH$_4^+$) m/z 378 (M+H)$^+$.

Example 20

N-[(5Z)-2-tert-butyl-4-(2,3-dihydroxypropyl)isothiazol-5(2H)-ylidene]-5-chloro-2-methoxybenzamide The product from Example 6B (160 mg, 0.44 mmol) in acetone (3 mL) and water (0.5 mL) was treated with 4-methymorpholine N-oxide (154 mg, 1.32 mmol) and osmium tetroxide (6 mg, 0.02 mmol). The mixture was stirred at rt for 12 hrs, quenched with saturated aqueous Na$_2$S$_2$O$_3$ and extracted twice with isopropanol/CH$_2$Cl$_2$ (1:3). The organics were combined, dried (MgSO$_4$), filtered and solvent evaporated. The residue was purified by reverse phase preparative HPLC on a Waters Symmetry C8 column (25 mm×100 mm, 7 µm particle size) using a gradient of 10% to 100% acetonitrile: 0.1% aqueous trifluoroacetic acid over 8 minutes (10 minutes run time) at a flow rate of 40 mL/minute to afford 67 mg (38%) of the title compound. $^1$H NMR (400 MHz, CDCl$_3$) δ ppm 1.68 (s, 9 H) 3.02-3.07 (m, 2 H) 3.53 (dd, J=4.60, 0.92 Hz, 2 H) 3.90-3.93 (m, 2 H) 3.93 (s, 3 H) 6.93 (d, J=8.90 Hz, 1 H) 7.37 (dd, J=8.90, 2.76 Hz, 1 H) 7.99 (d, J=2.76 Hz, 1 H) 8.00 (s, 1 H); MS (DCI/NH$_4^+$) m/z 399 (M+H)$^+$.

Example 21

N-[(5Z)-2-tert-butyl-4-[(methoxyimino)methyl]isothiazol-5(2H)-ylidene]-5-chloro-2-methoxybenzamide

Example 21A

N-[(5Z)-2-tert-butyl-4-formylisothiazol-5(2H)-ylidene]-5-chloro-2-methoxybenzamide The product from Example 6B (200 mg, 0.55 mmol) in acetone (6 mL) and water (3 mL) was treated with osmium tetroxide (5 mg, 0.02 mmol). The mixture was stirred at rt for 10 min, then to the mixture was added sodium periodate (258 mg, 1.2 mmol) in portions. The reaction was stirred at rt for 12 hrs, quenched with saturated aqueous Na$_2$S$_2$O$_3$ and extracted twice with isopropanol/CH$_2$Cl$_2$ (1:3). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 78 mg (40%) of the title compound. $^1$H NMR (500 MHz, CDCl$_3$) δ ppm 1.69 (s, 9 H) 3.96 (s, 3 H) 6.97 (d, J=8.85 Hz, 1 H) 7.43 (dd, J=8.85, 2.75 Hz, 1 H) 8.30 (d, J=2.75 Hz, 1 H) 8.67 (s, 1 H) 10.46 (s, 1 H); MS (DCI/NH$_4^+$) m/z 353 (M+H)$^+$.

Example 21B

N-[(5Z)-2-tert-butyl-4-[(methoxyimino)methyl]isothiazol-5(2H)-ylidene]-5-chloro-2-methoxybenzamide The title compound was prepared using the procedure as described in Example 15B substituting Example 21A for Example 15A. $^1$H NMR (500 MHz, CDCl$_3$) δ ppm 1.70 (s, 9H) 3.94 (s, 3 H) 3.95 (s, 3 H) 6.94 (d, J=8.85 Hz, 1 H) 7.38 (dd, J=8.85, 2.75 Hz, 1 H) 8.23 (d, J=2.75 Hz, 1 H) 8.57 (s, 1 H) 8.62 (s, 1 H); MS (DCI/NH$_4^+$) m/z 382 (M+H)$^+$.

Example 22

N-[(5Z)-2-tert-butyl-4-(1,3-dioxolan-2-ylmethyl) isothiazol-5(2H)-ylidene]-5-chloro-2-methoxybenzamide Example 22A 3-(1,3-dioxolan-2-yl)propanal To the solution of 2-(2-bromoethyl)-1,3-dioxolane (10 g, 55.2 mmol) in THF (50 mL) was added magnesium (1.6 g, 66.3 mmol) and trace amount of I$_2$ as initiator. The reaction mixture was stirred at rt for 2 hrs. After cooling to −78° C., the mixture was quenched with dry DMF (1.39 g, 66.3 mmol) and kept at −78° C. for 2 hrs. After dilution with H$_2$O the reaction mixture was extracted with CH$_2$Cl$_2$ (2×), followed by distillation (45-55° C. @ 8 mmHg) to afford 2 g (28%) of the title compound. MS (DCI/NH$_4^+$) m/z 131 (M+H)$^+$.

Example 22B

N-(3-(1,3-dioxolan-2-yl)propylidene)-2-methylpropan-2-amine

The title compound was prepared using the procedure as described in Example 1A substituting Example 22A for hexanal.

Example 22C

N-[(5Z)-2-tert-butyl-4-(1,3-dioxolan-2-ylmethyl) isothiazol-5(2H)-ylidene]-5-chloro-2-methoxybenzamide The title compound was prepared using the procedure as described in Example 1D substituting Example 22B for Example 1A. $^1$H NMR (400 MHz, CDCl$_3$) δ ppm 1.66 (s, 9 H) 3.23 (d, J=4.60 Hz, 2 H) 3.87-4.05 (m, 4 H) 3.92 (s, 3 H) 5.21 (t, J=4.91 Hz, 1 H) 6.91 (d, J=8.90 Hz, 1 H) 7.34 (dd, J=8.90, 2.76 Hz, 1 H) 8.15 (d, J=3.07 Hz, 1 H) 8.16 (s, 1 H); MS (DCI/NH$_4^+$) m/z 411 (M+H)$^+$.

Example 23

N-[(5Z)-2-tert-butyl-4-(1-hydroxy-2-methylpropyl) isothiazol-5(2H)-ylidene]-5-chloro-2-methoxybenzamide The product from Example 21A (50 mg, 0.14 mmol) in THF (5 mL) was cooled to −40° C. To the solution was dropwise added isopropylmagnesium bromide (3 M) (94 µL, 0.28 mmol). The reaction was kept at −40° C. for 30 min, quenched with saturated aqueous NH$_4$Cl, and the mixture was extracted with EtOAc (2×). The organics were combined, dried (MgSO$_4$), filtered and solvent evaporated. The residue was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minute to afford 7.8 mg (14%) of the title compound. $^1$H NMR (400 MHz, CDCl$_3$) δ ppm 0.99 (d, J=6.75 Hz, 6 H) 1.67 (s, 9 H) 2.11-2.26 (m, 1 H) 3.96 (s, 3 H) 4.59 (d, J=6.44 Hz, 1 H) 6.93 (d, J=8.90 Hz, 1 H) 7.39 (dd, J=8.90, 2.76 Hz, 1 H) 7.94 (s, 1 H) 8.10 (d, J=2.76 Hz, 1 H); MS (DCI/NH$_4^+$) m/z 397 (M+H)$^+$.

Example 24

N-[(5Z)-2-tert-butyl-4-(cyanomethyl)isothiazol-5 (2H)-ylidene]-5-chloro-2-methoxybenzamide Example 24A 4-oxobutanenitrile 4,4-Diethoxybutanenitrile (10 g, 63.6 mmol) in water (100 mL) was treated with 4-methylbenzenesulfonic acid (200 mg, 1.2 mmol) and refluxed for 2 hrs. The pH was adjusted to 7 and the mixture was extracted with CH$_2$Cl$_2$ (6×). The organics were combined, dried (MgSO$_4$), filtered and solvent evaporated to afford the crude product.

Example 24B 4-(tert-butylimino)butanenitrile

The title compound was prepared using the procedure as described in Example 1A substituting Example 24A for hexanal.

Example 24C

N-[(5Z)-2-tert-butyl-4-(cyanomethyl)isothiazol-5 (2H)-ylidene]-5-chloro-2-methoxybenzamide The title compound was prepared using the procedure as described in Example 1D substituting Example 24B for Example 1A. $^1$H NMR (500 MHz, CDCl$_3$) δ ppm 1.69 (s, 9 H) 3.93 (s, 3 H) 3.97 (s, 2 H) 6.94 (d, J=8.85 Hz, 1 H) 7.38 (dd, J=8.85, 2.75 Hz, 1 H) 8.16 (d, J=2.75 Hz, 1 H) 8.21 (s, 1 H); MS (DCI/NH$_4^+$) m/z 364 (M+H)$^+$.

Example 25

N-[(5Z)-4-[(1Z)-but-1-enyl]-2-tert-butylisothiazol-5 (2H)-ylidene]-5-chloro-2-methoxybenzamide Example 25A N—((Z)-hex-3-enylidene)-2-methylpropan-2-amine The title compound was prepared using the procedure as described in Example 1A substituting (Z)-hex-3-enal for hexanal.

Example 25B

N-[(5Z)-4-[(1Z)-but-1-enyl]-2-tert-butylisothiazol-5 (2H)-ylidene]-5-chloro-2-methoxybenzamide The title compound was prepared using the procedure as described in Example 1D substituting Example 25A for Example 1A. $^1$H NMR (400 MHz, CDCl$_3$) δ ppm 1.12 (t, J=7.67 Hz, 3 H) 1.69 (s, 9 H) 2.24-2.35 (m, 2 H) 3.92 (s, 3 H) 5.70 (dt, J=11.66, 7.06 Hz, 1H) 6.71 (dt, J=11.66, 1.53 Hz, 1 H) 6.91 (d, J=8.90 Hz, 1 H) 7.34 (dd, J=8.90, 2.76 Hz, 1 H) 8.16 (s, 1 H) 8.18 (d, J=3.07 Hz, 1 H); MS (DCI/NH$_4^+$) m/z 379 (M+H)$^+$.

Example 26

N-[(5Z)-4-butyl-2-tert-butylisothiazol-5(2H)-ylidene]-5-cyano-2-methoxybenzamide

Example 26A

Methyl 5-cyano-2-methoxybenzoate

3-Bromo-4-methoxybenzonitrile (10 g, 47 mmol) in MeOH (100 mL) was treated with triethyamine (9.1 g, 12.5 mL, 90 mmol) and $PdCl_2(dppf)CH_2Cl_2$ (1.0 g). The mixture was heated at 100° C. under CO at 60 psi for 4 hrs, then filtered and the filtrate concentrated. The residue was purified by column chromatography using an Analogix® Intelliflash280™ ($SiO_2$, 0-50% Hexane in ethyl acetate) to afford 8.2 g (93%) of the title compound. $^1$H NMR (500 MHz, $CDCl_3$) δ ppm 3.92 (s, 3 H) 3.98 (s, 3 H) 7.06 (d, J=8.54 Hz, 1 H) 7.76 (dd, J=8.54, 2.14 Hz, 1 H) 8.10 (d, J=2.14 Hz, 1 H).

Example 26B 5-cyano-2-methoxybenzoic acid

A mixture of the product from Example 26A (6.1 g, 31.9 mmol) and lithium hydroxide monohydrate (5.36 g, 128 mmol) in THF (100 mL) and $H_2O$ (50 mL) was stirred at rt for 3 hrs. The reaction pH was adjusted to 3 with 3N HCl, and the mixture was extracted twice with isopropanol/$CH_2Cl_2$ (1:3). The organics were combined, dried ($MgSO_4$), filtered and concentrated to afford 5.6 g (99%) of the title compound. $^1$H NMR (500 MHz, $CDCl_3$) δ ppm 4.15 (s, 3 H) 7.17 (d, J=8.85 Hz, 1 H) 7.86 (dd, J=8.85, 2.44 Hz, 1 H) 8.47 (d, J=2.14 Hz, 1 H).

Example 26C 5-cyano-2-methoxybenzoyl chloride

The title compound was prepared using the procedure as described in Example 1B substituting Example 26B for 5-chloro-2-methoxybenzoic acid.

Example 26D 5-cyano-2-methoxybenzoyl isothiocyanate

The title compound was prepared using the procedure as described in Example 1C substituting Example 26C for Example 1B.

Example 26E

N-[(5Z)-4-butyl-2-tert-butylisothiazol-5(2H)-ylidene]-5-cyano-2-methoxybenzamide The title compound was prepared using the procedure as described in Example 1D substituting Example 26D for Example 1C. $^1$H NMR (400 MHz, $CDCl_3$) δ ppm 0.99 (t, J=7.36 Hz, 3 H) 1.39-1.49 (m, 2 H) 1.66 (s, 9 H) 1.68-1.76 (m, 2 H) 2.83 (dd, J=7.67 Hz, 2H) 3.99 (s, 3 H) 7.04 (d, J=8.90 Hz, 1 H) 7.68 (dd, J=8.59, 2.15 Hz, 1 H) 7.97 (s, 1 H) 8.46 (d, J=2.15 Hz, 1 H); MS (DCI/$NH_4^+$) m/z 372 (M+H)$^+$.

Example 27

N-[(5Z)-2-tert-butyl-4-(2-ethylcyclopropyl)isothiazol-5(2H)-ylidene]-5-chloro-2-methoxybenzamide To a solution of $CH_2Cl_2$ (10 mL) and 1,2-dimethoxyethane (95 mg, 1.06 mmol) at −10° C. was added diethylzinc (130 mg, 1.06 mmol). To this solution was added dropwise diiodomethane (565 mg, 2.1 mmol). After the addition was complete, the resulting clear solution was stirred for 10 min at −10° C. A solution of Example 25B (200 mg, 0.53 mmol) was added to the reaction mixture, which was allowed to warm to room temperature and stir overnight. The reaction was quenched with $NH_4Cl$ then acetone and extracted with EtOAc (2×). The organics were combined, dried ($MgSO_4$), filtered and solvent evaporated. The residue was purified by column chromatography using an Analogix® Intelliflash280™ ($SiO_2$, 0-50% Hexane in ethyl acetate) to afford 159 mg (77%) of the title compound. $^1$H NMR (400 MHz, $CDCl_3$) δ ppm 0.59 (q, J=5.52 Hz, 1 H) 0.92 (t, J=7.36, 6.44 Hz, 3 H) 0.94-1.14 (m, 2 H) 1.16-1.29 (m, 2 H) 1.65 (s, 9 H) 2.11-2.33 (m, 1 H) 3.91 (s, 3 H) 6.91 (d, J=8.90 Hz, 1 H) 7.33 (dd, J=8.90, 2.76 Hz, 1 H) 7.81 (s, 1 H) 8.08 (d, J=2.76 Hz, 1 H); MS (DCI/$NH_4^+$) m/z 393 (M+H)$^+$.

Example 28

N-[(5Z)-2-tert-butyl-4-(methoxymethyl)isothiazol-5(2H)-ylidene]-5-chloro-2-methoxybenzamide

Example 28A

N-[(5Z)-2-tert-butyl-4-(hydroxymethyl)isothiazol-5(2H)-ylidene]-5-chloro-2-methoxybenzamide The product from Example 21A (50 mg, 0.14 mmol) in THF (10 mL) was treated with sodium borohydride (21 mg, 0.57 mmol) at −40° C. for 1 hr, quenched with saturated $NH_4Cl$, extracted with EtOAc (2×), dried over $MgSO_4$, filtered and concentrated to afford 50 mg of the title compound. $^1$H NMR (500 MHz, $CDCl_3$) δ ppm 1.67 (s, 9 H) 3.93 (s, 3 H) 4.88 (s, 2 H) 6.94 (d, J=8.85 Hz, 1 H) 7.37 (dd, J=8.85, 3.05 Hz, 1 H) 8.05 (s, 1 H) 8.08 (d, J=2.75 Hz, 1 H); MS (DCI/$NH_4^+$) m/z 355 (M+H)$^+$.

Example 28B

N-[(5Z)-2-tert-butyl-4-(methoxymethyl)isothiazol-5(2H)-ylidene]-5-chloro-2-methoxybenzamide The title compound was prepared using the procedure as described in Example 11E substituting Example 28A for Example 11D. $^1$H NMR (500 MHz, $CDCl_3$) δ ppm 1.67 (s, 3H) 3.51 (s, 3 H) 3.93 (s, 3 H) 4.73 (s, 2 H) 6.92 (d, J=8.85 Hz, 1 H) 7.35 (dd, J=8.85, 2.75 Hz, 1 H) 8.15 (d, J=2.75 Hz, 1 H) 8.18 (s, 1 H); MS (DCI/$NH_4^+$) m/z 369 (M+H)$^+$.

Example 29

N-[(5Z)-2-tert-butyl-4-(ethoxymethyl)isothiazol-5(2H)-ylidene]-5-chloro-2-methoxybenzamide The title compound was prepared using the procedure as described in Example 11E substituting Example 28A for Example 11D and iodoethane for iodomethane. $^1$H NMR (500 MHz, CDCl$_3$) δ ppm 1.30 (t, J=7.02 Hz, 3 H) 1.67 (s, 9 H) 3.69 (q, J=7.02 Hz, 2 H) 3.92 (s, 3H) 4.77 (s, 2 H) 6.92 (d, J=8.85 Hz, 1 H) 7.35 (dd, J=8.85, 2.75 Hz, 1 H) 8.14 (d, J=3.05 Hz, 1 H) 8.19 (s, 1 H); MS (DCI/NH$_4^+$) m/z 383 (M+H)$^+$.

Example 30

N-[(5Z)-2-tert-butyl-4-(3-cyanopropyl)isothiazol-5 (2H)-ylidene]-5-chloro-2-methoxybenzamide Example 30A 6-oxohexanenitrile The title compound was prepared using the procedure as described in Example 21A substituting hept-6-enenitrile for Example 6B.

Example 30B 6-(tert-butylimino)hexanenitrile

The title compound was prepared using the procedure as described in Example 1A substituting Example 30A for hexanal.

Example 30C

N-[(5Z)-2-tert-butyl-4-(3-cyanopropyl)isothiazol-5 (2H)-ylidene]-5-chloro-2-methoxybenzamide The title compound was prepared using the procedure as described in Example 1D substituting Example 30B for Example 1A. $^1$H NMR (400 MHz, CDCl$_3$) δ ppm 1.67 (s, 9 H) 2.13-2.24 (m, 2 H) 2.42 (t, J=7.06 Hz, 2 H) 2.98 (t, J=7.36 Hz, 2 H) 3.92 (s, 3 H) 6.92 (d, J=8.59 Hz, 1 H) 7.35 (dd, J=8.90, 2.76 Hz, 1 H) 8.01 (s, 1 H) 8.08 (d, J=2.76 Hz, 1 H); MS (DCI/NH$_4^+$) m/z 392 (M+H)$^+$.

Example 31

N-[(5Z)-2-tert-butyl-4-[hydroxy(phenyl)methyl] isothiazol-5(2H)-ylidene]-5-chloro-2-methoxybenzamide The title compound was prepared using the procedure as described in Example 23 substituting phenylmagnesium bromide for isopropylmagnesium bromide. $^1$H NMR (400 MHz, CDCl$_3$) δ ppm 1.57 (s, 9 H) 3.95 (s, 3 H) 6.25 (s, 1 H) 6.96 (t, J=9.21 Hz, 1 H) 7.30-7.46 (m, 4 H) 7.50-7.56 (m, 2 H) 8.18 (d, J=2.76 Hz, 1 H) 9.51 (s, 1 H); MS (DCI/NH$_4^+$) m/z 431 (M+H)$^+$.

Example 32

N-[(5Z)-4-(azidomethyl)-2-tert-butylisothiazol-5 (2H)-ylidene]-5-chloro-2-methoxybenzamide The title compound was prepared using the procedure as described in Example 14 substituting Example 28A for Example 11D. $^1$H NMR (500 MHz, CDCl$_3$) δ ppm 1.67 (s, 9H) 3.93 (s, 3 H) 4.65 (s, 2 H) 6.93 (d, J=8.85 Hz, 1 H) 7.37 (dd, J=8.85, 2.75 Hz, 1 H) 8.12 (m, 1 H) 8.20 (d, J=2.75 Hz, 1 H); MS (DCI/NH$_4^+$) m/z 380 (M+H)$^+$.

Example 33

N-[(5Z)-2-tert-butyl-4-(2-cyclobutyl-1-hydroxyethyl)isothiazol-5(2H)-ylidene]-5-chloro-2-methoxybenzamide To (bromomethyl)cyclobutane (211 mg, 1.42 mmol) in THF (20 mL) was added magnesium (41.3 mg, 1.7 mmol), and initiator iodine (10 mg). The mixture was stirred at rt for 2 hrs, then cooled to −40° C. and added to a solution of Example 21A (100 mg, 0.28 mmol) in THF (20 mL). The mixture was allowed to warm to room temperature, quenched with saturated aqueous NH$_4$Cl, and extracted with EtOAc (2×). The organics were combined, dried (MgSO$_4$), filtered and solvent evaporated. The residue was purified by column chromatography using an Analogix® Intelliflash280™ (SiO$_2$, 0-50% Hexane in ethyl acetate) to afford 63 mg (53%) of the title compound. $^1$H NMR (400 MHz, CDCl$_3$) δ ppm 1.62-1.78 (m, 2 H) 1.65 (s, 9 H) 1.76-1.94 (m, 2 H) 1.97-2.18 (m, 4 H) 2.47-2.59 (m, 1H) 3.92 (s, 3 H) 4.88 (dd, J=8.29, 6.14 Hz, 1 H) 6.93 (d, J=8.90 Hz, 1 H) 7.37 (dd, J=8.90, 3.07 Hz, 1 H) 7.95 (s, 1 H) 8.05 (d, J=2.76 Hz, 1 H); MS (DCI/NH$_4^+$) m/z 423 (M+H)$^+$.

Example 34

N-[(5Z)-2-tert-butyl-4-[cyclobutyl(hydroxy)methyl] isothiazol-5(2H)-ylidene]-5-chloro-2-methoxybenzamide The title compound was prepared using the procedure as described in Example 33 substituting bromocyclobutane for (bromomethyl)cyclobutane. $^1$H NMR (400 MHz, CDCl$_3$) δ ppm 1.65 (s, 9 H) 1.82-2.01 (m, 4 H) 2.08-2.20 (m, 2 H) 2.80-2.92 (m, 1 H) 3.94 (s, 3H) 4.85 (d, J=7.67 Hz, 1 H) 6.93 (d, J=8.90 Hz, 1 H) 7.37 (dd, J=8.59, 2.76 Hz, 1 H) 7.91 (s, 1 H) 8.03 (d, J=2.76 Hz, 1 H); MS (DCI/NH$_4^+$) m/z 409 (M+H)$^+$.

Example 35

N-[(5Z)-4-benzyl-2-tert-butylisothiazol-5(2H)-ylidene]-5-chloro-2-methoxybenzamide The product from Example 31 (20 mg, 0.05 mmol) in TFA (0.5 mL) was treated with triethylsilane (54 mg, 0.5 mmol). The mixture was heated at 60° C. for 12 hrs, solvent evaporated and the residue purified by reverse phase preparative HPLC on a Waters Symmetry C8 column (25 mm×100 mm, 7 µm particle size) using a gradient of 10% to 100% acetonitrile: 0.1% aqueous trifluoroacetic acid over 8 minutes (10 minutes run time) at a flow rate of 40 mL/minute to afford 4.8 mg (25%) of the title compound. $^1$H NMR (400 MHz, CDCl$_3$) δ ppm 1.61 (s, 9 H) 3.93 (s, 3 H) 4.18 (s, 2 H) 6.92 (d, J=8.90 Hz, 1 H) 7.20-7.28 (m, 1 H) 7.29-7.39 (m, 5 H) 7.78 (s, 1 H) 8.14 (d, J=2.76 Hz, 1 H); MS (DCI/NH$_4^+$) m/z 415 (M+H)$^+$.

Example 36

N-[(5Z)-2-tert-butyl-4-(2-cyclobutylethyl)isothiazol-5(2H)-ylidene]-5-chloro-2-methoxybenzamide Example 36A O-{1-[(5Z)-2-tert-butyl-5-{[(5-chloro-2-methoxyphenyl)carbonyl]imino}-2,5-dihydroisothiazol-4-yl]-2-cyclobutylethyl}O-phenyl thiocarbonate The product from Example 33 (32 mg, 0.07 mmol) in CH$_2$Cl$_2$ (5 mL) containing pyridine (17 mg, 0.2 mmol) was treated dropwise with O-phenyl carbonochloridothioate (18 mg, 0.11 mmol). The mixture was stirred at room temperature for 1 hr, solvent removed and the residue purified by column chromatography using an Analogix® Intelliflash280™ (SiO$_2$, 0-50% Hexane in ethyl acetate) to afford 32 mg (81%) of the title compound. MS (DCI/NH$_4^+$) m/z 559 (M+H)$^+$.

Example 36B

N-[(5Z)-2-tert-butyl-4-(2-cyclobutylethyl)isothiazol-5(2H)-ylidene]-5-chloro-2-methoxybenzamide The product from Example 36A (32 mg, 0.06 mmol) was immediately treated with 2 mL (0.03 mmol) of a stock solution of AIBN (12 mg (0.073 mmol in 5 mL of anhydrous toluene)) and tributylstannane (33.3 mg, 0.114 mmol), and the resulting mixture was heated to 85-90° C. After 30 min, additional tributylstannane (33.3 mg, 0.114 mmol) and AIBN stock solution (1 mL) were added. The reaction was refluxed for an additional 30 min, concentrated in vacuo and the residue purified by reverse phase preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 minutes run time) at a flow rate of 40 mL/minute to afford 13.2 mg (57%) of the title compound. $^1$H NMR (400 MHz, CDCl$_3$) δ ppm 1.61-1.75 (m, 2 H) 1.65 (s, 9 H) 1.77-1.94 (m, 4 H) 2.04-2.16 (m, 2 H) 2.30-2.41 (m, 1 H) 2.73 (dd, J=7.67 Hz, 2 H) 3.92 (s, 3 H) 6.91 (d, J=8.59 Hz, 1 H) 7.34 (dd, J=8.90, 3.07 Hz, 1 H) 7.93 (s, 1 H) 8.14 (d, J=2.76 Hz, 1 H); MS (DCI/NH$_4^+$) m/z 407 (M+H)$^+$.

Example 37

N-[(5Z)-2-tert-butyl-4-isobutylisothiazol-5(2H)-ylidene]-5-chloro-2-methoxybenzamide Example 37A O-{1-[(5Z)-2-tert-butyl-5-{[(5-chloro-2-methoxyphenyl)carbonyl]imino}-2,5-dihydroisothiazol-4-yl]-2-methylpropyl}O-phenyl thiocarbonate The title compound was prepared using the procedure as described in Example 36A substituting Example 23 for Example 33. MS (DCI/NH$_4^+$) m/z 533 (M+H)$^+$.

Example 37B

N-[(5Z)-2-tert-butyl-4-isobutylisothiazol-5(2H)-ylidene]-5-chloro-2-methoxybenzamide The title compound was prepared using the procedure as described in Example 36B substituting Example 37A for Example 36A. $^1$H NMR (400 MHz, CDCl$_3$) δ ppm 0.97 (d, J=6.44 Hz, 6 H) 1.66 (s, 9 H) 2.05-2.19 (m, 1 H) 2.70 (d, J=7.06 Hz, 2 H) 3.91 (s, 3 H) 6.91 (d, J=8.59 Hz, 1 H) 7.33 (dd, J=8.90, 2.76 Hz, 1 H) 7.91 (s, 1 H); MS (DCI/NH$_4^+$) m/z 381 (M+H)$^+$.

Example 38

N-[(5Z)-2-tert-butyl-4-(cyclobutylmethyl)isothiazol-5(2H)-ylidene]-5-chloro-2-methoxybenzamide Example 38A O-{[(5Z)-2-tert-butyl-5-{[(5-chloro-2-methoxyphenyl)carbonyl]imino}-2,5-dihydroisothiazol-4-yl](cyclobutyl)methyl}O-phenyl thiocarbonate The title compound was prepared using the procedure as described in Example 36A substituting Example 34 for Example 33. MS (DCI/NH$_4^+$) m/z 545 (M+H)$^+$.

Example 38B

N-[(5Z)-2-tert-butyl-4-(cyclobutylmethyl)isothiazol-5(2H)-ylidene]-5-chloro-2-methoxybenzamide The title compound was prepared using the procedure as described in Example 36B substituting Example 38A for Example 36A. $^1$H NMR (400 MHz, CDCl$_3$) δ ppm 1.65 (s, 9H) 1.73-1.84 (m, 2 H) 1.84-1.95 (m, 2 H) 2.04-2.16 (m, 2 H) 2.69-2.79 (m, 1 H) 2.92 (d, J=7.67 Hz, 2 H) 3.92 (s, 3 H) 6.91 (d, J=8.59 Hz, 1 H) 7.33 (dd, J=8.90, 2.76 Hz, 1 H) 7.89 (s, 1 H) 8.09 (d, J=2.76 Hz, 1 H); MS (DCI/NH$_4^+$) m/z 393 (M+H)$^+$.

Example 39

N-[(5Z)-2-tert-butyl-4-tetrahydro-2H-pyran-4-yl-isothiazol-5(2H)-ylidene]-5-chloro-2-methoxybenzamide Example 39A 2-methyl-N-(2-(tetrahydro-2H-pyran-4-yl)ethylidene)propan-2-amine The title compound was prepared using the procedure as described in Example 1A substituting 2-(tetrahydro-2H-pyran-4-yl)acetaldehyde for hexanal.

Example 39B

N-[(5Z)-2-tert-butyl-4-tetrahydro-2H-pyran-4-yl-isothiazol-5(2H)-ylidene]-5-chloro-2-methoxybenzamide The title compound was prepared using the procedure as described in Example 1D substituting Example 39A for Example 1A. $^1$H NMR (500 MHz, CDCl$_3$) δ ppm 1.64-1.68 (s, 9 H) 1.77 (qd, J=13.12, 12.21, 4.27 Hz, 2 H) 2.06 (dt, J=12.82, 1.83 Hz, 2 H) 3.36-3.45 (m, 1 H) 3.65 (td, J=11.90, 1.83 Hz, 2 H) 3.92 (s, 3 H) 4.08 (dd, J=11.29, 3.97 Hz, 2 H) 6.92 (d, J=8.85 Hz, 1 H) 7.35 (dd, J=8.85, 2.75 Hz, 1 H) 7.93 (s, 1 H) 8.08 (d, J=3.05 Hz, 1 H); MS (DCI/NH$_4^+$) m/z 409 (M+H)$^+$.

Example 40

N-[(5Z)-2-tert-butyl-4-[hydroxy(1,3-thiazol-2-yl)methyl]isothiazol-5(2H)-ylidene]-5-chloro-2-methoxybenzamide The title compound was prepared using the procedure as described in Example 23 substituting thiazol-2-yllithium for isopropylmagnesium bromide. $^1$H NMR (500 MHz, CDCl$_3$) δ ppm 1.82 (s, 9 H) 4.19 (s, 3 H) 6.83 (s, 1 H) 7.09 (d, J=8.85 Hz, 1 H) 7.40 (d, J=3.36 Hz, 1 H) 7.62 (dd, J=8.85, 2.75 Hz, 1 H) 7.79-7.82 (m, 1 H) 8.16 (d, J=2.75 Hz, 1 H) 8.94 (s, 1 H); MS (DCI/NH$_4$$^+$) m/z 438 (M+H)$^+$.

Example 41

N-[(5Z)-4-butyl-2-tert-butylisothiazol-5(2H)-ylidene]-2,5-dimethoxybenzamide

A mixture of the product from Example 110B (400 mg), 2,5-dimethoxybenzoic acid (86 mg, 0.47 mmol), EDCI (181 mg, 0.94 mmol), HOBt (145 mg, 0.94 mmol) and DMAP (12 mg, 0.1 mmol) in pyridine (10 mL) was stirred at rt for 1 hr. The solvent was removed in vacuo, the mixture diluted with water, and extracted with EtOAc. The organic extract was dried (Na$_2$SO$_4$), filtered and concentrated. The residue was washed with a small amount of EtOAc and filtered to afford 36 mg of the title compound. $^1$H NMR (400 MHz, CDCl$_3$) δ ppm 0.97 (t, J=7.36 Hz, 3 H) 1.38-1.48 (m, 2 H) 1.65 (s, 9 H) 1.68-1.78 (m, 2 H) 2.83 (dd, J=7.67 Hz, 2 H) 3.83 (s, 3 H) 3.89 (s, 3 H) 6.93-6.94 (m, 1 H) 6.95 (d, J=3.07 Hz, 1 H) 7.73 (d, J=2.76 Hz, 1 H) 7.93 (s, 1 H); MS (ESI) m/z 377 (M+H)$^+$.

Example 42

N-[(5Z)-4-butyl-2-tert-butylisothiazol-5(2H)-ylidene]-5-fluoro-2-methoxybenzamide The title compound was prepared using the procedure as described in Example 41 substituting 5-fluoro-2-methoxybenzoic acid for 2,5-dimethoxybenzoic acid. $^1$H NMR (400 MHz, CDCl$_3$) δ ppm 0.98 (t, J=7.36 Hz, 3 H) 1.37-1.48 (m, 2 H) 1.62-1.67 (s, 9 H) 1.67-1.77 (m, 2 H) 2.82 (dd, J=7.67 Hz, 2 H) 3.92 (s, 3 H) 6.92 (dd, J=8.90, 4.30 Hz, 1 H) 7.05-7.11 (m, 1 H) 7.88 (dd, J=9.51, 3.38 Hz, 1 H) 7.94 (s, 1 H); MS (DCI/NH$_4$$^+$) m/z 365 (M+H)$^+$.

Example 43

N-[(5Z)-4-butyl-2-tert-butylisothiazol-5(2H)-ylidene]-2-methoxy-5-methylbenzamide The title compound was prepared using the procedure as described in Example 41 substituting 2-methoxy-5-methylbenzoic acid for 2,5-dimethoxybenzoic acid. $^1$H NMR (400 MHz, CDCl$_3$) δ ppm 0.98 (t, J=7.36 Hz, 3 H) 1.38-1.50 (m, 2 H) 1.65 (s, 9 H) 1.67-1.79 (m, 2 H) 2.34 (s, 3 H) 2.84 (dd, J=7.98, 7.36 Hz, 2 H) 3.90 (s, 3 H) 6.88 (d, J=8.59 Hz, 1 H) 7.18 (dd, J=9.21, 2.46 Hz, 1 H) 7.92 (s, 1 H) 7.93 (d, J=2.45 Hz, 1 H); MS (DCI/NH$_4$$^+$) m/z 361 (M+H)$^+$.

Example 44

N-[(5Z)-2-tert-butyl-4-[hydroxy(thien-2-yl)methyl]isothiazol-5(2H)-ylidene]-5-chloro-2-methoxybenzamide To 2-bromothiophene (444 mg, 2.72 mmol) in THF (10 mL) was added dropwise n-butyllithium (2.5M) (1.09 mL, 2.72 mmol) at −78° C. The reaction was stirred at −78° C. for 15 min and treated with Example 21A (240 mg, 0.68 mmol) in THF (1 mL). The reaction was stirred at −78° C. for 1 hr, quenched with saturated aqueous NH$_4$Cl and extracted with EtOAc (2×). The organics were combined, dried (MgSO$_4$), filtered and solvent evaporated. The residue was purified by column chromatography using an Analogix® Intelliflash280™ (SiO$_2$, 0-75% Hexane in ethyl acetate) to afford 93 mg (31%) of the title compound. $^1$H NMR (400 MHz, CDCl$_3$) δ ppm 1.62 (s, 9 H) 3.94 (s, 3 H) 6.36 (s, 1 H) 6.94 (d, J=8.90 Hz, 1H) 7.01 (dd, J=4.91, 3.38 Hz, 1 H) 7.09 (d, J=3.38 Hz, 1 H) 7.30 (dd, J=4.91, 1.23 Hz, 1 H) 7.38 (dd, J=8.90, 2.45 Hz, 1 H) 7.78 (s, 1 H) 8.07 (d, J=2.76 Hz, 1 H); MS (DCI/NH$_4$$^+$) m/z 437 (M+H)$^+$.

Example 45

Methyl 4-{(5Z)-2-tert-butyl-5-[(5-chloro-2-methoxybenzoyl)imino]-2,5-dihydroisothiazol-4-yl}butanoate Example 45A Methyl 6-(tert-butylimino)hexanoate The title compound was prepared using the procedure as described in Example 1A substituting methyl 6-oxohexanoate for hexanal.

Example 45B

Methyl 4-{(5Z)-2-tert-butyl-5-[(5-chloro-2-methoxybenzoyl)imino]-2,5-dihydroisothiazol-4-yl}butanoate The title compound was prepared using the procedure as described in Example 1D substituting Example 45A for Example 1A. $^1$H NMR (400 MHz, CDCl$_3$) δ ppm 1.66 (s, 9 H) 2.01-2.15 (m, 2 H) 2.43 (t, J=7.36 Hz, 2 H) 2.87 (t, J=7.98, 7.36 Hz, 2 H) 3.68 (s, 3 H) 3.92 (s, 3 H) 6.92 (d, J=8.90 Hz, 1 H) 7.34 (dd, J=8.90, 2.76 Hz, 1 H) 7.98 (s, 1 H); MS (DCI/NH$_4$$^+$) m/z 425 (M+H)$^+$.

Example 46

Methyl 4-{(5Z)-2-tert-butyl-5-[(5-cyano-2-methoxybenzoyl)imino]-2,5-dihydroisothiazol-4-yl}butanoate The title compound was prepared using the procedure as described in Example 1D substituting Example 45A for Example 1A, and Example 26D for Example 1C. $^1$H NMR (400 MHz, CDCl$_3$) δ ppm 1.67 (s, 9 H) 2.04-2.14 (m, 2 H) 2.43 (t, J=7.36 Hz, 2 H) 2.87 (dd, J=7.36 Hz, 2 H) 3.69 (s, 3 H) 3.99 (s, 3 H) 7.04 (d, J=8.59 Hz, 1 H) 7.68 (dd, J=8.90, 2.45 Hz, 1 H) 8.01 (s, 1 H) 8.47 (d, J=2.46 Hz, 1 H); MS (DCI/NH$_4$$^+$) m/z 416 (M+H)$^+$.

Example 47

N-[(5Z)-4-butyl-2-tert-butylisothiazol-5(2H)-ylidene]-5-chloro-2-(2,2,2-trifluoroethoxy)benzamide Example 47A N-[(5Z)-4-butyl-2-tert-butylisothiazol-5(2H)-ylidene]-5-chloro-2-fluorobenzamide The title compound was prepared using the procedure as described in Example 41 substituting 5-chloro-2-fluorobenzoic acid for 2,5-dimethoxybenzoic acid. MS (DCI/NH$_4$$^+$) m/z 369 (M+H)$^+$.

Example 47B

N-[(5Z)-4-butyl-2-tert-butylisothiazol-5(2H)-ylidene]-5-chloro-2-(2,2,2-trifluoroethoxy)benzamide A mixture of the product from Example 47A (101 mg, 0.27 mmol), trifluoroethanol (33 mg, 0.32 mmol) and potassium tert-butoxide (2 M) (340 µL, 0.68 mmol) in THF (10 mL) was stirred at rt for 12 hrs. The mixture was diluted with water, and extracted with EtOAc. The organic extract was dried ($Na_2SO_4$), filtered and concentrated. The residue was purified by reverse phase preparative HPLC on a Waters Symmetry C8 column (25 mm×100 mm, 7 µm particle size) using a gradient of 10% to 100% acetonitrile:0.1% aqueous trifluoroacetic acid over 8 minutes (10 minutes run time) at a flow rate of 40 mL/minute to afford 34 mg (28%) of the title compound. $^1$H NMR (400 MHz, $CDCl_3$) δ ppm 0.97 (t, J=7.36 Hz, 3 H) 1.37-1.48 (m, 2 H) 1.65-1.75 (m, 2 H) 1.68 (s, 9 H) 4.50 (q, J=8.59 Hz, 2 H) 7.05 (d, J=8.59 Hz, 1 H) 7.34 (dd, J=8.90, 2.76 Hz, 1 H) 7.97 (s, 1 H) 8.11 (d, J=2.76 Hz, 1 H); MS (DCI/$NH_4^+$) m/z 449 (M+H)$^+$.

Example 48

N-[(5Z)-4-butyl-2-tert-butylisothiazol-5(2H)-ylidene]-2-methoxy-5-(methylsulfonyl)benzamide The title compound was prepared using the procedure as described in Example 41 substituting 2-methoxy-5-(methylsulfonyl)benzoic acid for 2,5-dimethoxybenzoic acid. $^1$H NMR (400 MHz, $CDCl_3$) δ ppm 0.98 (t, J=7.36 Hz, 3 H) 1.37-1.49 (m, 2 H) 1.67 (s, 9 H) 1.68-1.77 (m, 2 H) 2.83 (dd, J=7.67 Hz, 2 H) 3.06 (s, 3 H) 4.01 (s, 3 H) 7.10 (d, J=8.59 Hz, 1 H) 7.97 (dd, J=8.59, 2.46 Hz, 1 H) 7.96 (s, 1 H) 8.65 (d, J=2.46 Hz, 1 H); MS (DCI/$NH_4^+$) m/z 425 (M+H)$^+$.

Example 49

N-[(5Z)-2-tert-butyl-4-[hydroxy(1,3-thiazol-4-yl)methyl]isothiazol-5(2H)-ylidene]-5-chloro-2-methoxybenzamide The title compound was prepared using the procedure as described in Example 44 substituting 4-bromothiazole for 2-bromothiophene. $^1$H NMR (500 MHz, $CDCl_3$) δ ppm 1.66 (s, 9 H) 3.98 (s, 3 H) 6.38 (s, 1 H) 6.96 (d, J=8.85 Hz, 1 H) 7.34 (d, J=3.36 Hz, 1 H) 7.40 (dd, J=8.85, 2.75 Hz, 1 H) 7.77 (d, J=3.05 Hz, 1 H) 8.08 (d, J=2.75 Hz, 1 H) 8.28 (s, 1 H); MS (DCI/$NH_4^+$) m/z 438 (M+H)$^+$.

Example 50

N-[(5Z)-2-tert-butyl-4-(2-furylmethyl)isothiazol-5(2H)-ylidene]-5-chloro-2-methoxybenzamide

Example 50A 3-(furan-2-yl)propan-1-ol

To 3-(furan-2-yl)propanoic acid (1.4 g, 10 mmol) in THF (50 mL) was added dropwise borane (1M) (20 mL, 20 mmol). The mixture was stirred at rt for 12 hrs, quenched with MeOH, and the mixture was concentrated. The resulting residue was purified by column chromatography using an Analogix® Intelliflash280™ ($SiO_2$, 0-50% Hexane in ethyl acetate) to afford 1.0 g (79%) of the title compound. $^1$H NMR (500 MHz, $CDCl_3$) δ ppm 1.87-1.94 (m, 2 H) 2.74 (t, J=7.32 Hz, 2 H) 3.69 (t, J=6.10 Hz, 2 H) 6.28 (dd, J=3.05, 1.83 Hz, 1 H) 7.30 (d, J=0.92 Hz, 1 H).

Example 50B 3-(furan-2-yl)propanal

The product from Example 50A (2.0 g, 15.9 mmol) in $CH_2Cl_2$ (50 mL) was treated with Dess-Martin periodinane (8.1 g, 19.2 mmol) in portions. The mixture was stirred at rt for 2 hrs, quenched with saturated $NaS_2O_3$, and the mixture was extracted with $CH_2Cl_2$. The $CH_2Cl_2$ layer was washed with saturated $NaHCO_3$, dried over $MgSO_4$, filtered and concentrated. The resulting residue was purified by column chromatography using an Analogix® Intelliflash280™ ($SiO_2$, 0-50% Hexane in ethyl acetate) to afford 1.44 g (73%) of the title compound. $^1$H NMR (500 MHz, $CDCl_3$) δ ppm 2.80 (t, J=8.24, 6.41 Hz, 2 H) 2.98 (t, J=7.32 Hz, 2 H) 6.02 (d, J=3.97 Hz, 1 H) 6.19-6.36 (m, 1 H) 7.28-7.33 (m, 1 H) 9.82 (s, 1 H).

Example 50C

N-(3-(furan-2-yl)propylidene)-2-methylpropan-2-amine

The title compound was prepared using the procedure as described in Example 1A substituting Example 50B for hexanal.

Example 50D

Ethyl [(5Z)-2-tert-butyl-4-(furan-2-ylmethyl)isothiazol-5(2H)-ylidene]carbamate

The title compound was prepared using the procedure as described in Example 1D substituting Example 50C for Example 1A and o-ethyl carbonisothiocyanatidate for Example 1C. $^1$H NMR (400 MHz, $CDCl_3$) δ ppm 1.37 (t, J=7.36 Hz, 3 H) 1.58 (s, 9 H) 4.04 (s, 2 H) 4.29 (q, J=7.06 Hz, 2 H) 6.11 (d, J=3.38 Hz, 1 H) 6.31 (dd, J=3.07, 1.84 Hz, 1 H) 7.34 (d, J=1.84 Hz, 1 H) 7.76 (s, 1 H); MS (DCI/$NH_4^+$) m/z 309 (M+H)$^+$.

Example 50E 2-tert-butyl-4-(furan-2-ylmethyl)isothiazol-5(2H)-imine

The product from Example 50D (300 mg, 0.97 mmol) in chloroform (20 mL) was treated with TMSI (389 mg, 1.95 mmol). The reaction mixture was stirred at 65° C. for 12 hrs, diluted with $CH_2Cl_2$, the organic was washed with $H_2O$, dried over $MgSO_4$, filtered and concentrated to afford the title compound. MS (DCI/$NH_4^+$) m/z 237 (M+H)$^+$.

Example 50F

N-[(5Z)-2-tert-butyl-4-(2-furylmethyl)isothiazol-5(2H)-ylidene]-5-chloro-2-methoxybenzamide The title compound was prepared using the procedure as described in Example 41 substituting Example 51E for Example 110B and 5-chloro-2-methoxybenzoic acid for 2,5-dimethoxybenzoic acid. $^1$H NMR (400 MHz, $CDCl_3$) δ ppm 1.64 (s, 9 H) 3.92 (s, 3 H) 4.21 (s, 2 H) 6.17 (d, J=2.45 Hz, 1 H) 6.34 (dd, J=3.07, 1.84 Hz, 1 H) 6.92 (d, J=8.90 Hz, 1 H)

7.34 (dd, J=8.90, 2.76 Hz, 1 H) 7.36 (d, J=1.84 Hz, 1 H) 7.95 (s, 1 H) 8.14 (d, J=2.76 Hz, 1H); MS (DCI/NH$_4^+$) m/z 405 (M+H)$^+$.

Example 51

N-[(5Z)-2-tert-butyl-4-(2-furylmethyl)isothiazol-5 (2H)-ylidene]-5-cyano-2-methoxybenzamide The title compound was prepared using the procedure as described in Example 41 substituting Example 51E for Example 110B and Example 26B for 2,5-dimethoxybenzoic acid. $^1$H NMR (400 MHz, CDCl$_3$) δ ppm 1.65 (s, 9 H) 3.99 (s, 3 H) 4.21 (s, 2 H) 6.17 (d, J=3.07 Hz, 1 H) 6.35 (dd, J=3.07, 1.84 Hz, 1 H) 7.04 (d, J=8.59 Hz, 1 H) 7.37 (d, J=1.84 Hz, 1 H) 7.68 (dd, J=8.59, 2.15 Hz, 1 H) 7.98 (s, 1 H) 8.48 (d, J=2.15 Hz, 1 H); MS (DCI/NH$_4^+$) m/z 396 (M+H)$^+$.

Example 52

N-[(5Z)-2-tert-butyl-4-(1,3-thiazol-4-ylmethyl) isothiazol-5(2H)-ylidene]-5-chloro-2-methoxybenzamide

Example 52A

O-{[(5Z)-2-tert-butyl-5-{[(5-chloro-2-methoxyphenyl)carbonyl]imino}-2,5-dihydroisothiazol-4-yl](1,3-thiazol-4-yl)methyl}O-phenyl thiocarbonate The title compound was prepared using the procedure as described in Example 36A substituting Example 49 for Example 33. MS (DCI/NH$_4^+$) m/z 574 (M+H)$^+$.

Example 52B

N-[(5Z)-2-tert-butyl-4-(1,3-thiazol-4-ylmethyl) isothiazol-5(2H)-ylidene]-5-chloro-2-methoxybenzamide The title compound was prepared using the procedure as described in Example 36B substituting Example 52A for Example 36A. $^1$H NMR (500 MHz, CDCl$_3$) δ ppm 1.65 (s, 9H) 3.93 (s, 3 H) 4.58 (s, 2 H) 6.93 (d, J=8.85 Hz, 1 H) 7.24 (d, J=3.36 Hz, 1 H) 7.36 (dd, J=8.85, 3.05 Hz, 1 H) 7.71 (d, J=3.36 Hz, 1 H) 8.19 (s, 1 H) 8.23 (d, J=2.75 Hz, 1 H); MS (DCI/NH$_4^+$) m/z 422 (M+H)$^+$.

Example 53

N-[(5Z)-2-tert-butyl-4-(thien-2-ylmethyl)isothiazol-5 (2H)-ylidene]-5-cyano-2-methoxybenzamide

Example 53A 3-(thiophen-2-yl)propan-1-ol

The title compound was prepared using the procedure as described in Example 50A substituting 3-(thiophen-2-yl)propanoic acid for 3-(furan-2-yl)propanoic acid. MS (DCI/NH$_4^+$) m/z 143 (M+H)$^+$.

Example 53B 3-(thiophen-2-yl)propanal

The title compound was prepared using the procedure as described in Example 50B substituting Example 53A for Example 50A.

Example 53C 2-methyl-N-(3-(thiophen-2-yl)propylidene)propan-2-amine

The title compound was prepared using the procedure as described in Example 1A substituting Example 53B for hexanal.

Example 53D

Ethyl [(5Z)-2-tert-butyl-4-(thiophen-2-ylmethyl) isothiazol-5(2H)-ylidene]carbamate The title compound was prepared using the procedure as described in Example 1D substituting Example 53C for Example 1A and o-ethyl carbonisothiocyanatidate for Example 1C.MS (DCI/NH$_4^+$) m/z 325 (M+H)$^+$.

Example 53E 2-tert-butyl-4-(thiophen-2-ylmethyl)isothiazol-5 (2H)-imine

The title compound was prepared using the procedure as described in Example 50E substituting Example 53D for Example 50D. MS (DCI/NH$_4^+$) m/z 253 (M+H)$^+$.

Example 53F

N-[(5Z)-2-tert-butyl-4-(thien-2-ylmethyl)isothiazol-5 (2H)-ylidene]-5-cyano-2-methoxybenzamide The title compound was prepared using the procedure as described in Example 41 substituting Example 53D for Example 110B and Example 26B for 2,5-dimethoxybenzoic acid. $^1$H NMR (500 MHz, CDCl$_3$) δ ppm 1.64 (s, 9 H) 4.00 (s, 3 H) 4.39 (s, 2 H) 6.95-6.99 (m, 2 H) 7.05 (d, J=8.85 Hz, 1 H) 7.18 (dd, J=4.58, 2.14 Hz, 1 H) 7.69 (dd, J=8.54, 2.14 Hz, 1 H) 7.95 (s, 1 H) 8.52 (d, J=2.14 Hz, 1 H); MS (DCI/NH$_4^+$) m/z 412 (M+H)$^+$.

Example 54

N-[(5Z)-2-tert-butyl-4-(thien-2-ylmethyl)isothiazol-5 (2H)-ylidene]-5-chloro-2-methoxybenzamide The title compound was prepared using the procedure as described in Example 41 substituting Example 53E for Example 110B and 5-chloro-2-methoxybenzoic acid for 2,5-dimethoxybenzoic acid. $^1$H NMR (400 MHz, CDCl$_3$) δ ppm 1.62 (s, 9 H) 3.93 (s, 3 H) 4.39 (brs, 2 H) 6.90-6.98 (m, 3 H)

7.17 (dd, J=4.60, 2.15 Hz, 1 H) 7.35 (dd, J=8.90, 2.76 Hz, 1 H) 7.91 (s, 1 H) 8.18 (d, J=2.76 Hz, 1 H); MS (DCI/NH$_4^+$) m/z 421 (M+H)$^+$.

Example 55

5-amino-N-[(5Z)-4-butyl-2-tert-butylisothiazol-5(2H)-ylidene]-2-methoxybenzamide

Example 55A

Tert-butyl (3-{[(5Z)-4-butyl-2-tert-butylisothiazol-5(2H)-ylidene]carbamoyl}-4-methoxyphenyl)carbamate The title compound was prepared from Example 110B using the procedure as described in Example 41 substituting 5-(tert-butoxycarbonylamino)-2-methoxybenzoic acid for 2,5-dimethoxybenzoic acid. MS (DCI/NH$_4^+$) m/z 462 (M+H)$^+$.

Example 55B 5-amino-N-[(5Z)-4-butyl-2-tert-butylisothiazol-5(2H)-ylidene]-2-methoxybenzamide The product from Example 55A (71 mg, 0.15 mmol) was treated with TFA (1 mL) at rt for 10 min, solvent removed and the mixture treated with saturated aqueous NaHCO$_3$, and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 51 mg (92%) of the title compound. $^1$H NMR (500 MHz, CDCl$_3$) δ ppm 0.97 (t, J=7.32 Hz, 3 H) 1.36-1.47 (m, 2 H) 1.64 (s, 9 H) 1.67-1.77 (m, 2 H) 2.83 (dd, J=7.93 Hz, 2 H) 3.49 (brs, 2 H) 3.87 (s, 3 H) 6.76 (dd, J=8.54, 3.05 Hz, 1 H) 6.83 (d, J=8.54 Hz, 1 H) 7.54 (d, J=2.75 Hz, 1 H) 7.90 (s, 1 H); MS (DCI/NH$_4^+$) m/z 362 (M+H)$^+$.

Example 56

N-[(5Z)-4-butyl-2-tert-butylisothiazol-5(2H)-ylidene]-5-formyl-2-methoxybenzamide

Example 56A

N-[(5Z)-4-butyl-2-tert-butylisothiazol-5(2H)-ylidene]-5-formyl-2-hydroxybenzamide The title compound was prepared from Example 110B using the procedure as described in Example 41 substituting 5-formyl-2-hydroxybenzoic acid for 2,5-dimethoxybenzoic acid. MS (DCI/NH$_4^+$) m/z 361 (M+H)$^+$.

Example 56B

N-[(5Z)-4-butyl-2-tert-butylisothiazol-5(2H)-ylidene]-5-formyl-2-methoxybenzamide A mixture of Example 56A (350 mg, 0.97 mmol) and cesium carbonate (375 mg, 1.94 mmol) in DMF (20 mL) was treated with iodomethane (165 mg, 1.17 mmol). The mixture was stirred at rt for 2 hrs, diluted with H$_2$O and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 246 mg (68%) of the title compound. $^1$H NMR (400 MHz, CDCl$_3$) δ ppm 0.99 (t, J=7.36 Hz, 3 H) 1.36-1.51 (m, 2 H) 1.67 (s, 9 H) 1.68-1.78 (m, 2 H) 2.85 (dd, J=7.67 Hz, 2 H) 4.02 (s, 3 H) 7.11 (d, J=8.59 Hz, 1 H) 7.97 (dd, J=8.59, 2.15 Hz, 1 H) 7.96 (s, 1 H) 8.64 (d, J=2.15 Hz, 1 H) 9.96 (s, 1 H); MS (DCI/NH$_4^+$) m/z 375 (M+H)$^+$.

Example 57

N-[(5Z)-4-butyl-2-tert-butylisothiazol-5(2H)-ylidene]-2-methoxy-5-[(methoxyimino)methyl]benzamide The title compound was prepared using the procedure as described in Example 15B substituting Example 56B for Example 15A. $^1$H NMR (500 MHz, CDCl$_3$) δ ppm 0.99 (t, J=7.63 Hz, 3 H) 1.39-1.49 (m, 2 H) 1.66 (s, 9 H) 1.68-1.79 (m, 2 H) 2.83 (dd, J=7.63 Hz, 2H) 3.95 (s, 3 H) 3.96 (s, 3 H) 6.99 (d, J=8.85 Hz, 1 H) 7.72 (dd, J=8.54, 2.14 Hz, 1 H) 7.94 (s, 1 H) 8.07 (s, 1 H) 8.27 (d, J=2.14 Hz, 1 H); MS (DCI/NH$_4^+$) m/z 404 (M+H)$^+$.

Example 58

N-[(5Z)-4-butyl-2-tert-butylisothiazol-5(2H)-ylidene]-5-(formylamino)-2-methoxybenzamide The title compound was prepared using the procedure as described in Example 41 substituting Example 55B for Example 110B and formic acid for 2,5-dimethoxybenzoic acid. $^1$H NMR (400 MHz, CDCl$_3$) δ ppm 0.90-1.04 (m, 6 H) 1.34-1.47 (m, 4 H) 1.60-1.68 (m, 18 H) 1.65-1.77 (m, 4 H) 2.82 (t, J=7.98 Hz, 4 H) 3.89-3.96 (m, 6 H) 6.91-7.02 (m, 2 H) 7.09-7.16 (m, 1 H) 7.20-7.33 (m, 1 H) 7.86-8.01 (m, 4 H) 8.31-8.38 (m, 1 H) 8.52-8.60 (m, 1 H); MS (DCI/NH$_4^+$) m/z 390 (M+H)$^+$.

Example 59

N-[(5Z)-4-butyl-2-tert-butylisothiazol-5(2H)-ylidene]-5-[(hydroxyimino)methyl]-2-methoxybenzamide The title compound was prepared using the procedure as described in Example 15B substituting Example 56B for Example 15A and hydroxylamine hydrochloride for O-methylhydroxylamine hydrochloride. $^1$H NMR (400 MHz, CDCl$_3$) δ ppm 0.98 (t, J=7.36 Hz, 3 H) 1.38-1.48 (m, 2 H) 1.65 (s, 9 H) 1.67-1.77 (m, 2 H) 2.83 (dd, J=7.98 Hz, 2 H) 3.96 (s, 3 H) 7.00 (d, J=8.90 Hz, 1 H) 7.15 (s, 1 H) 7.69 (dd, J=8.59, 2.15 Hz, 1 H) 7.93 (s, 1 H) 8.14 (s, 1 H) 8.29 (d, J=2.15 Hz, 1 H); MS (DCI/NH$_4^+$) m/z 390 (M+H)$^+$.

Example 60

3-({[(5Z)-4-butyl-2-tert-butylisothiazol-5(2H)-ylidene]amino}carbonyl)-4-methoxybenzoic acid Aqueous sodium hydroxide (6M) (85 µL) was added dropwise to a stirred solution of urea hydrogen peroxide (223 mg, 2.4 mmol) and Example 56B (100 mg, 0.267 mmol) in MeOH (5 mL) at rt. The mixture was then heated at 65° C. for 2 hrs, acidified with HCl, and extracted with CH$_2$Cl$_2$/isopropanol (3:1). The organic layer was dried over MgSO$_4$, filtered and concentrated. The resulting residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford 26 mg (25%) of the title compound. $^1$H NMR (400 MHz, CDCl$_3$) δ ppm 0.98 (t, J=7.06 Hz, 3 H) 1.40-1.51 (m, 2 H) 1.63-1.75 (m, 2 H) 1.82 (s, 9 H) 2.90 (dd, J=8.29, 7.36 Hz, 2 H) 4.17 (s, 3 H) 7.16 (d, J=8.90 Hz, 1 H) 8.29 (dd, J=9.21, 2.15 Hz, 1 H) 8.69 (d, J=2.15 Hz, 3 H) 8.71 (s, 1 H); MS (DCI/NH$_4^+$) m/z 391 (M+H)$^+$.

Example 61

N-[(5Z)-4-butyl-2-tert-butylisothiazol-5(2H)-ylidene]-5-iodo-2-methoxybenzamide

The title compound was prepared from Example 110B using the procedure as described in Example 41 substituting 5-iodo-2-methoxybenzoic acid for 2,5-dimethoxybenzoic acid. $^1$H NMR (400 MHz, CDCl$_3$) δ ppm 0.99 (t, J=7.06 Hz, 3 H) 1.38-1.50 (m, 2 H) 1.65 (s, 9 H) 1.67-1.77 (m, 2 H) 2.83 (dd, J=7.67 Hz, 2 H) 3.90 (s, 3 H) 6.75 (d, J=8.59 Hz, 1 H) 7.65 (dd, J=8.59, 2.15 Hz, 1 H) 7.94 (s, 1 H) 8.40 (d, J=2.45 Hz, 1 H); MS (DCI/NH$_4^+$) m/z 473 (M+H)$^+$.

Example 62

N-[(5Z)-4-butyl-2-tert-butylisothiazol-5(2H)-ylidene]-5-ethynyl-2-methoxybenzamide

Example 62A

N-[(5Z)-4-butyl-2-tert-butylisothiazol-5(2H)-ylidene]-2-methoxy-5-[(trimethylsilyl)ethynyl]benzamide A mixture of the product from Example 61 (330 mg, 0.7 mmol), ethynyltrimethylsilane (206 mg, 2.1 mmol), PdCl$_2$(PPh$_3$)$_2$ (49 mg, 0.07 mmol), triethylamine (201 mg, 2.1 mmol) and CuI (33 mg, 0.18 mmol) in DMF (5 mL) was heated at 50° C. for 16 hrs, diluted with H$_2$O and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 300 mg (97%) of the title compound. MS (DCI/NH$_4^+$) m/z 443 (M+H)$^+$.

Example 62B

N-[(5Z)-4-butyl-2-tert-butylisothiazol-5(2H)-ylidene]-5-ethynyl-2-methoxybenzamide The product from Example 62A (300 mg, 0.68 mmol) in THF (10 mL) was treated with TBAF (1M) (1.7 mL, 1.7 mmol), stirred at rt for 1 hr, diluted with H$_2$O and extracted with EtOAc (2×). The organic layer was dried over MgSO$_4$, filtered and concentrated. The residue was purified by column chromatography using an Analogix® Intelliflash280™ (SiO$_2$, 0-50% Hexane in ethyl acetate) to afford 183 mg (73%) of the title compound. $^1$H NMR (400 MHz, CDCl$_3$) δ ppm 0.98 (t, J=7.36 Hz, 3 H) 1.36-1.50 (m, 2 H) 1.65 (s, 9 H) 1.67-1.77 (m, 2 H) 2.83 (dd, J=7.98 Hz, 2 H) 2.99 (s, 1 H) 3.94 (s, 3 H) 6.93 (d, J=8.59 Hz, 1 H) 7.52 (dd, J=8.59, 2.15 Hz, 1 H) 7.93 (s, 1 H) 8.28 (d, J=2.15 Hz, 1 H); MS (DCI/NH$_4^+$) m/z 371 (M+H)$^+$.

Example 63

N-[(5Z)-4-butyl-2-tert-butylisothiazol-5(2H)-ylidene]-2-methoxy-5-(trifluoromethoxy)benzamide The title compound was prepared from Example 110B using the procedure as described in Example 41 substituting 2-methoxy-5-(trifluoromethoxy)benzoic acid for 2,5-dimethoxybenzoic acid. $^1$H NMR (400 MHz, CDCl$_3$) δ ppm 0.98 (t, J=7.67 Hz, 3 H) 1.37-1.48 (m, 2 H) 1.65 (s, 9 H) 1.67-1.78 (m, 2 H) 2.82 (t, J=7.67 Hz, 2 H) 3.93 (s, 3 H) 6.96 (d, J=9.21 Hz, 1 H) 7.23 (d, J=3.38 Hz, 1 H) 7.94 (s, 1 H) 8.03 (d, J=3.07 Hz, 1 H); MS (DCI/NH$_4^+$) m/z 431 (M+H)$^+$.

Example 64

5-acetyl-N-[(5Z)-4-butyl-2-tert-butylisothiazol-5(2H)-ylidene]-2-methoxybenzamide

Example 64A 5-acetyl-N-[(5Z)-4-butyl-2-tert-butylisothiazol-5(2H)-ylidene]-2-hydroxybenzamide The title compound was prepared from Example 110B using the procedure as described in Example 41 substituting 5-acetyl-2-hydroxybenzoic acid for 2,5-dimethoxybenzoic acid. MS (DCI/NH$_4^+$) m/z 375 (M+H)$^+$.

Example 64B 5-acetyl-N-[(5Z)-4-butyl-2-tert-butylisothiazol-5(2H)-ylidene]-2-methoxybenzamide The title compound was prepared using the procedure as described in Example 56 substituting Example 64A for Example 56A. $^1$H NMR (500 MHz, CDCl$_3$) δ ppm 0.99 (t, J=7.32 Hz, 3 H) 1.40-1.49 (m, 2 H) 1.66 (s, 9 H) 1.70-1.80 (m, 2 H) 2.61 (s, 3 H) 2.85 (t, J=7.63 Hz, 2 H) 4.00 (s, 3 H) 7.04 (d, J=8.85 Hz, 1 H) 7.96 (s, 1 H) 8.07 (dd, J=8.54, 2.44 Hz, 1 H) 8.75 (d, J=2.44 Hz, 1 H); MS (DCI/NH$_4^+$) m/z 389 (M+H)$^+$.

Example 65

N-[(5Z)-4-butyl-2-tert-butylisothiazol-5(2H)-ylidene]-5-(difluoromethyl)-2-methoxybenzamide The product from Example 56B (140 mg, 0.37 mmol) was dissolved in CH$_2$Cl$_2$ (4 mL), treated with DAST (121 mg, 0.75 mmol) and a drop of MeOH to catalyze the reaction. The mixture was stirred at rt for 12 hrs, quenched with saturated aqueous NaHCO$_3$ and extracted with CH$_2$Cl$_2$ (2×). The combined organic layers were dried over MgSO$_4$, filtered and concentrated. The residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford the title compound. $^1$H NMR (500 MHz, CDCl$_3$) δ ppm 0.98 (t, J=7.63 Hz, 3 H) 1.44 (m, 2 H) 1.66 (s, 9 H) 1.73 (m, 2 H) 2.84 (t, J=7.63 Hz, 2 H) 3.96 (s, 3 H) 6.66 (t, J=56.76

Hz, 1 H) 7.05 (d, J=8.54 Hz, 1 H) 7.57 (d, J=9.76 Hz, 1 H) 7.96 (s, 1 H) 8.29 (s, 1 H); MS (DCI/NH$_4$$^+$) m/z 397 (M+H)$^+$.

Example 66

N-[(5Z)-4-butyl-2-tert-butylisothiazol-5(2H)-ylidene]-5-(fluoromethyl)-2-methoxybenzamide Example 66A N-[(5Z)-4-butyl-2-tert-butylisothiazol-5(2H)-ylidene]-5-(hydroxymethyl)-2-methoxybenzamide The title compound was prepared using the procedure as described in Example 28A substituting Example 56B for Example 21A. MS (DCI/NH$_4$$^+$) m/z 377 (M+H)$^+$.

Example 66B

N-[(5Z)-4-butyl-2-tert-butylisothiazol-5(2H)-ylidene]-5-(fluoromethyl)-2-methoxybenzamide The product from Example 66A (120 mg, 0.32 mmol) in CH$_2$Cl$_2$ (10 mL) at −78° C. was treated with bis(methoxyethyl)amino sulfurtrifluoride (106 mg, 0.48 mmol). The reaction was kept at −78° C. for 1 hr, quenched with saturated aqueous NaHCO$_3$ and extracted with CH$_2$Cl$_2$ (2×). The combined organic layers were dried over MgSO$_4$, filtered and concentrated. The residue was purified by column chromatography using an Analogix®Intelliflash280™ (SiO$_2$, 0-50% Hexane in ethyl acetate) to afford 56 mg (46%) of the title compound. $^1$H NMR (500 MHz, CDCl$_3$) δ ppm 0.99 (t, J=7.32 Hz, 3 H) 1.38-1.48 (m, 2 H) 1.65 (s, 9 H) 1.68-1.76 (m, 2 H) 2.84 (dd, J=7.93 Hz, 2 H) 3.95 (s, 3 H) 5.31 (s, 1 H) 5.41 (s, 1 H) 7.01 (d, J=8.54 Hz, 1 H) 7.45 (dt, J=8.54, 2.14 Hz, 1 H) 7.93 (s, 1 H) 8.18 (t, J=2.14 Hz, 1 H); MS (DCI/NH$_4$$^+$) m/z 379 (M+H)$^+$.

Example 67

N-[(5Z)-2-tert-butyl-4-(tetrahydrofuran-2-ylmethyl)isothiazol-5(2H)-ylidene]-5-chloro-2-methoxybenzamide Example 67A 3-(tetrahydrofuran-2-yl)propanoic acid (E)-3-(Furan-2-yl)acrylic acid (10 g, 72.4 mmol) was treated with Pd/C (1 g) in MeOH (100 mL). The mixture was heated at 60° C. at 60 psi under H$_2$ for 12 hrs. After filtering off the catalyst, the filtrate was concentrated to afford 9.8 g (93%) of the title compound. $^1$H NMR (500 MHz, CDCl$_3$) δ ppm 1.42-1.56 (m, 1 H) 1.77-1.96 (m, 4 H) 1.93-2.07 (m, 1H) 2.41-2.56 (m, 2 H) 3.71-3.79 (m, 1 H) 3.82-3.94 (m, 2 H); MS (DCI/NH$_4$$^+$) m/z 145 (M+H)$^+$.

Example 67B 3-(tetrahydrofuran-2-yl)propan-1-ol

The title compound was prepared using the procedure as described in Example 50A substituting Example 67A for 3-(furan-2-yl)propanoic acid. $^1$H NMR (500 MHz, CDCl$_3$) δ ppm 1.41-1.52 (m, 1 H) 1.64-1.73 (m, 4 H) 1.83-1.93 (m, 2 H) 1.95-2.03 (m, 1 H) 3.37-3.44 (m, 1 H) 3.61-3.71 (m, 2 H) 3.71-3.78 (m, 1 H) 3.80-3.86 (m, 1 H) 3.85-3.94 (m, 1H).

Example 67C 3-(tetrahydrofuran-2-yl)propanal

The title compound was prepared using the procedure as described in Example 50B substituting Example 67B for Example 50A.

Example 67D 2-methyl-N-(3-(tetrahydrofuran-2-yl)propylidene)propan-2-amine

The title compound was prepared using the procedure as described in Example 1A substituting Example 67C for hexanal.

Example 67E

N-[(5Z)-2-tert-butyl-4-(tetrahydrofuran-2-ylmethyl)isothiazol-5(2H)-ylidene]-5-chloro-2-methoxybenzamide The title compound was prepared using the procedure as described in Example 1D substituting Example 67D for Example 1A. $^1$H NMR (400 MHz, CDCl$_3$) δ ppm 1.46-1.59 (m, 1 H) 1.81 (s, 9 H) 1.79-1.88 (m, 1 H) 1.88-2.02 (m, 1 H) 2.06-2.23 (m, 1 H) 2.98-3.15 (m, 1 H) 3.26-3.47 (m, 1 H) 3.68-3.85 (m, 2 H) 4.10 (s, 3 H) 4.13-4.20 (m, 1 H) 7.08 (d, J=8.90 Hz, 1 H) 7.62 (dd, J=8.90, 2.45 Hz, 1 H) 8.15 (d, J=2.76 Hz, 1 H) 9.17-9.29 (m, 1 H); MS (DCI/NH$_4$$^+$) m/z 409 (M+H)$^+$.

Example 68

N-[(5Z)-4-butyl-2-tert-butylisothiazol-5(2H)-ylidene]-5-[(1Z)-N-hydroxyethanimidoyl]-2-methoxybenzamide The title compound was prepared using the procedure as described in Example 15B substituting Example 64B for Example 15A and hydroxylamine hydrochloride for O-methylhydroxylamine hydrochloride. $^1$H NMR (400 MHz, CDCl$_3$) δ ppm 0.98 (t, J=7.36 Hz, 3 H) 1.37-1.50 (m, 2 H) 1.65 (s, 9 H) 1.68-1.80 (m, 2 H) 2.29 (s, 3 H) 2.84 (dd, J=7.67 Hz, 2 H) 3.95 (s, 3 H) 6.98 (d, J=8.59 Hz, 1 H) 7.75 (dd, J=8.90, 2.45 Hz, 1 H) 7.93 (s, 1 H) 8.39 (d, J=2.45 Hz, 1 H); MS (DCI/NH$_4$$^+$) m/z 404 (M+H)$^+$.

Example 69

N-[(5Z)-4-butyl-2-tert-butylisothiazol-5(2H)-ylidene]-5-(1,1-difluoroethyl)-2-methoxybenzamide The product from Example 64B (50 mg, 0.13 mmol) was treated with bis(methoxyethyl)amino sulfurtrifluoride (57 mg, 0.26 mmol). The reaction was heated at 85° C. for 16 hrs, quenched with saturated aqueous NaHCO$_3$ and extracted with CH$_2$Cl$_2$ (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 12.1 mg (23%) of the title compound. $^1$H NMR (400 MHz, CDCl$_3$) δ ppm 0.98 (t, J=7.06 Hz, 3 H) 1.39-1.51 (m, 2 H)

1.65-1.75 (m, 2 H) 1.80 (s, 9 H) 1.95 (t, J=18.10 Hz, 3 H) 2.92 (dd, J=7.98 Hz, 2 H) 4.14 (s, 3 H) 7.17 (d, J=8.90 Hz, 1 H) 7.80 (dd, J=8.90, 2.45 Hz, 1 H) 8.22 (d, J=2.45 Hz, 1 H) 8.79-8.83 (m, 1 H); MS (DCI/NH$_4^+$) m/z 389 (M+H)$^+$.

Example 70

N-[(5Z)-2-tert-butyl-4-(2-furylmethyl)isothiazol-5 (2H)-ylidene]-2-fluoro-3-(trifluoromethyl)benzamide The title compound was prepared using the procedure as described in Example 41 substituting Example 50E for Example 110B and 2-fluoro-3-(trifluoromethyl)benzoic acid for 2,5-dimethoxybenzoic acid. $^1$H NMR (400 MHz, CDCl$_3$) δ ppm 1.65 (s, 9 H) 4.22 (s, 2 H) 6.17 (d, J=3.38 Hz, 1 H) 6.31-6.35 (m, 1 H) 7.25 (s, 1 H) 7.30 (t, J=7.67 Hz, 1 H) 7.69 (td, J=6.14, 1.23 Hz, 1 H) 8.00 (s, 1 H) 8.44 (td, J=7.98, 1.53 Hz, 1 H); MS (DCI/NH$_4^+$) m/z 427 (M+H)$^+$.

Example 71

N-[(5Z)-2-tert-butyl-4-(2-furylmethyl)isothiazol-5 (2H)-ylidene]-2-methoxy-5-(trifluoromethyl)benzamide The title compound was prepared using the procedure as described in Example 41 substituting Example 50E for Example 110B and 2-methoxy-5-(trifluoromethyl)benzoic acid for 2,5-dimethoxybenzoic acid. $^1$H NMR (400 MHz, CDCl$_3$) δ ppm 1.64 (s, 9 H) 3.98 (s, 3 H) 4.21 (s, 2 H) 6.18 (dd, J=3.07, 0.92 Hz, 1 H) 6.34 (dd, J=3.07, 1.84 Hz, 1 H) 7.06 (d, J=8.59 Hz, 1 H) 7.35-7.37 (m, 1 H) 7.65 (dd, J=8.90, 2.46 Hz, 1 H) 7.96 (s, 1 H) 8.43 (d, J=2.15 Hz, 1 H); MS (DCI/NH$_4^+$) m/z 439 (M+H)$^+$.

Example 72

N-[(5Z)-2-tert-butyl-4-(isopropoxymethyl)isothiazol-5(2H)-ylidene]-5-chloro-2-methoxybenzamide The product from Example 28A (50 mg, 0.14 mmol) in dioxane (5 mL) was treated with NaH (60%) (7 mg, 0.17 mmol) stirred at rt for 10 min and treated with isopropyl methanesulfonate (78 mg, 0.56 mmol). The reaction was heated at 85° C. for 12 hrs, quenched with H$_2$O, the mixture was extracted with EtOAc (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 5.2 mg (9%) of the title compound. $^1$H NMR (400 MHz, CDCl$_3$) δ ppm 1.22 (d, J=6.14 Hz, 6 H) 1.81 (s, 9 H) 3.75-3.83 (m, 1 H) 4.12 (s, 3 H) 4.92 (s, 2 H) 7.10 (d, J=9.21 Hz, 1 H) 7.63 (dd, J=9.21, 2.76 Hz, 1 H) 8.18 (d, J=2.45 Hz, 1 H) 9.28 (s, 1 H); MS (DCI/NH$_4^+$) m/z 397 (M+H)$^+$.

Example 73

N-[(5Z)-4-butyl-2-tert-butylisothiazol-5(2H)-ylidene]-2-fluoro-3-(trifluoromethyl)benzamide The title compound was prepared using the procedure as described in Example 41 substituting 2-fluoro-3-(trifluoromethyl)benzoic acid for 2,5-dimethoxybenzoic acid. $^1$H NMR (500 MHz, CDCl$_3$) δ ppm 0.98 (t, J=7.32 Hz, 3 H) 1.38-1.47 (m, 2 H) 1.67 (s, 9 H) 1.68-1.76 (m, 2 H) 2.84 (dd, J=7.63 Hz, 2 H) 7.30 (t, J=7.63 Hz, 1 H) 7.69 (td, J=7.63, 1.53 Hz, 1 H) 7.99 (s, 1 H) 8.43 (td, J=8.24, 1.53 Hz, 1 H); MS (DCI/NH$_4^+$) m/z 403 (M+H)$^+$.

Example 74

Methyl 3-({[(5Z)-4-butyl-2-tert-butylisothiazol-5 (2H)-ylidene]amino}carbonyl)-4-methoxybenzoate The product from Example 61 (199 mg, 0.42 mmol) in MeOH (5 mL) was added to PdCl$_2$(dppf)CH$_2$Cl$_2$ (Heraeus) (15.4 mg, 0.02 mmol) and Et$_3$N (117 μL, 0.84 mmol) in a 20 mL pressure bottle. The mixture was pressurized with CO (60 psi), and stirred 16 hr at 100° C. The solvent was removed and the resulting residue was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to afford 15 mg (9%) of the title compound. $^1$H NMR (500 MHz, CDCl$_3$) δ ppm 1.00 (t, J=7.32 Hz, 3 H) 1.40-1.49 (m, 2H) 1.66 (s, 9 H) 1.70-1.79 (m, 2 H) 2.85 (t, J=7.63 Hz, 2 H) 3.89 (s, 3 H) 3.99 (s, 3 H) 7.01 (d, J=8.85 Hz, 1 H) 7.95 (s, 1 H) 8.09 (dd, J=8.54, 2.14 Hz, 1 H) 8.80 (d, J=2.14 Hz, 1 H); MS (DCI/NH$_4^+$) m/z 405 (M+H)$^+$.

Example 75

N-[(5Z)-2-tert-butyl-4-(4-oxopentyl)isothiazol-5 (2H)-ylidene]-5-chloro-2-methoxybenzamide Example 75A 6-oxoheptanal The title compound was prepared using the procedure as described in Example 21A substituting 1-methylcyclohex-1-ene for Example 6B.

Example 75B 7-(tert-butylimino)heptan-2-one

The title compound was prepared using the procedure as described in Example 1A substituting Example 75A for hexanal.

Example 75C

Ethyl [(5Z)-2-tert-butyl-4-(4-oxopentyl)isothiazol-5 (2H)-ylidene]carbamate

The title compound was prepared using the procedure as described in Example 1D substituting Example 75B for Example 1A and o-ethyl carbonisothiocyanatidate for Example 1C. MS (DCI/NH$_4^+$) m/z 313 (M+H)$^+$.

Example 75D 5-(2-tert-butyl-5-imino-2,5-dihydroisothiazol-4-yl) pentan-2-one

The title compound was prepared using the procedure as described in Example 110B substituting Example 75C for Example 110A. MS (DCI/NH$_4^+$) m/z 241 (M+H)$^+$.

Example 75E

N-[(5Z)-2-tert-butyl-4-(4-oxopentyl)isothiazol-5 (2H)-ylidene]-5-chloro-2-methoxybenzamide The title compound was prepared using the procedure as described in Example 41 substituting Example 75D for Example 110B. $^1$H NMR (400 MHz, CDCl$_3$) δ ppm 1.65 (s, 9 H) 1.98-2.07 (m, 2 H) 2.14 (s, 3 H) 2.56 (t, J=7.06 Hz, 2 H) 2.83 (t, J=7.98, 7.36 Hz, 2 H) 3.91 (s, 3 H) 6.92 (d, J=8.90 Hz, 1 H) 7.34 (dd, J=8.90, 2.76 Hz, 1 H) 7.97 (s, 1 H) 8.11 (d, J=2.76 Hz, 1 H); MS (DCI/NH$_4$$^+$) m/z 409 (M+H)$^+$.

Example 76

N-[(5Z)-2-tert-butyl-4-(4-oxopentyl)isothiazol-5 (2H)-ylidene]-2-methoxy-5-(trifluoromethyl)benzamide The title compound was prepared using the procedure as described in Example 41 substituting Example 75D for Example 110B and 2-methoxy-5-(trifluoromethyl)benzoic acid for 5-chloro-2-methoxybenzoic acid. $^1$H NMR (400 MHz, CDCl$_3$) δ ppm 1.67 (s, 9 H) 1.99-2.08 (m, 2 H) 2.14 (s, 3 H) 2.56 (t, J=7.36 Hz, 2 H) 2.84 (t, J=7.67 Hz, 2 H) 3.98 (s, 3 H) 7.06 (d, J=8.90 Hz, 1 H) 7.65 (dd, J=8.90, 2.45 Hz, 1 H) 7.99 (s, 1 H) 8.40 (d, J=2.45 Hz, 1 H) MS (DCI/NH$_4$$^+$) m/z 443 (M+H)$^+$.

Example 77

N-[(5Z)-2-tert-butyl-4-(4-oxopentyl)isothiazol-5 (2H)-ylidene]-2-fluoro-3-(trifluoromethyl)benzamide The title compound was prepared using the procedure as described in Example 41 substituting Example 75D for Example 110B and 2-fluoro-3-(trifluoromethyl)benzoic acid for 5-chloro-2-methoxybenzoic acid. $^1$H NMR (400 MHz, CDCl$_3$) δ ppm 1.67 (s, 9 H) 1.99-2.08 (m, 2 H) 2.13 (s, 3 H) 2.56 (t, J=7.06 Hz, 2 H) 2.85 (t, J=7.36 Hz, 2 H) 7.30 (t, J=7.67 Hz, 1 H) 7.69 (td, J=7.67, 1.84, 1.23 Hz, 1 H) 8.02 (s, 1 H) 8.40 (td, J=7.67, 1.53 Hz, 1 H); MS (DCI/NH$_4$$^+$) m/z 431 (M+H)$^+$.

Example 78

N$^3$-[(5Z)-4-butyl-2-tert-butylisothiazol-5(2H)-ylidene]-4-methoxyisophthalamide The product from Example 26E (110 mg, 0.3 mmol) was treated with concentrated sulfuric acid (1 mL). The mixture was heated at 40° C. for 1 hr, diluted with H$_2$O, neutralized with saturated Na$_2$CO$_3$, and extracted with EtOAc (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 107 mg (93%) of the title compound. $^1$H NMR (500 MHz, CDCl$_3$) δ ppm 0.99 (t, J=7.32 Hz, 3 H) 1.40-1.48 (m, 2 H) 1.66 (s, 9 H) 1.69-1.76 (m, 2 H) 2.84 (dd, J=7.63 Hz, 2 H) 3.99 (s, 3 H) 7.06 (d, J=8.54 Hz, 1 H) 7.96 (s, 1 H) 8.02 (dd, J=8.85, 2.44 Hz, 1 H) 8.51 (d, J=2.44 Hz, 1 H); MS (DCI/NH$_4$$^+$) m/z 390 (M+H)$^+$.

Example 79

N-[(5Z)-2-tert-butyl-4-(4-hydroxy-4-methylpentyl)isothiazol-5(2H)-ylidene]-2-fluoro-3-ftrifluoromethyl)benzamide To the suspension of cerium(III) chloride (86 mg, 0.35 mmol) in THF (3 mL) was added the product from Example 77 (100 mg, 0.23 mmol) in THF (0.5 mL). The mixture was stirred at rt for 1 hr. The above mixture was cooled to −40° C. and methylmagnesium bromide (41.6 mg, 0.348 mmol) was added dropwise. The reaction was stirred for 40 min at −40° C., quenched with saturated aqueous NH$_4$Cl and extracted with CH$_2$Cl$_2$ (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 57 mg (55%) of the title compound. $^1$H NMR (500 MHz, CDCl$_3$) δ ppm 1.23 (s, 6 H) 1.57-1.61 (m, 2 H) 1.68 (s, 9 H) 1.74 (s, 1 H) 1.81-1.89 (m, 2 H) 2.88 (t, J=7.63 Hz, 2 H) 7.30 (t, J=7.93 Hz, 1 H) 7.69 (t, J=6.41 Hz, 1 H) 8.01-8.04 (m, 1 H) 8.39 (td, J=7.93, 1.53 Hz, 1 H); MS (DCI/NH$_4$$^+$) m/z 447 (M+H)$^+$.

Example 80

N-[(5Z)-2-tert-butyl-4-(4-hydroxy-4-methylpentyl)isothiazol-5(2H)-ylidene]-5-chloro-2-methoxybenzamide The title compound was prepared using the procedure as described in Example 79 substituting Example 75E for Example 77. $^1$H NMR (400 MHz, CDCl$_3$) δ ppm 1.24 (s, 6 H) 1.55-1.62 (m, 2 H) 1.65 (s, 9 H) 1.79-1.90 (m, 2 H) 2.87 (t, J=7.67 Hz, 2 H) 3.91 (s, 3 H) 6.91 (d, J=8.90 Hz, 1 H) 7.33 (dd, J=8.90, 2.76 Hz, 1 H) 7.97 (s, 1 H) 8.09 (d, J=2.76 Hz, 1H); MS (DCI/NH$_4$$^+$) m/z 425 (M+H)$^+$.

Example 81

N-[(5Z)-2-tert-butyl-4-(4-hydroxy-4-methylpentyl)isothiazol-5(2H)-ylidene]-2-methoxy-5-(trifluoromethyl)benzamide The title compound was prepared using the procedure as described in Example 79 substituting Example 76 for Example 77. $^1$H NMR (500 MHz, CDCl$_3$) δ ppm 1.23 (s, 6 H) 1.56-1.71 (m, 2 H) 1.67 (s, 9 H) 1.80-1.90 (m, 2 H) 2.87 (t, J=7.63 Hz, 2 H) 3.97 (s, 3 H) 7.05 (d, J=8.85 Hz, 1 H) 7.64 (dd, J=8.54, 2.14 Hz, 1 H) 7.99 (s, 1 H) 8.37 (d, J=2.44 Hz, 1H); MS (DCI/NH$_4$$^+$) m/z 459 (M+H)$^+$.

Example 82

N-[(5Z)-4-butyl-2-tert-butylisothiazol-5(2H)-ylidene]-5-isopropyl-2-methoxybenzamide

Example 82A 5-isopropyl-2-methoxybenzoic acid

5-Isopropyl-2-methoxybenzaldehyde (2.8 g, 15.7 mmol) was dissolved in acetone (40 mL). To this solution was added sulfamic acid (2.29 g, 23.57 mmol) and sodium chlorite (1.71 g, 18.85 mmol) in water (40 mL). The mixture was stirred at rt in an open flask for 12 hrs. The acetone was removed and the mixture was extracted with Et$_2$O. The organic layer was dried over MgSO$_4$, filtered and concentrated to afford the title compound. MS (DCI/NH$_4^+$) m/z 212 (M+NH$_4$)$^+$.

Example 82B

N-[(5Z)-4-butyl-2-tert-butylisothiazol-5(2H)-ylidene]-5-isopropyl-2-methoxybenzamide The title compound was prepared using the procedure as described in Example 41 substituting Example 82A for 2,5-dimethoxybenzoic acid. $^1$H NMR (300 MHz, CDCl$_3$) δ ppm 0.98 (t, J=7.14 Hz, 3 H) 1.26 (d, J=7.14 Hz, 6 H) 1.37-1.50 (m, 2 H) 1.65 (s, 9 H) 1.68-1.80 (m, 2 H) 2.84 (dd, J=7.54 Hz, 2 H) 2.86-2.98 (m, 1 H) 3.91 (s, 3 H) 6.91 (d, J=8.72 Hz, 1 H) 7.25 (dd, J=9.91, 2.78 Hz, 1 H) 7.92 (s, 1 H) 7.99 (d, J=2.78 Hz, 1 H); MS (DCI/NH$_4^+$) m/z 389 (M+H)$^+$.

Example 83

N-[(5Z)-2-tert-butyl-4-(4-fluoro-4-methylpentyl)isothiazol-5(2H)-ylidene]-5-chloro-2-methoxybenzamide The product from Example 80 (50 mg, 0.12 mmol) in CH$_2$Cl$_2$ (4 mL) was treated with DAST (38 mg, 0.24 mmol) at −78° C. The mixture was stirred at −78° C. for 1.5 hrs, quenched with saturated aqueous NaHCO$_3$ and extracted with CH$_2$Cl$_2$ (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 29 mg (58%) of the title compound. $^1$H NMR (400 MHz, CDCl$_3$) δ ppm 1.38 (d, J=21.48 Hz, 6 H) 1.65 (s, 9 H) 1.68-1.80 (m, 2 H) 1.81-1.93 (m, 2 H) 2.84 (t, J=7.67 Hz, 2 H) 3.91 (s, 3 H) 6.91 (d, J=8.90 Hz, 1 H) 7.33 (dd, J=8.59, 2.76 Hz, 1 H) 7.97 (s, 1 H) 8.11 (d, J=2.76 Hz, 1 H); MS (DCI/NH$_4^+$) m/z 427 (M+H)$^+$.

Example 84

N-[(5Z)-2-tert-butyl-4-(3-oxobutyl)isothiazol-5(2H)-ylidene]-5-chloro-2-methoxybenzamide Example 84A 5-oxohexanal The title compound was prepared using the procedure as described in Example 21A substituting 1-methylcyclopent-1-ene for Example 6B.

Example 84B 6-(tert-butylimino)hexan-2-one

The title compound was prepared using the procedure as described in Example 1A substituting Example 84A for hexanal.

Example 84C

Ethyl [(5Z)-2-tert-butyl-4-(3-oxobutyl)isothiazol-5(2H)-ylidene]carbamate

The title compound was prepared using the procedure as described in Example 1D substituting Example 84B for Example 1A and o-ethyl carbonisothiocyanatidate for Example 1C. $^1$H NMR (300 MHz, CDCl$_3$) δ ppm 1.37 (t, J=7.14 Hz, 3 H) 1.60 (s, 9 H) 2.09 (s, 3 H) 2.88 (t, J=4.36, 3.17 Hz, 4 H) 4.29 (q, J=7.14 Hz, 2 H) 7.94 (s, 1 H); MS (DCI/NH$_4^+$) m/z 299 (M+H)$^+$.

Example 84D 4-(2-tert-butyl-5-imino-2,5-dihydroisothiazol-4-yl)butan-2-one

The title compound was prepared using the procedure as described in Example 110B substituting Example 84C for Example 110A. MS (DCI/NH$_4^+$) m/z 227 (M+H)$^+$.

Example 84E

N-[(5Z)-2-tert-butyl-4-(3-oxobutyl)isothiazol-5(2H)-ylidene]-5-chloro-2-methoxybenzamide The title compound was prepared using the procedure as described in Example 41 substituting Example 84D for Example 110B. $^1$H NMR (400 MHz, CDCl$_3$) δ ppm 1.64 (s, 9 H) 2.14 (s, 3 H) 2.95-3.08 (m, 4 H) 3.92 (s, 3 H) 6.92 (d, J=8.90 Hz, 1 H) 7.35 (dd, J=8.59, 2.76 Hz, 1 H) 8.07 (s, 1 H) 8.09 (d, J=2.76 Hz, 1 H); MS (DCI/NH$_4^+$) m/z 395 (M+H)$^+$.

Example 85

N-[(5Z)-2-tert-butyl-4-[(2,2,2-trifluoroethoxy)methyl]isothiazol-5(2H)-ylidene]-5-chloro-2-methoxybenzamide Example 85A

[(5Z)-2-tert-butyl-5-{[(5-chloro-2-methoxyphenyl)carbonyl]imino}-2,5-dihydroisothiazol-4-yl]methyl methanesulfonate The product from Example 28A (300 mg, 0.85 mmol) in CH$_2$Cl$_2$ (10 mL) containing triethylamine (257 mg, 2.54 mmol) was treated with methanesulfonyl chloride (145 mg, 1.27 mmol) at 0° C. The mixture was stirred for 30 min at 0° C., diluted with water and extracted with CH$_2$Cl$_2$ (2×). The combined organic layers were dried over MgSO$_4$, filtered and concentrated to afford the title compound.

Example 85B

N-[(5Z)-2-tert-butyl-4-[(2,2,2-trifluoroethoxy)methyl]isothiazol-5(2H)-ylidene]-5-chloro-2-methoxybenzamide 2,2,2-Trifluoroethanol (48 mg, 0.48 mmol) in DMF (2 mL) and THF (2.0 mL) was treated for sodium hydride (23 mg, 0.58 mmol). The reaction was stirred at rt for 10 min, treated with Example 85A (80 mg, 0.19 mmol) in THF (0.5 mL), heated at 85° C. for 1.5 hrs, diluted with H$_2$O and extracted with EtOAc (2×). The combined organic layers were dried over MgSO$_4$, filtered and concentrated. The residue was purified by column chromatography using an Analogix® Intelliflash280™ (SiO$_2$, 0-50% Hexane in ethyl acetate) to afford 24 mg (29%) of the title compound. $^1$H NMR (500 MHz, CDCl$_3$) δ ppm 1.68 (s, 9 H) 3.93 (s, 3 H) 4.05 (q, J=8.85 Hz, 2 H) 4.94 (s, 2 H) 6.93 (d, J=8.85 Hz, 1 H) 7.37 (dd, J=8.85, 2.75 Hz, 1H) 8.12 (d, J=2.75 Hz, 1 H) 8.19 (s, 1 H); MS (DCI/NH$_4^+$) m/z 437 (M+H)$^+$.

Example 86

N-[(5Z)-2-tert-butyl-4-(4,4-difluoropentyl)isothiazol-5(2H)-ylidene]-5-chloro-2-methoxybenzamide The title compound was prepared using the procedure as described in Example 69 substituting Example 75E for Example 64B. $^1$H NMR (400 MHz, CDCl$_3$) δ ppm 1.63 (t, J=18.41 Hz, 3 H) 1.65 (s, 9 H) 1.91-2.01 (m, 4 H) 2.87 (t, J=7.36 Hz, 2 H) 3.92 (s, 3 H) 6.92 (d, J=8.90 Hz, 1 H) 7.34 (dd, J=8.90, 2.76 Hz, 1 H) 7.96 (s, 1 H) 8.10 (d, J=2.76 Hz, 1H); MS (DCI/NH$_4^+$) m/z 431 (M+H)$^+$.

Example 87

N-[(5Z)-2-tert-butyl-4-(3-fluoro-3-methylbutyl)isothiazol-5(2H)-ylidene]-5-chloro-2-methoxybenzamide

Example 87A

N-[(5Z)-2-tert-butyl-4-(3-hydroxy-3-methylbutyl)isothiazol-5(2H)-ylidene]-5-chloro-2-methoxybenzamide The title compound was prepared using the procedure as described in Example 79 substituting Example 84E for Example 75E. MS (DCI/NH$_4^+$) m/z 411 (M+H)$^+$.

Example 87B

N-[(5Z)-2-tert-butyl-4-(3-fluoro-3-methylbutyl)isothiazol-5(2H)-ylidene]-5-chloro-2-methoxybenzamide The title compound was prepared using the procedure as described in Example 83 substituting Example 87A for Example 80. $^1$H NMR (400 MHz, CDCl$_3$) δ ppm 1.47 (d, J=21.48 Hz, 6 H) 1.65 (s, 9 H) 2.02-2.14 (m, 2 H) 2.90-2.97 (m, 2 H) 3.92 (s, 3 H) 6.92 (d, J=8.90 Hz, 1 H) 7.34 (dd, J=8.90, 2.76 Hz, 1 H) 7.98 (s, 1 H) 8.16 (d, J=2.76 Hz, 1 H); MS (DCI/NH$_4^+$) m/z 413 (M+H)$^+$.

Example 88

N-[(5Z)-2-tert-butyl-4-(4-fluoro-4-methylpentyl)isothiazol-5(2H)-ylidene]-2-methoxy-5-(trifluoromethyl)benzamide The title compound was prepared using the procedure as described in Example 83 substituting Example 81 for Example 80. $^1$H NMR (400 MHz, CDCl$_3$) δ ppm 1.37 (d, J=21.48 Hz, 6 H) 1.66 (s, 9 H) 1.67-1.78 (m, 2 H) 1.83-1.94 (m, 2 H) 2.84 (t, J=7.98, 7.36 Hz, 2 H) 3.97 (s, 3 H) 7.05 (d, J=8.29 Hz, 1 H) 7.64 (dd, J=7.98, 2.45 Hz, 1 H) 7.96-7.99 (m, 1 H) 8.40 (d, J=2.45 Hz, 1 H); MS (DCI/NH$_4^+$) m/z 461 (M+H)$^+$.

Example 89

N-[(5Z)-2-tert-butyl-4-{[(2R)-tetrahydrofuran-2-ylmethoxy]methyl}isothiazol-5(2H)-ylidene]-5-chloro-2-methoxybenzamide The title compounds was obtained from Example 85A using the procedure as described in Example 85B substituting (R)-(tetrahydrofuran-2-yl)methanol for 2,2,2-trifluoroethanol. $^1$H NMR (400 MHz, CDCl$_3$) δ ppm 1.59-1.69 (m, 1 H) 1.66 (s, 9 H) 1.86-2.04 (m, 3 H) 3.58-3.70 (m, 2 H) 3.76-3.84 (m, 1 H) 3.86-3.94 (m, 1 H) 3.92 (s, 3 H) 4.10-4.19 (m, 1 H) 4.84 (s, 2 H) 6.92 (d, J=8.90 Hz, 1 H) 7.34 (dd, J=8.90, 2.76 Hz, 1 H) 8.13 (d, J=2.76 Hz, 1 H) 8.24 (s, 1 H); MS (DCI/NH$_4^+$) m/z 439 (M+H)$^+$.

Example 90

N-[(5Z)-2-tert-butyl-4-[(2-fluoroethoxy)methyl]isothiazol-5(2H)-ylidene]-5-chloro-2-methoxybenzamide The title compounds was obtained from Example 85A using the procedure as described in Example 85B substituting 2-fluoroethanol for 2,2,2-trifluoroethanol. $^1$H NMR (400 MHz, CDCl$_3$) δ ppm 1.67 (s, 9 H) 3.82-3.95 (m, 2 H) 3.92 (s, 3 H) 4.62 (dt, J=47.56, 3.99 Hz, 2 H) 4.86 (s, 2 H) 6.92 (d, J=8.90 Hz, 1 H) 7.35 (dd, J=8.29, 2.76 Hz, 1 H) 8.13 (d, J=2.76 Hz, 1 H) 8.21 (s, 1 H); MS (DCI/NH$_4^+$) m/z 401 (M+H)$^+$.

Example 91

N-[(5Z)-2-tert-butyl-4-[(2,2-difluoroethoxy)methyl]isothiazol-5(2H)-ylidene]-5-chloro-2-methoxybenzamide The title compounds was obtained from Example 85A using the procedure as described in Example 85B substituting 2,2-difluoroethanol for 2,2,2-trifluoroethanol. $^1$H NMR (400 MHz, CDCl$_3$) δ ppm 3.86 (td, J=14.12, 3.99 Hz, 2 H) 3.92 (s, 3 H) 4.88 (s, 2 H) 5.95 (tt, J=55.24, 4.30 Hz, 1 H) 6.93 (d, J=8.90 Hz, 1 H) 7.36 (dd, J=8.90, 2.76 Hz, 1 H) 8.12 (d, J=2.76 Hz, 1 H) 8.18 (s, 1 H); MS (DCI/NH$_4^+$) m/z 419 (M+H)$^+$.

Example 92

Methyl 3-({[(5Z)-4-butyl-2-tert-butylisothiazol-5(2H)-ylidene]amino}carbonyl)-2,2,3-trimethylcyclopentanecarboxylate

Example 92A

Ethyl [(5Z)-4-butyl-2-tert-butylisothiazol-5(2H)-ylidene]carbamate

To a solution of hexanal (Aldrich, 20.0 g, 200 mmol) in acetonitrile (20 mL) in a 100-mL, round-bottomed flask containing molecular sieves (10 g) was added neat t-butylamine (Aldrich, 16.1 g, 220 mmol). The mixture was stirred at room temperature overnight. The solids were removed by vacuum filtration through a glass frit and the liquor was concentrated by rotary evaporator to give the crude imine as a pale yellow oil. The crude imine was dissolved in anhydrous tetrahydrofuran (200 mL) containing pyridine (Aldrich, 15.8 g, 200 mmol) and O-ethyl carbonisothiocyanatidate (Aldrich, 15.7 g, 120 mmol) was added dropwise. The resulting yellow mixture was stirred at room temperature for 1 hour. Anhydrous methanol (100 mL) and iodine (Aldrich, 30.5 g, 120 mmol) were added to form a brown slurry. The mixture was stirred at room temperature for 2 hours. The excess iodine was quenched by addition of solid sodium metabisulfite until the mixture changed to yellow. Saturated aqueous sodium bicarbonate solution was added and the mixture was stirred at room temperature for 15 minutes. The mixture was extracted with dichloromethane (3×75 mL). The combined organic extracts were dried (MgSO$_4$), filtered, and concentrated by rotary evaporator to give a brown oil. The product was purified by flash chromatography (silica gel: 25-95% ethyl acetate in hexanes) to afford 31.6 g (56%) of the title compound. $^1$H NMR (DMSO-d$_6$) δ ppm 0.90 (t, J=7.3 Hz, 3H), 1.22 (t, J=7.1 Hz, 3H), 1.23-1.36 (m, 2H), 1.50-1.60 (m, 2H), 1.55 (s, 9H), 2.51 (t, J=7.5 Hz, 2H), 4.10 (q, J=7.1 Hz, 2H), 8.45 (s, 1H); MS (ESI+) m/z 285 (M+H)$^+$.

Example 92B 2-tert-butyl-4-butylisothiazol-5(2H)-imine

To a 250-mL, round-bottomed flask containing a magnetic stir bar were added the product from Example 92A (7.11 g, 25.0 mmol) and chloroform (100 mL). Neat iodotrimethylsilane (Aldrich, 6.25 g, 31.1 mmol) was added. A reflux condenser with nitrogen inlet was attached and a heating mantle was applied. The yellow reaction mixture was heated to 60° C. and stirred overnight. After cooling to room temperature, saturated aqueous sodium bicarbonate solution was added. The organic layer was separated and the aqueous layer was extracted with dichloromethane (2×50 mL). The combined organic layers were dried (MgSO$_4$), filtered, and concentrated by rotary evaporator to give a yellow semi-solid. The product was purified by flash chromatography (silica get: 30-90% ethyl acetate in hexanes) to afford the title compound. LC-MS (ESI+) m/z 213 (M+H)$^+$ Example 92C Methyl 3-({[(5Z)-4-butyl-2-tert-butylisothiazol-5 (2H)-ylidene]amino}carbonyl)-2,2,3-trimethylcyclopentanecarboxylate To a 20-mL scintillation vial containing a magnetic stir bar were added the product from Example 92B (637 mg, 3.00 mmol), racemic 3-(methoxycarbonyl)-1,2,2-trimethylcyclopentanecarboxylic acid (Maybridge, 771 mg, 3.60 mmol), and 2-(1H-benzo[d][1,2,3]triazol-1-yl)-1,1,3,3-tetramethylisouronium tetrafluoroborate (TBTU, Bachem, 1.16 g, 3.60 mmol). Anhydrous acetontirile (8 mL) was added to form a white slurry. Neat triethylamine (Aldrich, 1.09 g, 10.8 mm0l) was added via syringe to form a tan solution. The reaction flask was heated to 60° C. in a shaker block and mixed for 2 hours. The volatiles were removed by rotary evaporator to give a brown oil. The product was purified by flash chromatography (silica gel: 2-20% ethyl acetate in hexanes) to afford the title compound. $^1$H NMR (DMSO-d$_6$) δ ppm 0.50 (s, 3H), 0.90 (t, J=7.5 Hz, 3H), 1.21 (s, 3H), 1.24-1.36 (m, 2H), 1.30 (s, 3H), 1.41-1.51 (m, 1H), 1.57 (s, 9H), 1.57-1.67 (m, 2H), 1.73-1.87 (m, 1H), 2.01-2.11 (m, 1H), 2.62-2.67 (m, 2H), 2.70-2.81 (m, 1H), 2.85-2.91 (m, 1H), 3.60 (s, 3H), 8.50 (s, 1H). MS (ESI+) m/z 409 (M+H)$^+$. Anal. calcd. for C$_{22}$H$_{36}$N$_2$O$_3$S: C, 64.67; H, 8.88; N, 6.86. Found: C, 64.20; H, 8.71; N, 6.59.

Example 93

Methyl 3-({[(5Z)-4-butyl-2-tert-butylisothiazol-5 (2H)-ylidene]amino}carbonyl)-1,2,2-trimethylcyclopentanecarboxylate The product from Example 92B and racemic 3-(methoxycarbonyl)-2,2,3-trimethylcyclopentanecarboxylic (May-bridge) were processed using the method described in Example 92C to afford the title compound. $^1$H NMR (DMSO-d$_6$) δ ppm 0.53 (s, 3H), 0.90 (t, J=7.3 Hz, 3H), 1.20 (s, 3H), 1.23 (s, 3H), 1.23-1.40 (m, 2H), 1.41-1.50 (m, 1H), 1.57 (s, 9H), 1.57-1.67 (m, 2H), 1.71-1.84 (m, 1H), 2.24-2.36 (m, 1H), 2.41-2.48 (m, 1H), 2.61-2.67 (m, 2H), 3.00-3.06 (m, 1H), 3.59 (s, 3H), 8.51 (s, 1H). MS (ESI+) m/z 409 (M+H)$^+$. Anal. calcd. for C$_{22}$H$_{36}$N$_2$O$_3$S: C, 64.67; H, 8.88; N, 6.86. Found: C, 64.37; H, 8.67; N, 6.50.

Example 94

N-[(5Z)-4-butyl-2-tert-butylisothiazol-5(2H)-ylidene]-1-phenylcyclohexanecarboxamide The product from Example 92B and 1-phenylcyclohexanecarboxylic acid (Aldrich) were processed using the method described in Example 92C to afford the title compound. $^1$H NMR (DMSO-d$_6$) δ ppm 0.90 (t, J=7.3 Hz, 3H), 1.20-1.77 (m, 21H), 2.61-2.69 (m, 4H), 7.10-7.15 (m, 1H), 7.21-7.27 (m, 2H), 7.35-7.39 (m, 2H), 8.51 (s, 1H). MS (ESI+) m/z 399 (M+H)$^+$. Anal. calcd. for C$_{24}$H$_{34}$N$_2$OS: C, 72.32; H, 8.60; N, 7.03. Found: C, 72.24; H, 8.59; N, 7.10.

Example 95

N-[(5Z)-4-butyl-2-tert-butylisothiazol-5(2H)-ylidene]-1-(2-chloro-4-fluorophenyl)cyclohexanecarboxamide The product from Example 92B and (2-chloro-4-fluorophenyl)cyclohexanecarboxylic acid (Acros) were processed using the method described in Example 92C to afford the title compound. $^1$H NMR (DMSO-d$_6$) δ ppm 0.76 (t, J=7.3 Hz, 3H), 1.06-1.18 (m, 2H), 1.33-1.53 (m, 8H), 1.56 (s, 9H), 1.71-1.81 (m, 2H), 1.92-2.00 (m, 2H), 2.34-2.42 (m, 2H), 7.14-7.22 (m, 2H), 7.57 (dd, J=8.6, 6.3 Hz, 1H), 8.46 (s, 1H). MS (ESI+) m/z 451 (M+H)$^+$. Anal. calcd. for C$_{24}$H$_{32}$ClFN$_2$OS: C, 63.91; H, 7.15; N, 6.21. Found: C, 64.04; H, 7.08; N, 6.10.

Example 96

3-({[(5Z)-4-butyl-2-tert-butylisothiazol-5(2H)-ylidene]amino}carbonyl)-2,2,3-trimethylcyclopentanecarboxylic acid To a 20-mL scintillation vial containing a magnetic stir bar were added the product from Example 92C (102 mg, 0.250 mmol) and potassium hydroxide (84 mg, 1.50 mmol). Ethanol (1 mL) and water (0.25 mL) were added. The vial was heated to 60° C. and the reaction mixed for 24 hours. After cooling to room temperature, the pH was adjusted to ~1 by addition of 1N hydrochloric acid. The mixture was extracted with dichloromethane (3×10 mL). The combined organic extracts were dried (MgSO$_4$), filtered, and concentrated by rotary evaporator to afford a tan solid. The product was recrystallized from ethyl acetate/hexanes to afford 74 mg (75%) of the title compound. $^1$H NMR (DMSO-d$_6$) δ ppm 0.63 (br s, 3H), 0.91 (t, J=7.3 Hz, 3H), 1.23-1.38 (m, 8H), 1.57-1.68 (m, 12H), 1.76-1.87 (m, 1H), 2.00-2.11 (m, 1H), 2.65-2.84 (m, 4H), 8.7 (br s, 1H), 11.7 (br s, 1H). MS (ESI+) m/z 395 (M+H)$^+$.

Example 97

N-[(5Z)-4-butyl-2-tert-butylisothiazol-5(2H)-ylidene]-3-oxocyclopentanecarboxamide The product from Example 92B and 3-oxocyclopentanecarboxylic acid (Aldrich) were processed using the method described in Example 92C to afford the title compound. $^1$H NMR (DMSO-d$_6$) δ ppm 0.91 (t, J=7.5 Hz, 3H), 1.25-1.36 (m, 2H), 1.57 (s, 9H), 1.55-1.84 (m, 2H), 1.98-2.06 (m, 1H), 2.13-2.28 (m, 3H), 2.39-2.42 (m, 2H), 2.61-2.66 (m, 2H), 3.27-3.34 (m, 1H), 8.55 (s, 1H). MS (ESI+) m/z 323 (M+H)$^+$. Anal. calcd. for C$_{17}$H$_{26}$N$_2$O$_2$S: C, 63.32; H, 8.13; N, 8.69. Found: C, 63.19; H, 8.07; N, 8.66.

Example 98

N-[(5Z)-4-butyl-2-tert-butylisothiazol-5(2H)-ylidene]-1-phenylcyclopentanecarboxamide The product from Example 92B and 1-phenylcyclopentanecarboxylic acid (Aldrich) were processed using the method described in Example 92C to afford the title compound. $^1$H NMR (DMSO-d$_6$) δ ppm 0.90 (t, J=7.3 Hz, 3H), 1.23-1.35 (m, 2H), 1.54 (s, 9H), 1.54-1.69 (m, 6H), 1.78-1.87 (m, 2H), 2.61-2.66 (m, 2H), 2.86-2.93 (m, 2H), 7.10-7.16 (m, 1H), 7.21-7.26 (m, 2H), 7.31-7.38 (m, 2H), 8.50 (s, 1H). MS (ESI+) m/z 385 (M+H)$^+$. Anal. calcd. for C$_{23}$H$_{32}$N$_2$OS: C, 71.83; H, 8.39; N, 7.28. Found: C, 71.58; H, 8.21; N, 7.05.

Example 99

N$^1$-[(5Z)-4-butyl-2-tert-butylisothiazol-5(2H)-ylidene]-N$^3$,N$^3$,1,2,2-pentamethylcyclopentane-1,3-dicarboxamide To a 20-mL scintillation vial were added the product from Example 96 (118 mg, 0.300 mmol), dimethylamine hydrochloride (Aldrich, 36.7 mg, 0.450 mmol), and 2-(1H-benzo[d][1,2,3]tria-zol-1-yl)-1,1,3,3-tetramethylisouronium tetrafluoroborate (TBTU, Bachem, 144 mg, 0.450 mmol). Anhydrous acetonitrile (3 mL) was added to form a yellow slurry. Neat triethylamine (Aldrich, 182 mg, 1.80 mmol) was added to form a tan solution. The reaction was stirred at 25° C. in a shaker block for 24 hr. The volatiles removed by rotary evaporator to give a brown oil. The product was purified by flash chromatography (silica gel: 10-45% ethyl acetate in hexanes). The product was recrystallized from hexanes to afford 67.0 mg (53%) of the title compound. $^1$H NMR (DMSO-d$_6$) δ ppm 0.49 (s, 3H), 0.90 (t, J=7.3 Hz, 3H), 1.25 (s, 3H), 1.26 (s, 3H), 1.28-1.33 (m, 2H), 1.37-1.46 (m, 1H), 1.57 (s, 9H), 1.57-1.70 (m, 3H), 2.01-2.10 (m, 1H), 2.62-2.67 (m, 2H), 2.74-2.83 (m, 1H), 2.83 (s, 3H), 3.05 (s, 3H), 3.33-3.39 (m, 1H), 8.49 (s., 1H). MS (ESI+) m/z 422 (M+H)$^+$. Anal. calcd. for C$_{23}$H$_{39}$N$_3$O$_2$S: C, 65.52; H, 9.32; N, 9.97. Found: C, 65.13; H, 9.22; N, 9.55.

Example 100

N$^1$-[(5Z)-4-butyl-2-tert-butylisothiazol-5(2H)-ylidene]-N$^3$,1,2,2-tetramethylcyclopentane-1,3-dicarboxamide The product from Example 96 and methylamine hydrochloride (Aldrich) were processed using the method described in Example 99 to afford the title compound. $^1$H NMR (DMSO-d$_6$) δ ppm 0.47 (s, 3H), 0.90 (t, J=7.3 Hz, 3H), 1.19 (s, 3H), 1.22 (s, 3H), 1.26-1.33 (m, 2H), 1.36-1.45 (m, 1H), 1.57 (s, 9H), 1.57-1.68 (m, 3H), 1.95-2.07 (m, 1H), 2.57 (d, J=4.7 Hz, 3H), 2.60-2.67 (m, 3H), 2.72-2.83 (m, 1H), 4.78 (q, J=4.5 Hz, 1H), 8.49 (s, 1H). MS (ESI+) m/z 408 (M+H)$^+$. Anal. calcd. for C$_{22}$H$_{37}$N$_3$O$_2$S: C, 64.83; H, 9.15; N, 10.31. Found: C, 64.55; H, 9.02; N, 10.29.

Example 101

N-[(5Z)-4-butyl-2-tert-butylisothiazol-5(2H)-ylidene]-3-[3,3-difluoroazetidin-1-yl)carbonyl]-1,2,2-trimethylcyclopentanecarboxamide The product from Example 96 and 3,3-difluoroazetidine hydrochloride (Oakwood)) were processed using the method described in Example 99 to afford the title compound. $^1$H NMR (DMSO-d$_6$) δ ppm 0.51 (s, 3H), 0.90 (t, J=7.3 Hz, 3H), 1.22 (s, 3H), 1.25 (s, 3H), 1.26-1.36 (m, 2H), 1.39-1.48 (m, 1H), 1.57 (s, 9H), 1.57-1.78 (m, 3H), 1.93-2.07 (m, 1H), 2.62-2.67 (m, 2H), 2.72-2.83 (m, 1H), 2.88-2.94 (m, 1H), 4.14-4.37 (m, 2H), 4.41-4.52 (m, 1H), 4.73-4.86 (m, 1H), 8.50 (s, 1H). MS (ESI+) m/z 470 (M+H)$^+$. Anal. calcd. for C$_{24}$H$_{37}$F$_2$N$_3$O$_2$S: C, 61.38; H, 7.94; N, 8.95. Found: C, 61.35; H, 7.84; N, 8.96.

Example 102

(1S,4R)—N-[(5Z)-4-butyl-2-tert-butylisothiazol-5(2H)-ylidene]-4,7,7-trimethyl-3-oxo-2-oxabicyclo[2.2.1]heptane-1-carboxamide To a 20-mL scintillation vial containing a magnetic stir bar were added the product from Example 92B (327 mg, 1.75 mmol) and (1S)-(−)-camphanic acid chloride (Aldrich, 474 mg, 2.19 mmol) and anhydrous tetrahydrofuran (12 mL). Triethylamine (797 mg, 7.88 mmol) was added via syringe and the resulting yellow slurry was stirred at room temperature for 24 h. The volatiles removed by rotary evaporator to give a brown oil. The product was purified by flash chromatography (silica gel: 20-80% ethyl acetate in hexanes) to afford 527 mg (77%) of the title compound. $^1$H NMR (DMSO-d$_6$) δ ppm 0.79 (s, 3H), 0.90 (t, J=7.3 Hz, 3H), 1.01 (s, 3H), 1.07 (s, 3H), 1.22-1.39 (m, 2H), 1.60 (s, 9H), 1.50-1.67 (m, 3H), 1.61-2.02 (m, 2H), 2.45-2.54 (m, 1H), 2.65-2.70 (m, 2H), 8.66 (s, 1H). MS (ESI+) m/z 393 (M+H)$^+$. Anal. calcd. for C$_{21}$H$_{32}$N$_2$O$_3$S: C, 64.25; H, 8.22; N, 7.14. Found: C, 64.04; H, 8.22; N, 7.01.

Example 103

(1R,4S)—N-[(5Z)-4-butyl-2-tert-butylisothiazol-5(2H)-ylidene]-4,7,7-trimethyl-3-oxo-2-oxabicyclo[2.2.1]heptane-1-carboxamide The product from Example 92B and (1R)-(+)-camphanic acid chloride (Fluka) were processed using the method described in Example 102 to afford the title compound. $^1$H NMR (DMSO-d$_6$) δ ppm 0.79 (s, 3H), 0.90 (t, J=7.3 Hz, 3H), 1.01 (s, 3H), 1.06 (s, 3H), 1.25-1.37 (m, 2H), 1.60 (s, 9H), 1.50-1.67 (m, 3H), 1.61-2.02 (m, 2H), 2.45-2.54 (m, 1H), 2.65-2.70 (m, 2H), 8.66 (s, 1H). MS (ESI+) m/z 393 (M+H)$^+$. Anal. calcd. for C$_{21}$H$_{32}$N$_2$O$_3$S: C, 64.25; H, 8.22; N, 7.14. Found: C, 64.16; H, 8.05; N, 7.03.

Example 104

Ethyl 3-({[(5Z)-4-butyl-2-tert-butylisothiazol-5(2H)-ylidene]amino}carbonyl)pyrrolidine-1-carboxylate

Example 104A

Tert-butyl 3-{[(5Z)-4-butyl-2-tert-butylisothiazol-5(2H)-ylidene]carbamoyl}pyrrolidine-1-carboxylate The product from Example 92B and 1-(tert-butoxycarbonyl)pyrrolidine-3-carboxylic acid (Aldrich) were processed using the method described in Example 92C to afford the title compound. MS (ESI+) m/z 410 (M+H)$^+$.

Example 104B

N-[(5Z)-4-butyl-2-tert-butylisothiazol-5(2H)-ylidene]pyrrolidine-3-carboxamide

To a 20-mL scintillation vial containing a magnetic stir bar were added the product from Example 104A (143 mg, 0.350 mmol), anhydrous dichloromethane (5 mL), and trifluoroacetic acid (200 mg, 1.75 mmol). The pale yellow solution was stirred at room temperature for 4 hours. The pH of the reaction mixture was adjusted to ~9 by addition of saturated aqueous sodium bicarbonate solution. The mixture was extracted with dichloromethane (3×10 mL). The combined organic extracts were dried (MgSO$_4$), filtered, and concentrated by rotary evaporator to afford the title compound. The crude product was used without purification for the next step. MS (ESI+) m/z 310 (M+H)$^+$.

Example 104C

Ethyl 3-({[(5Z)-4-butyl-2-tert-butylisothiazol-5(2H)-ylidene]amino}carbonyl)pyrrolidine-1-carboxylate The product from Example 104B and ethylchloroformate (Aldrich) were processed using the method described in Example 102 to afford the title compound. $^1$H NMR (DMSO-d$_6$) δ ppm 0.91 (t, J=7.3 Hz, 3H), 1.18 (t, J=6.9 Hz, 3H), 1.24-1.37 (m, 3H), 1.51-1.64 (m, 3H), 1.58 (s, 9H), 2.05-2.14 (m, 2H), 2.61-2.66 (m, 2H), 3.21-3.28 (m, 1H), 3.49-3.64 (m, 2H), 4.02 (q, J=7.1 Hz, 2H), 8.57 (s, 1H). (ESI+) m/z 410 (M+H)$^+$.

Example 105

3-({[(5Z)-4-butyl-2-tert-butylisothiazol-5(2H)-ylidene]amino}carbonyl)-1,2,2-trimethylcyclopentanecarboxylic acid The product from Example 93 was processed using the method described in Example 96 to afford the title compound. $^1$H NMR (DMSO-d$_6$) δ ppm 0.75 (s, 3H), 0.92 (t, J=7.3 Hz, 3H), 1.19 (s, 3H), 1.23 (s, 3H), 1.30-1.42 (m, 2H), 1.45-1.66 (m, 4H), 1.69 (br s, 9H), 1.84-1.96 (m, 1H), 2.00-2.13 (m, 1H), 2.78-2.92 (m, 3H), 9.1 (br s, 1H), 13.1 (br s, 1H). MS (ESI+) m/z 395 (M+H)$^+$.

Example 106

Tert-butyl 3-({[(5Z)-4-butyl-2-tert-butylisothiazol-5(2H)-ylidene]amino}carbonyl)pyrrolidine-1-carboxylate The product from Example 92B and 1-(tert-butoxycarbonyl)pyrrolidine-3-carboxylic acid (Aldrich) were processed using the method described in Example 92C to afford the title compound. $^1$H NMR (DMSO-d$_6$) δ 0.91 (t, J=7.3 Hz, 3H), 1.27-1.35 (m, 2H), 1.39 (s, 9H), 1.55-1.65 (m, 12H), 2.06-2.11 (m, 2H), 2.62-2.67 (m, 2H), 3.19-3.30 (m, 2H), 3.45-3.54 (m, 2H), 8.56 (s, 1H). MS (ESI+) m/z 410 (M+H)$^+$.

Example 107

N-[(5Z)-4-butyl-2-tert-butylisothiazol-5(2H)-ylidene]-1-(3-cyanopyridin-2-yl)pyrrolidine-3-carboxamide To a 20-mL scintillation vial were added the product from Example 104B (54.2 mg, 0.175 mmol), the 2-fluoronicotinonitrile (Aldrich, 32.1 mg, 0.263 mmol), and anhydrous acetonitrile (2 mL). Neat triethylamine (53.1 mg, 0.525 mmol) was added. The reaction mixture was heated to 60° C. in a heated shaker block and mixed for 24 hours. After cooling to room temperature, the volatiles were removed by rotary evaporator. The product was purified by flash chromatography (silica gel: 20-65% ethyl acetate in hexanes) to give 54.6 mg (76%) of the title compound. $^1$H NMR (DMSO-d$_6$) δ ppm 0.88 (t, J=7.3 Hz, 3H), 1.21-1.34 (m, 3H), 1.52-1.62 (m, 1H), 1.57 (s, 9H), 2.20-2.27 (m, 2H), 2.59-2.64 (m, 2H), 3.35-3.43 (m, 1H), 3.69-3.78 (m, 2H), 3.88-3.95 (m, 1H), 4.04-4.09 (m, 1H), 6.69 (dd, J=7.5, 4.8 Hz, 1H), 7.93 (dd, J=7.9, 2.0 Hz, 1H), 8.31 (dd, J=4.8, 2.0 Hz, 1H), 8.57 (s, 1H). MS (ESI+) m/z 412 (M+H)$^+$.

Example 108

Methyl 4-({[(5Z)-4-butyl-2-tert-butylisothiazol-5(2H)-ylidene]amino}carbonyl)bicyclo[2.2.2]octane-1-carboxylate The product from Example 92B and 4-(methoxycarbonyl)bicyclo[2.2.2]octane-1-carboxylic acid (Oakwood) were processed using the method described in Example 92C to afford the title compound. $^1$H NMR (DMSO-d$_6$) δ ppm 0.91 (t, J=7.3 Hz, 3H), 1.23-1.36 (m, 2H), 1.58 (s, 9H), 1.58-1.66 (m, 2H), 1.70-1.83 (m, 12H), 2.61-2.66 (m, 2H), 3.58 (s, 3H), 8.49 (s, 1H). (ESI+) m/z 407 (M+H)$^+$. Anal. calcd. for $C_{22}H_{34}N_2O_3S$: C, 64.99; H, 8.43; N, 6.89. Found: C, 64.65; H, 8.24; N, 6.72.

Example 109

N-[(5Z)-4-butyl-2-tert-butylisothiazol-5(2H)-ylidene]-5-oxo-1-phenylpyrrolidine-3-carboxamide The product from Example 92B and 5-oxo-1-phenylpyrrolidine-3-carboxylic acid (Princeton Bio) were processed using the method described in Example 92C to afford the title compound. $^1$H NMR (DMSO-d$_6$) δ ppm 0.91 (t, J=7.3 Hz, 3H), 1.26-1.38 (m, 2H), 1.58-1.66 (m, 2H), 1.61 (s, 9H), 2.64-2.69 (m, 2H), 2.85-2.89 (m, 2H), 3.49-3.58 (m, 1H), 4.12 (s, 1H), 4.14 (d, J=1.7 Hz, 1H), 7.08-7.14 (m, 1H), 7.31-7.38 (m, 2H), 7.62-7.68 (m, 2H), 8.48 (s, 1H). (ESI+) m/z 400 (M+H)$^+$.

Example 110

N-[(5Z)-4-butyl-2-tert-butylisothiazol-5(2H)-ylidene]-5-chloro-N'-cyano-2-methoxybenzenecarboximidamide

Example 110A

Ethyl [(5Z)-4-butyl-2-tert-butylisothiazol-5(2H)-ylidene]carbamate

To a solution of Example 1A (4.2 g, 27 mmol) in THF (100 mL) at room temperature under $N_2$ was added O-ethyl carbonisothiocyanatidate (3.55 g, 27 mmol). The reaction mixture was stirred for 1 hour and iodine (6.8 g, 27 mmol), MeOH (100 mL) and pyridine (10 mL) were added. The reaction mixture was stirred for 2 hours. The reaction mixture was poured into saturated $NaHCO_3/Et_2O$ and stirred for 30 minutes. Additional saturated $NaHCO_3$ and $Et_2O$ were added and the organic layer was separated. The aqueous layer was extracted with $Et_2O$ (2×) and combined organics were dried ($MgSO_4$) and concentrated in vacuo. Toluene and acetonitrile were added and evaporated to remove water and pyridine. The crude compound was purified by flash chromatography using 0-100% EtOAc in hexane as eluent to give 5.2 g of the title compound as yellow solid. $^1$H NMR (300 MHz, $CDCl_3$) δ ppm 0.93 (t, J=7.3 Hz, 3 H), 1.27-1.47 (m, 5 H), 1.54-1.73 (m, 11 H), 2.59-2.74 (m, 2 H), 4.28 (q, J=7.1 Hz, 2 H), 7.78 (s, 1 H). MS ($DCI/NH_3$) m/z 285 $(M+H)^+$.

Example 110B 2-tert-butyl-4-butylisothiazol-5(2H)-imine

A solution of Example 110A (3.95 g, 13.89 mmol) in chloroform (35 mL) was treated with TMSI (2.65 mL, 19.5 mmol). The reaction mixture was stirred at 65° C. for 8 hours, cooled to room temperature, quenched with water and extracted between $CH_2Cl_2$ and saturated $NaHCO_3$, dried ($MgSO_4$) and concentrated to give the title compound (2.45 g, 83% yield). $^1$H NMR (300 MHz, $CDCl_3$) δ ppm 0.84-1.02 (m, 3 H), 1.30-1.51 (m, 2 H), 1.56-1.68 (m, 11 H), 2.73 (t, J=7.6 Hz, 2 H), 7.82 (s, 1 H), 11.68 (d, J=6.1 Hz, 1 H). MS ($DCI/NH_3$) m/z 213 $(M+H)^+$.

Example 110C

Methyl N-[(5Z)-4-butyl-2-tert-butylisothiazol-5(2H)-ylidene]-N'-cyanoimidothiocarbamate A mixture of Example 110B (2.06 g, 9.71 mmol) and dimethyl cyanocarbonimidodithioate (1.36 g, 9.3 mmol) in THF (35 mL) was treated with $Et_3N$ (0.98 g, 9.71 mmol) and stirred at 45° C. for 12 h. The mixture was concentrated under reduced pressure and the residue was purified by chromatography (hexane-EtOAc 1:1) to afford 1.65 g, (55% yield) of the title compound. $^1$H NMR (300 MHz-DMSO-$d_6$) δ ppm 1.31 (s, 9H), 1.60 (m, 1H), 1.82 (quintet, J=7 Hz, 2H), 1.95 (m, 1H), 2.53 (s, 3H), 3.65 (m, 1H), 3.75 (m, 1H), 4.26 (m, 3H), 7.43 (s, 1H); MS ($DCI/NH_3$) m/z 339 $(M+H)^+$.

Example 110D

N-[(5Z)-4-butyl-2-tert-butylisothiazol-5(2H)-ylidene]-5-chloro-N'-cyano-2-methoxybenzenecarboximidamide To a mixture of Example 110C (0.67 g, 2.15 mol), 2-methoxy-5-chlorophenylboronic acid (1.046 g, 5.6 mmol), copper (I) acetate (0.794 g, 6.47 mmol) in dimethoxyethane (35 mL) were added tris(dibenzylideneacetone)dipalladium(0) 0.289 g, 0.315 mmol) and triethyl phosphite (0.170 mg, 1.0 mmol) and the mixture was refluxed for 16 h. The mixture was then concentrated under reduced pressure and the residue was chromatographed (hexane-EtOAc 1:1) to afford 550 mg (62% yield) of the title compound. $^1$H NMR (300 MHz, $CDCl_3$) δ ppm 0.96 (t, J=7.3 Hz, 3 H), 1.29-1.50 (m, 2 H), 1.60-1.75 (m, 11 H), 2.75-2.93 (m, 2 H), 3.92 (s, 3 H), 6.94 (d, J=8.8 Hz, 1 H), 7.37 (dd, J=8.8, 2.7 Hz, 1 H), 7.47 (d, J=2.7 Hz, 1 H), 8.06 (s, 1 H). MS ($DCI/NH_3$) m/z 405 $(M+H)^+$. Anal. calculated for $C_{20}H_{25}ClN_4OS$: C, 59.32; H, 6.22; N, 13.84. Found: C, 59.10; H, 5.85; N, 13.27

Example 111

N-[(5Z)-4-butyl-2-tert-butylisothiazol-5(2H)-ylidene]-5-chloro-2-methoxybenzenecarbothioamide To a solution of Example 1D (380 mg, 1 mmol) in toluene (25 mL) was added $P_2S_5$ (220 mg, 1 mmol) and the reaction mixture was heated at 82° C. for 75 minutes, concentrated under reduced pressure and purified via column chromatography ($SiO_2$, 0-25% EtOAc in hexanes) to provide the title compound (0.14 g, 34% yield). $^1$H NMR (300 MHz, $CDCl_3$) δ ppm 0.95 (t, J=7.3 Hz, 3 H), 1.40 (dd, J=15.1, 7.5 Hz, 2 H), 1.61-1.78 (m, 11 H), 2.84-3.00 (m, 2 H), 3.84 (s, 3 H), 6.90 (d, J=8.7 Hz, 1 H), 7.27-7.35 (m, 1 H), 7.66 (d, J=2.8 Hz, 1 H), 8.13 (s, 1 H). MS ($DCI/NH_3$) m/z 398 $(M+H)^+$.

Example 112

N-[(3Z)-1-tert-butyl-5-(trifluoromethyl)-4,5,6,7-tetrahydro-2,1-benzisothiazol-3(1H)-ylidene]-5-chloro-2-methoxybenzamide The title compound was prepared using the procedure as described in Example 9, substituting 4-(trifluoromethyl)cyclohexanone for 4-propylcyclohexanone. $^1$H NMR (300 MHz, $CDCl_3$) δ ppm 1.74 (s, 9 H), 1.78-2.03 (m, 1 H), 2.33 (dd, J=7.8, 2.4 Hz, 1 H), 2.40-2.63 (m, 1 H), 2.74-2.99 (m, 2 H), 3.16-3.47 (m, 2 H), 3.84-3.97 (m, 3 H), 6.84-7.04 (m, 1 H), 7.34 (dd, J=8.8, 2.7 Hz, 1 H), 8.07 (d, J=2.7 Hz, 1 H). MS ($DCI/NH_3$) m/z 447 $(M+H)^+$. Anal. calculated for $C_{20}H_{22}ClF_3N_2O_2S$: C, 53.75; H, 4.96; N, 6.27. Found: C, 53.71; H, 4.81; N, 6.25.

Example 113

Tert-butyl (3Z)-1-tert-butyl-3-[5-chloro-2-methoxybenzoyl)imino]-1,4,6,7-tetrahydroisothiazolo[4,3-c]pyridine-5(3H)-carboxylate The title compound was prepared using the procedure as described in Example 9, substituting commercially available tert-butyl 4-oxopiperidine-1-carboxylate for 4-propylcyclohexanone. $^1$H NMR (300 MHz, $CDCl_3$) δ ppm 1.45-1.60 (m, 9 H), 1.73 (s, 9 H), 3.03 (t, J=5.6 Hz, 2 H), 3.76 (t, J=5.8 Hz, 2 H), 3.91 (s, 3 H), 4.72 (s, 2 H), 6.91 (d, J=8.8 Hz, 1 H), 7.34 (dd, J=8.8, 2.7 Hz, 1 H), 8.09 (s, 1 H). MS ($DCI/NH_3$) m/z 481

(M+H)⁺. Anal. calculated for $C_{23}H_{30}ClN_3O_4S$: C, 57.55; H, 6.30; N, 8.75. Found: C, 57.41; H, 6.37; N, 8.64

Example 114

N-[(3Z)-1-tert-butyl-4,5,6,7-tetrahydroisothiazolo[4,3-c]pyridin-3(1H)-ylidene]-5-chloro-2-methoxybenzamide Example 113 (800 mg, 1.66 mmol) in $CH_2Cl_2$ (10 mL) was treated with TFA (1.5 mL) and the reaction mixture was stirred at room temperature for 24 hours. The reaction mixture was concentrated under reduced pressure and the residue was partitioned between saturated $NaHCO_3$/EtOAc, organics were dried ($MgSO_4$), filtered and solvent evaporated. The crude was flash chromatographed on silica gel, eluting with 0-20% methanol in $CH_2Cl_2$ to provide 600 mg of the title compound. ¹H NMR (300 MHz, DMSO-d₆) δ ppm 1.69 (s, 9 H), 2.34-2.51 (m, 2 H), 2.97 (s, 2 H), 3.78 (s, 3 H), 3.85 (s, 2 H), 7.11 (d, J=9.2 Hz, 1 H), 7.45 (dd, J=8.8, 2.7 Hz, 1 H), 7.69 (d, J=2.7 Hz, 1 H). MS (DCI/NH₃) m/z 380 (M+H)⁺.

Example 115

N-[(5Z)-4-butyl-2-tert-butylisothiazol-5(2H)-ylidene]-5-chloro-2-methoxybenzenesulfonamide Example 110B (294 mg, 1.4 mmol) in $CH_2Cl_2$ (20 mL) was treated with triethylamine (0.193 mL, 1.4 mmol) and commercially available 5-chloro-2-methoxybenzene-1-sulfonyl chloride (334 mg, 1.4 mmol). The reaction mixture was stirred at room temperature for 18 hours, partitioned between $CH_2Cl_2$ and saturated $NaHCO_3$, dried ($MgSO_4$) and concentrated. The residue was purified by flash chromatography with 0-60% EtOAc in hexane to give the title compound (320 mg, 55%) ¹H NMR (300 MHz, DMSO-d₆) δ ppm 0.80 (t, J=7.3 Hz, 3 H), 1.11-1.29 (m, 2 H), 1.32-1.52 (m, 2 H), 1.57 (s, 9 H), 2.29-2.43 (m, 2 H), 3.65 (s, 3 H), 7.18 (d, J=8.8 Hz, 1 H), 7.58 (dd, J=8.8, 2.7 Hz, 1 H), 7.71 (d, J=2.7 Hz, 1 H), 8.46 (s, 1 H). MS (DCI/NH₃) m/z 417 (M+H)⁺.

Example 116

N-[(5Z)-4-butyl-2-tert-butylisothiazol-5(2H)-ylidene]naphthalene-1-sulfonamide

The title compound was prepared using the procedure as described in Example 115, substituting 5-chloro-2-methoxybenzene-1-sulfonyl chloride with naphthalene-1-sulfonyl chloride. ¹H NMR (300 MHz, CDCl₃) δ ppm 0.78 (t, J=7.3 Hz, 3 H), 1.12-1.32 (m, 2 H), 1.33-1.51 (m, 2 H), 1.56 (s, 9 H), 2.36-2.52 (m, 2 H), 7.39-7.71 (m, 4 H), 7.86 (d, J=8.7 Hz, 1 H), 7.96 (d, J=8.3 Hz, 1 H), 8.25 (d, J=7.5 Hz, 1 H), 8.90 (d, J=8.7 Hz, 1 H)). MS (DCI/NH₃) m/z 403 (M+H)⁺. Anal. calculated for $C_{21}H_{26}N_2O_2S_2$: C, 62.65; H, 6.51; N, 6.96. Found: C, 62.45, H, 6.44; N, 6.91.

Example 117

N-[(5Z)-4-butyl-2-tert-butylisothiazol-5(2H)-ylidene]-5-(dimethylamino)naphthalene-1-sulfonamide The title compound was prepared using the procedure as described in Example 115, substituting 5-chloro-2-methoxybenzene-1-sulfonyl chloride with 5-(dimethylamino)naphthalene-1-sulfonyl chloride. ¹H NMR (300 MHz, CDCl₃) δ ppm 0.80 (t, J=7.1 Hz, 3 H), 1.15-1.33 (m, 2 H), 1.33-1.52 (m, 2 H), 1.52-1.64 (m, 9 H), 2.36-2.53 (m, 2 H), 2.85 (s, 6 H), 7.14 (d, J=7.8 Hz, 1 H), 7.38-7.58 (m, 2 H), 7.61 (s, 1 H), 8.25 (dd, J=7.1, 1.4 Hz, 1 H), 8.43 (d, J=8.5 Hz, 1 H), 8.57 (d, J=8.8 Hz, 1 H). MS (DCI/NH₃) m/z 446 (M+H)⁺. Anal. calculated for $C_{23}H_{31}N_3O_2S_2$: C, 61.99; H, 7.01; N, 9.43. Found: C, 61.94; H, 7.04; N, 9.34

Example 118

N-[(5Z)-4-butyl-2-tert-butylisothiazol-5(2H)-ylidene]cyclohexanesulfonamide

The title compound was prepared using the procedure described in Example 115, substituting 5-chloro-2-methoxybenzene-1-sulfonyl chloride with cyclohexanesulfonyl chloride. ¹H NMR (300 MHz, CDCl₃) δ ppm 0.82-1.00 (m, 3 H), 1.20-1.52 (m, 16 H), 1.66-1.82 (m, 1 H), 1.89-2.29 (m, 8 H), 6.94 (d, J=14.2 Hz, 1 H), 9.61 (s, 1 H). MS (DCI/NH₃) m/z 359 (M+H)⁺. Anal. calculated for $C_{17}H_{30}N_2O_2S_2$: C, 56.94; H, 8.43; N, 7.81. Found: C, 56.55; H, 8.22; N, 7.49.

Example 119

N-[(5Z)-4-butyl-2-tert-butylisothiazol-5(2H)-ylidene]benzenesulfonamide

The title compound was prepared using the procedure as described in Example 115, substituting 5-chloro-2-methoxybenzene-1-sulfonyl chloride with benzenesulfonyl chloride. ¹H NMR (300 MHz, CDCl₃) δ ppm 0.87 (t, J=7.3 Hz, 3 H), 1.20-1.39 (m, 2 H), 1.43-1.63 (m, 11 H), 2.37-2.53 (m, 2 H), 7.37-7.54 (m, 4 H), 7.63 (s, 1 H), 7.93 (dd, J=8.1, 1.7 Hz, 1 H). MS (DCI/NH₃) m/z 353 (M+H)⁺. Anal. calculated for $C_{17}H_{24}N_2O_2S_2$: C, 57.92; H, 6.86; N, 7.95. Found: C, 57.61; H, 6.82; N, 8.0;

Example 120

N-[(5Z)-4-butyl-2-tert-butylisothiazol-5(2H)-ylidene]quinoline-8-sulfonamide

The title compound was prepared using the procedure as described in Example 115, substituting 5-chloro-2-methoxybenzene-1-sulfonyl chloride with quinoline-8-sulfonyl chloride. ¹H NMR (300 MHz, CDCl₃) δ ppm 0.64-0.79 (m, 3 H), 1.09-1.30 (m, 2 H), 1.32-1.49 (m, 2 H), 1.59-1.69 (m, 9 H), 2.37-2.52 (m, 2 H), 7.40 (dd, J=8.5, 4.1 Hz, 1 H), 7.51-7.62 (m, 1 H), 7.65 (s, 1 H), 7.93 (dd, J=8.1, 1.4 Hz, 1 H), 8.16 (dd, J=8.3, 1.9 Hz, 1 H), 8.55 (dd, J=7.5, 1.4 Hz, 1 H), 8.88 (dd, J=4.2, 1.9 Hz, 1 H). MS (DCI/NH₃) m/z 404 (M+H)⁺. Anal. calculated for $C_{20}H_{25}N_3O_2S_2$: C, 59.52; H, 6.24; N, 10.41. Found: C, 59.59; H, 6.35; N, 10.08.

Example 121

N-[(5Z)-4-butyl-2-tert-butylisothiazol-5(2H)-ylidene]-2,2,3,3-tetramethylcyclopropanecarboxamide The title compound was prepared using the procedure as described in Example 115, substituting 5-chloro-2-methoxybenzene-1-sulfonyl chloride with 2,2,3,3-tetramethylcyclopropanecarbonyl chloride. ¹H NMR (300 MHz, CDCl₃) δ ppm 0.88-1.05 (m, 3 H), 1.19-1.28 (m, 6 H), 1.31-1.50 (m, 8 H), 1.54-1.72 (m, 12 H), 2.66-2.82 (m, 2 H), 7.82 (s, 1 H). MS (DCI/NH$_3$) m/z 337 (M+H)$^+$. Anal. calculated for C$_{19}$H$_{32}$N$_2$OS: C, 67.81; H, 9.58; N, 8.32. Found: C, 67.73; H, 9.59; N, 8.45.

Example 122

N-[(5Z)-4-butyl-2-tert-butylisothiazol-5(2H)-ylidene]-2,3-dichlorobenzenesulfonamide The title compound was prepared using the procedure as described in Example 115, substituting 5-chloro-2-methoxybenzene-1-sulfonyl chloride with 2,3-dichlorobenzene-1-sulfonyl chloride. $^1$H NMR (300 MHz, CDCl$_3$) δ ppm 0.88 (t, J=7.3 Hz, 3 H), 1.18-1.40 (m, 2 H), 1.46-1.57 (m, 2 H), 1.57-1.65 (m, 9 H), 2.41-2.56 (m, 2 H), 7.28-7.36 (m, 1 H), 7.58 (dd, J=8.3, 1.6 Hz, 1 H), 7.69 (s, 1 H), 8.16 (dd, J=7.9, 1.6 Hz, 1 H). MS (DCI/NH$_3$) m/z 422 (M+H)$^+$. Anal. calculated for C$_{17}$H$_{22}$N$_2$Cl$_2$O$_2$S$_2$: C, 48.45; H, 5.26; N, 6.65. Found: C, 48.67; H, 5.35; N, 6.56.

Example 123

N-[(5Z)-4-butyl-2-tert-butylisothiazol-5(2H)-ylidene]adamantane-1-carboxamide

The title compound was prepared using the procedure as described in Example 115, substituting 5-chloro-2-methoxybenzene-1-sulfonyl chloride with 1-adamantanecarbonyl-chloride. $^1$H NMR (300 MHz, CDCl$_3$) δ ppm 0.96 (t, J=7.3 Hz, 3 H), 1.29-1.48 (m, 2 H), 1.60 (s, 9 H), 1.62-1.72 (m, 2 H), 1.76 (s, 6 H), 2.04 (s, 9 H), 2.71-2.81 (m, 2 H), 7.85 (s, 1 H). MS (DCI/NH$_3$) m/z 375 (M+H)$^+$. Anal. calculated for C$_{22}$H$_{34}$N$_2$OS: C, 70.54; H, 9.15; N, 7.48. Found: C, 70.51; H, 9.21; N, 8.06.

Example 124

N-[(5Z)-4-butyl-2-tert-butylisothiazol-5(2H)-ylidene]-N'-cyano-2-methoxy-5-(trifluoromethyl)benzenecarboximidamide The title compound was prepared using the procedure as described in Example 110D, substituting 2-methoxy-5-chlorophenylboronic acid with 2-methoxy-5-trifluoromethylphenylboronic acid. $^1$H NMR (300 MHz, CDCl$_3$) δ ppm 0.96 (t, J=7.3 Hz, 3 H), 1.31-1.51 (m, 2 H), 1.58-1.76 (m, 11 H), 2.75-2.91 (m, 2 H), 3.99 (s, 3 H), 7.08 (d, J=8.8 Hz, 1 H), 7.68 (dd, J=8.8, 1.7 Hz, 1 H), 7.77 (d, J=2.4 Hz, 1 H), 8.07 (s, 1 H). MS (DCI/NH$_3$) m/z 439 (M+H)$^+$. Anal. calculated for C$_{21}$H$_{25}$F$_3$N$_4$OS: C, 57.52; H, 5.75; N, 12.78. Found: C, 57.44; H, 5.22; N, 12.84.

Example 125

N-[(5Z)-4-butyl-2-tert-butylisothiazol-5(2H)-ylidene]-2,2-dimethyl-4-oxo-3,4-dihydro-2H-pyran-6-carboxamide The title compound was prepared using the procedure as described in Example 115, substituting 5-chloro-2-methoxybenzene-1-sulfonyl chloride with 2,2-dimethyl-4-oxo-3,4-dihydro-2H-pyran-6-carbonyl chloride. $^1$H NMR (300 MHz, DMSO-d$_6$) δ ppm 0.88-0.98 (m, 3 H), 1.22-1.38 (m, 1.38-1.46 (m, 6 H), 1.55-1.70 (m, 11 H), 2.57 (s, 2 H), 2.65-2.77 (m, 2 H), 6.24 (s, 1 H), 8.73 (s, 1 H). MS (DCI/NH$_3$) m/z 365 (M+H)$^+$.

Example 126

N-[(5Z)-4-butyl-2-tert-butylisothiazol-5(2H)-ylidene]-N'-cyano-2-ethoxy-5-(trifluoromethyl)benzenecarboximidamide The title compound was prepared using the procedure as described in Example 110D, substituting 2-methoxy-5-chlorophenylboronic acid with 2-ethoxy-5-trifluoromethylphenylboronic acid. $^1$H NMR (300 MHz, CDCl$_3$) δ ppm 0.96 (t, J=7.3 Hz, 3 H), 1.33-1.46 (m, 2 H), 1.46-1.55 (m, 3 H), 1.60-1.78 (m, 11 H), 2.74-2.92 (m, 2 H), 4.23 (q, J=7.0 Hz, 2 H), 7.05 (d, J=8.7 Hz, 1 H), 7.65 (dd, J=9.1, 2.0 Hz, 1 H), 7.77 (d, J=2.4 Hz, 1 H), 8.07 (s, 1 H)). MS (DCI/NH$_3$) m/z 453 (M+H)$^+$. Anal. calculated for C$_{22}$H$_{27}$F$_3$N$_4$OS: C, 58.39; H, 6.01; N, 12.38. Found: C, 58.04; H, 5.84; N, 12.26.

Example 127

N-[(5Z)-4-butyl-2-tert-butylisothiazol-5(2H)-ylidene]-2-methoxy-5-(trifluoromethyl)benzamide To a solution of Example 110B (1.0 g, 4.7 mmol) in THF (50 mL) were added 2-methoxy-5-(trifluoromethyl)benzoic acid (1.1 g, 5.2 mmol, JRD Fluorochemicals Ltd), N-(3-dimethylaminopropyl)-N-ethylcarbodimide hydrochloride (1.0 g, 5.2 mmol, Aldrich), 1-hydroxybenzotriazole (0.8 g, 5.2 mmol, Aldrich) and triethylamine (2.0 mL, 14.3 mmol, Aldrich). The mixture was stirred at 60° C. for 12 hr. The reaction mixture was then cooled to room temperature, diluted with 1 M aqueous NaHCO$_3$ (50 mL) and extracted with ethyl acetate (2×50 mL). The combined organic extracts were dried (Na$_2$SO$_4$), filtered and concentrated. The residue was purified by column chromatography using an Analogix® Intelliflash280™ (SiO$_2$, 0-50% ethyl acetate in hexanes) to afford 1.23 g (63%) of the title compound. $^1$H NMR (300 MHz, DMSO-d$_6$) δ ppm 0.93 (t, J=7.3 Hz, 3 H), 1.17-1.45 (m, 2 H), 1.62 (s, 9 H), 1.64-1.73 (m, 2 H), 2.64-2.80 (m, 2 H), 3.88 (s, 3 H), 7.30 (d, J=8.7 Hz, 1 H), 7.80 (dd, J=8.3, 2.8 Hz, 1 H), 8.08 (d, J=2.4 Hz, 1 H), 8.64 (s, 1 H); MS (ESI+) m/z 415 (M+H)$^+$; Anal. Calculated C$_{20}$H$_{25}$F$_3$N$_2$O$_2$S: C, 57.95; H, 6.08; N, 6.76. Found: C, 57.82; H, 5.92; N, 7.07.

Example 128

N-[(5Z)-2-tert-butyl-4-(3-cyanopropyl)isothiazol-5(2H)-ylidene]-5-chloro-N'-cyano-2-methoxybenzenecarboximidamide

Example 128A

Ethyl [(5Z)-2-tert-butyl-4-(3-cyanopropyl)isothiazol-5(2H)-ylidene]carbamate

Example 30A, 2-methylpropan-2-amine (Aldrich), O-ethyl carbonisothiocyanatidate (Aldrich) and iodine (EMD chemicals) were processed using the method described in Example 110A to afford the title compound. MS (ESI$^+$) m/z 296 (M+H)$^+$.

Example 128B 4-(2-tert-butyl-5-imino-2,5-dihydroisothiazol-4-yl)butanenitrile Example 128A and iodotrimethylsilane (Aldrich) were processed using the method described in Example 110B to afford the title compound. MS (ESI$^+$) m/z 224 (M+H)$^+$.

Example 128C

Ethyl 5-chloro-2-methoxybenzimidate hydrochloride

A cooled solution of 5-chloro-2-methoxybenzonitrile (9.3 g, 0.056 mol, Maybridge) and ethanol (16.2 mL, 0.28 mol) in $CH_2Cl_2$ (40 mL) was bubbled with HCl gas at 0° C. for 30 min. The reaction mixture was kept in refrigerator for 5 days. The reaction mixture was then concentrated and triturated with diethyl ether to remove unreacted starting material. The precipitate was dried under reduced pressure to obtain 7.1 g (51%) of the title compound. MS (ESI$^+$) m/z 214 (M+H)$^+$.

Example 128D

Ethyl 5-chloro-N-cyano-2-methoxybenzimidate

A solution of ethyl 5-chloro-2-methoxybenzimidate (1.3 g, 6.2 mmol, obtained after aqueous bicarbonate wash of Example 128C) in MeCN (2 mL) was added to a solution of sodium phosphate monobasic monohydrate (3.4 g, 24.7 mmol), sodium phosphate dibasic heptahydrate (3.3 g, 12.4 mmol) and cyanamide (0.52 g, 12.4 mmol) in water (20 mL). The reaction mixture was stirred at room temperature overnight and then extracted with dichloromethane (3×15 mL). The combined organic extracts were dried ($Na_2SO_4$), filtered and concentrated. The residue contained about 30% of starting material. The residue was reprocessed with half the amounts of the reagents to drive the reaction to completion and that yielded 1.32 g (90%) of the title compound. MS (ESI$^+$) m/z 239 (M+H)$^+$.

Example 128E

N-[(5Z)-2-tert-butyl-4-(3-cyanopropyl)isothiazol-5 (2H)-ylidene]-5-chloro-N'-cyano-2-methoxybenzenecarboximidamide A mixture of Example 128B (0.2 g, 0.9 mmol, crude), Example 128D (0.25 g, 1.0 mmol), and triethylamine (0.25 mL, 1.8 mmol) in ethanol (1 mL) was heated in a 20 mL scintillation vial at 80° C. for 2 hr. The reaction mixture was cooled to room temperature, concentrated and then diluted with saturated $NaHCO_3$ (10 mL). The aqueous layer was extracted with ethyl acetate (3×15 mL). The combined organic extracts were dried ($Na_2SO_4$), filtered and concentrated. The residue was purified by column chromatography using an Analogix® Intelliflash280™ ($SiO_2$, 0-50% ethyl acetate in dichloromethane) to afford 115 mg (15%) of the title compound. $^1$H NMR (300 MHz, DMSO-d$_6$) δ ppm 1.67 (s, 9 H), 1.83-2.07 (m, 2 H), 2.49-2.58 (m, 2 H), 2.77-2.90 (m, 2 H), 3.82 (s, 3 H), 7.22 (d, J=8.8 Hz, 1 H), 7.38 (d, J=2.7 Hz, 1 H), 7.54 (dd, J=8.8, 2.7 Hz, 1 H), 8.92 (s, 1 H); MS (ESI$^+$) m/z 416 (M+H)$^+$; Anal. Calculated $C_{20}H_{22}ClN_5OS$: C, 57.75; H, 5.33; N, 16.84. Found: C, 57.59; H, 5.13; N, 16.38.

Example 129

N-[(5Z)-4-butyl-2-tert-butylisothiazol-5(2H)-ylidene]-5-cyano-2-hydroxybenzamide The title compound was obtained as a byproduct from Example 130B. $^1$H NMR (300 MHz, DMSO-d$_6$) δ ppm 0.83-1.11 (m, 3 H), 1.22-1.51 (m, 2 H), 1.56-1.74 (m, 2 H), 1.66 (s, 9 H), 2.63-2.79 (m, 2 H), 7.08 (d, J=8.8 Hz, 1 H), 7.82 (dd, J=8.6, 2.2 Hz, 1 H), 8.24 (d, J=2.4 Hz, 1 H), 8.87 (s, 1 H), 14.99 (s, 1 H); MS (ESI$^+$) m/z 358 (M+H)$^+$.

Example 130

N-[(5Z)-4-butyl-2-tert-butylisothiazol-5(2H)-ylidene]-5-cyano-2-(2,2,2-trifluoroethoxy)benzamide

Example 130A

5-cyano-2-(2,2,2-trifluoroethoxy)benzoic acid

To a refluxing mixture of acetone (20 mL), methyl 5-cyano-2-hydroxybenzoate (2.0 g, 11.3 mmol, Astatech) and potassium carbonate (3.1 g, 22.6 mmol) in a 40 mL sealed vial was added dropwise 2,2,2-trifluoroethyl trifluoromethanesulfonate (3.9 g, 16.9 mmol, TCI). The mixture was stirred at reflux overnight and then concentrated under reduced pressure. The residue was dissolved in water (50 mL) and dichloromethane (50 mL). The layers were separated and the aqueous layer was extracted with dichloromethane (3×50 mL). The combined organic extracts were dried ($Na_2SO_4$), filtered and concentrated to afford 1.8 g of crude methyl 5-cyano-2-(2,2,2-trifluoroethoxy)benzoate that was suspended in methanol/water (1:1, 100 mL) and treated with an aqueous solution of 5N sodium hydroxide (2.8 mL, 13.9 mmol). After stirring at 40° C. for 16 h, the reaction mixture was concentrated and then washed with methylene chloride. The aqueous layer was acidified to pH~2 with aqueous 2N HCl solution to precipitate the product. The precipitate was filtered and dried under reduced pressure to afford 1.1 g of a product mixture of the title compound with unreacted 5-cyano-2-hydroxybenzoic acid (5:2 ratio). MS (ESI$^+$) m/z 263 (M+NH$_4$)$^+$.

Example 130B

N-[(5Z)-4-butyl-2-tert-butylisothiazol-5(2H)-ylidene]-5-cyano-2-(2,2,2-trifluoroethoxy)benzamide Example 130A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.91 (t, 3 H), 1.20-1.47 (m, 2 H), 1.53-1.72 (m, 2 H), 1.63 (s, 9 H), 2.57-2.85 (m, 2 H), 4.94 (q, J=8.9 Hz, 2 H), 7.40 (d, J=8.7 Hz, 1 H), 7.97 (dd, J=8.7, 2.4 Hz, 1 H), 8.17 (d, J=2.0 Hz, 1 H), 8.67 (s, 1 H); MS (ESI$^+$) m/z 440 (M+H)$^+$.

Example 131

N-[(5Z)-2-tert-butyl-4-(3-cyanopropyl)isothiazol-5 (2H)-ylidene]-5-cyano-2-(2,2,2-trifluoroethoxy)benzamide Example 128B, Example 130A, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.90-2.04 (m, 2 H), 2.52-2.57 (m, 2 H), 2.76-2.87 (m, 2 H), 4.94 (q, J=8.8 Hz, 2 H), 7.40 (d, J=8.8 Hz, 1 H), 7.97 (dd, J=8.6, 2.2 Hz, 1 H), 8.21 (d, J=2.0 Hz, 1 H), 8.71 (s, 1 H); MS (ESI$^+$) m/z 451 (M+H)$^+$; Anal. Calculated $C_{21}H_{21}F_3N_4O_2S$: C, 55.99; H, 4.70; N, 12.44. Found: C, 56.15; H, 4.83; N, 12.25.

Example 132

N-[(5Z)-2-tert-butyl-4-(3-cyanopropyl)isothiazol-5(2H)-ylidene]-5-cyano-2-hydroxybenzamide The title compound was obtained as byproduct for Example 131. $^1$H NMR (300 MHz, DMSO-$d_6$) δ ppm 1.67 (s, 9 H), 1.92-2.12 (m, 2 H), 2.58 (t, J=7.1 Hz, 2 H), 2.77-2.91 (m, 2 H), 7.09 (d, J=8.8 Hz, 1 H), 7.82 (dd, J=8.6, 2.2 Hz, 1 H), 8.26 (d, J=2.0 Hz, 1 H), 8.88 (s, 1 H), 14.75 (s, 1 H); MS (ESI$^+$) m/z 369 (M+H)$^+$; Anal. Calculated $C_{19}H_{20}N_4O_2S$: C, 61.94; H, 5.47; N, 15.21. Found: C, 61.49; H, 5.40; N, 14.87.

Example 133

N-[(5Z)-2-tert-butyl-4-(3-cyanopropyl)isothiazol-5(2H)-ylidene]-5-chloro-2-(2,2,2-trifluoroethoxy)benzamide

Example 133A

5-chloro-2-(2,2,2-trifluoroethoxy)benzoic acid

Commercially available, methyl 5-chloro-2-hydroxybenzoate (Maybridge), potassium carbonate, 2,2,2-trifluoroethyl trifluoromethanesulfonate (TCI) and sodium hydroxide were processed according to the method of Example 130A to obtain the title compound. MS (ESI$^+$) m/z 253 (M–H)$^+$.

Example 133B

N-[(5Z)-2-tert-butyl-4-(3-cyanopropyl)isothiazol-5(2H)-ylidene]-5-chloro-2-(2,2,2-trifluoroethoxy)benzamide Example 128B, Example 133A, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 1.63 (s, 9 H), 1.90-2.14 (m, 2 H), 2.50-2.61 (m, 2 H), 2.76-2.91 (m, 2 H), 4.79 (q, J=9.0 Hz, 2 H), 7.25 (d, J=8.8 Hz, 1 H), 7.53 (dd, J=9.0, 2.9 Hz, 1 H), 7.85 (s, 1 H), 8.70 (s, 1 H); MS (ESI$^+$) m/z 460 (M+H)$^+$; Anal. Calculated $C_{20}H_{21}ClF_3N_3O_2S$: C, 52.23; H, 4.60; N, 9.14. Found: C, 51.97; H, 4.32; N, 8.74.

Example 134

N-[(5Z)-2-tert-butyl-4-(3-cyanopropyl)isothiazol-5(2H)-ylidene]-2-methoxy-5-(trifluoromethyl)benzamide Example 128B, 2-methoxy-5-(trifluoromethyl)benzoic acid (JRD fluorochemicals), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 1.63 (s, 9 H), 1.92-2.07 (m, 2 H), 2.55 (t, J=7.1 Hz, 2 H), 2.77-2.89 (m, 2 H), 3.79-3.95 (m, 3 H), 7.30 (d, J=8.5 Hz, 1 H), 7.80 (dd, J=9.0, 2.9 Hz, 1 H), 8.07 (d, J=2.0 Hz, 1 H), 8.69 (s, 1 H); MS (ESI$^+$) m/z 426 (M+H)$^+$; Anal. Calculated $C_{20}H_{22}F_3N_3O_2S$: C, 56.46; H, 5.21; N, 9.88. Found: C, 56.26; H, 5.15; N, 9.78.

Example 135

N-[(5Z)-4-butyl-2-tert-butylisothiazol-5(2H)-ylidene]-5-chloro-2-hydroxybenzamide Example 110B, 5-chloro-2-hydroxybenzoic acid (Aldrich), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-$d_6$) δ ppm 0.85-1.02 (m, 3 H), 1.26-1.49 (m, 2 H), 1.57-1.71 (m, 2 H), 1.65 (s, 9 H), 2.64-2.81 (m, 2 H), 6.96 (d, J=8.8 Hz, 1 H), 7.42 (dd, J=8.8, 2.7 Hz, 1 H), 7.84 (d, J=3.1 Hz, 1 H), 8.83 (s, 1 H), 13.92 (s, 1 H); LCMS (ESI$^+$) m/z 367 (M+H)$^+$.

Example 136

N-[(5Z)-2-tert-butyl-4-(cyclopentylmethyl)isothiazol-5(2H)-ylidene]-5-chloro-2-methoxybenzamide

Example 136A

3-cyclopentylpropanal

To $CH_2Cl_2$ (100 mL) at –78° C. were added oxalyl chloride (4.1 mL, 46.8 mmol, Aldrich) and dry DMSO (5.5 mL, 78.0 mmol, Aldrich), dropwise. After 5 min, 3-cyclopentylpropan-1-ol (5.0 g, 39.0 mmol, Aldrich) in 5 mL of $CH_2Cl_2$ was added. The mixture was stirred for an additional 0.5 hr at –78° C., and triethylamine (27.2 mL, 195.0 mmol) was added. The mixture was then allowed to warm to room temperature over 0.5 hr. After stirring for 3 hr, 100 mL of water was added. The phases were separated, and the aqueous phase was extracted with diethyl ether (3×100 mL). The combined organic extracts were washed successively with 50 mL of aqueous 1% HCl, 50 mL of water, 50 mL of aqueous 5% $NaHCO_3$ and 50 mL of saturated aqueous NaCl. The organic layer was dried ($MgSO_4$), filtered and concentrated to provide 4.1 g (83%) of the title compound. MS (ESI$^+$) m/z 144 (M+$NH_4$)$^+$.

Example 136B

N-[(5Z)-2-tert-butyl-4-(cyclopentylmethyl)isothiazol-5(2H)-ylidene]-5-chloro-2-methoxybenzamide Example 136A, 2-methylpropan-2-amine (Aldrich), Example 1C and iodine were processed using the method described in Example 110A to afford the title compound. $^1$H NMR (300 MHz, DMSO-$d_6$) δ ppm 1.13-1.36 (m, 2 H), 1.43-1.57 (m, 2 H), 1.53-1.71 (m, 2 H), 1.62 (s, 9 H), 2.17-2.38 (m, 1 H), 2.69 (d, J=7.5 Hz, 2 H), 3.79 (s, 3 H), 7.13 (d, J=8.7 Hz, 1 H), 7.47 (dd, J=8.9, 3.0 Hz, 1 H), 7.72 (d, J=2.8 Hz, 1 H), 8.64 (s, 1 H); MS (ESI$^+$) m/z 407 (M+H)$^+$; Anal. Calculated $C_{21}H_{27}ClN_2O_2S$: C, 61.98; H, 6.69; N, 6.88. Found: C, 61.55; H, 6.46; N, 6.88.

Example 137

N-[(5Z)-2-tert-butyl-4-(3-cyano-3-methylbutyl)isothiazol-5(2H)-ylidene]-5-chloro-2-methoxybenzamide

Example 137A

2,2-dimethyl-6-oxohexanenitrile

To a suspension of trimethylamine oxide (1.5 g, 19.6 mmol, Aldrich) in DMSO (10 mL) was added 6-bromo-2,2- dimethylhexanenitrile (0.84 mL, 4.9 mmol, Aldrich). After stirring at room temperature overnight, the reaction mixture was quenched with water (10 mL) and extracted with hexanes (4×10 mL). The combined organic extracts were washed with brine (20 mL), dried (NaSO$_4$), filtered and concentrated to afford 0.65 g (80% pure) of the title compound. MS (ESI$^+$) m/z 157 (M+NH$_4$)$^+$.

Example 137B

N-[(5Z)-2-tert-butyl-4-(3-cyano-3-methylbutyl) isothiazol-5(2H)-ylidene]-5-chloro-2-methoxybenzamide Example 137A, 2-methylpropan-2-amine (Aldrich), Example 1C and iodine were processed using the method described in Example 110A to afford the title compound. $^1$H NMR (300 MHz, DMSO-d$_6$) δ ppm 1.39 (s, 6 H), 1.62 (s, 9 H), 1.88-2.06 (m, 2 H), 2.80-2.91 (m, 2 H), 3.81 (s, 3 H), 7.14 (d, J=8.9 Hz, 1 H), 7.47 (dd, J=8.9, 2.8 Hz, 1 H), 7.84 (d, J=2.8 Hz, 1 H), 8.71 (s, 1 H); MS (ESI$^+$) m/z 420 (M+H)$^+$.

Example 138

N-[(5Z)-2-tert-butyl-4-(4-cyanobutyl)isothiazol-5 (2H)-ylidene]-5-chloro-2-methoxybenzamide Example 138A 7-oxoheptanenitrile 7-bromoheptanenitrile and trimethylamine oxide were processed using the method described in Example 137A to afford the title compound. MS (ESI$^+$) m/z 143 (M+NH$_4$)$^+$.

Example 138B

N-[(5Z)-2-tert-butyl-4-(4-cyanobutyl)isothiazol-5 (2H)-ylidene]-5-chloro-2-methoxybenzamide Example 138A, 2-methylpropan-2-amine (Aldrich), Example 1C and iodine were processed using the method described in Example 110A to afford the title compound. $^1$H NMR (300 MHz, DMSO-d$_6$) δ ppm 1.52-1.61 (m, 2 H), 1.62 (s, 9 H), 1.71-1.89 (m, 2 H), 2.55 (t, J=7.1 Hz, 2 H), 2.74 (t, J=7.4 Hz, 2 H), 3.80 (s, 3 H), 7.13 (d, J=8.9 Hz, 1 H), 7.47 (dd, J=8.9, 2.8 Hz, 1 H), 7.74 (d, J=2.8 Hz, 1 H), 8.65 (s, 1 H); MS (ESI$^+$) m/z 406 (M+H)$^+$.

Example 139

N-[(5Z)-4-butyl-2-tert-butylisothiazol-5(2H)-ylidene]-5-chloro-2-(2-fluoroethoxy)benzamide Example 139A 5-chloro-2-(2-fluoroethoxy)benzoic acid The title compound was obtained from 5-chloro-2-hydroxybenzoic acid (Aldrich) using the method described in Journal of Labelled Compounds & Radiopharmaceuticals (2001), 44(2), 127-139. MS (ESI$^+$) m/z 236 (M+NH$_4$)$^+$.

Example 139B

N-[(5Z)-4-butyl-2-tert-butylisothiazol-5(2H)-ylidene]-5-chloro-2-(2-fluoroethoxy)benzamide Example 139A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.80-1.00 (m, 3 H), 1.16-1.43 (m, 2 H), 1.52-1.72 (m, 2 H), 1.62 (s, 9 H), 2.62-2.84 (m, 2 H), 4.20-4.29 (m, 1 H), 4.30-4.41 (m, 1 H), 4.60-4.67 (m, 1 H), 4.75-4.83 (m, 1 H), 7.16 (d, J=8.7 Hz, 1 H), 7.47 (dd, J=8.7, 2.8 Hz, 1 H), 7.76 (d, J=2.8 Hz, 1 H), 8.63 (s, 1 H); MS (ESI$^+$) m/z 413 (M+H)$^+$; Anal. Calculated C$_{20}$H$_{26}$ClFN$_2$O$_2$S: C, 58.17; H, 6.35; N, 6.78. Found: C, 58.10; H, 6.24; N, 6.75.

Example 140

2-(2-amino-2-oxoethoxy)-N-[(5Z)-4-butyl-2-tert-butylisothiazol-5(2H)-ylidene]-5-chlorobenzamide Example 140A 2-(2-amino-2-oxoethoxy)-5-chlorobenzoic acid Commercially available, methyl 5-chloro-2-hydroxybenzoate (Maybridge), potassium carbonate, 2-chloroacetonitrile (Aldrich) and sodium hydroxide were processed according to the method described for Example 130A to obtain the title compound. MS (ESI$^+$) m/z 248 (M+H$_2$O)$^+$.

Example 140B 2-(2-amino-2-oxoethoxy)-N-[(5Z)-4-butyl-2-tert-butylisothiazol-5(2H)-ylidene]-5-chlorobenzamide Example 140A, Example 110B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.80-1.02 (m, 3 H), 1.21-1.44 (m, 2 H), 1.54-1.74 (m, 2 H), 1.63 (s, 9 H), 2.62-2.80 (m, 2 H), 4.59 (s, 2 H), 7.22 (d, J=8.8 Hz, 1 H), 7.50 (dd, J=8.8, 2.7 Hz, 1 H), 7.59 (s, 1 H), 7.88 (d, J=2.7 Hz, 1 H), 8.22 (s, 1 H), 8.68 (s, 1 H); MS (ESI$^+$) m/z 424 (M+H)$^+$.

Example 141

2-(2-amino-2-oxoethoxy)-N-[(5Z)-2-tert-butyl-4-(3-cyanopropyl)isothiazol-5(2H)-ylidene]-5-chlorobenzamide Example 140A, Example 128B, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.91-2.09 (m, 2 H), 2.54 (t, J=7.1 Hz, 2 H), 2.77-2.91 (m, 2 H), 4.59 (s, 2 H), 7.22 (d, J=8.8 Hz, 1 H), 7.51 (dd, J=9.0, 2.9 Hz, 1 H), 7.61 (s, 1 H), 7.90 (d, J=2.7 Hz, 1 H), 8.17 (s, 1 H), 8.73 (s, 1 H); LC/MS (ESI$^+$) m/z 435 (M+H)$^+$.

Example 142

N-[(5Z)-2-tert-butyl-4-(4,4,4-trifluorobutyl)isothiazol-5(2H)-ylidene]-5-chloro-2-methoxybenzamide Example 142A 6,6,6-trifluorohexanal Commercially available 6-bromo-1,1,1-trifluorohexane (Oakwood) and trimethylamine oxide were processed using the method described in example 137A to afford the title compound. MS (ESI⁺) m/z 154 (M+NH₄—H₂O)⁺.

Example 142B

N-[(5Z)-2-tert-butyl-4-(4,4,4-trifluorobutyl)isothiazol-5(2H)-ylidene]-5-chloro-2-methoxybenzamide Example 142A, 2-methylpropan-2-amine (Aldrich), Example 1C and iodine were processed using the method described in Example 110A to afford the title compound. ¹H NMR (300 MHz, DMSO-d₆) δ ppm 1.62 (s, 9 H), 1.81-2.06 (m, 2 H), 2.19-2.43 (m, 2 H), 2.79 (t, J=7.5 Hz, 2 H), 3.79 (s, 3 H), 7.13 (d, J=9.1 Hz, 1 H), 7.47 (dd, J=8.7, 2.8 Hz, 1 H), 7.75 (d, J=2.8 Hz, 1 H), 8.67 (s, 1 H); MS (ESI⁺) m/z 435 (M+H)⁺; Anal. Calculated C₁₉H₂₂ClF₃N₂O₂S: C, 52.47; H, 5.10; N, 6.44. Found: C, 52.35; H, 5.02; N, 6.44.

Example 143

N-[(5Z)-2-tert-butyl-4-isobutylisothiazol-5(2H)-ylidene]-2-methoxy-5-(trifluoromethyl)benzamide

Example 143A 4-methylpentanal

Commercially available 4-methylpentan-1-ol, oxalyl chloride, DMSO, and triethylamine were processed using the method described in Example 136A to afford the title compound. MS (ESI⁺) m/z 100 (M+NH₄—H₂O)⁺.

Example 143B

Ethyl [(5Z)-2-tert-butyl-4-(2-methylpropyl)isothiazol-5(2H)-ylidene]carbamate

Example 143A, 2-methylpropan-2-amine (Aldrich), O-ethyl carbonisothiocyanatidate (Aldrich) and iodine (EMD chemicals) were processed using the method described in Example 110A to afford the title compound. MS (ESI⁺) m/z 285 (M+H)⁺.

Example 143C 2-tert-butyl-4-isobutylisothiazol-5(2H)-imine

Example 143B and iodotrimethylsilane (Aldrich) were processed using the method described in Example 110B to afford the title compound. MS (ESI⁺) m/z 213 (M+H)⁺.

Example 143D

N-[(5Z)-2-tert-butyl-4-isobutylisothiazol-5(2H)-ylidene]-2-methoxy-5-(trifluoromethyl)benzamide Example 143C, 2-methoxy-5-(trifluoromethyl)benzoic acid (JRD fluorochemicals), N-(3-dimethylaminopropyl)-N-ethylcarbodimide hydrochloride, 1-hydroxybenzotriazole and triethylamine were processed using the method described in Example 127 to afford the title compound. ¹H NMR (300 MHz, DMSO-d₆) δ ppm 0.89 (d, J=6.3 Hz, 6 H), 1.63 (s, 9 H), 1.94-2.16 (m, 1 H), 2.59 (d, J=7.1 Hz, 2 H), 3.88 (s, 3 H), 7.30 (d, J=8.7 Hz, 1 H), 7.79 (dd, J=9.1, 2.0 Hz, 1 H), 8.06 (d, J=2.4 Hz, 1 H), 8.63 (s, 1 H); MS (ESI⁺) m/z 415 (M+H)⁺; Anal. Calculated C₂₀H₂₅F₃N₂O₂S: C, 57.95; H, 6.08; N, 6.76. Found: C, 58.04; H, 6.09; N, 6.79.

Example 144

N-[(5Z)-2-tert-butyl-4-isobutylisothiazol-5(2H)-ylidene]-5-chloro-2-(2-fluoroethoxy)benzamide Example 143C, Example 139A, N-(3-dimethylaminopropyl)-N-ethylcarbodimide hydrochloride, 1-hydroxybenzotriazole and triethylamine were processed using the method described in Example 127 to afford the title compound. ¹H NMR (300 MHz, DMSO-d₆) δ ppm 0.89 (d, J=6.7 Hz, 6 H), 1.63 (s, 9 H), 1.81-2.17 (m, 1 H), 2.60 (d, J=7.1 Hz, 2 H), 4.16-4.29 (m, 1 H), 4.31-4.45 (m, 1 H), 4.59-4.69 (m, 1 H), 4.75-4.87 (m, 1 H), 7.16 (d, J=8.7 Hz, 1 H), 7.47 (dd, J=8.7, 2.8 Hz, 1 H), 7.75 (d, J=2.8 Hz, 1 H), 8.62 (s, 1 H); MS (ESI⁺) m/z 413 (M+H)⁺; Anal. Calculated C₂₀H₂₆ClFN₂O₂S: C, 58.17; H, 6.35; N, 6.78. Found: C, 58.21; H, 6.44; N, 6.80.

Example 145

N-[(5Z)-2-tert-butyl-4-isobutylisothiazol-5(2H)-ylidene]-5-cyano-2-methoxybenzamide Example 143C, Example 26B, N-(3-dimethylaminopropyl)-N-ethylcarbodimide hydrochloride, 1-hydroxybenzotriazole and triethylamine were processed using the method described in Example 127 to afford the title compound. ¹H NMR (300 MHz, DMSO-d₆) δ ppm 0.89 (d, J=6.3 Hz, 6 H), 1.63 (s, 9 H), 1.91-2.19 (m, 1 H), 2.59 (d, J=7.1 Hz, 2 H), 3.88 (s, 3 H), 7.29 (d, J=8.7 Hz, 1 H), 7.91 (dd, J=8.7, 2.4 Hz, 1 H), 8.08 (d, J=2.4 Hz, 1 H), 8.64 (s, 1 H); MS (ESI⁺) m/z 372 (M+H)⁺; Anal. Calculated C₂₀H₂₅N₃O₂S: C, 64.66; H, 6.78; N, 11.31. Found: C, 64.64; H, 6.62; N, 11.18.

Example 146

N-[(5Z)-2-tert-butyl-4-isobutylisothiazol-5(2H)-ylidene]-2-ethoxy-5-(trifluoromethyl)benzamide

Example 146A

Ethyl 2-fluoro-5-(trifluoromethyl)benzoate

To a solution of 2-fluoro-5-(trifluoromethyl)benzoyl chloride (5.0 g, 22.0 mmol) in THF (25 mL) was added Et₃N (3.1 mL, 22.0 mmol) followed by EtOH (1.3 mL, 22.0 mmol). This mixture was stirred at ambient temperature for 1 h and quenched with saturated, aqueous NH₄Cl (10 mL). The layers were separated and the aqueous layer was extracted with 3×10 mL EtOAc and the combined organics were dried over anhydrous Na₂SO₄, filtered and concentrated under reduced pressure. The crude material was purified by column chromatography (SiO₂, 60% hexanes in EtOAc) to give the title compound (4.8 g, 20.3 mmol, 92% yield). ¹H NMR (300 MHz, CDCl₃) δ ppm 1.42 (t, J=7.1 Hz, 3 H), 4.43 (q, J=7.1 Hz, 2 H), 7.23-7.34 (m, 1 H), 7.74-7.82 (m, 1 H), 8.23 (dd, J=6.3, 2.4 Hz, 1 H).

Example 146B

Ethyl 2-ethoxy-5-(trifluoromethyl)benzoate

To EtOH (2.5 mL, 42.7 mmol) in 25 mL THF was added KOt-Bu (4.6 g, 40.6 mmol). The mixture stirred at ambient temperature for 20 min then Example 146A in 25 mL THF was added via cannula. The mixture stirred for 1 h at ambient temperature then was quenched with saturated, aqueous NH$_4$Cl. The layers were separated the aqueous layer was extracted with 3×10 mL EtOAc. The combined organics were dried over Na$_2$SO$_4$, filtered and concentrated under reduced pressure. Purification via column chromatography (SiO$_2$, 60% hexanes in EtOAc then 100% EtOAc) gave the title compound. MS (DCI/NH$_3$) m/z 263 (M+H)$^+$.

Example 146C 2-ethoxy-5-(trifluoromethyl)benzoic acid

To a solution of Example 146B (1.63 g, 6.2 mmol) in EtOH (50 mL) was added 40% aqueous KOH (5.81 g, 31.1 mmol). The mixture was allowed to stir for 1 h then was partially concentrated under reduced pressure. The material was diluted with 20 mL EtOAc and the solution was acidified with 10% aqueous HCl. The layers were separated and the aqueous layer was extracted with EtOAc (3×20 mL). The combined organics were dried over Na$_2$SO$_4$, filtered and concentrated under reduced pressure to give the title compound (1.39 g, 5.94 mmol, 95% yield). MS (DCI/NH$_3$) m/z 252 (M+NH$_4$)$^+$.

Example 146D

N-[(5Z)-2-tert-butyl-4-isobutylisothiazol-5(2H)-ylidene]-2-ethoxy-5-(trifluoromethyl)benzamide Example 143C, Example 146C, N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 0.89 (d, J=6.3 Hz, 6 H), 1.35 (t, J=6.9 Hz, 3 H), 1.63 (s, 9 H), 1.94-2.19 (m, 1 H), 2.60 (d, J=7.1 Hz, 2 H), 4.18 (q, J=6.9 Hz, 2 H), 7.29 (d, J=8.7 Hz, 1 H), 7.76 (dd, J=9.1, 2.4 Hz, 1 H), 8.04 (d, J=2.4 Hz, 1 H), 8.63 (s, 1 H); MS (ESI$^+$) m/z 429 (M+H)$^+$; Anal. Calculated C$_{20}$H$_{27}$F$_3$N$_2$O$_2$S: C, 58.86; H, 6.35; N, 6.54. Found: C, 59.01; H, 6.38; N, 6.58.

Example 147

N-[(5Z)-2-tert-butyl-4-pentylisothiazol-5(2H)-ylidene]-5-chloro-2-methoxybenzamide Commercially available heptanal (Aldrich), 2-methylpropan-2-amine (Aldrich), Example 1C and iodine were processed using the method described in Example 110A to afford the title compound. $^1$H NMR (300 MHz, DMSO-d$_6$) δ ppm 0.80-0.98 (m, 3 H), 1.17-1.49 (m, 4 H), 1.62 (s, 9 H), 1.63-1.72 (m, 2 H), 2.62-2.89 (m, 2 H), 3.79 (s, 3 H), 7.13 (d, J=8.7 Hz, 1 H), 7.47 (dd, J=8.7, 2.8 Hz, 1 H), 7.75 (d, J=2.8 Hz, 1 H), 8.63 (s, 1 H); MS (ESI$^+$) m/z 395 (M+H)$^+$; Anal. Calculated C$_{20}$H$_{27}$ClN$_2$O$_2$S: C, 60.82; H, 6.89; N, 7.09. Found: C, 60.67; H, 6.96; N, 7.03.

Example 148

N-[(5Z)-2-tert-butyl-4-(4-fluorobutyl)isothiazol-5(2H)-ylidene]-5-chloro-2-methoxybenzamide

Example 148A 6-fluorohexanal

Commercially available, 1-bromo-6-fluorohexane (Narchem) and trimethylamine oxide were processed using the method described in example 137A to afford the title compound. MS (ESI$^+$) m/z 136 (M+NH$_4$)$^+$.

Example 148B

Ethyl [(5Z)-2-tert-butyl-4-(4-fluorobutyl)isothiazol-5(2H)-ylidene]carbamate

Example 148A, 2-methylpropan-2-amine (Aldrich), O-ethyl carbonisothiocyanatidate (Aldrich) and iodine were processed using the method described in Example 110A to afford the title compound. MS (ESI$^+$) m/z 303 (M+H)$^+$.

Example 148C 2-tert-butyl-4-(4-fluorobutyl)isothiazol-5(2H)-imine

Example 148B and iodotrimethylsilane (Aldrich) were processed using the method described in Example 110B to afford the title compound. MS (ESI$^+$) m/z 231 (M+H)$^+$.

Example 148D

N-[(5Z)-2-tert-butyl-4-(4-fluorobutyl)isothiazol-5(2H)-ylidene]-5-chloro-2-methoxybenzamide Example 148C, 5-chloro-2-methoxybenzoic acid (Aldrich), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.62 (s, 9 H), 1.68-1.86 (m, 4 H), 2.74 (t, J=7.3 Hz, 2 H), 3.79 (s, 3 H), 4.41 (t, J=5.9 Hz, 1 H), 4.50-4.64 (m, 1 H), 7.13 (d, J=9.1 Hz, 1 H), 7.47 (dd, J=8.7, 2.8 Hz, 1 H), 7.74 (d, J=2.8 Hz, 1 H), 8.65 (s, 1 H); MS (ESI$^+$) m/z 399 (M+H)$^+$; Anal. Calculated C$_{19}$H$_{24}$ClFN$_2$O$_2$S: C, 57.20; H, 6.06; N, 7.02. Found: C, 57.12; H, 6.11; N, 7.06.

Example 149

N-[(5Z)-2-tert-butyl-4-(4-fluorobutyl)isothiazol-5(2H)-ylidene]-2-methoxy-5-(trifluoromethyl)benzamide Example 148C, 2-methoxy-5-(trifluoromethyl)benzoic acid (JRD Fluorochemicals Ltd), N-(3-dimethylaminopropyl)-N-ethylcarbodimide hydrochloride, 1-hydroxybenzotriazole and triethylamine were processed using the method described in Example 127 to afford the title compound. $^1$H NMR (300 MHz, DMSO-d$_6$) δ ppm 1.63 (s, 9 H), 1.66-1.87 (m, 4 H), 2.75 (t, J=7.3 Hz, 2 H), 3.88 (s, 3 H), 4.41 (t, J=5.9 Hz, 1 H), 4.51-4.67 (m, 1 H), 7.30 (d, J=8.5 Hz, 1 H), 7.79 (dd, J=8.5, 3.1 Hz, 1 H), 8.07 (d, J=2.0 Hz, 1 H), 8.67 (s, 1 H); MS (ESI$^+$) m/z 433 (M+H)$^+$; Anal. Calculated C$_{20}$H$_{24}$F$_4$N$_2$O$_2$S: C, 55.54; H, 5.59; N, 6.48. Found: C, 55.87; H, 5.61; N, 6.49.

Example 150

N-[(5Z)-4-butyl-2-tert-butylisothiazol-5(2H)-ylidene]-5-chloro-2-[2-(dimethylamino)-2-oxoethoxy]benzamide To a mixture of 3-pentanone (10 mL), potassium carbonate (0.28 g, 2.0 mmol) and Example 135 (0.25 g, 0.7 mmol) was added dropwise 2-chloro-N,N-dimethylacetamide (0.25 g, 2.0 mmol, Fluka). After refluxing for 36 hr, the reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 50 mg (16%) of the title compound. $^1$H NMR (300 MHz, DMSO-d$_6$) δ ppm 0.92 (t, J=7.3 Hz, 3 H), 1.33 (t, 2 H), 1.62 (s, 9 H), 1.63-1.71 (m, 2 H), 2.66-2.76 (m, 2 H), 2.83 (s, 3 H), 3.00 (s, 3 H), 4.87 (s, 2 H), 6.98 (d, J=9.2 Hz, 1 H), 7.42 (dd, J=9.0, 2.9 Hz, 1 H), 7.76 (d, J=3.1 Hz, 1 H), 8.62 (s, 1 H); MS (ESI$^+$) m/z 452 (M+H)$^+$; Anal. Calculated C$_{22}$H$_{30}$ClN$_3$O$_3$S: C, 58.46; H, 6.69; N, 9.30. Found: C, 58.41; H, 6.83; N, 9.26.

Example 151

N-[(5Z)-4-butyl-2-(2,2,2-trifluoro-1,1-dimethylethyl) isothiazol-5(2H)-ylidene]-5-chloro-2-methoxybenzamide Example 151A Ethyl [(5Z)-4-butyl-2-(2,2,2-trifluoro-1,1-dimethylethyl)isothiazol-5(2H)-ylidene]carbamate Commercially available hexanal (Aldrich), 1,1,1-trifluoro-2-methylpropan-2-amine (Chemcollect), O-ethyl carbonisothiocyanatidate (Aldrich) and iodine were processed using the method described in Example 110A to afford the title compound. MS (ESI$^+$) m/z 339 (M+H)$^+$.

Example 151B 4-butyl-2-(1,1,1-trifluoro-2-methylpropan-2-yl) isothiazol-5(2H)-imine Example 151A and iodotrimethylsilane (Aldrich) were processed using the method described in Example 110B to afford the title compound. MS (ESI$^+$) m/z 267 (M+H)$^+$.

Example 151C

N-[(5Z)-4-butyl-2-(2,2,2-trifluoro-1,1-dimethylethyl) isothiazol-5(2H)-ylidene]-5-chloro-2-methoxybenzamide Example 151B, 5-chloro-2-methoxybenzoic acid (Aldrich), N-(3-dimethylaminopropyl)-N-ethylcarbodiimide hydrochloride, 1-hydroxybenzotriazole and triethylamine were processed using the method described in Example 127 to afford the title compound. $^1$H NMR (300 MHz, DMSO-d$_6$) δ ppm 0.76-1.03 (m, 3 H), 1.14-1.43 (m, 2 H), 1.57-1.76 (m, 2 H), 1.92 (s, 6 H), 2.65-2.85 (m, 2 H), 3.82 (s, 3 H), 7.16 (d, J=8.7 Hz, 1 H), 7.52 (dd, J=8.9, 3.0 Hz, 1 H), 7.84 (d, J=3.2 Hz, 1 H), 8.77 (s, 1 H); MS (ESI$^+$) m/z 435 (M+H)$^+$; Anal. Calculated C$_{19}$H$_{22}$ClF$_3$N$_2$O$_2$S: C, 52.47; H, 5.10; N, 6.44. Found: C, 52.71; H, 5.18; N, 6.50.

Example 152

N-[(5Z)-4-butyl-2-(2-fluoro-1,1-dimethylethyl) isothiazol-5(2H)-ylidene]-2-methoxy-5-(trifluoromethyl)benzamide Example 152A 1-fluoro-N-hexylidene-2-methylpropan-2-amine To a suspension of 1-fluoro-2-methylpropan-2-amine hydrochloride (ABCR) (2 g, 15.7 mmol), anhydrous magnesium sulfate (3.77 g, 31.4 mmol) and potassium carbonate (2.17 g, 15.68 mmol) in dichloromethane (100 mL) was added drop wise hexanal (1.93 mL, 15.7 mmol) at 0° C. The reaction mixture was stirred for 10 h at room temperature, then filtered and concentrated to obtain the title compound as a pale yellow liquid.

Example 152B

Ethyl [(5Z)-4-butyl-2-(2-fluoro-1,1-dimethylethyl) isothiazol-5(2H)-ylidene]carbamate Example 152A, O-ethyl carbonisothiocyanatidate (Aldrich) and iodine were processed using the method described in Example 1D to afford the title compound. The product was purified by column chromatography using an Analogix® Intelliflash280™ (SiO$_2$, 0-50% ethyl acetate in Hexane) to provide the title compound. MS (ESI+) m/z 303 (M+H)$^+$.

Example 152C 4-butyl-2-(1-fluoro-2-methylpropan-2-yl)isothiazol-5(2H)-imine

Example 152B and iodotrimethylsilane (Aldrich) were processed using the method described in Example 110B to afford the title compound. MS (ESI$^+$) m/z 231 (M+H)$^1$.

Example 152D

N-[(5Z)-4-butyl-2-(2-fluoro-1,1-dimethylethyl) isothiazol-5(2H)-ylidene]-2-methoxy-5-(trifluoromethyl)benzamide To a solution of Example 152C (0.46 g, 2.0 mmol) in THF (10 mL) were added 2-methoxy-5-(trifluoromethyl)benzoyl chloride (0.52 g, 2.2 mmol, JRD Fluorochemicals Ltd) and triethylamine (0.84 mL, 6.0 mmol). After stirring at 60° C. for 14 hr, the reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 75 mg of the title compound. $^1$H NMR (300 MHz, DMSO-d$_6$) δ ppm 0.93 (t, J=7.3 Hz, 3 H), 1.22-1.46 (m, 2 H), 1.65 (s, 2 H), 1.65 (s, 6 H), 2.63-2.83 (m, 2 H), 3.89 (s, 3 H), 4.60 (d, J=47.1 Hz, 2 H), 7.31 (d, J=8.8 Hz, 1 H), 7.80 (dd, J=8.6, 2.5 Hz, 1 H), 8.10 (d, J=2.4 Hz, 1 H), 8.63 (s, 1 H); MS (ESI$^+$) m/z 433 (M+H)$^+$; Anal. Calculated C$_{20}$H$_{24}$F$_4$N$_2$O$_2$S: C, 55.54; H, 5.59; N, 6.48. Found: C, 55.75; H, 5.23; N, 6.43.

Example 153

N-[(5Z)-4-butyl-2-tert-butylisothiazol-5(2H)-ylidene]-5-chloro-2-(cyanomethoxy)benzamide To a solution of Example 135 (300 mg, 0.82 mmol) in THF/DMF (1:1, 4 mL) were added sodium hydride (39.2 mg, 0.98 mmol) and 2-bromoacetonitrile (65 μl, 0.98 mmol). The reaction was stirred at 40° C. for 4 hrs and at 80° C. for overnight. The reaction mixture was cooled to room temperature, quenched with saturated NaHCO$_3$ (10 mL) and extracted with ethyl acetate (3×20 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 15 mg of the title compound. $^1$H NMR (300 MHz, DMSO-d$_6$) δ ppm 0.93 (t, J=7.3 Hz, 3 H), 1.20-1.48 (m, 2 H), 1.53-1.77 (m, 2 H), 1.63 (s, 9 H), 2.62-2.82 (m, 2 H), 5.22 (s, 2 H), 7.29 (d, J=9.1 Hz, 1H), 7.58 (dd, J=8.7, 2.8 Hz, 1 H), 7.86 (d, J=2.8 Hz, 1 H), 8.67 (s, 1 H); MS (ESI$^+$) m/z 406 (M+H)$^+$; Anal. Calculated C$_{20}$H$_{24}$ClN$_3$O$_2$S: C, 59.17; H, 5.96; N, 10.35. Found: C, 59.18; H, 5.78; N, 10.37.

Example 154

N-[(5Z)-4-butyl-2-(2-fluoro-1,1-dimethylethyl) isothiazol-5(2H)-ylidene]-5-chloro-2-methoxybenzamide The title compound was prepared using the procedure as described in Example 1D, substituting Example 152A for Example 1A. The product was purified by column chromatography using an Analogix® Intelliflash280™ (SiO$_2$, gradient 0-50% ethyl acetate in hexane) to provide the title compound. $^1$H NMR (400 MHz, CDCl$_3$) δ ppm 0.98 (t, J=7.4 Hz, 3 H), 1.36-1.48 (m, 2 H), 1.71 (s, 6 H), 1.70-1.78 (m, 2 H), 2.70-2.90 (m, 2 H), 3.92 (s, 3 H), 4.44 (d, J=47.3 Hz, 2 H), 6.92 (d, J=8.9 Hz, 1 H), 7.35 (dd, J=8.9, 3.1 Hz, 1 H), 8.00 (s, 1 H), 8.13 (d, J=3.1 Hz, 1 H). MS (ESI$^+$) m/z 399 (M+H)$^+$.

Example 155

N-[(5Z)-4-(benzyloxy)-2-tert-butylisothiazol-5(2H)-ylidene]-5-chloro-2-methoxybenzamide The title compound was prepared according to the procedure of Example 9 by replacing 4-propylcyclohexanone with 2-(benzyloxy)acetaldehyde. $^1$H NMR (300 MHz, DMSO-d$_6$) δ ppm 1.58 (s, 9 H), 3.80 (s, 3 H), 5.28 (s, 2 H), 7.14 (d, J=9.2 Hz, 1 H), 7.31-7.42 (m, 3 H), 7.44-7.54 (m, 3 H), 7.79 (d, J=2.7 Hz, 1 H), 8.73 (s, 1 H); MS (DCI/NH$_3$) m/z 431 (M+H)$^+$. Anal. calculated for C$_{22}$H$_{23}$ClN$_2$O$_3$S: C, 61.32; H, 5.38; N, 6.50. Found: C, 61.09; H, 5.43; N, 6.49.

Example 156

N-[(5Z)-2-tert-butyl-4-(1-methylethoxy)isothiazol-5 (2H)-ylidene]-5-chloro-2-methoxybenzamide

Example 156A

N-[(5Z)-2-tert-butyl-4-hydroxyisothiazol-5(2H)-ylidene]-5-chloro-2-methoxybenzamide A solution of Example 155 (500 mg, 1.16 mmol) in anhydrous CH$_2$Cl$_2$ (20 mL) was treated at 0° C. with triflic acid (1741 mg, 11.6 mmol) for 1 h. A saturated solution of sodium bicarbonate was added and the organic layer was separated, dried with anhydrous MgSO$_4$ and concentrated under reduced pressure to afford 400 mg of crude material, which was used directly without purification in the next reactions. $^1$H NMR (300 MHz, DMSO-d$_6$) δ 1.55-1.71 (m, 9 H), 3.77-3.87 (m, 3 H), 7.18 (d, J=9.1 Hz, 1 H), 7.54 (dd, J=8.9, 2.2 Hz, 1 H), 7.81 (d, J=2.4 Hz, 1 H), 8.65 (s, 1 H); MS (DCI/NH$_3$) m/z 341 (M+H)$^+$.

Example 156B

N-[(5Z)-2-tert-butyl-4-(1-methylethoxy)isothiazol-5 (2H)-ylidene]-5-chloro-2-methoxybenzamide A mixture of product from Step 1 (70 mg, 0.2 mmol), 2-iodopropane (85 mg, 0.5 mmol) and potassium carbonate (42 mg, 0.3 mmol) in DMF (10 mL) was stirred at 50° C. for 12 h. The mixture was then poured into water and extracted with ethyl acetate. The acetate layer was washed with water, brine, dried with MgSO$_4$ and concentrated under reduced pressure. The residue was purified by chromatography (hexane EtOAc 1:1) to afford 49 mg of the title compound. $^1$H NMR (300 MHz, DMSO-d$_6$) δ ppm 1.27 (d, J=6.1 Hz, 6 H), 1.61 (s, 9 H), 3.80 (s, 3 H), 4.62-4.89 (m, 1 H), 7.13 (d, J=8.8 Hz, 1 H), 7.47 (dd, J=8.8, 2.7 Hz, 1 H), 7.75 (d, J=2.7 Hz, 1 H), 8.70 (s, 1 H); MS (DCI/NH$_3$) m/z 383 (M+H)$^+$. Anal. calculated for C$_{18}$H$_{23}$ClN$_2$O$_3$S: C, 56.46; H, 6.05; N, 7.32. Found: C, 57.13; H, 5.95; N, 6.93.

Example 157

N-[(5Z)-2-tert-butyl-4-(1-methylpropoxy)isothiazol-5(2H)-ylidene]-5-chloro-2-methoxybenzamide The title compound was prepared according to the procedure of Example 156B by replacing 2-iodopropane with 2-iodobutane. $^1$H NMR (300 MHz, DMSO-d$_6$) δ ppm 0.99 (t, J=7.5 Hz, 3 H), 1.21 (d, 3 H), 1.49-1.79 (m, 11 H), 3.80 (s, 3 H), 4.46-4.68 (m, J=5.9 Hz, 1 H), 7.13 (d, J=9.1 Hz, 1 H), 7.48 (dd, J=8.7, 2.8 Hz, 1 H), 7.80 (d, J=3.2 Hz, 1 H), 8.69 (s, 1 H); MS (DCI/NH$_3$) m/z 397 (M+H)$^+$.

Example 158

N-[(5Z)-2-tert-butyl-4-(4-fluorobutoxy)isothiazol-5 (2H)-ylidene]-5-chloro-2-methoxybenzamide The title compound was prepared according to the procedure of Example 156B by replacing 2-iodopropane with 1-bromo-4-fluorobutane. $^1$H NMR (300 MHz, DMSO-d$_6$) δ ppm 1.53-1.63 (m, 9 H), 1.72-1.93 (m, 4 H), 3.79 (s, 3 H), 4.21 (t, J=6.3 Hz, 2 H), 4.46 (t, J=5.9 Hz, 1 H), 4.62 (t, J=5.9 Hz, 1 H), 7.13 (d, J=8.7 Hz, 1 H), 7.48 (dd, J=8.7, 2.8 Hz, 1 H), 7.76 (d, J=3.2 Hz, 1 H), 8.76 (s, 1 H); MS (DCI/NH$_3$) m/z 415 (M+H)$^+$.

Example 159

N-[(5Z)-2-tert-butyl-4-(cyanomethoxy)isothiazol-5 (2H)-ylidene]-5-chloro-2-methoxybenzamide The title compound was prepared according to the procedure of Example 156B by replacing 2-iodopropane with 2-bromoacetonitrile. $^1$H NMR (300 MHz, DMSO-d$_6$) δ ppm 1.62 (s, 9 H), 3.82 (s, 3 H), 5.35 (s, 2 H), 7.15 (d, J=9.2 Hz, 1 H), 7.50 (dd, J=9.0, 2.9 Hz, 1 H), 7.86 (d, J=2.7 Hz, 1 H), 8.93 (s, 1 H); MS (DCI/NH$_3$) m/z 380 (M+H)$^+$.

Example 160

N-[(5Z)-2-tert-butyl-4-{[(2S)-5-oxopyrrolidin-2-yl] methoxy}isothiazol-5(2H)-ylidene]-5-chloro-2-methoxybenzamide The title compound was prepared according to the procedure of Example 156B by replacing 2-iodopropane with (S)-(5-oxopyrrolidin-2-yl)methyl 4-methylbenzenesulfonate. $^1$H NMR (300 MHz, DMSO-d$_6$) δ ppm 1.61 (s, 9 H), 1.83-1.98 (m, 1 H), 2.08-2.34 (m, 3 H), 3.80 (s, 3 H), 3.82-3.90 (m, 1 H), 3.96-4.08 (m, 1 H), 4.23 (dd, J=10.3, 4.8 Hz, 1 H), 7.14 (d, J=9.1 Hz, 1 H), 7.49 (dd, J=8.7, 2.8 Hz, 1 H), 7.78 (d, J=2.8 Hz, 1 H), 7.88 (s, 1 H), 8.81 (s, 1 H); MS (DCI/NH$_3$) m/z 438 (M+H)$^+$.

Example 161

N-[(5Z)-2-tert-butyl-4-{[(2R)-5-oxopyrrolidin-2-yl]methoxy}isothiazol-5(2H)-ylidene]-5-chloro-2-methoxybenzamide The title compound was prepared according to the procedure of Example 156B by replacing 2-iodopropane with (R)-(5-oxopyrrolidin-2-yl)methyl 4-methylbenzenesulfonate. $^1$H NMR (300 MHz, DMSO-$d_6$) δ ppm 1.54-1.65 (m, 9 H), 1.86-1.92 (m, 1 H), 2.06-2.32 (m, 3 H), 3.80 (s, 3 H), 3.82-3.86 (m, J=5.6, 5.6 Hz, 1 H), 3.95-4.07 (m, 1 H), 4.23 (dd, J=9.9, 4.8 Hz, 1 H), 7.14 (d, J=8.7 Hz, 1 H), 7.49 (dd, J=8.9, 3.0 Hz, 1 H), 7.78 (d, J=2.8 Hz, 1 H), 7.88 (s, 1 H), 8.81 (s, 1 H); MS (DCI/NH$_3$) m/z 438 (M+H)$^+$.

Example 162

Tert-butyl [(5Z)-2-tert-butyl-5-{[(5-chloro-2-methoxyphenyl)carbonyl]imino}-3-methyl-2,5-dihydroisothiazol-4-yl]carbamate

Example 162A

Ethyl (5Z)-2-tert-butyl-5-{[(5-chloro-2-methoxyphenyl)carbonyl]imino}-3-methyl-2,5-dihydroisothiazole-4-carboxylate To a solution of ethyl 3-oxobutanoate (1.3 g, 10 mmol) and 2-methylpropan-2-amine (0.73 g, 10 mmol) in toluene (15 mL) were added anhydrous magnesium sulfate (3.0 g, 25 mmol) and Montmorillonite K10 (3.0 g, 10 mmol). The resulting mixture was stirred at 45° C. for 14 h and then cooled to room temperature. The mixture was diluted with anhydrous ethyl ether, filtered and washed with ethyl ether. The filtrate and washings were combined and concentrated under reduced pressure. The residue was dissolved in THF (60 mL), 5-chloro-2-methoxybenzoyl isothiocyanate (2.16 g, 9.5 mmol) was added and the mixture was stirred at ambient temperature for 2 h. Iodine (2.4 g, 9.5 mmol) was added followed by addition of MeOH (100 mL) and pyridine (10 mL). The mixture was left overnight at room temperature and then treated with ethyl acetate and a saturated solution of sodium bicarbonate for additional 1 h. The layers were separated and the aqueous layer was extracted with ethyl acetate. The extracts were combined, washed with brine, dried with MgSO$_4$ and concentrated under reduced pressure. The solid was triturated with hexane-ethyl ether (1:1) to provide 2.8 g of the title compound. $^1$H NMR (300 MHz, DMSO-$d_6$) δ ppm 1.37 (t, 3 H), 1.74 (s, 9 H), 2.76 (s, 3 H), 3.82 (s, 3 H), 4.32 (q, J=6.9 Hz, 2 H), 7.16 (d, J=8.7 Hz, 1 H), 7.52 (dd, J=8.7, 2.8 Hz, 1 H), 8.01 (d, J=3.2 Hz, 1 H); MS (DCI/NH$_3$) m/z 411 (M+H)$^+$.

Example 162B (5Z)-2-tert-butyl-5-{[(5-chloro-2-methoxyphenyl)carbonyl]imino}-3-methyl-2,5-dihydroisothiazole-4-carboxylic acid To a solution of product from Example 162A (1.45 g, 3.5 mmol) in dioxane (7.5 mL) and ethanol (15 mL) was added 1N NaOH (5 mL, 5 mmol) and the mixture was stirred at room temperature for 16 h. Another portion of 1N NaOH (2.5 mL, 2.5 mmol) was added and reaction was continued for an additional 9 h. Water (15 mL) was added and organics were removed under reduced pressure. The solution was acidified to pH 4 and the solid was filtered, washed with water and dried under reduced pressure to provide 1.2 g of the title compound. $^1$H NMR (300 MHz, DMSO-$d_6$) δ ppm 1.74 (s, 9 H), 2.85 (s, 3 H), 3.85 (s, 3 H), 7.19 (d, J=8.7 Hz, 1 H), 7.54 (dd, J=9.1, 2.8 Hz, 1 H), 7.81 (d, J=2.8 Hz, 1 H); MS (DCI/NH$_3$) m/z 383 (M+H)$^+$.

Example 162C

Tert-butyl [(5Z)-2-tert-butyl-5-{[(5-chloro-2-methoxyphenyl)carbonyl]imino}-3-methyl-2,5-dihydroisothiazol-4-yl]carbamate A mixture of Example 162B (784 mg, 2 mmol), triethylamine (0.57 mL, 4.1 mmol) and diphenyl phosphorazidate (1.13 g, 4.1 mmol) in dioxane (10 mL) was refluxed at 80° C. for 3 h. tert-Butanol (30 mL) was added heating at 80° C. was continued for another 8 h. The mixture was cooled to room temperature and concentrated under reduced pressure. Water was added and the mixture was extracted with EtOAc. The acetate layer was washed with 10% NaHCO$_3$, brine and concentrated under reduced pressure. Chromatography (EtOAc-MeOH 9:1) afforded 10 mg of product. $^1$H NMR (300 MHz, DMSO-$d_6$) δ ppm 1.47 (s, 9 H), 1.68-1.76 (m, 9 H), 2.50-2.54 (m, 3 H), 3.79 (s, 3 H), 7.12 (d, J=8.7 Hz, 1 H), 7.47 (dd, J=8.9, 3.0 Hz, 1 H), 7.82 (d, J=2.8 Hz, 1 H), 8.45 (s, 1 H); MS (DCI/NH$_3$) m/z 454 (M+H)$^+$.

Example 163

N-[(5Z)-2-tert-butyl-4-(1-hydroxyethyl)isothiazol-5(2H)-ylidene]-5-chloro-2-methoxybenzamide The product from Example 21A (450 mg, 1.28 mmol) in THF (20 mL) was treated dropwise with methylmagnesium bromide (0.85 mL, 2.55 mmol) at −40° C. The reaction was stirred at −40° C. for 1.5 hrs, quenched with saturated NH$_4$Cl and the mixture was extracted with EtOAc (2×). The organics were combined, dried over MgSO$_4$, filtered and concentrated. The residue was purified by column chromatography using an Analogix® Intelliflash280™ (SiO$_2$, 10-80% ethyl acetate/hexane) to afford 220 mg (47%) of the title compound. $^1$H NMR (400 MHz, CDCl$_3$) δ ppm 1.64 (d, J=6.44 Hz, 3 H) 1.67 (s, 9 H) 3.70-3.78 (m, 1 H) 3.93 (s, 3 H) 5.19 (q, J=6.44 Hz, 1 H) 6.93 (d, J=8.90 Hz, 1 H) 7.37 (dd, J=8.59, 2.76 Hz, 1 H) 7.97 (s, 1 H) 8.06 (d, J=2.76 Hz, 1 H); MS (DCI/NH$_4^+$) m/z 369 (M+H)$^+$.

Example 164

N-[(5Z)-2-tert-butyl-4-(1-ethoxyethyl)isothiazol-5(2H)-ylidene]-5-chloro-2-methoxybenzamide The title compound was prepared using the procedure as described in Example 11E substituting Example 163 for Example 11D and iodoethane for iodomethane. $^1$H NMR (500 MHz, CDCl$_3$) δ ppm 1.24 (t, J=7.02 Hz, 3 H) 1.56 (d, J=6.71 Hz, 3 H) 1.67 (s, 9 H) 3.47-3.56 (m, 1 H) 3.58-3.66 (m, 1 H) 3.92 (s, 3 H) 5.09 (q, J=6.41 Hz, 1 H) 6.92 (d, J=8.85 Hz, 1 H) 7.35 (dd, J=8.54, 2.75 Hz, 1 H) 8.10 (d, J=2.75 Hz, 1 H) 8.16 (s, 1 H); MS (DCI/NH$_3$) m/z 397 (M+H)$^+$.

Example 165

N-[(5Z)-2-tert-butyl-4-(1-methoxyethyl)isothiazol-5(2H)-ylidene]-5-chloro-2-methoxybenzamide The title compound was prepared using the procedure as described in Example 11E substituting Example 163 for Example 11D. $^1$H NMR (400 MHz, CDCl$_3$) δ ppm 1.56 (d, J=6.44 Hz, 3 H) 1.66 (s, 9 H) 3.42 (s, 3 H) 3.91 (s, 3 H) 5.00 (q, J=6.44 Hz, 1 H) 6.92 (d, J=8.90 Hz, 1 H) 7.35 (ddd, J=8.90, 2.76, 0.61 Hz, 1 H) 8.10 (d, J=2.45 Hz, 1 H) 8.15 (s, 1 H); MS (DCI/NH$_3$) m/z 383 (M+H)$^+$.

Example 166

N-[(5Z)-2-tert-butyl-4-[1-(2,2,2-trifluoroethoxy) ethyl]isothiazol-5(2H)-ylidene]-5-chloro-2-methoxybenzamide Example 166A 1-[(5Z)-2-tert-butyl-5-{[(5-chloro-2-methoxyphenyl) carbonyl]imino}-2,5-dihydroisothiazol-4-yl]ethyl methanesulfonate A mixture of the product of Example 163 (220 mg, 0.6 mmol) in CH$_2$Cl$_2$ (20 mL) and triethylamine (181 mg, 1.8 mmol) was cooled to 0° C., and treated dropwise with methanesulfonyl chloride (102 mg, 0.9 mmol). The reaction was stirred at 0° C. for 30 min., poured into water, and the mixture was extracted with CH$_2$Cl$_2$ (2×). The organics were combined, dried over MgSO$_4$, filtered and concentrated to afford the title compound (234 mg, 88%). MS (DCI/NH$_3$) m/z 383 (M−Ms+15)$^+$.

Example 166B

N-[(5Z)-2-tert-butyl-4-[1-(2,2,2-trifluoroethoxy) ethyl]isothiazol-5(2H)-ylidene]-5-chloro-2-methoxybenzamide 2,2,2-Trifluoroethanol (39.3 mg, 0.39 mmol) in THF (2 mL) was treated with NaH (60%)(19 mg, 0.47 mmol). The reaction was stirred at rt for 20 min. To the above mixture was added Example 166A (117 mg, 0.262 mmol) in THF (1 mL). The mixture was heated at 80° C. for 12 hrs, poured into water, and the mixture was extracted with EtOAc (2×). The organics were combined, dried over MgSO$_4$, filtered and concentrated. The residue was purified by column chromatography using an Analogix® Intelliflash280™ (SiO$_2$, 0-80% ethyl acetate/hexane) to afford 11 mg (9%) of the title compound. $^1$H NMR (400 MHz, CDCl$_3$) δ ppm 1.62 (d, J=6.44 Hz, 3 H) 1.67 (s, 9 H) 3.75-3.86 (m, 1 H) 3.92 (s, 3 H) 3.99-4.10 (m, 1 H) 5.27 (q, J=6.75 Hz, 1 H) 6.93 (d, J=8.90 Hz, 1 H) 7.36 (dd, J=8.90, 2.76 Hz, 1 H) 8.08 (d, J=2.76 Hz, 1 H) 8.19 (s, 1 H) MS (DCI/NH$_3$) m/z 451 (M+H)$^+$.

Example 167

N-[(5Z)-2-tert-butyl-4-vinylisothiazol-5(2H)-ylidene]-5-chloro-2-methoxybenzamide The title compound was obtained as a by-product in the reaction to prepare Example 166B (18 mg, 20%). $^1$H NMR (400 MHz, CHLOROFORM-D) δ ppm 1.67 (s, 9 H) 3.94 (s, 3 H) 5.35 (dd, J=11.35, 1.53 Hz, 1 H) 6.13 (dd, J=17.80, 1.84 Hz, 1 H) 6.93 (d, J=8.90 Hz, 1 H) 6.97 (dd, J=17.49, 11.05 Hz, 1 H) 7.36 (dd, J=8.90, 2.76 Hz, 1 H) 8.18 (s, 1 H) 8.22 (d, J=2.76 Hz, 1 H); MS (DCI/NH$_3$) m/z 351 (M+H)$^+$.

Example 168

(1R,3S)-3-({[(5Z)-4-butyl-2-tert-butylisothiazol-5 (2H)-ylidene]amino}carbonyl)-3-hydroxy-1,2,2-trimethylcyclopentanecarboxylic acid A mixture of the product from Example 102 (50.0 mg, 0.127 mmol) and potassium hydroxide (71.5 mg, 1.27 mmol) in ethanol (1 mL) and water (0.2 mL) was heated to 60° C. for 24 hours. After cooling to ambient temperature, 1N HCl (aq) was added to adjust the pH to ~1. The mixture was extracted with ethyl acetate. The extract was dried (MgSO$_4$), filtered, and concentrated by rotary evaporator to give a white solid. Recrystallization of the solid from ethyl acetate afforded 39.2 mg (75%) of the title compound. $^1$H NMR (DMSO-d$_6$) δ 0.79 (s, 3H), 0.92 (t, J=7.2 Hz, 3H), 1.07 (br s, 3H), 1.18 (br s, 3H), 1.27-1.40 (m, 3H), 1.50-1.63 (m, 3H), 1.68 (s, 9H), 1.85 (br s, 1H), 2.51-2.59 (m, 2H), 2.91 (br s, 2H), 9.07 (br s, 1H), 12.10 (br s, 1H). MS (ESI$^+$) m/z 411 (M+H)$^+$.

Example 169

(1S,3R)-3-({[(5Z)-4-butyl-2-tert-butylisothiazol-5 (2H)-ylidene]amino}carbonyl)-3-hydroxy-1,2,2-trimethylcyclopentanecarboxylic acid The product of Example 103 (200 mg, 0.509 mmol) was processed using the method described in Example 168 to afford the title compound. $^1$H NMR (DMSO-d$_6$) δ 0.79 (s, 3H), 0.92 (t, J=7.2 Hz, 3H), 1.07 (br s, 3H), 1.18 (br s, 3H), 1.27-1.40 (m, 3H), 1.50-1.63 (m, 3H), 1.68 (s, 9H), 1.85 (br s, 1H), 2.51-2.59 (m, 2H), 2.91 (br s, 2H), 9.07 (br s, 1H), 12.10 (br s, 1H). MS (ESI+) m/z 411 (M+H)$^+$.

Example 170

Methyl (1R,3S)-3-({[(5Z)-4-butyl-2-tert-butyl-isothiazol-5(2H)-ylidene]amino}carbonyl)-1,2,2-trimethylcyclopentanecarboxylate A mixture of (+)-camphoric acid (Aldrich, 2.00 g, 10.0 mmol) and phosphorus pentachloride (Aldrich, 4.16 g, 20.0 mmol) in hexane (75 mL) was heated to reflux and stirred for 24 hours. After cooling to ambient temperature, the reaction mixture was concentrated by rotary evaporator to give a pale yellow oil. The crude bis acid chloride (474 mg, 2.00 mmol) was added to a mixture of the product from Example 92B (425 mg, 2.00 mmol) and triethylamine (1.01 g, 10.0 mmol) in anhydrous tetrahydrofuran (12 mL). The mixture was stirred for 2 hours Anhydrous methanol (10 mL) was added and the resulting mixture was stirred overnight. The mixture was concentrated by rotary evaporator to give a brown oil. Flash chromatography (silica gel, 5-25% ethylacetate in hexanes) afforded 343 mg (42%) of the title compound. $^1$H NMR (DMSO-d$_6$) δ 0.53 (s, 3H), 0.90 (t, J=7.3 Hz, 3H), 1.20 (s, 3H), 1.23 (s, 3H), 1.23-1.40 (m, 2H), 1.41-1.50 (m, 1H), 1.57 (s, 9H), 1.57-1.67 (m, 2H), 1.71-1.84 (m, 1H), 2.24-2.36 (m, 1H), 2.41-2.48 (m, 1H), 2.61-2.67 (m, 2H), 3.00-3.06 (m, 1H), 3.59 (s, 3H), 8.52 (s, 1H). MS (ESI+) m/z 409 (M+H)$^+$. Anal. calcd. for C$_{22}$H$_{36}$N$_2$O$_3$S: C, 64.67; H, 8.88; N, 6.86. Found: C, 64.52; H, 8.76; N, 6.84.

Example 171

(1R,3S)—N$^3$-[(5Z)-4-butyl-2-tert-butylisothiazol-5 (2H)-ylidene]-1,2,2-trimethylcyclopentane-1,3-dicarboxamide The product from Example 92B and the (+) camphoric acid (Aldrich) were processed using the method described in Example 170 except that the methanol used to trap the intermediate was saturated with ammonia solution instead of methanol to afford the title compound. $^1$H NMR (DMSO-$d_6$) δ 0.50 (s, 3H), 0.90 (t, J=7.2 Hz, 3H), 1.19 (s, 3H), 1.23-1.44 (m, 3H), 1.26 (s, 3H), 1.57 (s, 9H), 1.57-1.71 (m, 3H), 1.93-2.06 (m, 1H), 2.71-2.82 (m, 1H), 2.62-2.69 (m, 3H), 7.01 (s, 1H), 6.75 (s, 1H), 8.50 (s, 1H). MS (ESI+) m/z 394 (M+H)$^+$. Anal. calcd. for $C_{11}H_{35}N_3O_2S$: C, 64.08; H, 8.96; N, 10.68. Found: C, 64.26; H, 9.10; N, 10.65.

Example 172

(1S,3R)—N-[(5Z)-4-butyl-2-tert-butylisothiazol-5 (2H)-ylidene]-1,2,2-trimethyl-3-(pyrrolidin-1-ylcarbonyl)cyclopentanecarboxamide Example 172A (1R,3S)-1,2,2-trimethyl-3-(pyrrolidine-1-carbonyl) cyclopentanecarboxylic acid (+)-Camphoric acid (Aldrich, 2.00 g, 10.0 mmol), tosyl chloride (Aldrich, 1.14 g, 6.00 mmol), and potassium carbonate (6.22 g, 45.0 mmol) were ground by mortar and pestle for 1 hour. The sticky paste was washed with dichloromethane, and the rinse was concentrated by rotary evaporator to give an intermediate anhydride as a white solid. This crude anhydride (356 mg, 1.00 mmol), pyrrolidine (Aldrich 356 mg, 5.00 mmol), and anhydrous acetonitrile were mixed at room temperature for 24 hours. The pH of the mixture was adjusted to ~1 by addition of 1N hydrochloric acid, and the mixture was extracted with dichloromethane. The extracts were dried (MgSO$_4$), filtered, and concentrated by rotary evaporator to give 238 mg (94%) of the title compound.

Example 172B (1S,3R)—N-[(5Z)-4-butyl-2-tert-butylisothiazol-5 (2H)-ylidene]-1,2,2-trimethyl-3-(pyrrolidin-1-ylcarbonyl)cyclopentanecarboxamide The products from Example 172A and Example 92B were processed using the method described in Example 92C to afford the title compound. $^1$H NMR (DMSO-$d_6$) δ 0.54 (s, 3H), 0.90 (t, J=7.3 Hz, 3H), 1.24 (s, 6H), 1.26-1.36 (m, 3H), 1.37-1.46 (m, 1H), 1.57 (s, 9H), 1.57-1.67 (m, 2H), 1.69-1.87 (m, 4H), 1.94-2.07 (m, 1H), 2.62-2.67 (m, 2H), 2.75-2.86 (m, 1H), 3.09-3.15 (m, 1H), 3.20-3.37 (m, 2H), 3.42-3.48 (m, 1H), 3.55-3.63 (m, 1H), 8.50 (s, 1H). MS (ESI+) m/z 448 (M+H)$^+$. Anal. calcd. for $C_{25}H_{41}N_3O_2S$: C, 67.07; H, 9.23; N, 9.39. Found: C, 66.64; H, 9.11; N, 9.33.

Example 173

(1S,3R)-3-({[(5Z)-4-butyl-2-tert-butylisothiazol-5 (2H)-ylidene]amino}carbonyl)-2,2,3-trimethylcyclopentanecarboxylic acid The product from Example 177 was processed using the method described in Example 96 to afford the title compound. MS (ESI+) m/z 395 (M+H)$^+$.

Example 174

(1R,3S)-3-({[(5Z)-4-butyl-2-tert-butylisothiazol-5 (2H)-ylidene]amino}carbonyl)-2,2,3-trimethylcyclopentanecarboxylic acid The product from Example 186 was processed using the method described in Example 96 to afford the title compound. MS (ESI+) m/z 395 (M+H)$^+$.

Example 175

Ethyl (1S,3R)-3-({[(5Z)-4-butyl-2-tert-butylisothiazol-5(2H)-ylidene]amino}carbonyl)-2,2,3-trimethylcyclopentanecarboxylate A mixture of (+)-camphoric acid (Aldrich, 2.00 g, 10.0 mmol) and phosphorus pentachloride (Aldrich, 4.16 g, 20.0 mmol) in hexane (75 mL) was heated to reflux and stirred for 24 hours. After cooling to ambient temperature, the reaction mixture was concentrated by rotary evaporator to give a pale yellow oil. The crude bis acid chloride (356 mg, 1.50 mmol) was added to a mixture of the product from Example 92B (319 mg, 1.50 mmol) and triethylamine (455 g, 4.50 mmol) in anhydrous tetrahydrofuran (12 mL). The mixture was stirred for 2 hours Anhydrous ethanol (20 mL) was added and the resulting mixture was stirred overnight. The mixture was concentrated by rotary evaporator to give a brown oil. Flash chromatography (silica gel, 5-25% ethyl acetate in hexanes) afforded 327 mg (52%) of the title compound. $^1$H NMR (DMSO-$d_6$) δ 0.51 (s, 3H), 0.90 (7.3 Hz, 3H), 1.18 (t, J=7.0 Hz, 3H), 1.21 (s, 3H), 1.23-1.36 (m, 2H), 1.31 (s, 3H), 1.40-1.50 (m, 1H), 1.57 (s, 9H), 1.57-1.67 (m, 2H), 1.71-1.85 (m, 1H), 1.98-2.10 (m, 1H), 2.62-2.67 (m, 2H), 2.70-2.81 (m, 1H), 2.82-2.89 (m, 1H), 3.98-4.16 (m, 2H), 8.51 (s, 1H)). MS (ESI+) m/z 423 (M+H)$^+$. Anal. calcd. for $C_{22}H_{36}N_2O_3S$: C, 65.36; H, 9.06; N, 6.63. Found: C, 65.02; H, 8.97; N, 6.49.

Example 176

Ethyl (1R,3S)-3-({[(5Z)-4-butyl-2-tert-butylisothiazol-5(2H)-ylidene]amino}carbonyl)-2,2,3-trimethylcyclopentanecarboxylate The product from Example 92B and the (−) camphoric acid (Aldrich) were processed using the method described in Example 175 to afford the title compound. $^1$H NMR (DMSO-$d_6$) δ 0.51 (s, 3H), 0.90 (7.3 Hz, 3H), 1.18 (t, J=7.0 Hz, 3H), 1.21 (s, 3H), 1.23-1.36 (m, 2H), 1.31 (s, 3H), 1.40-1.50 (m, 1H), 1.57 (s, 9H), 1.57-1.67 (m, 2H), 1.71-1.85 (m, 1H), 1.98-2.10 (m, 1H), 2.62-2.67 (m, 2H), 2.70-2.81 (m, 1H), 2.82-2.89 (m, 1H), 3.98-4.16 (m, 2H), 8.51 (s, 1H)). MS (ESI+) m/z 423 (M+H)$^+$. Anal. calcd. for $C_{22}H_{36}N_2O_3S$: C, 65.36; H, 9.06; N, 6.63. Found: C, 65.02; H, 8.97; N, 6.49.

Example 177

Methyl (1S,3R)-3-({[(5Z)-4-butyl-2-tert-butylisothiazol-5(2H)-ylidene]amino}carbonyl)-2,2,3-trimethylcyclopentanecarboxylate A mixture of (+)-camphoric acid (Aldrich, 2.00 g, 10.0 mmol) and phosphorus pentachloride (Aldrich, 4.16 g, 20.0 mmol) in hexane (75 mL) was heated to reflux and stirred for 24 hours. After cooling to ambient temperature, the reaction mixture was concentrated by rotary evaporator to give a pale yellow oil. The crude bis acid chloride (474 mg, 2.00 mmol)

was added to a mixture of the product from Example 92B (425 mg, 2.00 mmol) and triethylamine (1.01 g, 10.0 mmol) in anhydrous tetrahydrofuran (12 mL). The mixture was stirred for 2 hours Anhydrous methanol (10 mL) was added and the resulting mixture was stirred overnight. The mixture was concentrated by rotary evaporator to give a brown oil. Flash chromatography (silica gel, 5-25% ethyl acetate in hexanes) afforded 331 mg (41%) of the title compound. $^1$H NMR (DMSO-$d_6$) δ 0.50 (s, 3H), 0.90 (t, J=7.5 Hz, 3H), 1.21 (s, 3H), 1.24-1.36 (m, 2H), 1.30 (s, 3H), 1.42-1.50 (m, 1H), 1.57 (s, 9H), 1.57-1.67 (m, 2H), 1.73-1.86 (m, 1H), 1.98-2.11 (m, 1H), 2.62-2.67 (m, 2H), 2.70-2.81 (m, 1H), 2.85-2.92 (m, 1H), 3.60 (s, 3H), 8.51 (s, 1H). MS (ESI+) m/z 409 (M+H)$^+$. Anal. calcd. for $C_{22}H_{36}N_2O_3S$: C, 64.67; H, 8.88; N, 6.86. Found: C, 64.60; H, 8.63; N, 6.64.

Example 178

(1R,3S)-3-(azetidin-1-ylcarbonyl)-N-[(5Z)-4-butyl-2-tert-butylisothiazol-5(2H)-ylidene]-1,2,2-trimethylcyclopentanecarboxamide Solid N-(3-dimethylaminopropyl)-n'-ethylcarbodiimide hydrochloride (EDC) (Aldrich, 216 mg, 1.12 mmol), the product from Example 173 (296 mg, 0.750 mmol), hydroxybenzotriazole (Aldrich, 152 mg, 1.12 mmol), azetidine hydrochloride (Aldrich, 105 mg, 1.12 mmol), triethylamine (Aldrich, 152 mg, 1.50 mmol) and anhydrous N,N-dimethylformamide (4 mL) were mixed together at room temperature. Water was added to quench and the mixture was extracted with dichloromethane. The extracts were dried over sodium sulfate and concentrated by rotary evaporator to give a brown oil. Flash chromatography (silica gel: 20-75% ethyl acetate in hexanes) afforded 189 mg (58%) of the title compound. $^1$H NMR (DMSO-$d_6$) δ 0.50 (s, 3H), 0.90 (t, J=7.8 Hz, 3H), 1.22 (s, 3H), 1.23 (s, 3H), 1.23-1.35 (m, 4H), 1.37-1.46 (m, 1H), 1.56 (s, 9H), 1.56-1.67 (m, 2H), 1.90-2.03 (m, 1H), 2.08-2.22 (m, 2H), 2.71-2.76 (m, 2H), 2.77-2.83 (m, 1H), 3.73-3.81 (m, 1H), 3.82-3.91 (m, 1H), 4.06-4.14 (m, 1H), 4.18-4.26 (m, 1H), 8.50 (s, 1H). MS (ESI+) m/z 434 (M+H)$^+$. Anal. calcd. for $C_{24}H_{39}N_3O_2S$: C, 66.47; H, 9.06; N, 9.69. Found: C, 66.60; H, 9.02; N, 9.47.

Example 179

(1R,3S)—$N^1$-[(5Z)-4-butyl-2-tert-butylisothiazol-5(2H)-ylidene]-$N^3,N^3$,1,2,2-pentamethylcyclopentane-1,3-dicarboxamide The product from Example 173 and dimethylamine hydrochloride (Aldrich) were processed using the method described in Example 178 to afford the title compound. $^1$H NMR (DMSO-$d_6$) δ 0.49 (s, 3H), 0.90 (t, J=7.3 Hz, 3H), 1.25 (s, 3H), 1.26 (s, 3H), 1.28-1.33 (m, 2H), 1.37-1.46 (m, 1H), 1.57 (s, 9H), 1.57-1.70 (m, 3H), 2.01-2.10 (m, 1H), 2.62-2.67 (m, 2H), 2.74-2.83 (m, 1H), 2.83 (s, 3H), 3.05 (s, 3H), 3.33-3.39 (m, 1H), 8.50 (s, 1H). MS (ESI+) m/z 422 (M+H)$^+$. Anal. calcd. for $C_{23}H_{39}N_3O_2S$: C, 65.52; H, 9.32; N, 9.97. Found: C, 65.26; H, 9.15; N, 9.88.

Example 180

(1R,3S)—N-[(5Z)-4-butyl-2-tert-butylisothiazol-5(2H)-ylidene]-3-[(3-hydroxyazetidin-1-yl)carbonyl]-1,2,2-trimethylcyclopentanecarboxamide The product from Example 173 and 3-hydroxyazetidine hydrochloride (Oakwood) were processed using the method described in Example 178 to afford the title compound. $^1$H NMR δ 0.49-0.50 (m, 3H), 0.90 (t, J=7.2 Hz, 3H), 1.22 (s, 6H), 1.24-1.46 (m, 3H), 1.56 (s, 9H), 1.56-1.67 (m, 3H), 1.90-2.03 (m, 1H), 2.62-2.67 (m, 2H), 2.71-2.86 (m, 2H), 3.50-3.61 (m, 1H), 4.23-4.45 (m, 1H), 4.41 (br s, 1H), 3.83-4.09 (m, 2H), 3.50-3.61 (m, 1H), 8.50 (s, 1H). MS (ESI+) m/z 450 (M+H)$^+$.

Example 181

(1R,3S)-3-({[(5Z)-4-butyl-2-tert-butylisothiazol-5(2H)-ylidene]amino}carbonyl)-1,2,2-trimethylcyclopentanecarboxylic acid The product from Example 170 was processed using the method described in Example 96 to afford the title compound. MS (ESI+) m/z 395 (M+H)$^+$.

Example 182

(1R,3S)—N-[(5Z)-4-butyl-2-tert-butylisothiazol-5(2H)-ylidene]-$N^1$,1,2,2-tetramethylcyclopentane-1,3-dicarboxamidetetramethylcyclopentane-1,3-dicarboxamide The product from Example 181 and methylamine hydrochloride (Aldrich) were processed using the method described in Example 178 to afford the title compound. $^1$H NMR (DMSO-$d_6$) δ 0.48 (s, 3H), 0.89 (t, J=7.2 Hz, 3H), 1.13 (s, 3H), 1.23 (s, 3H), 1.26-1.42 (m, 3H), 1.57 (s, 9H), 1.57-1.66 (m, 2H), 1.69-1.82 (m, 1H), 2.24-2.45 (m, 2H), 2.54-2.56 (m, 3H), 2.61-2.67 (m, 2H), 2.96-3.02 (m, 1H), 7.24-7.28 (m, 1H), 8.50 (s, 1H). MS (ESI+) m/z 408 (M+H)$^+$. Anal. calcd. for $C_{22}H_{37}N_3O_2S$: C, 64.83; H, 9.15; N, 10.31. Found: C, 64.68; H, 9.18; N, 10.25.

Example 183

(1R,3S)—$N^3$-[(5Z)-4-butyl-2-tert-butylisothiazol-5(2H)-ylidene]-$N^1,N^1$,1,2,2-pentamethylcyclopentane-1,3-dicarboxamide The product from Example 181 and dimethylamine hydrochloride (Aldrich) were processed using the method described in Example 178 to afford the title compound. $^1$H NMR (DMSO-$d_6$) δ 0.49 (s, 3H), 0.90 (t, J=7.3 Hz, 3H), 1.25 (s, 3H), 1.26 (s, 3H), 1.26-1.33 (m, 2H), 1.37-1.46 (m, 1H), 1.57 (s, 9H), 1.57-1.70 (m, 3H), 1.98-2.10 (m, 1H), 2.62-2.67 (m, 2H), 2.74-2.83 (m, 1H), 2.83 (s, 3H), 3.05 (s, 3H), 3.33-3.39 (m, 1H), 8.50 (s, 1H). MS (ESI+) m/z 422 (M+H)$^+$. Anal. calcd. for $C_{23}H_{39}N_3O_2S$: C, 65.52; H, 9.32; N, 9.97. Found: C, 65.19; H, 9.18; N, 9.88.

Example 184

(1R,3S)—$N^1$-[(5Z)-4-butyl-2-tert-butylisothiazol-5(2H)-ylidene]-$N^3$,1,2,2-tetramethylcyclopentane-1,3-dicarboxamide The product from Example 173 and methylamine hydrochloride (Aldrich) were processed using the method described in Example 178 to afford the title compound. $^1$H NMR (DMSO-$d_6$) δ 0.47 (s, 3H), 0.90 (t, J=7.3 Hz, 3H), 1.19 (s, 3H), 1.22 (s, 3H), 1.26-1.33 (m, 2H), 1.36-1.45 (m, 1H), 1.57 (s, 9H), 1.57-1.68 (m, 3H), 1.96-2.08 (m, 1H), 2.57 (d, J=4.7 Hz, 3H), 2.60-2.67 (m, 3H), 2.72-2.83 (m, 1H), 4.78 (q, J=4.5 Hz, 1H), 8.50 (s, 1H). MS (ESI+) m/z 408 (M+H)$^+$.

Anal. calcd. for $C_{22}H_{37}N_3O_2S$: C, 64.83; H, 9.15; N, 10.31. Found: C, 64.20; H, 9.03; N, 10.25.

Example 185

(1R,3S)—N-[(5Z)-4-butyl-2-tert-butylisothiazol-5 (2H)-ylidene]-3-[(3,3-difluoroazetidin-1-yl)carbonyl]-1,2,2-trimethylcyclopentanecarboxamide The product from Example 173 and 3,3-difluoroazetidine hydrochloride (Oakwood) were processed using the method described in Example 178 to afford the title compound. $^1$H NMR (DMSO-$d_6$) δ 0.51 (s, 3H), 0.90 (t, J=7.3 Hz, 3H), 1.22 (s, 3H), 1.25 (s, 3H), 1.26-1.36 (m, 2H), 1.39-1.48 (m, 1H), 1.57 (s, 9H), 1.57-1.78 (m, 3H), 1.93-2.05 (m, 1H), 2.62-2.67 (m, 2H), 2.73-2.83 (m, 1H), 2.88-2.94 (m, 1H), 4.14-4.37 (m, 2H), 4.41-4.53 (m, 1H), 4.74-4.86 (m, 1H), 8.51 (s, 1H). (ESI+) m/z 470 (M+H)$^+$.

Example 186

Methyl (1R,3S)-3-({[(5Z)-4-butyl-2-tert-butylisothiazol-5(2H)-ylidene]amino}carbonyl)-2,2,3-trimethylcyclopentanecarboxylate A mixture of (-)-camphoric acid (Aldrich, 2.00 g, 10.0 mmol) and phosphorus pentachloride (Aldrich, 4.16 g, 20.0 mmol) in hexane (75 mL) was heated to reflux and stirred for 24 hours. After cooling to ambient temperature, the reaction mixture was concentrated by rotary evaporator to give a pale yellow oil. The crude bis acid chloride (474 mg, 2.00 mmol) was added to a mixture of the product from Example 92B (425 mg, 2.00 mmol) and triethylamine (1.01 g, 10.0 mmol) in anhydrous tetrahydrofuran (12 mL). The mixture was stirred for 2 hours Anhydrous methanol (10 mL) was added and the resulting mixture was stirred overnight. The mixture was concentrated by rotary evaporator to give a brown oil. Flash chromatography (silica gel, 5-25% ethyl acetate in hexanes) afforded 212 mg (26%) of the title compound. $^1$H NMR (DMSO-$d_6$) δ 0.50 (s, 3H), 0.90 (t, J=7.5 Hz, 3H), 1.21 (s, 3H), 1.24-1.36 (m, 2H), 1.30 (s, 3H), 1.42-1.50 (m, 1H), 1.57 (s, 9H), 1.57-1.67 (m, 2H), 1.78-1.86 (m, 1H), 1.98-2.11 (m, 1H), 2.62-2.67 (m, 2H), 2.70-2.81 (m, 1H), 2.85-2.92 (m, 1H), 3.60 (s, 3H), 8.51 (s, 1H). MS (ESI+) m/z 409 (M+H)$^+$. Anal. calcd. for $C_{22}H_{36}N_2O_3S$: C, 64.67; H, 8.88; N, 6.86. Found: C, 64.63; H, 8.82; N, 6.71.

Example 187

Neopentyl (5Z)-4-butyl-2-tert-butylisothiazol-5(2H)-ylidenecarbamate

A mixture of Example 110B (0.106 g, 0.5 mmol), triethylamine (0.073 mL, 0.5 mmol), and neopentyl carbonochloridate (0.074 mL, 0.5 mmol) in dichloromethane (10 mL) was stirred at room temp for 18 hrs. The reaction mixture was concentrated in vacuo. Purification by gradient flash chromatography over silica gel (0 to 100% ethyl acetate/hexane) afforded the title compound (145 mg, 89% yield). $^1$H NMR (300 MHz, CDCl$_3$) δ ppm 0.89-1.08 (m, 12 H), 1.28-1.52 (m, 2 H), 1.53-1.71 (m, 12 H), 2.59-2.78 (m, 2 H), 3.97 (s, 1 H), 7.78 (s, 1 H). MS (DCI/NH$_3$) m/z 327 (M+H)$^+$. Anal. calculated for $C_{17}H_{30}N_2O_2S$: C, 62.54; H, 9.26; N, 8.58. Found: C, 61.92; H, 9.48; N, 7.10.

Example 188

2,2,2-trichloroethyl (5Z)-4-butyl-2-tert-butylisothiazol-5(2H)-ylidenecarbamate

The title compound was prepared from 2,2,2-trichloroethyl carbonochloridate and Example 110B using the procedure as described in Example 187 (117 mg, 16% yield). $^1$H NMR (300 MHz, CDCl$_3$) δ ppm 0.95 (t, J=7.3 Hz, 3 H), 1.30-1.49 (m, 2 H), 1.52-1.57 (m, 2 H), 1.57-1.71 (m, 9 H), 2.64-2.78 (m, 2 H), 4.93 (s, 2 H), 7.84 (s, 1 H). MS (DCI/NH$_3$) m/z 388 (M+H)$^+$. Anal. calculated for $C_{14}H_{21}Cl_3N_2O_2S$: C, 43.37; H, 5.46; N, 7.22. Found: C, 43.49; H, 5.53; N, 7.11.

Example 189

1-adamantyl (5Z)-4-butyl-2-tert-butylisothiazol-5(2H)-ylidenecarbamate

The title compound was prepared from 1-adamantane carbonofluoridate and Example 110B using the procedure as described in Example 187 (187 mg, 79% yield). $^1$H NMR (300 MHz, CDCl$_3$) δ ppm 0.86-1.02 (m, 3 H), 1.33-1.47 (m, 2 H), 1.52-1.77 (m, 17 H), 2.18 (s, 3 H), 2.25 (d, J=2.7 Hz, 6 H), 2.61-2.75 (m, 2 H), 7.75 (s, 1 H). MS (DCI/NH$_3$) m/z 391 (M+H)$^+$. Anal. calculated for $C_{22}H_{34}N_2O_2S$: C, 67.65; H, 8.77; N, 7.17. Found: C, 67.43; H, 8.94; N, 6.86

Example 190

$N^2$-({[(5Z)-4-butyl-2-tert-butylisothiazol-5(2H)-ylidene]amino}carbonyl)-$N^1$,3-dimethyl-L-valinamide

Example 190A 4-nitrophenyl [(5Z)-4-butyl-2-tert-butylisothiazol-5(2H)-ylidene]carbamate A mixture of Example 110B (1.48 g, 7 mmol) and 4-nitrophenylcarbonochloridate (1.41 g, 7 mmol) in dichloromethane was treated with triethylamine (0.78 g, 7.7 mmol). The reaction mixture was stirred at room temperature for 18 hr, diluted with CH$_2$Cl$_2$ and washed with water, dried over MgSO$_4$ and concentrated in vacuo. Purification by flash chromatography (0-50% ethyl acetate/hexane) afforded the title compound (1.8 g, 68% yield).

Example 190B $N^2$-({[(5Z)-4-butyl-2-tert-butylisothiazol-5(2H)-ylidene]amino}carbonyl)-$N^1$,3-dimethyl-L-valinamide Example 190A (120 mg, 0.3 mmol) in acetonitrile (5 mL) was treated with commercially available (S)-2-amino-N,3,3-trimethylbutanamide (115 mg, 0.79 mmol). The reaction mixture was heated and microwave irradiation at 100° C. for 60 min and then concentrated in vacuo. Purification by flash chromatography (50 to 100% ethyl acetate in hexane) afforded the title compound (105 mg, 86% yield). $^1$H NMR (300 MHz, DMSO-$d_6$) δ ppm 0.81-0.98 (m, 12 H), 1.22-1.39 (m, 2 H), 1.44-1.51 (s, 9 H), 1.51-1.63 (m, 2 H), 2.40-2.54 (m, 2 H), 2.57 (d, J=4.4 Hz, 3 H), 4.00 (d, J=9.9 Hz, 1 H), 6.34 (d, J=9.5 Hz, 1 H), 7.85 (d, J=4.4 Hz, 1 H), 8.20 (s, 1 H). MS

Example 191

N-[(5Z)-4-butyl-2-tert-butylisothiazol-5(2H)-ylidene]-N'-(4-methylcyclohexyl)urea The title compound was prepared from 4-methylcyclohexane amine and Example 190A using the procedure described in Example 190B (105 mg, 86% yield). $^1$H NMR (300 MHz, DMSO-$d_6$) δ ppm 0.80-1.01 (m, 6 H), 1.10-1.90 (m, 21 H), 2.42-2.58 (m, 2 H), 3.22-3.38 (m, 2 H), 6.84-7.06 (m, 1 H), 8.12 (d, J=3.2 Hz, 1 H). MS (DCI/NH$_3$) m/z 352 (M+H)$^+$. Anal. calculated for $C_{19}H_{33}N_3OS$: C, 64.91; H, 9.46; N, 11.95. Found: C, 64.29; H, 9.34; N, 11.43.

Example 192

N-[(5Z)-4-butyl-2-tert-butylisothiazol-5(2H)-ylidene]-2-{[(2S)-1-methylpyrrolidin-2-yl]methoxy}-5-(trifluoromethyl)benzamide

Example 192A

N-[(5Z)-4-butyl-2-tert-butylisothiazol-5(2H)-ylidene]-2-fluoro-5-(trifluoromethyl)benzamide Example 110B (2 g, 9.42 mmol) in CH$_2$Cl$_2$ (20 mL) was treated with triethylamine (2.63 mL, 18.8 mmol) and commercially available 2-fluoro-5-(trifluoromethyl)benzoyl chloride (2.13 g, 9.4 mmol). The reaction mixture was stirred at room temperature for 18 hours, partitioned between CH$_2$Cl$_2$ and saturated NaHCO$_3$, dried (MgSO$_4$) and concentrated. The residue was purified by flash chromatography using 0-60% EtOAc in hexane to afford the title compound (2.83 g, 74%) MS (DCI/NH$_3$) m/z 403 (M+H)$^+$.

Example 192B

N-[(5Z)-4-butyl-2-tert-butylisothiazol-5(2H)-ylidene]-2-{[(2S)-1-methylpyrrolidin-2-yl]methox}-5-trifluoromethyl)benzamide To (S)-(1-methylpyrrolidin-2-yl)methanol (0.23 mL, 2 mmol) in tetrahydrofuran (3 mL) was added 1M potassium t-butoxide in THF (2 mL, 2 mmol) and the mixture was stirred for 10 minutes. Example 192A (402 mg, 1 mmol) was added and the mixture stirred at ambient temperature for 24 hours. The mixture was diluted with EtOAc, washed with aqueous NH$_4$Cl, water, brine, dried with MgSO$_4$ and the solvent removed. The product was purified by silica gel chromatography (0-20% MeOH/CH$_2$Cl$_2$ (0.1% NH$_4$OH)) to afford title compound (263 mg, 53% yield). $^1$H NMR (300 MHz, CDCl$_3$) δ ppm 0.98 (t, J=7.3 Hz, 3 H), 1.31-1.51 (m, 2 H), 1.56-1.88 (m, 14 H), 1.98-2.14 (m, 1 H), 2.18-2.36 (m, 1 H), 2.45 (s, 3 H), 2.72-2.92 (m, 3 H), 3.06 (t, J=7.3 Hz, 1 H), 3.96 (dd, J=9.3, 6.5 Hz, 1 H), 4.14 (dd, J=9.1, 5.6 Hz, 1 H), 7.03 (d, J=8.7 Hz, 1 H), 7.60 (dd, J=8.7, 2.4 Hz, 1 H), 7.95 (s, 1 H), 8.22 (d, J=2.4 Hz, 1 H). MS (DCI/NH$_3$) m/z 498 (M+H)$^+$. Anal. calculated for $C_{25}H_{34}F_3N_3O_2S$: C, 60.34; H, 6.89; N, 8.44. Found: C, 60.25; H, 6.77; N, 8.26.

Example 193

N-[(5Z)-4-butyl-2-tert-butylisothiazol-5(2H)-ylidene]-N'-cyano-2-{[(2S)-1-methylpyrrolidin-2-yl]methoxy}-5-trifluoromethyl)benzenecarboximidamide

Example 193A

To a mixture of Example 110C (500 mg, 1.61 mmol), 2-fluoro-5-(trifluoromethyl)phenylboronic acid (871 mg, 2.6 mmol), copper(I) acetate (0.592 g, 4.83 mmol) in DME (35 mL) were added tris(dibenzylideneacetone)dipalladium(0) (0.22 g, 0.15 mmol) and triethyl phosphate (0.132 mL, 0.47 mmol) and the mixture was refluxed for 16 h. The mixture was then concentrated under reduced pressure and the residue was chromatographed over silica gel (hexane:EtOAc, 1:1) to afford the title compound (200 mg, 29% yield). MS (DCI/NH$_3$) m/z 427 (M+H)$^+$.

Example 193B

N-[(5Z)-4-butyl-2-tert-butylisothiazol-5(2H)-ylidene]-N'-cyano-2-{[(2S)-1-methylpyrrolidin-2-yl]methoxy}-5-(trifluoromethyl)benzenecarboximidamide The title compound was prepared using the procedure described in Example 192B substituting Example 193A for Example 192A. $^1$H NMR (300 MHz, CDCl$_3$) δ ppm 0.87-1.03 (m, 3 H), 1.31-1.50 (m, 2 H), 1.52-1.88 (m, 14 H), 1.96-2.16 (m, 1 H), 2.21-2.37 (m, 1 H), 2.40 (s, 3 H), 2.74-2.94 (m, 3 H), 3.05 (d, J=6.4 Hz, 1 H), 4.01 (dd, J=8.8, 6.4 Hz, 1 H), 4.09-4.24 (m, 1 H), 7.08 (d, J=8.5 Hz, 1 H), 7.59-7.70 (m, 1 H), 7.74 (d, J=2.4 Hz, 1 H), 8.08 (s, 1 H). MS (DCI/NH$_3$) m/z 522 (M+H)$^+$. Anal. calculated for $C_{26}H_{34}F_3N_5OS$: C, 59.86; H, 6.57; N, 13.43. Found: C, 59.33; H, 6.44; N, 12.74.

Example 194

N-[(5Z)-4-butyl-2-tert-butylisothiazol-5(2H)-ylidene]-2-{[(2S)-5-oxopyrrolidin-2-yl]methoxy}-5-(trifluoromethyl)benz amide The title compound was prepared from (S)-5-(hydroxymethyl)-pyrrolidine-2-one and Example 192A using the procedure as described in Example 192B (225 mg, 45% yield). $^1$H NMR (300 MHz, CDCl$_3$) δ ppm 0.98 (t, J=7.3 Hz, 3 H), 1.33-1.54 (m, 2 H), 1.69 (s, 9 H), 1.70-1.87 (m, 2 H), 2.22-2.36 (m, 1 H), 2.36-2.47 (m, 2 H), 2.76-2.93 (m, 2 H), 3.76-3.89 (m, 1 H), 4.12-4.27 (m, 1 H), 4.36 (dd, J=9.2, 3.4 Hz, 1 H), 7.01 (d, J=8.5 Hz, 1 H), 7.16 (s, 1 H), 7.63 (dd, J=8.6, 1.9 Hz, 1 H), 7.98 (s, 1 H), 8.34 (s, 1 H), 8.38 (s, 1 H). MS (DCI/NH$_3$) m/z 498 (M+H)$^+$. Anal. calculated for $C_{24}H_{30}F_3N_3O_3S$: C, 57.93; H, 6.08; N, 8.45. Found: C, 57.38; H, 6.02; N, 8.34.

Example 195

N-[(5Z)-4-butyl-2-tert-butylisothiazol-5(2H)-ylidene]-2-{[(4R)-2-oxo-1,3-oxazolidin-4-yl]methoxy}-5-(trifluoromethyl)benzamide The title compound was prepared from (R)-4-hydroxymethyl oxazolidinone and Example 192A using the procedure as described in Example 192B (45 mg, 10% yield). $^1$H NMR (300 MHz, CDCl$_3$) δ ppm 0.90-1.06 (m, 3 H), 1.33-1.52 (m,

---

(DCI/NH$_3$) m/z 382 (M+H)$^+$. Anal. calculated for $C_{19}H_{34}N_4O_2S$: C, 59.09; H, 8.98; N, 14.51. Found: C, 58.90; H, 9.21; N, 14.08.

2 H), 1.62-1.80 (m, 11 H), 2.84 (dd, J=8.6, 7.0 Hz, 2 H), 3.94-4.22 (m, 2 H), 4.29-4.47 (m, 2 H), 4.53 (t, J=8.5 Hz, 1 H), 7.03 (d, J=8.5 Hz, 1 H), 7.11 (s, 1 H), 7.64 (dd, J=8.6, 2.5 Hz, 1 H), 7.99 (s, 1 H), 8.35 (d, J=2.0 Hz, 1 H). MS (DCI/NH$_3$) m/z 499 (M+H)$^+$. Anal. calculated for $C_{23}H_{27}F_3N_3O_4S$: C, 55.41; H, 5.46; N, 8.43. Found: C, 55.32; H, 5.81; N, 8.25

Example 196

N-[(5Z)-4-butyl-2-tert-butylisothiazol-5(2H)-ylidene]-2-[(1-methylpiperidin-2-yl)methoxy]-5-(trifluoromethyl)benzamide The title compound was prepared from (1-methylpiperidine)-2-ylmethanol and Example 192A using the procedure as described in Example 192B (310 mg, 81% yield). $^1$H NMR (300 MHz, CDCl$_3$) δ ppm 0.98 (t, J=7.3 Hz, 3 H), 1.22-1.52 (m, 4 H), 1.64-1.85 (m, 14 H), 1.92-2.06 (m, 1 H), 2.07-2.25 (m, 1 H), 2.35 (s, 3 H), 2.40-2.57 (m, 1 H), 2.72-2.93 (m, 3 H), 3.96 (dd, J=9.5, 5.4 Hz, 1 H), 4.30 (dd, J=9.5, 5.4 Hz, 1 H), 7.01 (d, J=8.8 Hz, 1 H), 7.60 (dd, J=8.6, 1.9 Hz, 1 H), 7.88-8.04 (m, 1 H), 8.23 (d, J=2.0 Hz, 1 H). MS (DCI/NH$_3$) m/z 512 (M+H)$^+$. Anal. calculated for $C_{26}H_{36}F_3N_3O_2S$: C, 61.03; H, 7.03; N, 8.21. Found: C, 60.88; H, 6.73; N, 7.98.

Example 197

N-[(5Z)-2-tert-butyl-4-isobutylisothiazol-5(2H)-ylidene]-2-{[(2S)-1-methylpyrrolidin-2-yl]methoxy}-5-(trifluoromethyl)benzamide Example 197A N-[(5Z)-2-tert-butyl-4-(2-methylpropyl)isothiazol-5(2H)-ylidene]-2-fluoro-5-(trifluoromethyl)benzamide Example 143C (2 g, 9.42 mmol) in CH$_2$Cl$_2$ (20 mL) was treated with triethylamine (2.63 mL, 18.8 mmol) and commercially available 2-fluoro-5-(trifluoromethyl)benzoyl chloride (2.13 g, 9.4 mmol). The reaction mixture was stirred at room temperature for 18 hours, partitioned between CH$_2$Cl$_2$ and saturated NaHCO$_3$, dried (MgSO$_4$) and concentrated. The residue was purified by flash chromatography using 0-60% EtOAc in hexane to afford the title compound (3.1 g, 82% yield). MS (DCI/NH$_3$) m/z 403 (M+H)$^+$.

Example 197B

N-[(5Z)-2-tert-butyl-4-isobutylisothiazol-5(2H)-ylidene]-2-{[(2S)-1-methylpyrrolidin-2-yl]methoxy}-5-(trifluoromethyl)benzamide The title compound was prepared using the procedure as described in Example 192B replacing Example 192A with Example 197A (290 mg, 78% yield). $^1$H NMR (300 MHz, CDCl$_3$) δ ppm 0.96 (dd, J=6.8, 1.7 Hz, 6 H), 1.63-1.86 (m, 12 H), 1.95-2.21 (m, 2 H), 2.19-2.37 (m, 1 H), 2.45 (s, 3 H), 2.69 (d, J=7.1 Hz, 2 H), 2.73-2.89 (m, 1 H), 2.99-3.15 (m, 1 H), 3.96 (dd, J=9.2, 6.4 Hz, 1 H), 4.14 (dd, J=9.2, 5.4 Hz, 1 H), 7.03 (d, J=8.5 Hz, 1 H), 7.59 (dd, J=8.6, 2.5 Hz, 1 H), 7.93 (s, 1 H), 8.21 (d, J=2.4 Hz, 1 H). MS (DCI/NH$_3$) m/z 498 (M+H)$^+$.

Example 198

N-[(5Z)-4-butyl-2-tert-butylisothiazol-5(2H)-ylidene]-2-(pyrazin-2-ylmethoxy)-5-(trifluoromethyl)benzamide The title compound was prepared from pyrazine-2-ylmethanol and Example 192A using the procedure as described in Example 192B (70 mg, 19% yield). $^1$H NMR (300 MHz, CDCl$_3$) δ ppm 0.94 (t, J=7.3 Hz, 3 H), 1.27-1.50 (m, 2 H), 1.61-1.80 (m, 11 H), 2.75-2.97 (m, 2 H), 5.40 (s, 2 H), 7.11 (d, J=8.5 Hz, 1 H), 7.55-7.77 (m, 1 H), 7.98 (s, 1 H), 8.39 (d, J=2.4 Hz, 1 H), 8.53 (s, 2 H), 9.15 (s, 1 H). MS (DCI/NH$_3$) m/z 493 (M+H)$^+$. Anal. calculated for $C_{24}H_{27}F_3N_4O_2S$: C, 58.52; H, 5.53; N, 11.37. Found: C, 58.56; H, 5.42; N, 11.41.

Example 199

N-[(5Z)-2-tert-butyl-4-isobutylisothiazol-5(2H)-ylidene]-2-(pyrazin-2-ylmethoxy)-5-(trifluoromethyl)benzamide The title compound was prepared from pyrazine-2-ylmethanol and Example 197A using the procedure as described in Example 192B (225 mg, 61% yield). $^1$H NMR (300 MHz, CDCl$_3$) δ ppm 0.88-1.01 (m, 6 H), 1.69 (s, 9 H), 1.98-2.21 (m, 1 H), 2.70 (d, J=7.1 Hz, 2 H), 5.42 (s, 2 H), 7.10 (d, J=8.5 Hz, 1 H), 7.63 (dd, J=8.6, 1.9 Hz, 1 H), 7.95 (s, 1 H), 8.39 (d, J=2.4 Hz, 1 H), 8.49-8.59 (m, 2 H), 9.13 (s, 1 H). MS (DCI/NH$_3$) m/z 493 (M+H)$^+$. Anal. calculated for $C_{24}H_{27}F_3N_4O_2S$: C, 58.52; H, 5.53; N, 11.37. Found: C, 58.50; H, 5.40; N, 11.56.

Example 200

N-[(5Z)-2-tert-butyl-4-isobutylisothiazol-5(2H)-ylidene]-2-(pyridin-2-ylmethoxy)-5-(trifluoromethyl)benzamide The title compound was prepared from pyridine-2-ylmethanol and Example 197A using the procedure as described in Example 192B (313 mg, 64% yield). $^1$H NMR (300 MHz, DMSO-d$_6$) δ ppm 0.78-0.92 (m, 6 H), 1.55-1.72 (m, 9 H), 1.93-2.14 (m, 1 H), 2.60 (d, J=7.1 Hz, 2 H), 5.38 (s, 2 H), 7.25-7.45 (m, 2 H), 7.64-7.92 (m, 3 H), 8.08 (d, J=2.4 Hz, 1 H), 8.57 (d, J=4.0 Hz, 1 H), 8.65 (s, 1 H). MS (DCI/NH$_3$) m/z 492 (M+H)$^+$. Anal. calculated for $C_{25}H_{28}F_3N_3O_2S$: C, 61.08; H, 5.74; N, 8.55. Found: C, 60.94; H, 5.71; N, 8.52.

Example 201

(1R,3S)—N$^1$-[(5Z)-4-butyl-2-tert-butylisothiazol-5(2H)-ylidene]-N$^3$-ethyl-1,2,2-trimethylcyclopentane-1,3-dicarboxamide The product from Example 173 and ethylamine hydrochloride (Aldrich) were processed using the method described in Example 178 to afford the title compound. $^1$H NMR (DMSO-d$_6$) δ 0.48 (s, 3H), 0.90 (t, J=7.0 Hz, 3H), 1.00 (t, J=7.2 Hz, 3H), 1.23 (2, 3H), 1.19 (s, 3H), 1.26-1.44 (m, 3H), 1.57 (s, 9H), 1.57-1.70 (m, 3H), 1.96-2.09 (m, 1H), 2.59-2.67 (m, 3H), 2.72-2.82 (m, 1H), 2.94-3.19 (m, 2H), 7.53-7.57 (m, 1H), 8.50 (s, 1H). MS (ESI+) m/z 422 (M+H)$^+$. Anal. calcd. for $C_{23}H_{39}N_3O_2S$: C, 65.52; H, 9.32; N, 9.97. Found: C, 65.03; H, 9.26; N, 9.86.

Example 202

(1R,3S)—N¹-[(5Z)-4-butyl-2-tert-butylisothiazol-5 (2H)-ylidene]-1,2,2-trimethyl-N³-propylcyclopentane-1,3-dicarboxamide The product from Example 173 and propylamine hydrochloride (Aldrich) were processed using the method described in Example 178 to afford the title compound. $^1$H NMR $^1$H NMR (DMSO-d$_6$) δ 0.48 (s, 3H), 0.83 (t, J=7.3 Hz, 3H), 0.90 (t, J=7.3 Hz, 3H), 1.19 (s, 3H), 1.23 (s, 3H), 1.26-1.43 (m, 5H), 1.56 (s, 9H), 1.56-1.67 (m, 3H), 1.96-2.09 (m, 1H), 2.62-2.69 (m, 3H), 2.72-2.95 (m, 2H), 3.06-3.17 (m, 1H), 7.53-7.57 (m, 1H), 8.50 (s, 1H). MS (ESI+) m/z 436 (M+H)$^+$. Anal. calcd. for C$_{24}$H$_{41}$N$_3$O$_2$S: C, 66.16; H, 9.49; N, 9.65. Found: C, 65.76; H, 9.51; N, 9.68.

Example 203

(1R,3S)—N¹-[(5Z)-4-butyl-2-tert-butylisothiazol-5 (2H)-ylidene]-N³-(2-hydroxyethyl)-1,2,2-trimethylcyclopentane-1,3-dicarboxamide The product from Example 173 and ethanolamine hydrochloride (Aldrich) were processed using the method described in Example 178 to afford the title compound. $^1$H NMR (DMSO-d$_6$) δ 0.47 (s, 3H), 0.90 (t. J=7.0 Hz, 3H), 1.19 (s, 3H), 1.23 (s, 3H), 1.26-1.48 (m, 4H), 1.57 (s, 9H), 1.57-1.67 (m, 3H), 1.96-2.08 (m, 1H), 2.62-2.68 (m, 2H), 2.71-2.82 (m, 1H), 3.00-3.10 (m, 1H), 3.14-2.25 (m, 1H), 3.33-3.39 (m, 2H), 4.62 (t, J=4.6 Hz, 1H), 7.52 (t, J=5.7 Hz, 1H), 8.50 (s, 1H). MS (ESI+) m/z 438 (M+H)$^+$.

Example 204

Methyl (1S,3R)-3-({[(5Z)-4-butyl-2-tert-butyl-isothiazol-5(2H)-ylidene]amino}carbonyl)-1,2,2-trimethylcyclopentanecarboxylate The product from Example 92B and (−)-camphoric acid (Aldrich) were processed using the method described in Example 170 to afford the title compound. $^1$H NMR (DMSO-d$_6$) δ 0.53 (s, 3H), 0.90 (t, J=7.3 Hz, 3H), 1.20 (s, 3H), 1.23 (s, 3H), 1.23-1.40 (m, 2H), 1.41-1.50 (m, 1H), 1.57 (s, 9H), 1.57-1.67 (m, 2H), 1.71-1.84 (m, 1H), 2.24-2.36 (m, 1H), 2.41-2.48 (m, 1H), 2.61-2.67 (m, 2H), 3.00-3.06 (m, 1H), 3.59 (s, 3H), 8.51 (s, 1H). (ESI+) m/z 409 (M+H)$^+$. Anal. calcd. for C$_{22}$H$_{36}$N$_2$O$_3$S: C, 64.67; H, 8.88; N, 6.86. Found: C, 64.52; H, 8.94; N, 6.70.

Example 205

(1S,3R)-3-({[(5Z)-4-butyl-2-tert-butylisothiazol-5 (2H)-ylidene]amino}carbonyl)-1,2,2-trimethylcyclopentanecarboxylic acid The product from Example 204 was processed using the method described in Example 96 to afford the title compound. MS (ESI+) m/z 395 (M+H)$^+$.

Example 206

(1R,3S)—N¹-[(5Z)-4-butyl-2-tert-butylisothiazol-5 (2H)-ylidene]-N³-isopropyl-1,2,2-trimethylcyclopentane-1,3-dicarboxamide The product from Example 173 and isopropylamine (Aldrich) were processed using the method described in Example 178 to afford the title compound. $^1$H NMR (DMSO-d$_6$) δ 0.48 (s, 3H), 0.90 (t, J=7.3 Hz, 3H), 1.02-1.05 (m, 6H), 1.19 (s, 3H), 1.23 (s, 3H), 1.26-1.44 (m, 3H), 1.56 (s, 9H), 1.56-1.67 (m, 3H), 1.95-2.08 (m, 1H), 2.60-2.67 (m, 3H), 2.72-2.82 (m, 1H), 3.80-3.92 (m, 1H), 7.39 (d J=7.4 Hz, 1H), 8.50 (s, 1H). (ESI+) m/z 436 (M+H)$^+$. Anal. calcd. for C$_{24}$H$_{41}$N$_2$O$_3$S: C, 66.16; H, 9.49; N, 9.65. Found: C, 65.80; H, 9.54; N, 9.50.

Example 207

(1R,3S)—N¹-[(5Z)-4-butyl-2-tert-butylisothiazol-5 (2H)-ylidene]-N³-cyclobutyl-1,2,2-trimethylcyclopentane-1,3-dicarboxamide The product from Example 173 and cyclobutylamine hydrochloride (Aldrich) were processed using the method described in Example 178 to afford the title compound. $^1$H NMR (DMSO-d$_6$) δ 0.00 (s, 3H), 0.44 (t, J=7.3 Hz, 3H), 0.74 (s, 3H), 0.77 (s, 3H), 0.80-0.98 (m, 3H), 1.11 (s, 9H), 1.11-1.21 (m, 5H), 1.32-1.57 (m, 3H), 1.62-1.72 (m, 2H), 2.13-2.21 (m, 3H), 2.26-2.36 (m, 1H), 3.67-3.80 (m, 1H), 7.32 (d, J=7.7 Hz, 1H), 8.04 (s, 1H). (ESI+) m/z 448 (M+H)$^+$. Anal. calcd. for C$_{25}$H$_{41}$N$_3$O$_2$S: C, 67.07; H, 9.23; N, 9.39. Found: C, 66.48; H, 9.40; N, 9.24.

Example 208

(1R,3S)—N¹-[(5Z)-4-butyl-2-tert-butylisothiazol-5 (2H)-ylidene]-N³-cyclopropyl-1,2,2-trimethylcyclopentane-1,3-dicarboxamide The product from Example 173 and cyclopropylamine hydrochloride (Aldrich) were processed using the method described in Example 178 to afford the title compound. $^1$H NMR (DMSO-d$_6$) δ 0.30-0.42 (m, 2H), 0.47 (s, 3H), 0.56-0.60 (m, 2H), 0.90 (7.3 Hz, 3H), 1.17 (s, 3H), 1.18 (s, 3H), 1.23-1.44 (m, 3H), 1.56 (s, 9H), 1.56-1.67 (m, 3H), 1.95-2.07 (m, 1H), 2.56-2.67 (m, 4H), 2.71-2.82 (m, 1H), 7.63 (d, J=4.0 Hz, 1H), 8.50 (s, 1H). (ESI+) m/z 434 (M+H)$^+$. Anal. calcd. for C$_{24}$H$_{39}$N$_3$O$_2$S: C, 66.47; H, 9.06; N, 9.69. Found: C, 65.95; H, 9.13; N, 9.44.

Example 209

(1S,3R)—N³-[(5Z)-4-butyl-2-tert-butylisothiazol-5 (2H)-ylidene]-N¹,1,2,2-tetramethylcyclopentane-1,3-dicarboxamide The product from Example 205 and methylamine hydrochloride (Aldrich) were processed using the method described in Example 178 to afford the title compound. $^1$H NMR (DMSO-d$_6$) δ 0.48 (s, 3H), 0.90 (t, J=7.3 Hz, 3H), 1.13 (s, 3H), 1.23 (s, 3H), 1.26-1.42 (m, 3H), 1.57 (s, 9H), 1.57-1.66 (m, 2H), 1.72-1.82 (m, 1H), 2.24-2.45 (m, 2H), 2.54-2.56 (m, 3H), 2.61-2.67 (m, 2H), 2.96-3.02 (m, 1H), 7.24-7.28 (m, 1H), 8.50 (s, 1H). (ESI+) m/z 408 (M+H)$^+$.

Example 210

(1S,3R)—N³-[(5Z)-4-butyl-2-tert-butylisothiazol-5 (2H)-ylidene]-N¹-ethyl-1,2,2-trimethylcyclopentane-1,3-dicarboxamide The product from Example 205 and ethylamine hydrochloride (Aldrich) were processed using the method described in Example 178 to afford the title compound. $^1$H NMR (DMSO-d$_6$) δ 0.49 (s, 3H), 0.90 (t, J=7.3 Hz, 3H), 0.98 (t, J=7.7 Hz, 3H), 1.13 (s, 3H), 1.23 (s, 3H), 1.26-1.40 (m, 3H), 1.57 (s, 9H), 1.57-1.66 (m, 2H), 1.71-1.82 (m, 1H), 2.24-2.47 (m, 2H), 2.61-2.67 (m, 2H), 2.96-3.11 (m, 3H), 7.28-7.31 (m, 1H), 8.50 (s, 1H). (ESI+) m/z 422 (M+H)$^+$.

Example 211

(1S,3R)—N$^3$-[(5Z)-4-butyl-2-tert-butylisothiazol-5 (2H)-ylidene]-1,2,2-trimethyl-N$^1$-propylcyclopentane-1,3-dicarboxamide The product from Example 205 and propylamine hydrochloride (Aldrich) were processed using the method described in Example 178 to afford the title compound. $^1$H NMR (DMSO-d$_6$) δ 0.50 (s, 3H), 0.80 (t, J=7.3 Hz, 3H), 0.90 (t, J=7.3 Hz, 3H), 1.14 (s, 3H), 1.24 (s, 3H), 1.28-1.43 (m, 5H), 1.57 (s, 9H), 1.57-1.67 (m, 2H), 1.72-1.82 (m, 1H), 2.25-2.47 (m, 2H), 2.61-2.67 (m, 2H), 2.96-3.03 (m, 3H), 7.25-7.29 (m, 1H), 8.50 (s, 1H). (ESI+) m/z 436 (M+H)$^+$. Anal. calcd. for C$_{24}$H$_{41}$N$_3$O$_2$S: C, 66.16; H, 9.49; N, 9.65. Found: C, 65.94; H, 9.63; N, 9.44.

Example 212

(1S,3R)—N$^3$-[(5Z)-4-butyl-2-tert-butylisothiazol-5 (2H)-ylidene]-N$^1$-(2-hydroxyethyl)-1,2,2-trimethylcyclopentane-1,3-dicarboxamide The product from Example 205 and ethanolamine hydrochloride (Aldrich) were processed using the method described in Example 178 to afford the title compound. $^1$H NMR (DMSO-d$_6$) δ 0.49 (s, 3H), 0.90 (t, J=7.3 Hz, 3H), 1.14 (s, 3H), 1.23 (s, 3H), 1.26-1.42 (m, 3H), 1.57 (s, 9H), 1.57-1.67 (m, 2H), 1.69-1.82 (m, 1H), 2.25-2.47 (m, 2H), 2.61-2.67 (m, 2H), 2.96-3.02 (m, 1H), 3.09-3.15 (m, 2H), 3.33-3.39 (m, 2H), 4.61 (t, J=5.3 HZ, 1H), 7.20 (t, J=5.5 Hz, 1H), 8.50 (s, 1H). (ESI+) m/z 438 (M+H)$^+$. Anal. calcd. for C$_{23}$H$_{39}$N$_3$O$_3$S: C, 63.12; H, 8.98; N, 9.60. Found: C, 62.89; H, 8.84; N, 9.72.

Example 213

(1R,3S)—N$^1$-[(5Z)-4-butyl-2-tert-butylisothiazol-5 (2H)-ylidene]-N$^3$-(3-hydroxypropyl)-1,2,2-trimethylcyclopentane-1,3-dicarboxamide The product from Example 173 and propanolamine (Aldrich) were processed using the method described in Example 178 to afford the title compound. $^1$H NMR (DMSO-d$_6$) δ 0.48 (s, 3H), 0.90 (t, J=7.3 Hz, 3H), 1.19 (s, 3H), 1.23 (s, 3H), 1.26-1.45 (m, 3H), 1.49-1.57 (m, 2H), 1.57 (s, 9H), 1.57-1.67 (m, 3H), 1.96-2.08 (m, 1H), 2.62-2.68 (m, 3H), 2.72-2.83 (m, 1H), 2.95-3.06 (m, 1H), 3.13-3.26 (m, 1H), 3.37-3.43 (m, 2H), 4.42 (t, J=5.3 Hz, 1H), 7.56 (t, J=5.7 Hz, 1H), 8.50 (s, 1H). (ESI+) m/z 452 (M+H)$^+$. Anal. calcd. for C$_{24}$H$_{41}$N$_3$O$_3$S: C, 63.82; H, 9.15; N, 9.30. Found: C, 63.12; H, 8.91; N, 9.25.

Example 214

(1R,3S)—N$^1$-[(5Z)-4-butyl-2-tert-butylisothiazol-5 (2H)-ylidene]-1,2,2-trimethyl-N$^3$-[(2R)-tetrahydrofuran-2-ylmethyl]cyclopentane-1,3-dicarboxamide The product from Example 173 and (R)-(tetrahydrofuran-2-yl)methanamine (Aldrich) were processed using the method described in Example 178 to afford the title compound. $^1$H NMR (DMSO-d$_6$) δ 0.48 (s, 3H), 0.90 (t, J=7.3 Hz, 3H), 1.19 (s, 3H), 1.24 (s, 3H), 1.26-1.52 (m, 5H), 1.57 (s, 9H), 1.57-1.67 (m, 2H), 1.74-1.89 (m, 3H), 1.95-2.08 (m, 1H), 2.62-2.83 (m, 4H), 2.91-2.99 (m, 1H), 3.22-3.33 (m, 2H), 3.56-3.84 (m, 2H), 7.58-7.62 (m, 1H), 8.50 (s, 1H). (ESI+) m/z 478 (M+H)$^+$. Anal. calcd. for C$_{26}$H$_{43}$N$_3$O$_3$S: C, 65.37; H, 9.07; N, 8.80. Found: C, 65.39; H, 8.91; N, 8.66.

Example 215

Methyl (1S,3R)-3-({[(5Z)-4-butyl-2-tert-butylisothiazol-5(2H)-ylidene]amino}carbonyl)-2,2,3-trimethylcyclopentylcarbamate To a 100-mL, round-bottomed flask containing a magnetic stir bar were added Example 173 (1.18 g, 3.00 mmol), diphenylphosphoryl azide (Aldrich, 90.8 mg, 3.30 mmol) anhydrous toluene (45 mL) and triethylamine (Aldrich, 1.25 mL, 9.00 mmol). The mixture was heated to reflux under nitrogen atmosphere for 4 h. After cooling, the volatiles were removed by rotary evaporator to give a clear liquid. The crude intermediate (235 mg, 0.600 mmol) was dissolved in anhydrous methanol and the mixture was stirred overnight. The volatiles were removed by rotary evaporator to give a light brown oil. Flash chromatography (silica gel, 25-75% ethyl acetate in hexanes) afforded 86 mg (34%) of the title compound. $^1$H NMR (DMSO-d$_6$) δ 0.48 (s, 3H), 0.90 (t, J=7.2 Hz, 3H), 1.03 (s, 3H), 1.19 (s, 3H), 1.24-1.41 (m, 3H), 1.45-1.67 (m, 3H), 1.57 (s, 9H), 1.86-1.97 (m, 1H), 2.62-2.77 (m, 3H), 3.51 (s, 3H), 3.89-3.98 (m, 1H), 6.93 (d, J=9.6 Hz, 1H), 8.51 (s, 1H). MS (ESI+) m/z 424 (M+H)$^+$.

Example 216

Ethyl (1S,3R)-3-({[(5Z)-4-butyl-2-tert-butylisothiazol-5(2H)-ylidene]amino}carbonyl)-2,2,3-trimethylcyclopentylcarbamate The title compound was prepared as described in Example 215 substituting ethanol for methanol. $^1$H NMR (DMSO-d$_6$) δ 0.48 (s, 3H), 0.90 (t, J=7.3 Hz, 3H), 1.03 (s, 3H), 1.15 (t, J=7.1 Hz, 3H), 1.19 (s, 3H), 1.24-1.40 (m, 3H), 1.46-1.67 (m, 3H), 1.57 (s, 9H), 1.86-1.99 (m, 1H), 2.63-2.77 (m, 3H), 3.89-4.04 (m, 3H), 6.89 (d, J=9.6 Hz, 1H), 8.51 (s, 1H). MS (ESI+) m/z 438 (M+H)$^+$.

Example 217

(1R,3S)—N-[(5Z)-4-butyl-2-tert-butylisothiazol-5 (2H)-ylidene]-3-(4,5-dihydro-1,3-oxazol-2-yl)-1,2,2-trimethylcyclopentanecarboxamide To a 20-mL scintillation vial containing a magnetic stir bar were added Example 203 (219 mg, 0.500 mmol), solid tosyl chloride (Aldrich, 105 mg, 0.550 mmol), and a crystal of dimethylaminopyridine (Aldrich). Anhydrous tetrahydrofuran was added to form a colorless solution, and the triethylamine (Aldrich, 0.139 mL, 1.00 mmol) was added. The reaction mixture was stirred at room temperature overnight. Water (10 mL) was added, and the mixture was extracted with dichloromethane (3×10 mL). The combined organic extracts were dried over sodium sulfate, filtered, and concentrated by rotary evaporator to give a sticky solid. Flash chromatography (silica gel, 40-100% ethyl acetate in hexanes) afforded 134 mg (64%) of the title compound. $^1$H NMR (DMSO-d$_6$) δ 0.51 (s, 3H), 0.90 (t, J=7.3 Hz, 3H), 1.29 (s, 3H), 1.21 (s, 3H), 1.23-1.36 (m, 2H), 1.39-1.48 (m, 1H), 1.57 (s, 9H), 1.57-1.67 (m, 2H), 1.76-1.90 (m, 1H), 2.07-2.19 (m, 1H), 2.62-2.67 (m, 2H), 2.72-2.82 (m, 2H), 3.68 (t, J=9.3 Hz, 2H), 4.15 (t, J=9.2 Hz, 2H), 8.50 (s, 1H). MS (ESI+) m/z 420 (M+H)+. Anal. calcd. for $C_{23}H_{37}N_3O_2S$: C, 65.83; H, 8.89; N, 10.01. Found: C, 65.52; H, 8.85; N, 9.93.

Example 218

(1S,3R)—$N^1$-[(5Z)-4-butyl-2-tert-butylisothiazol-5 (2H)-ylidene]-$N^3$,1,2,2-tetramethylcyclopentane-1,3-dicarboxamide Example 174 and methylamine hydrochloride (Aldrich) were processed as described in Example 178 to afford the title compound. $^1$H NMR (DMSO-$d_6$) δ 0.47 (s, 3H), 0.90 (t, J=7.3 Hz, 3H), 1.19 (s, 3H), 1.22 (s, 3H), 1.26-1.45 (m, 3H), 1.57 (s, 9H), 1.57-1.68 (m, 3H), 1.96-2.08 (m, 1H), 2.57 (d, J=4.4 Hz, 3H), 2.61-2.67 (m, 3H), 2.72-2.83 (m, 1H), 7.48 (q, J=4.4 Hz, 1H), 8.49 (s, 1H). MS (ESI+) m/z 408 (M+H)+. Anal. calcd. for $C_{22}H_{37}N_3O_2S$: C, 64.83; H, 9.15; N, 10.31. Found: C, 64.76; H, 9.29; N, 10.28.

Example 219

(1S,3R)—$N^1$-[(5Z)-4-butyl-2-tert-butylisothiazol-5 (2H)-ylidene]-1,2,2-trimethyl-$N^3$-propylcyclopentane-1,3-dicarboxamide Example 174 and propylamine hydrochloride (Aldrich) were processed as described in Example 178 to afford the title compound. $^1$H NMR (DMSO-$d_6$) δ 0.48 (s, 3H), 0.83 (t, J=7.5 Hz, 3H), 0.90 (t, J=7.5 Hz, 3H), 1.19 (s, 3H), 1.24 (s, 3H), 1.26-1.45 (m, 5H), 1.57 (s, 9H), 1.57-1.67 (m, 3H), 1.96-2.09 (m, 1H), 2.62-2.69 (m, 3H), 2.72-2.83 (m, 1H), 2.86-2.95 (m, 1H), 3.06-3.19 (m, 1H), 7.54 (dd, J=5.6, 5.6 Hz, 1H), 8.49 (s, 1H). MS (ESI+) m/z 436 (M+H)+. Anal. calcd. for $C_{24}H_{41}N_3O_2S$: C, 66.16; H, 9.49; N, 9.65. Found: C, 65.77; H, 9.60; N, 9.49.

Example 220

(1S,3R)—$N^1$-[(5Z)-4-butyl-2-tert-butylisothiazol-5 (2H)-ylidene]-$N^3$-(2-methoxyethyl)-1,2,2-trimethyl-cyclopentane-1,3-dicarboxamide Example 174 and 2-methoxyethanamine (Aldrich) were processed as described in Example 178 to afford the title compound. $^1$H NMR (DMSO-$d_6$) δ 0.48 (s, 3H), 0.90 (t, J=7.2 Hz, 3H), 1.19 (s, 3H), 1.23 (s, 3H), 1.26-1.46 (m, 4H), 1.57 (s, 9H), 1.57-1.67 (m, 3H), 1.96-2.09 (m, 1H), 2.62-2.69 (m, 3H), 2.72-2.82 (m, 1H), 3.07-3.15 (m, 1H), 3.22 (s, 3H), 3.28-3.34 (m, 2H), 7.56 (dd, J=5.1, 5.1 Hz, 1H), 8.49 (s, 1H). MS (ESI+) m/z 452 (M+H)+. Anal. calcd. for $C_{24}H_{41}N_3O_3S$: C, 63.82; H, 9.15; N, 9.30. Found: C, 63.60; H, 9.35; N, 9.23.

Example 221

(1S,3R)—$N^1$-[(5Z)-4-butyl-2-tert-butylisothiazol-5 (2H)-ylidene]-$N^3$-(3-hydroxypropyl)-1,2,2-trimethylcyclopentane-1,3-dicarboxamide Example 174 and 3-aminopropan-1-ol (Aldrich) were processed as described in Example 178 to afford the title compound. $^1$H NMR (DMSO-$d_6$) δ 0.48 (s, 3H), 0.90 (t, J=7.5 Hz, 3H), 1.19 (s, 3H), 1.23 (s, 3H), 1.26-1.33 (m, 2H), 1.36-1.45 (m, 1H), 1.49-1.57 (m, 2H), 1.57 (s, 9H), 1.57-1.67 (m, 3H), 1.96-2.08 (m, 1H), 2.62-2.68 (m, 3H), 2.72-2.83 (m, 1H), 2.95-3.06 (m, 1H), 3.13-3.24 (m, 1H), 3.37-3.43 (m, 2H), 4.40 (t, J=5.3 Hz, 1H), 7.53 (dd, J=5.6, 5.6 Hz, 1H), 8.49 (s, 1H). MS (ESI+) m/z 452 (M+H)+. Anal. calcd. for $C_{24}H_{41}N_3O_3S$: C, 63.82; H, 9.15; N, 9.30. Found: C, 63.96; H, 9.30; N, 9.28.

Example 222

(1S,3R)-3-(azetidin-1-ylcarbonyl)-N-[(5Z)-4-butyl-2-tert-butylisothiazol-5(2H)-ylidene]-1,2,2-trimethylcyclopentanecarboxamide Example 174 and azetidine hydrochloride (Aldrich) were processed as described in Example 178 to afford the title compound. $^1$H NMR (DMSO-$d_6$) δ 0.50 (s, 3H), 0.90 (t, J=7.5 Hz, 3H), 1.22 (s, 3H), 1.24 (s, 3H), 1.24-1.35 (m, 2H), 1.37-1.46 (m, 1H), 1.57 (s 9H), 1.57-1.68 (m, 3H), 1.90-2.03 (m, 1H), 2.09-2.19 (m, 2H), 2.62-2.67 (m, 2H), 2.71-2.83 (m, 2H), 3.73-3.81 (m, 1H), 3.82-3.91 (m, 1H), 4.06-4.14 (m, 1H), 4.18-4.26 (m, 1H), 8.49 (s, 1H). MS (ESI+) m/z 434 (M+H)+.

Example 223

(1S,3R)—$N^1$-[(5Z)-4-butyl-2-tert-butylisothiazol-5 (2H)-ylidene]-$N^3$,$N^3$,1,2,2-pentamethylcyclopentane-1,3-dicarboxamide Example 174 and dimethylamine hydrochloride (Aldrich) were processed as described in Example 178 to afford the title compound. $^1$H NMR (DMSO-$d_6$) δ 0.49 (s, 3H), 0.90 (t, J=7.3 Hz, 3H), 1.25 (s, 3H), 1.26 (s, 3H), 1.27-1.46 (m, 3H), 1.57 (s, 9H), 1.57-1.70 (m, 3H), 1.96-2.10 (m, 1H), 2.62-2.67 (m, 2H), 2.74-2.81 (m, 1H), 2.83 (s, 3H), 3.05 (s, 3H), 3.33-3.38 (m, 1H), 8.49 (s, 1H). MS (ESI+) m/z 422 (M+H)+. Anal. calcd. for $C_{23}H_{39}N_3O_2S$: C, 65.52; H, 9.32; N, 9.97. Found: C, 65.46; H, 9.43; N, 9.98.

Example 224

(1R,3S)—N-[(5Z)-4-butyl-2-tert-butylisothiazol-5 (2H)-ylidene]-3-(4,5-dihydro-1,3-oxazol-2-yl)-2,2,3-trimethylcyclopentanecarboxamide Example 212, tosyl chloride (Aldrich), and triethylamine (Aldrich) were processed as described in Example 217 to afford the title compound. $^1$H NMR (DMSO-$d_6$) δ 0.54 (s, 3H), 0.89 (t, J=7.5 Hz, 3H), 1.18 (s, 3H), 1.23 (s, 3H), 1.24-1.36 (m, 2H), 1.44-1.52 (m, 1H), 1.57 (s, 9H), 1.53-1.72 (m, 2H), 1.74-1.85 (m, 1H), 2.24-2.37 (m, 1H), 2.56-2.73 (m, 3H), 3.01-3.07 (m, 1H), 3.63-3.67 (m, 2H), 4.12-4.19 (m, 2H), 8.50 (s, 1H). MS (ESI+) m/z 420 (M+H)+. Anal. calcd. for $C_{23}H_{37}N_3O_2S$: C, 65.83; H, 8.89; N, 10.01. Found: C, 65.49; H, 9.13; N, 9.94.

Example 225

(1S,3R)—$N^1$-[(5Z)-4-butyl-2-tert-butylisothiazol-5 (2H)-ylidene]-$N^3$-cyclobutyl-1,2,2-trimethylcyclopentane-1,3-dicarboxamide Example 174 and aminocyclobutane hydrochloride (Aldrich) were processed as described in Example 178 to afford the title compound. $^1$H NMR (DMSO-$d_6$) δ 0.46 (s, 3H), 0.90 (t, J=7.3 Hz, 3H), 1.19 (s, 3H), 1.23 (s, 3H), 1.26-1.44 (m, 3H), 1.57 (s, 9H), 1.57-1.69 (m, 5H), 1.78-2.06 (m, 3H), 2.08-2.18 (m, 2H), 2.58-2.67 (m, 3H), 2.71-2.82 (m, 1H), 4.12-4.26 (m, 1H), 7.75 (d, J=7.5 Hz, 1H), 8.49 (s, 1H). MS (ESI+) m/z 448 (M+H)⁺. Anal. calcd. for $C_{25}H_{41}N_3O_2S$: C, 67.07; H, 9.23; N, 9.39. Found: C, 67.24; H, 9.46; N, 9.34.

Example 226

(1R,3S)—N¹-[(5Z)-4-butyl-2-tert-butylisothiazol-5 (2H)-ylidene]-1,2,2-trimethyl-N³-[(2S)-tetrahydrofuran-2-ylmethyl]cyclopentane-1,3-dicarboxamide Example 173 and (S)-(tetrahydrofuran-2-yl)methanamine (Aldrich) were processed as described in Example 178 to afford the title compound. ¹H NMR (DMSO-d₆) δ 0.49 (s, 3H), 0.90 (t, J=7.3 Hz, 3H), 1.19 (s, 3H), 1.23 (s, 3H), 1.26-1.54 (m, 4H), 1.57 (s, 9H), 1.57-1.67 (m, 3H), 1.73-1.89 (m, 3H), 1.95-2.08 (m, 1H), 2.62-2.83 (m, 4H), 2.94-3.02 (m, 1H), 3.23-3.29 (m, 1H), 3.56-3.63 (m, 1H), 3.71-3.86 (m, 2H), 7.59 (dd, J=6.0, 6.0 Hz, 1H), 8.49 (s, 1H). MS (ESI+) m/z 478 (M+H)⁺. Anal. calcd. for $C_{26}H_{43}N_3O_3S$: C, 65.37; H, 9.07; N, 8.80. Found: C, 65.67; H, 9.20; N, 8.83.

Example 227

(1S,3R)—N³-[(5Z)-4-butyl-2-tert-butylisothiazol-5 (2H)-ylidene]-1,2,2-trimethyl-N¹-[(2S)-tetrahydrofuran-2-ylmethyl]cyclopentane-1,3-dicarboxamide Example 205 and (S)-(tetrahydrofuran-2-yl)methanamine (Aldrich) were processed as described in Example 178 to afford the title compound. ¹H NMR (DMSO-d₆) δ 0.50 (s, 3H), 0.90 (t, J=7.3 Hz, 3H), 1.14 (s, 3H), 1.24 (s, 3H), 1.25-1.43 (m, 3H), 1.57 (s, 9H), 1.50-1.66 (m, 3H), 1.72-1.84 (4H), 2.25-2.46 (m, 2H), 2.59-2.69 (m, 2H), 2.96-3.17 (m, 3H), 3.54-3.62 (m, 1H), 3.69-3.76 (m, 1H), 3.81-3.90 (m, 1H), 7.22 (dd, J=5.8, 5.8 Hz, 1H), 8.49 (s, 1H). MS (ESI+) m/z 478 (M+H)⁺.

Example 228

(1S,3R)—N¹-[(5Z)-4-butyl-2-tert-butylisothiazol-5 (2H)-ylidene]-N³-(2-hydroxyethyl)-1,2,2-trimethyl-cyclopentane-1,3-dicarboxamide Example 174 and 2-aminoethanol hydrochloride (Aldrich) were processed as described in Example 178 to afford the title compound. ¹H NMR (DMSO-d₆) δ 0.48 (s, 3H), 0.90 (t, J=7.3 Hz, 3H), 1.19 (s, 3H), 1.24 (s, 3H), 1.26-1.45 (m, 3H), 1.57 (s, 9H), 2.57-1.67 (m, 3H), 1.96-2.09 (m, 1H), 2.62-2.68 (m, 3H), 2.71-2.82 (m, 1H), 3.00-3.11 (m, 1H), 3.15-3.25 (m, 1H), 3.34-3.41 (m, 2H), 4.59 (dd, J=4.6, 4.6 Hz, 1H), 7.49 (dd, J=4.6, 4.6 Hz, 1H), 8.49 (s, 1H). MS (ESI+) m/z 438 (M+H)⁺.

Example 229

(1R,3S)—N³-[(5Z)-4-butyl-2-tert-butylisothiazol-5 (2H)-ylidene]-N¹-ethyl-1,2,2-trimethylcyclopentane-1,3-dicarboxamide Example 181 and ethylamine hydrochloride (Aldrich) were processed as described in Example 178 to afford the title compound. ¹H NMR (DMSO-d₆) δ 0.50 (s, 3H), 0.90 (t, J=7.3 Hz, 3H), 0.98 (dd, J=7.1, 7.1 Hz, 3H), 1.19 (s, 3H), 1.23 (s, 3H), 1.23-1.41 (m, 3H), 1.57 (s, 9H), 1.57-1.82 (m, 3H), 2.24-2.44 (m, 2H), 2.59-2.72 (m, 2H), 2.95-3.11 (m, 3H), 7.27 (dd, J=5.8, 5.8 Hz, 1H), 8.49 (s, 1H). MS (ESI+) m/z 422 (M+H)⁺.

Example 230

(1R,3S)—N³-[(5Z)-4-butyl-2-tert-butylisothiazol-5 (2H)-ylidene]-N¹-(2-hydroxyethyl)-1,2,2-trimethyl-cyclopentane-1,3-dicarboxamide Example 181 and 2-aminoethanol hydrochloride (Aldrich) were processed as described in Example 178 to afford the title compound. ¹H NMR (DMSO-d₆) δ 0.50 (s, 3H), 0.90 (t, J=7.3 Hz, 3H), 1.14 (s, 3H), 1.23 (s, 3H), 1.26-1.43 (m, 3H), 1.57 (s, 9H), 1.57-1.67 (m, 2H), 1.69-1.82 (m, 1H), 2.25-2.47 (m, 2H), 2.61-2.67 (m, 2H), 2.96-3.02 (m, 1H), 3.07-3.18 (m, 2H), 3.34-3.40 (m, 2H), 4.59 (dd, J=5.6, 5.6 Hz, 1H), 7.19 (dd, J=5.6, 5.6 Hz, 1H), 8.50 (s, 1H). MS (ESI+) m/z 438 (M+H)⁺. Anal. calcd. for $C_{23}H_{39}N_3O_3S$: C, 63.12; H, 8.98; N, 9.60. Found: C, 62.77; H, 9.10; N, 9.59.

Example 231

(1S,3R)—N-[(5Z)-4-butyl-2-tert-butylisothiazol-5 (2H)-ylidene]-3-(4,5-dihydro-1,3-oxazol-2-yl)-1,2,2-trimethylcyclopentanecarboxamide Example 228, tosyl chloride (Aldrich), and triethylamine (Aldrich) were processed as described in Example 217 to afford the title compound. ¹H NMR (DMSO-d₆) δ 0.51 (s, 3H), 0.90 (t, J=7.3 Hz, 3H), 1.21 (s, 3H), 1.28 (s, 3H), 1.26-1.35 (m, 2H), 1.39-1.50 (m, 1H), 1.57 (s, 9H), 1.57-1.67 (m, 2H), 1.76-1.90 (m, 1H), 2.07-2.19 (m, 1H), 2.62-2.67 (m, 2H), 2.71-2.82 (m, 2H), 3.65-3.71 (m, 2H), 4.12-4.18 (m, 2H), 8.50 (s, 1H). MS (ESI+) m/z 420 (M+H)⁺. Anal. calcd. for $C_{23}H_{37}N_3O_2S$: C, 65.83; H, 8.89; N, 10.01. Found: C, 65.56; H, 8.83; N, 9.81.

Example 232

(1S,3R)—N-[(5Z)-4-butyl-2-tert-butylisothiazol-5 (2H)-ylidene]-3-(4,5-dihydro-1,3-oxazol-2-yl)-2,2,3-trimethylcyclopentanecarboxamide Example 230, tosyl chloride (Aldrich), and triethylamine (Aldrich) were processed as described in Example 217 to afford the title compound. ¹H NMR (DMSO-d₆) δ 0.54 (s, 3H), 0.89 (t, J=7.3 Hz, 3H), 1.18 (s, 3H), 1.23 (s, 3H), 1.23-1.36 (m, 2H), 1.44-1.52 (m, 1H), 1.57 (s, 9H), 1.57-1.67 (m, 2H), 1.72-1.85 (m, 1H), 2.24-2.37 (m, 1H), 2.51-2.73 (m, 3H), 3.01-3.07 (m, 1H), 3.63-3.70 (m, 2H), 4.12-4.19 (m, 2H), 8.50 (s, 1H). MS (ESI+) m/z 420 (M+H)⁺. Anal. calcd. for $C_{23}H_{37}N_3O_2S$: C, 65.83; H, 8.89; N, 10.01. Found: C, 65.66; H, 8.96; N, 9.83.

Example 233

(1R,3S)—N³-benzyl-N¹-[(5Z)-4-butyl-2-tert-butyl-isothiazol-5(2H)-ylidene]-1,2,2-trimethylcyclopentane-1,3-dicarboxamide Example 173 and benzylamine (Aldrich) were processed as described in Example 178 to afford the title compound. ¹H NMR (DMSO-d₆) δ 0.50 (s, 3H), 0.90 (t, J=7.2 Hz, 3H), 1.20 (s, 3H), 1.25 (s, 3H), 1.26-1.46 (m, 3H), 1.57 (s, 9H), 1.57-1.72 (m, 3H), 2.00-2.12 (m, 1H), 2.62-2.67 (m, 2H), 2.72-2.85 (m, 2H), 4.16-4.23 (m, 1H), 4.31-4.38 (m, 1H), 7.18-7.33 (m, 5H), 8.09 (dd, J=5.9, 5.9 Hz, 1H), 8.49 (s, 1H). MS (ESI+) m/z 484 (M+H)⁺. Anal. calcd. for $C_{28}H_{41}N_3O_2S$: C, 69.53; H, 8.54; N, 8.69. Found: C, 69.19; H, 8.51; N, 8.60.

Example 234

(1R,3S)—N$^1$-[(5Z)-4-butyl-2-tert-butylisothiazol-5(2H)-ylidene]-1,2,2-trimethyl-N$^3$-(pyridin-2-ylmethyl)cyclopentane-1,3-dicarboxamide Example 173 and 2-aminomethylpyridine (Aldrich) were processed as described in Example 178 to afford the title compound. $^1$H NMR (DMSO-d$_6$) δ 0.50 (s, 3H), 0.90 (t, J=7.3 Hz, 3H), 1.21 (s, 3H), 1.29 (s, 3H), 1.26-1.47 (m, 3H), 1.57 (s, 9H), 1.57-1.78 (m, 3H), 2.01-2.12 (m, 1H), 2.62-2.67 (m, 2H), 2.77-2.85 (m, 2H), 4.27-4.34 (m, 1H), 4.40-4.47 (m, 1H), 7.22-7.26 (m, 1H), 7.27 (d, J=7.8 Hz, 1H), 7.74 (ddd, J=7.6, 7.6, 1.7 Hz, 1H), 8.15 (dd, J=5.9, 5.9 Hz, 1H), 8.47-8.49 (m, 1H), 8.49 (s, 1H). MS (ESI+) m/z 485 (M+H)$^+$. Anal. calcd. for C$_{27}$H$_{40}$N$_4$O$_2$S: C, 66.91; H, 8.32; N, 11.56. Found: C, 66.53; H, 8.17; N, 11.46.

Example 235

(1R,3S)—N$^1$-[(5Z)-4-butyl-2-tert-butylisothiazol-5(2H)-ylidene]-1,2,2-trimethyl-N$^3$-(pyridin-3-ylmethyl)cyclopentane-1,3-dicarboxamide Example 173 and 3-aminomethylpyridine (Aldrich) were processed as described in Example 178 to afford the title compound. $^1$H NMR (DMSO-d$_6$) δ 0.47 (s, 3H), 0.90 (t, J=7.3 Hz, 3H), 1.20 (s, 3H), 1.24 (s, 3H), 1.26-1.46 (m, 3H), 1.57 (s, 9H), 1.57-1.78 (m, 3H), 1.98-2.11 (m, 1H), 2.62-2.67 (m, 2H), 2.70-2.84 (m, 2H), 4.19-4.26 (m, 1H), 4.32-4.39 (m, 1H), 7.31-7.35 (m, 1H), 7.63-7.67 (m, 1H), 8.18 (dd, J=5.9, 5.9 Hz, 1H), 8.42-8.44 (m, 1H), 8.48-8.49 (m, 1H), 8.49 (s, 1H). MS (ESI+) m/z 485 (M+H)$^+$.

Example 236

(1R,3S)—N$^1$-[(5Z)-4-butyl-2-tert-butylisothiazol-5(2H)-ylidene]-1,2,2-trimethyl-N$^3$-(pyridin-4-ylmethyl)cyclopentane-1,3-dicarboxamide Example 173 and 4-aminomethylpyridine (Aldrich) were processed as described in Example 178 to afford the title compound. $^1$H NMR (DMSO-d$_6$) δ 0.50 (s, 3H), 0.90 (t, J=7.3 Hz, 3H), 1.21 (s, 3H), 1.28 (s, 3H), 1.26-1.48 (m, 3H), 1.57 (s, 9H), 1.57-1.78 (m, 3H), 1.99-2.11 (m, 1H), 2.62-2.68 (m, 2H), 2.73-2.85 (m, 2H), 4.20-4.27 (m, 1H), 4.31-4.38 (m, 1H), 7.24 (d, J=6.0 Hz, 2H), 8.22 (dd, J=5.9 Hz, 1H), 8.47-8.50 (m, 2H). 8.50 (s, 1H). MS (ESI+) m/z 485 (M+H)$^+$.

Example 237

(1R,3S)—N$^1$-[(5Z)-4-butyl-2-tert-butylisothiazol-5(2H)-ylidene]-1,2,2-trimethyl-N$^3$-prop-2-ynylcyclopentane-1,3-dicarboxamide Example 173 and propargylamine hydrochloride (Aldrich) were processed as described in Example 178 to afford the title compound. $^1$H NMR (DMSO-d$_6$) δ 0.49 (s, 3H), 0.90 (t, J=7.3 Hz, 3H), 1.19 (s, 3H), 1.24 (s, 3H), 1.26-1.46 (m, 3H), 1.57 (s, 9H), 1.57-1.73 (m, 3H), 1.96-2.08 (m, 1H), 2.62-2.83 (m, 4H), 3.03 (s, 1H), 3.75-3.83 (m, 1H), 3.85-3.94 (m, 1H), 7.99 (dd, J=5.6, 5.6 Hz, 1H), 8.49 (s, 1H). MS (ESI+) m/z 432 (M+H)$^+$. Anal. calcd. for C$_{24}$H$_{37}$N$_3$O$_2$S: C, 66.78; H, 8.64; N, 9.74. Found: C, 66.64; H, 8.74; N, 9.74.

Example 238

(1R,3S)—N$^1$-[(5Z)-4-butyl-2-tert-butylisothiazol-5(2H)-ylidene]-1,2,2-trimethyl-N$^3$-(2,2,2-trifluoroethyl)cyclopentane-1,3-dicarboxamide Example 173 and 2,2,2-trifluoroethanamine hydrochloride (Aldrich) were processed as described in Example 178 to afford the title compound. $^1$H NMR (DMSO-d$_6$) δ 0.48 (s, 3H), 0.90 (t, J=7.3 Hz, 3H), 1.21 (s, 3H), 1.25 (s, 3H), 1.26-1.48 (m, 3H), 1.57 (s, 9H), 1.57-1.78 (m, 3H), 1.97-2.10 (m, 1H), 2.62-2.67 (m, 2H), 2.72-2.85 (m, 2H), 3.62-3.79 (m, 1H), 3.99-4.13 (m, 1H), 8.23 (dd, J=6.4, 6.4 Hz, 1H), 8.49 (s, 1H). MS (ESI+) m/z 476 (M+H)$^+$. Anal. calcd. for C$_{23}$H$_{36}$F$_3$N$_3$O$_2$S: C, 58.08; H, 7.63; N, 8.83. Found: C, 57.61; H, 7.66; N, 8.59.

Example 239

(1S,3R)—N$^1$-[(5Z)-4-butyl-2-tert-butylisothiazol-5(2H)-ylidene]-1,2,2-trimethyl-N$^3$-prop-2-ynylcyclopentane-1,3-dicarboxamide Example 174 and propargylamine hydrochloride (Aldrich) were processed as described in Example 178 to afford the title compound. $^1$H NMR (DMSO-d$_6$) δ 0.48 (s, 3H), 0.90 (t, J=7.3 Hz, 3H), 1.19 (s, 3H), 1.24 (s, 3H), 1.26-1.46 (m, 3H), 1.57 (s, 9H), 1.57-1.72 (m, 3H), 1.96-2.08 (m, 1H), 2.62-2.83 (m, 4H), 3.05-3.06 (m, 1H), 3.75-3.94 (m, 2H), 8.03 (dd, J=5.6, 5.6 Hz, 1H), 8.50 (s, 1H). MS (ESI+) m/z 432 (M+H)$^+$. Anal. calcd. for C$_{24}$H$_{37}$N$_3$O$_2$S: C, 66.78; H, 8.64; N, 9.74. Found: C, 66.79; H, 8.84; N, 9.67.

Example 240

(1S,3R)—N$^1$-[(5Z)-4-butyl-2-tert-butylisothiazol-5(2H)-ylidene]-1,2,2-trimethyl-N$^3$-(2,2,2-trifluoroethyl)cyclopentane-1,3-dicarboxamide Example 174 and 2,2,2-trifluoroethanamine hydrochloride (Aldrich) were processed as described in Example 178 to afford the title compound. $^1$H NMR (DMSO-d$_6$) δ 0.47 (s, 3H), 0.90 (t, J=7.5 Hz, 3H), 1.20 (s, 3H), 1.25 (s, 3H), 1.25-1.33 (m, 2H), 1.38-1.47 (m, 1H), 1.57 (s, 9H), 1.57-1.78 (m, 3H), 1.97-2.10 (m, 1H), 2.62-2.67 (m, 2H), 2.73-2.85 (m, 2H), 3.62-3.79 (m, 1H), 3.99-4.13 (m, 1H), 8.26 (t, J=6.4, 6.4 Hz, 1H), 8.51 (s, 1H). MS (ESI+) m/z 476 (M+H)$^+$. Anal. calcd. for C$_{23}$H$_{36}$F$_3$N$_3$O$_2$S: C, 58.08; H, 7.63; N, 8.83. Found: C, 57.97; H, 7.85; N, 8.81.

Example 241

(1R,3S)—N$^1$-[(5Z)-4-butyl-2-tert-butylisothiazol-5(2H)-ylidene]-N$^3$-methoxy-N$^3$,1,2,2-tetramethylcyclopentane-1,3-dicarboxamide Example 173 and N,O-dimethylhydroxylamine hydrochloride (Aldrich) were processed as described in Example 178 to afford the title compound. $^1$H NMR (DMSO-d$_6$) δ 0.52 (s, 3H), 0.90 (t, J=7.3 Hz, 3H), 1.23 (s, 3H), 1.24 (s, 3H), 1.23-1.36 (m, 3H), 1.41-1.50 (m, 1H), 1.57 (s, 9H), 1.57-1.67 (m, 2H), 1.70-1.80 (m, 1H), 1.93-2.04 (m, 1H), 2.62-2.67 (m, 2H), 2.72-2.89 (m, 1H), 3.11 (s, 3H), 3.65 (s, 3H), 8.50 (s, 1H). MS (ESI+) m/z 438 (M+H)⁺. Anal. calcd. for C₂₃H₃₉N₃O₃S: C, 63.12; H, 8.98; N, 9.60. Found: C, 63.47; H, 9.18; N, 9.56.

Example 242

(1S,3R)—N-[(5Z)-4-butyl-2-tert-butylisothiazol-5 (2H)-ylidene]-3-(5,6-dihydro-4H-1,3-oxazin-2-yl)-1, 2,2-trimethylcyclopentanecarboxamide Example 221, tosyl chloride (Aldrich), and triethylamine (Aldrich) were processed as described in Example 217 to afford the title compound. ¹H NMR (DMSO-d₆) δ 0.51 (s, 3H), 0.90 (t, J=7.3 Hz, 3H), 1.19 (s, 3H), 1.25 (s, 3H), 1.23-1.42 (m, 3H), 1.57 (s, 9H), 1.57-1.78 (m, 4H), 2.06-2.19 (m, 1H), 2.56-2.74 (m, 4H), 3.22-3.26 (m, 2H), 4.06-4.10 (m, 2H), 8.50 (s, 1H). MS (ESI+) m/z 434 (M+H)⁺.

Example 243

(1R,3S)—N-[(5Z)-4-butyl-2-tert-butylisothiazol-5 (2H)-ylidene]-3-(5,6-dihydro-4H-1,3-oxazin-2-yl)-1, 2,2-trimethylcyclopentanecarboxamide Example 213, tosyl chloride (Aldrich), and triethylamine (Aldrich) were processed as described in Example 217 to afford the title compound. ¹H NMR (DMSO-d₆) δ 0.51 (s, 3H), 0.90 (t, J=7.5 Hz, 3H), 1.19 (s, 3H), 1.25 (s, 3H), 1.23-1.41 (m, 3H), 1.57 (s, 9H), 1.57-1.77 (m, 5H), 2.06-2.19 (m, 1H), 2.56-2.74 (m, 4H), 3.22-3.26 (m, 2H), 4.06 (m, 2H), δ 8.50 (s, 1H). MS (ESI+) m/z 434 (M+H)⁺.

Example 244

N-[(1S,3R)-3-({[(5Z)-4-butyl-2-tert-butylisothiazol-5(2H)-ylidene]amino}carbonyl)-2,2,3-trimethylcyclopentyl]pyrrolidine-1-carboxamide Example 173, diphenylphosphoryl azide (Aldrich), triethylamine (Aldrich), and pyrrolidine (Aldrich) were processed as described in Example 215 to afford the title compound. ¹H NMR (DMSO-d₆) δ 0.52 (s, 3H), 0.90 (t, J=7.3 Hz, 3H), 0.99 (s, 3H), 1.20 (s, 3H), 1.26-1.44 (m, 4H), 1.57 (s, 9H), 1.57-1.67 (m, 2H), 1.73-1.78 (m, 4H), 1.90-2.02 (m, 1H), 2.63-2.73 (m, 3H), 3.08-3.16 (m, 2H), 3.19-3.27 (m, 2H), 4.09-4.18 (m, 1H), 5.42 (d, J=9.1 Hz, 1H), 8.51 (s, 1H). MS (ESI+) m/z 463 (M+H)⁺.

Example 245

(1R,3S)-3-[(aminocarbonyl)amino]-N-[(5Z)-4-butyl-2-tert-butylisothiazol-5(2H)-ylidene]-1,2,2-trimethylcyclopentanecarboxamide Example 173, diphenylphosphoryl azide (Aldrich), triethylamine (Aldrich), and ammonium hydroxide (Aldrich) were processed as described in Example 215 to afford the title compound. ¹H NMR (DMSO-d₆) δ 0.48 (s, 3H), 0.90 (t, J=7.3 Hz, 3H), 1.02 (s, 3H), 1.20 (s, 3H), 1.23-1.37 (m, 4H), 1.57 (s, 9H), 1.57-1.67 (m, 2H), 1.85-1.96 (m, 1H), 2.62-2.62 (m, 2H), 2.71-2.80 (m, 1H), 3.96-3.06 (m, 1H), 5.37 (br s, 2H), 5.73 (d, J=9.8 Hz, 1H), 8.51 (s, 1H). MS (ESI+) m/z 409 (M+H)⁺.

Example 246

(1R,3S)-3-[(aminocarbonyl)amino]-N-[(5Z)-4-butyl-2-tert-butylisothiazol-5(2H)-ylidene]-2,2,3-trimethylcyclopentanecarboxamide Example 205, diphenylphosphoryl azide (Aldrich), triethylamine (Aldrich), and ammonium hydroxide (Aldrich) were processed as described in Example 215 to afford the title compound. ¹H NMR (DMSO-d₆) δ 0.48-0.60 (m, 3H), 0.90 (t, J=7.3 Hz, 3H), 1.02-1.14 (m, 3H), 1.20 (s, 3H), 1.24-1.38 (m, 3H), 1.57 (s, 9H), 1.57-1.67 (m, 2H), 1.85-2.28 (m, 2H), 2.62-2.91 (m, 3H), 3.96-4.06 (m, 1H), 5.24-5.37 (m, 2H), 5.71-5.74 (m, 1H), 8.51 (s, 1H). MS (ESI+) m/z 409 (M+H)⁺. Anal. calcd. for C₂₁H₃₆N₄O₂S: C, 61.73; H, 8.88; N, 13.71. Found: C, 61.13; H, 8.74; N, 13.86.

Example 247

(1R,3S)—N-[(5Z)-4-butyl-2-tert-butylisothiazol-5 (2H)-ylidene]-2,2,3-trimethyl-3-{[(methylamino) carbonyl]amino}cyclopentanecarboxamide Example 205, diphenylphosphoryl azide (Aldrich), triethylamine (Aldrich), and methylamine hydrochloride (Aldrich) were processed as described in Example 215 to afford the title compound. ¹H NMR (DMSO-d₆) δ 0.47-0.59 (m, 3H), 0.90 (t, J=7.3 Hz, 3H), 1.01-1.13 (m, 3H), 1.20-1.27 (m, 3H), 1.23-1.36 (m, 3H), 1.57 (s, 9H), 1.57-1.74 (m, 2H), 1.85-2.31 (m, 2H), 2.52-2.54 (m, 3H), 2.62-2.91 (m, 3H), 3.99-4.09 (m, 1H), 0.5.60-5.64 (m, 2H), 8.50 (s, 1H). MS (ESI+) m/z 423 (M+H)⁺.

Example 248

(1R,3S)—N-[(5Z)-4-butyl-2-tert-butylisothiazol-5 (2H)-ylidene]-1,2,2-trimethyl-3-(morpholin-4-ylcarbonyl)cyclopentanecarboxamide Example 173 and morpholine (Aldrich) were processed as described in Example 178 to afford the title compound. ¹H NMR (DMSO-d₆) δ 0.49 (s, 3H), 0.90 (t, J=7.3 Hz, 3H), 1.25 (s, 6H), 1.25-1.47 (m, 3H), 1.57 (s, 9H), 1.57-1.74 (m, 3H), 2.03-2.15 (m, 1H), 2.62-2.67 (m, 2H), 2.73-2.85 (m, 1H), 3.29-3.37 (m, 1H), 3.48-3.56 (m, 8H), 8.50 (s, 1H). MS (ESI+) m/z 464 (M+H)⁺.

Example 249

(1R,3S)—N¹-[(5Z)-4-butyl-2-tert-butylisothiazol-5 (2H)-ylidene]-1,2,2-trimethyl-N³-pyrrolidin-1-ylcyclopentane-1,3-dicarboxamide Example 173 and pyrrolidin-1-amine hydrochloride (Aldrich) were processed as described in Example 178 to afford the title compound. ¹H NMR (DMSO-d₆) δ 0.49-0.54 (m, 3H), 0.90 (t, J=7.3 Hz, 3H), 1.18 (s, 3H), 1.22 (s, 3H), 1.26-1.44 (m, 3H), 1.57 (s, 9H), 1.57-1.70 (m, 7H), 1.94-2.06 (m, 1H), 2.55-2.80 (m, 1H), 2.62-2.67 (m, 2H), 2.71-2.89 (m, 5H), 8.08-8.47 (m, 1H), 8.49 (s, 1H). MS (ESI+) m/z 463 (M+H)⁺. Anal. calcd. for C₂₅H₄₂N₄O₂S: C, 64.90; H, 9.15; N, 12.11. Found: C, 64.43; H, 8.85; N, 12.37.

Example 250

N-[(1S,3R)-3-({[(5Z)-4-butyl-2-tert-butylisothiazol-5(2H)-ylidene]amino}carbonyl)-2,2,3-trimethylcyclopentyl]morpholine-4-carboxamide Example 173, diphenylphosphoryl azide (Aldrich), triethylamine (Aldrich), and morpholine (Aldrich) were processed as described in Example 215 to afford the title compound. $^1$H NMR (DMSO-$d_6$) δ 0.51 (s, 3H), 0.90 (t, J=7.3 Hz, 3H), 1.00 (s, 3H), 1.20 (s, 3H), 1.24-1.43 (m, 3H), 1.57 (s, 9H), 1.57-1.67 (m, 3H), 1.87-2.00 (m, 1H), 2.62-2.76 (m, 3H), 3.15-3.28 (m, 4H), 3.49-3.52 (m, 4H), 4.14-4.22 (m, 1H), 5.97 (d, J=8.7 Hz, 1H), 8.51 (s, 1H). MS (ESI+) m/z 479 (M+H)$^+$. Anal. calcd. for $C_{25}H_{42}N_4O_3S$: C, 62.73; H, 8.84; N, 11.70. Found: C, 62.45; H, 8.25; N, 11.85.

Example 251

N-[(1S,3R)-3-({[(5Z)-4-butyl-2-tert-butylisothiazol-5(2H)-ylidene]amino}carbonyl)-2,2,3-trimethylcyclopentyl]benzamide To a 100-mL, round-bottomed flask containing a magnetic stir bar were added Example 173 (1.18 g, 3.00 mmol), diphenylphosphorylazide (Aldrich, 908 mg, 3.30 mmol), and anhydrous toluene (45 mL). Neat triethylamine (Aldrich, 0.418 mL, 3.00 mmol) was added to form a pale yellow solution. The mixture was heated to reflux under nitrogen atmosphere and stirred for 8 h. After cooling, water (30 mL) was added and the resulting mixture was extracted with dichloromethane (3×25 mL). The combined organic extracts over sodium sulfate and filtered. The volatiles were removed by rotary evaporator. Flash chromatography (silica gel, 5-50% ethylacetate in hexanes) afforded the isocyanate as a colorless oil.

To a 20-mL vial were added the isocyanate (98 mg, 0.25 mmol) and anhydrous tetrahydrofuran (3 mL). The vial was cooled in an ice bath and a solution of phenylmagnesium bromide (Aldrich, 1.00M in tetrahydrofuran, 0.500 mL, 0.500 mmol) was added dropwise. After the addition, the mixture was allowed to warm to room temperature and stirred overnight. Water (10 mL) was added carefully. The mixture was extracted with dichloromethane (3×10 mL). The combined organic extracts were dried over sodium sulfate, filtered, and concentrated by rotary evaporator to give a brown oil. Flash chromatography (silica gel, 30-90% ethyl acetate in hexanes) afforded 43 mg (36%) of the title compound. $^1$H NMR (DMSO-$d_6$) δ 0.51 (s, 3H), 0.89 (t, J=7.3 Hz, 3H), 1.09 (s, 3H), 1.27 (s, 3H), 1.25-1.37 (2H), 1.42-1.54 (m, 1H), 1.57 (s, 9H), 1.57-1.66 (m, 2H), 1.72-1.85 (m, 1H), 1.96-2.09 (m, 1H), 2.62-2.67 (m, 2H), 2.73-2.83 (m, 1H), 4.47-4.56 (m, 1H), 7.39-7.53 (m, 3H), 7.76-7.79 (m, 2H), 7.99 (d, J=9.1 Hz, 1H), 8.53 (s, 1H). MS (ESI+) m/z 470 (M+H)$^+$.

Example 252

(1R,3S)—N-[(5Z)-4-butyl-2-tert-butylisothiazol-5(2H)-ylidene]-1,2,2-trimethyl-3-{[(methylamino)carbonyl]amino}cyclopentanecarboxamide Example 173, diphenylphosphoryl azide (Aldrich), triethylamine (Aldrich), and methylamine hydrochloride (Aldrich) were processed as described in Example 215 to afford the title compound. $^1$H NMR (DMSO-$d_6$) δ 0.48 (s, 3H), 0.90 (t, J=7.5 Hz, 3H), 1.01 (s, 3H), 1.20 (s, 3H), 1.24-1.38 (m, 4H), 1.57 (s, 9H), 1.57-1.67 (m, 2H), 1.85-1.97 (m, 1H), 2.53 (d, J=4.7 Hz, 3H), 2.62-2.67 (m, 2H), 2.69-2.79 (m, 1H), 3.99-4.09 (m, 1H), 5.57-5.65 (m, 2H), 8.49 (s, 1H). MS (ESI+) m/z 423 (M+H)$^+$.

Example 253

(1S,3R)-3-[(aminocarbonyl)amino]-N-[(5Z)-4-butyl-2-tert-butylisothiazol-5(2H)-ylidene]-1,2,2-trimethylcyclopentanecarboxamide Example 174, diphenylphosphoryl azide (Aldrich), triethylamine (Aldrich), and ammonium hydroxide (Aldrich) were processed as described in Example 215 to afford the title compound. $^1$H NMR (DMSO-$d_6$) δ 0.48 (s, 3H), 0.90 (t, J=7.3 Hz, 3H), 1.02 (s, 3H), 1.20 (s, 3H), 1.24-1.38 (m, 4H), 1.57 (s, 9H), 1.57-1.67 (m, 2H), 1.85-1.96 (m, 1H), 2.62-2.68 (m, 2H), 2.71-2.80 (m, 1H), 3.96-4.06 (m, 1H), 5.35 (s, 2H), 5.71 (d, J=9.5 Hz, 1H), 8.49 (s, 1H). MS (ESI+) m/z 409 (M+H)$^+$. Anal. calcd. for $C_{21}H_{36}N_4O_2S$: C, 61.73; H, 8.88; N, 13.71. Found: C, 61.34; H, 8.67; N, 13.88.

Example 254

(1S,3R)—N-[(5Z)-4-butyl-2-tert-butylisothiazol-5(2H)-ylidene]-1,2,2-trimethyl-3-{[(methylamino)carbonyl]amino}cyclopentanecarboxamide Example 174, diphenylphosphoryl azide (Aldrich), triethylamine (Aldrich), and methylamine hydrochloride (Aldrich) were processed as described in Example 215 to afford the title compound. $^1$H NMR (DMSO-$d_6$) δ 0.48 (s, 3H), 0.90 (t, J=7.3 Hz, 3H), 1.01 (s, 3H), 1.20 (s, 3H), 1.24-1.38 (m, 4H), 1.57 (s, 9H), 1.57-1.67 (m, 2H), 1.86-1.95 (m, 1H), 2.54 (d, J=4.7 Hz, 3H), 2.62-2.67 (m, 2H), 2.69-2.79 (m, 1H), 3.99-4.09 (m, 1H), 5.58-5.65 (m, 2H), 8.49 (s, 1H). MS (ESI+) m/z 423 (M+H)$^+$.

Example 255

N-[(1R,3S)-3-({[(5Z)-4-butyl-2-tert-butylisothiazol-5(2H)-ylidene]amino}carbonyl)-2,2,3-trimethylcyclopentyl]benzamide Example 174, diphenylphosphoryl azide (Aldrich), triethylamine (Aldrich), and phenylmagnesium bromide (Aldrich) were processed as described in Example 251 to afford the title compound. $^1$H NMR (DMSO-$d_6$) δ 0.61 (s, 3H), 0.89 (t, J=7.3 Hz, 3H), 1.09 (s, 3H), 1.27 (s, 3H), 1.25-1.35 (m, 2H), 1.43-1.53 (m, 1H), 1.57-1.66 (m, 2H), 1.58 (s, 9H), 1.74-1.85 (m, 1H), 1.96-2.10 (m, 1H), 2.62-2.67 (m, 2H), 2.73-2.83 (m, 1H), 4.47-4.56 (m, 1H), 7.39-7.53 (m, 3H), 7.76-7.79 (m, 2H), 7.98 (d, J=9.2 Hz, 1H), 8.52 (s, 1H). MS (ESI+) m/z 470 (M+H)$^+$.

Example 256

(1R,3S)-3-(acetylamino)-N-[(5Z)-4-butyl-2-tert-butylisothiazol-5(2H)-ylidene]-1,2,2-trimethylcyclopentanecarboxamide Example 173, diphenylphosphoryl azide (Aldrich), triethylamine (Aldrich), and methyllithium (Aldrich) were processed as described in Example 251 to afford the title compound. $^1$H NMR (DMSO-$d_6$) δ 0.51 (s, 3H), 0.90 (t, J=7.3 Hz, 3H), 1.02 (s, 3H), 1.21 (s, 3H), 1.24-1.36 (m, 3H), 1.35-1.45 (m, 1H), 1.57 (s, 9H), 1.57-1.67 (m, 2H), 1.82 (s, 3H), 1.83-

1.92 (m, 1H), 2.62-2.67 (m, 2H), 2.75-2.81 (m, 1H), 4.20-4.29 (m, 1H), 7.47 (d, J=9.1 Hz, 1H), 8.50 (s, 1H). MS (ESI+) m/z 408 (M+H)$^+$.

Example 257

(1R,3S)—N-[(5Z)-4-butyl-2-tert-butylisothiazol-5(2H)-ylidene]-3-({[(2-hydroxyethyl)amino]carbonyl}amino)-1,2,2-trimethylcyclopentanecarboxamide Example 173, diphenylphosphoryl azide (Aldrich), triethylamine (Aldrich), and 2-aminoethanol (Aldrich) were processed as described in Example 215 to afford the title compound. $^1$H NMR (DMSO-d$_6$) δ 0.48-0.60 (m, 3H), 0.86-0.92 (m, 3H), 1.02 (s, 3H), 1.13-1.20 (m, 3H), 1.22-1.38 (m, 4H), 1.57 (s, 9H), 1.54-1.67 (m, 2H), 1.86-1.99 (m, 1H), 2.14-2.37 (m, 1H), 2.62-2.67 (m, 2H), 2.71-2.91 (m, 1H), 2.99-3.07 (m, 2H), 3.34-3.39 (m, 2H), 3.97-4.08 (m, 1H), 4.63-4.66 (m, 1H), 5.73-5.76 (m, 1H), 5.85-5.88 (m, 1H), 8.49 (s, 1H). MS (ESI+) m/z 453 (M+H)$^+$. Anal. calcd. for C$_{23}$H$_{40}$N$_4$O$_3$S: C, 61.03; H, 8.91; N, 12.38. Found: C, 61.10; H, 9.07; N, 12.23.

Example 258

(1R,3S)—N-[(5Z)-4-butyl-2-tert-butylisothiazol-5(2H)-ylidene]-3-[({[(2S)-2-hydroxypropyl]amino}carbonyl)amino]-1,2,2-trimethylcyclopentanecarboxamide Example 173, diphenylphosphoryl azide (Aldrich), triethylamine (Aldrich), and (S)-1-aminopropan-2-ol (Aldrich) were processed as described in Example 215 to afford the title compound. $^1$H NMR (DMSO-d$_6$) δ 0.48-0.60 (m, 3H), 0.87-0.90 (m, 3H), 0.98-1.02 (m, 6H), 1.14-1.20 (m, 3H), 1.24-1.38 (m, 4H), 1.57 (s, 9H), 1.57-1.67 (m, 2H), 1.86-1.97 (m, 1H), 2.62-2.67 (m, 2H), 2.71-3.04 (m, 3H), 3.54-3.61 (m, 1H), 3.97-4.08 (m, 1H), 4.64-4.67 (m, 1H), 5.75-5.78 (m, 1H), 5.82-5.86 (m, 1H), 8.49 (s, 1H). MS (ESI+) m/z 467 (M+H)$^+$.

Example 259

(1R,3S)—N-[(5Z)-4-butyl-2-tert-butylisothiazol-5(2H)-ylidene]-3-[({[(2R)-2-hydroxypropyl]amino}carbonyl)amino]-1,2,2-trimethylcyclopentanecarboxamide Example 173, diphenylphosphoryl azide (Aldrich), triethylamine (Aldrich), and (R)-1-aminopropan-2-ol (Aldrich) were processed as described in Example 215 to afford the title compound. $^1$H NMR (DMSO-d$_6$) δ 0.48-0.60 (m, 3H), 0.86-0.92 (m, 3H), 0.98-1.02 (m, 6H), 1.14-1.20 (m, 3H), 1.24-1.38 (m, 4H), 1.57 (s, 9H), 1.53-1.67 (m, 2H), 1.85-2.32 (m, 1H), 2.62-2.67 (m, 2H), 2.71-2.91 (m, 2H), 2.94-3.04 (s, 1H), 3.52-3.61 (m, 1H), 3.97-4.09 (m, 1H), 4.65-4.67 (m, 1H), 5.75-5.79 (m, 1H), 5.83-5.87 (m, 1H), 8.49 (s, 1H). MS (ESI+) m/z 467 (M+H)$^+$.

Example 260

N-[(1S,3R)-3-({[(5Z)-4-butyl-2-tert-butylisothiazol-5(2H)-ylidene]amino}carbonyl)-2,2,3-trimethylcyclopentyl]-3-hydroxyazetidine-1-carboxamide Example 173, diphenylphosphoryl azide (Aldrich), triethylamine (Aldrich), and 3-hydroxyazetidine hydrochloride (Oakwood) were processed as described in Example 215 to afford the title compound. $^1$H NMR (DMSO-d$_6$) δ 0.50-0.65 (m, 3H), 0.90 (t, J=7.3 Hz, 3H), 0.99-1.10 (m, 3H), 1.19-1.29 (m, 3H), 1.24-1.41 (m, 3H), 1.57 (s, 9H), 1.51-1.67 (m, 3H), 1.75-1.96 (m, 1H), 2.62-2.94 (m, 3H), 3.44-3.61 (m, 2H), 3.84-4.11 (m, 3H), 4.28-4.38 (m, 1H), 5.49-5.52 (m, 1H), 5.69-5.78 (m, 1H), 8.51-8.54 (m, 1H). MS (ESI+) m/z 465 (M+H)$^+$. Anal. calcd. for C$_{24}$H$_{40}$N$_4$O$_3$S: C, 62.04; H, 8.68; N, 12.06. Found: C, 61.76; H, 8.54; N, 11.94.

Example 261

N-[(1S,3R)-3-({[(5Z)-4-butyl-2-tert-butylisothiazol-5(2H)-ylidene]amino}carbonyl)-2,2,3-trimethylcyclopentyl]-3,3-difluoroazetidine-1-carboxamide Example 173, diphenylphosphoryl azide (Aldrich), triethylamine (Aldrich), and 3,3-difluororoazetidine hydrochloride (Oakwood) were processed as described in Example 215 to afford the title compound. $^1$H NMR (DMSO-d$_6$) δ 0.90 (t, J=7.3 Hz, 3H), 0.51 (s, 3H), 1.02 (s, 3H), 1.21 (s, 3H), 1.24-1.41 (m, 3H), 1.57 (s, 9H), 1.52-1.67 (m, 3H), 1.83-1.99 (m, 1H), 2.63-2.80 (m, 3H), 4.05-4.29 (m, 5H), 6.28 (d, J=8.7 Hz, 1H), 8.51 (s, 1H). MS (ESI+) m/z 485 (M+H)$^+$. Anal. calcd. for C$_{24}$H$_{38}$F$_2$N$_4$O$_2$S: C, 59.48; H, 7.90; N, 11.56. Found: C, 59.32; H, 8.18; N, 11.24.

Example 262

N-[(5Z)-4-butyl-2-tert-butylisothiazol-5(2H)-ylidene]-2-(2-hydroxy-2-methylpropoxy)-5-(trifluoromethyl)benzamide Example 192A (150 mg, 0.37 mmol) in THF (5 mL) was treated with NaH (60% dispersion) (44.7 mg, 1.12 mmol) and stirred for 10 min. To this mixture was added 2-methylpropane-1,2-diol (101 mg, 1.12 mmol). The reaction mixture was stirred at room temperature for 2 hours. Water (10 mL) was added, and the mixture was extracted with dichloromethane (3×10 mL). The combined organic extracts were dried over sodium sulfate, filtered, and concentrated. Purification by flash chromatography (silica gel, 40-100% ethyl acetate in hexanes) afforded 61 mg (35%) of the title compound. $^1$H NMR (500 MHz, CDCl$_3$) δ ppm 0.97 (t, J=7.32 Hz, 3 H) 1.34 (s, 6 H) 1.38-1.49 (m, 2 H) 1.58 (s, 2 H) 2.71-3.05 (m, 2 H) 4.02 (s, 2 H) 5.09 (s, 1 H) 7.04 (d, J=8.54 Hz, 1 H) 7.48-7.76 (m, 1 H) 7.97 (s, 1 H) 8.34 (s, 1 H); MS (ESI+) m/z 473 (M+H)$^+$.

Example 263

N-[(1S,3R)-3-({[(5Z)-4-butyl-2-tert-butylisothiazol-5(2H)-ylidene]amino}carbonyl)-2,2,3-trimethylcyclopentyl]azetidine-1-carboxamide Example 173, diphenylphosphoryl azide (Aldrich), triethylamine (Aldrich), and azetidine hydrochloride (Aldrich) were processed as described in Example 215 to afford the title compound. $^1$H NMR (DMSO-d$_6$) δ 0.50-0.64 (m, 3H), 0.90 (t, J=7.3 Hz, 3H), 0.99-1.10 (m, 3H), 1.19-1.31 (m, 3H), 1.24-1.41 (m, 3H), 1.50-1.67 (m, 3H), 1.57 (s, 9H), 1.75-1.96 (m, 1H), 2.03-2.13 (m, 2H), 2.62-2.93 (m, 3H), 3.66-3.82 (m, 4H), 3.99-4.11 (m, 1H), 5.63-5.69 (m, 1H), 8.49-8.54 (m, 1H). MS (ESI+) m/z 449 (M+H)$^+$.

Example 264

(1R,3S)—N-[(5Z)-4-butyl-2-tert-butylisothiazol-5 (2H)-ylidene]-1,2,2-trimethyl-3-({[methyl(phenyl) amino]carbonyl}amino)cyclopentanecarboxamide Example 173, diphenylphosphoryl azide (Aldrich), triethylamine (Aldrich), and N-methylaniline (Aldrich) were processed as described in Example 215 to afford the title compound. $^1$H NMR (DMSO-$d_6$) δ 0.89 (t, J=7.3 Hz, 3H), 0.47 (s, 3H), 1.03 (s, 3H), 1.07 (s, 3H), 1.24-1.40 (m, 3H), 1.43-1.53 (m, 3H), 1.57 (s, 9H), 1.92-2.04 (m, 1H), 2.50-2.58 (m, 3H), 3.13 (s, 3H), 4.12-4.21 (m, 1H), 5.23 (d, J=9.1 Hz, 1H), 7.14-7.23 (m, 3H), 7.30-7.35 (m, 2H), 8.47 (s, 1H). MS (ESI+) m/z 499 (M+H)$^+$. Anal. calcd. for $C_{28}H_{42}N_4O_2S$: C, 67.43; H, 8.49; N, 11.23. Found: C, 67.74; H, 8.52; N, 10.97.

Example 265

Methyl 3-({[(5Z)-4-butyl-2-tert-butylisothiazol-5 (2H)-ylidene]amino}carbonyl)adamantane-1-carboxylate To a 250-mL, roundbottomed flask containing a magnetic stir bar were added 1,3-adamantanedicarboxylic acid (Aldrich, 2.02 g, 9.00 mol), phosphorus pentachloride (3.75 g, 18.0 mmol), and hexane (75 mL). The mixture was heated to reflux under nitrogen atmosphere and refluxed overnight. After cooling, the solids were removed by filtration and the volatiles were removed by rotary evaporator to afford the diacid chloride.

To a 20-mL vial containing a magnetic stir bar were added the crude diacid chloride (392 mg, 1.50 mmol) and anhydrous tetrahydrofuran (10 mL). A solution of Example 92B (212 mg, 1.00 mmol) and triethylamine (0.836 mL, 6.00 mmol) in dry tetrahydrofuran was added drop wise and slowly to form a dark orange slurry. The mixture was stirred at room temperature for 4 hours. Methanol (10 mL) was added and the mixture was stirred for an additional 4 hours. Water (15 mL) was added and the resulting mixture was extracted with dichloromethane (3×10 mL). The combined organic extracts were dried over sodium sulfate, filtered, concentrated by rotary evaporator to give a brown oil. Flash chromatography (silica gel, 5-25% ethylacetate in hexanes) afforded 119 mg (27%) of the title compound. $^1$H NMR (DMSO-$d_6$) δ 0.92 (t, J=7.3 Hz, 3H), 1.24-1.37 (m, 2H), 1.57 (s, 9H), 1.60-1.65 (m, 4H), 1.74-1.89 (m, 9H), 1.97 (br s, 2H), 2.10 (br s, 2H), 2.65 (t, J=7.5 Hz, 2H), 3.59 (s, 3H), 8.50 (s, 1H). MS (ESI+) m/z 433 (M+H)$^+$. Anal. calcd. for $C_{24}H_{36}N_2O_3S$: C, 66.63; H, 8.39; N, 6.48. Found: C, 66.73; H, 8.49; N, 6.15.

Example 266

3-({[(5Z)-4-butyl-2-tert-butylisothiazol-5(2H)-ylidene]amino}carbonyl)adamantane-1-carboxylic acid Example 265 was processed as described in Example 96 to afford the title compound. MS (ESI$^+$) m/z 419 (M+H)$^+$.

Example 267

2-[(tert-butylamino)oxy]-N-[(5Z)-4-butyl-2-tert-butylisothiazol-5(2H)-ylidene]-5-(trifluoromethyl) benzamide Example 192A (210 mg, 0.52 mmol) in THF (5 mL) was treated with NaH (60% dispersion) (42 mg, 1.04 mmol). After 10 min, the mixture was cooled to 0° C. and N-tert-butylhydroxylamine (93 mg, 1.04 mmol) was added. The mixture was allowed to warm to room temperature and stirred for 4 hours. Water (10 mL) was added, and the mixture was extracted with dichloromethane (3×10 mL). The combined organic extracts were dried over sodium sulfate, filtered, and concentrated. Purification of the residue by flash chromatography (silica gel, 40-100% ethyl acetate in hexanes) afforded 42 mg (17%) of the title compound. $^1$H NMR (500 MHz, CDCl$_3$) δ ppm 0.97 (t, J=7.32 Hz, 3 H) 1.22 (s, 9 H) 1.39-1.46 (m, 2 H) 1.67 (s, 9 H) 1.67-1.74 (m, 2 H) 2.75-2.96 (m, 2 H) 5.79 (s, 1 H) 7.57 (dd, J=8.54, 1.83 Hz, 1 H) 7.79 (d, J=8.85 Hz, 1 H) 7.95 (s, 1 H) 8.34 (d, J=1.83 Hz, 1 H); MS (ESI+) m/z 472 (M+H)$^+$.

e. Biological Data (i) In Vitro Methods—$CB_2$ and $CB_1$ Radioligand Binding Assays:

The $CB_1$ and $CB_2$ radioligand binding assays described herein are utilized to determine the selectivity of present compounds for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. The compounds tested were found to bind to $CB_1$ receptors with $K_i$ of about 10 fold to about 1000 fold higher than that for $CB_2$ receptors. These results demonstrate that certain compounds tested preferably bind to $CB_2$ vs. $CB_1$ receptors, and thus are selective ligands for the $CB_2$ receptor.

$CB_2$ and $CB_1$ Cyclase Functional Assays:

The cyclase functional assays were performed using the HitHunter™ cAMP assay kit from DiscoveRx (Fremont, Calif.) according to vendor's protocol. Briefly, HEK cells expressing $CB_2$ or $CB_1$ receptors (rat or human) were detached using cell dissociation buffer (Invitrogen, Carlsbad, Calif.), dispersed and placed in suspension at 10,000 cells per well in 96 well plates prior to the assay. Cell suspensions were incubated at 37° C. for 20 min with variable concentrations of test ligands and or 10 μM CP 55,940-positive control in the presence of a fixed concentration of forskolin (18 μM for rat $CB_2$ and 37 μM for rat $CB_1$) in Dulbescco's phosphate-buffered saline (Invitrogen, Carlsbad, Calif.) supplemented with bovine serum albumin (0.01% final concentration). The reactions were terminated by the addition of lysis buffer and the luminescence was detected following the procedure according to the manufacturer's instructions. $EC_{50}$ values were calculated using sigmoidal dose-response curve fitting from Prism (GraphPad). Compounds tested are about 100-fold to about >10,000-fold more potent at activating rat $CB_2$ vs. rat $CB_1$ receptors in the described cyclase assays.

TABLE 1

| Example | human $CB_2$ ($K_i$, nM) | rat $CB_2$ ($K_i$, nM) | rat $CB_2$ cyclase ($EC_{50}$, nM) |
|---|---|---|---|
| 1 | 16 | 1.5 | 0.72 |
| 3 | 410 | 11 | |
| 4 | 3.8 | 3.2 | |
| 5 | 30 | 2.2 | |
| 6 | 210 | 16 | 2.4 |
| 7 | 370 | 8.8 | 2.7 |
| 8 | 4.0 | 1.1 | 1.0 |
| 9 | 0.9 | 0.42 | |
| 10 | 190 | 42 | |

TABLE 1-continued

| Example | human $CB_2$ ($K_i$, nM) | rat $CB_2$ ($K_i$, nM) | rat $CB_2$ cyclase ($EC_{50}$, nM) |
|---|---|---|---|
| 11 | | 29 | |
| 12 | 230 | 12 | |
| 14 | 26 | 2.4 | 0.71 |
| 15 | 170 | 15 | 1.1 |
| 18 | 86 | 4.3 | 2.7 |
| 19 | 44 | 7.1 | 0.57 |
| 22 | 67 | 6.2 | 0.24 |
| 23 | 14 | 2.7 | 0.89 |
| 25 | 51 | 1.6 | 1.7 |
| 26 | 14 | 1.0 | 0.23 |
| 27 | 240 | 23 | |
| 29 | 180 | 13 | 0.41 |
| 30 | 17 | 2.6 | 0.20 |
| 31 | 63 | 5.8 | |
| 32 | 170 | 20 | |
| 33 | 3.7 | 1.0 | |
| 34 | 3.6 | 1.2 | 0.40 |
| 35 | 9.1 | 1.1 | |
| 36 | 1.3 | 0.16 | 0.91 |
| 37 | 31 | 5.8 | 1.3 |
| 38 | 2.5 | 0.61 | 1.7 |
| 39 | 99 | 26 | 1.6 |
| 41 | 45 | 6.3 | 0.21 |
| 42 | 24 | 2.3 | 0.31 |
| 43 | 18 | 2.6 | 0.23 |
| 44 | 27 | 2.1 | |
| 45 | 120 | 5.6 | |
| 46 | | 17 | 0.56 |
| 47 | 7.3 | 1.8 | |
| 48 | | 22 | 0.56 |
| 50 | 19 | 2.5 | 0.13 |
| 51 | 140 | 8.1 | 0.30 |
| 52 | 43 | 4.8 | 0.15 |
| 53 | 59 | 2.6 | |
| 54 | 17 | 1.0 | |
| 56 | 11 | 1.2 | 0.076 |
| 57 | 190 | 18 | |
| 59 | 54 | 3.3 | 0.12 |
| 61 | 7.6 | 0.51 | |
| 62 | 27 | 3.1 | |
| 63 | 33 | 3.4 | |
| 64 | 14 | 0.63 | 0.050 |
| 65 | 9.3 | 1.6 | 0.052 |
| 66 | 103 | 12 | |
| 67 | 32 | 3.0 | 3.7 |
| 68 | 59 | 8.3 | 0.022 |
| 69 | 18 | 1.6 | 0.043 |
| 70 | 34 | 4.2 | |
| 71 | 28 | 1.9 | 0.36 |
| 72 | 19 | 7.4 | 0.054 |
| 74 | 27 | 2.5 | 0.095 |
| 75 | 31 | 4.0 | 0.29 |
| 76 | 24 | 2.2 | 0.13 |
| 80 | 74 | 8.5 | 0.046 |
| 81 | 45 | 2.6 | 0.061 |
| 82 | 160 | 15 | |
| 83 | 12 | 0.79 | 0.073 |
| 84 | 42 | 2.7 | 0.88 |
| 85 | 17 | 3.5 | 0.42 |
| 86 | 4.4 | 0.64 | 0.12 |
| 87 | 12 | 0.74 | 0.15 |
| 89 | 190 | 7.9 | |
| 90 | 280 | 27 | |
| 91 | 45 | 12 | 0.10 |
| 92 | 0.20 | 0.25 | 0.45 |
| 94 | 4.8 | 1.1 | 0.25 |
| 95 | 7.5 | 2.3 | |
| 96 | 20 | 27 | 1.4 |
| 98 | 10 | 4.8 | |
| 99 | 56 | 42 | 4.8 |
| 100 | 10 | 9.9 | 0.99 |
| 105 | 19 | 17 | 0.11 |
| 108 | 180 | 13 | |
| 110 | 3.0 | 1.6 | 0.12 |
| 112 | 0.24 | 0.30 | 0.21 |
| 115 | 53 | 33 | |
| 116 | 50 | 45 | 2.4 |

TABLE 1-continued

| Example | human CB$_2$ (K$_i$, nM) | rat CB$_2$ (K$_i$, nM) | rat CB$_2$ cyclase (EC$_{50}$, nM) |
|---|---|---|---|
| 118 | 43 | 119 | 5.1 |
| 119 | 170 | 33 | |
| 121 | 0.8 | 0.52 | 0.33 |
| 122 | 18 | 11 | 1.9 |
| 123 | 0.31 | 0.17 | 0.13 |
| 124 | 3.0 | 2.3 | 0.027 |
| 125 | 31 | 1.0 | 2.6 |
| 126 | 0.6 | 1.2 | 0.076 |
| 127 | 3.7 | 0.43 | 0.16 |
| 128 | 15 | 5.8 | 0.26 |
| 130 | 81 | 2.8 | |
| 133 | 15 | 1.1 | 1.4 |
| 134 | 18 | 1.1 | 1.6 |
| 136 | 1.9 | 0.51 | 0.051 |
| 137 | 7.5 | 2.6 | 2.2 |
| 138 | 5.9 | 0.90 | 12.8 |
| 139 | 5.5 | 2.0 | 0.059 |
| 140 | 11 | 3.9 | 0.15 |
| 141 | 56 | 15 | 0.094 |
| 142 | 2.2 | 0.43 | 0.062 |
| 143 | 11 | 1.8 | 0.10 |
| 144 | 8.8 | 1.2 | 0.10 |
| 145 | 58 | 6.1 | 0.078 |
| 146 | 24 | 3.1 | 0.29 |
| 147 | 1.6 | 0.15 | 0.062 |
| 148 | 7.6 | 0.24 | 0.11 |
| 149 | 8.3 | 0.15 | 0.23 |
| 151 | 9.1 | 0.40 | 0.072 |
| 152 | 5.1 | 0.79 | 0.071 |
| 153 | 13 | 2.1 | 0.061 |
| 154 | 5.7 | 0.32 | 0.065 |
| 158 | 48 | 6.1 | 0.046 |
| 162 | 120 | 47 | |
| 170 | 1.4 | 1.7 | 0.043 |
| 171 | 9.0 | 5.8 | 0.19 |
| 173 | 107 | 77 | 3.5 |
| 174 | 62 | 33 | 3.4 |
| 175 | 3.8 | 1.5 | 0.54 |
| 176 | 16 | 7.0 | 1.1 |
| 177 | 0.16 | 0.10 | 0.15 |
| 178 | 170 | 46 | |
| 179 | 160 | 67 | |
| 180 | 260 | 37 | |
| 181 | 160 | 15 | |
| 182 | 350 | 327 | |
| 183 | 210 | 40 | |
| 184 | 6.5 | 3.2 | 0.41 |
| 185 | 113 | 49 | |
| 186 | 1.7 | 1.4 | 0.38 |
| 187 | 38 | 8.2 | |
| 189 | 39 | 5.3 | |
| 190 | 2.4 | 2.4 | |
| 191 | 15 | 1.8 | 0.51 |
| 192 | 46 | 18 | 3.4 |
| 193 | 37 | 97 | 2.7 |
| 194 | 170 | 41 | |
| 195 | 16 | 7.6 | 1.4 |
| 196 | 18 | 28.8 | 2.4 |
| 197 | 260 | 156 | |
| 198 | 250 | 111 | |
| 200 | 470 | 391 | |
| 201 | 180 | | 3.5 |
| 203 | 70 | | 3.9 |
| 204 | 0.6 | | 0.34 |
| 205 | 21 | | 11.7 |
| 208 | 200 | 11 | |
| 209 | 12 | 7.3 | 0.44 |
| 210 | 36 | 49 | 0.19 |
| 211 | 270 | 111 | |
| 212 | 180 | 257 | 6.2 |
| 213 | 140 | 45 | |
| 214 | 130 | 83 | |
| 215 | 69 | 91 | |
| 216 | 160 | 299 | |
| 217 | 0.7 | 0.73 | 0.16 |
| 218 | 53 | 29 | 1.1 |
| 219 | 204 | 159 | |
| 222 | 170 | 70 | 5.7 |
| 223 | 92 | 62 | 5.8 |
| 224 | 38 | 20 | |
| 225 | 290 | 423 | |
| 226 | 250 | 132 | |
| 231 | 51 | 11 | |
| 232 | 45 | 18 | |
| 234 | 320 | 142 | |
| 235 | 320 | 258 | |
| 237 | 23 | 18 | |
| 238 | 23 | 14 | |
| 239 | 72 | 70 | |
| 240 | 100 | 156 | 2.5 |
| 241 | 20 | 24 | |
| 243 | 41 | 14 | |
| 244 | 42 | 150 | |
| 245 | 32 | 35 | 9.6 |
| 246 | 150 | 38 | |
| 247 | 41 | 40 | |
| 249 | 110 | 325 | |
| 250 | 48 | 75 | |
| 251 | 60 | 60 | |
| 252 | 6.2 | 18.8 | |
| 253 | 160 | 45 | |
| 254 | 84 | 107 | |
| 255 | 25 | 69 | |
| 256 | 19 | 28 | |
| 260 | 190 | 361 | |
| 261 | 54 | 44 | |
| 262 | 6.0 | 4.4 | |
| 263 | 33 | 77 | |
| 264 | 11 | 33.0 | |
| 265 | 0.32 | 0.07 | |
| 267 | 19 | 1.0 | | ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441.

Certain compounds tested showed a statistically significant change in paw withdrawal latency versus a saline vehicle at less than about 300 micromoles/kg in the incision model of postoperative pain, for example, at less than about 50 micromoles/kg in the incision model of postoperative pain.

Spinal Nerve Ligation Model of Neuropathic Pain:

A model of spinal nerve ligation-induced (SNL model) neuropathic pain was produced using the procedure originally described in Kim, S. H. and J. M. Chung, 1992, An experimental model for peripheral neuropathy produced by segmental spinal nerve ligation in the rat, Pain, 50, 355. The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and were acclimated to the test chambers for 20 minutes. The von Frey filaments were presented perpendicularly to the plantar surface of the selected hind paw, and were then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats.

A representative compound showed a statistically significant change in paw withdrawal latency versus a saline vehicle at less than about 50 micromoles/kg in the spinal nerve ligation model of neuropathic pain.

Capsaicin-induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compounds tested showed a statistically significant change in paw withdrawal latency versus a saline vehicle at less than about 300 micromoles/kg in the capsaicin model, for example, at less than about 50 micromoles/kg in the capsaicin model.

MIA-induced Knee Joint Osteoarthritic Pain Model

Unilateral knee joint osteoarthritis was induced in the rats by a single intra-articular (i.a.) injection of sodium monoiodoacetate (MIA, 3 mg in 0.05 mL sterile isotonic saline) into the right knee joint cavity under light isoflurane anesthesia using a 26G needle. The dose of the MIA (3 mg/i.a. injection) was selected based on results obtained from preliminary studies wherein an optimal pain behavior was observed at this dose. Pain behavioral assessment of hind limb grip force were conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of MIA. The vehicle control group for each compound being tested was assigned 0% whereas the age matched naïve group was assigned as being 100% (normal). The % effects for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than one day. A typical duration of repeated daily dosing is about 5 days to about 12 days.

Compounds tested showed a statistically significant change in hind limb grip force strength versus a saline vehicle at less than about 300 micromoles/kg, for example, at less than about 50 micromoles/kg, in the MIA model of osteoarthritic pain following a single dose administration. Certain compound showed a statistically significant change in hind limb grip force strength versus a saline vehicle at less than about 30 micromoles/kg in the MIA model of osteoarthritic pain following repeated daily administration for 5 to 12 days.

f. Methods of Using the Compounds

One embodiment provides methods for treating pain (for example, chronic pain, inflammatory pain, post-operative pain, neuropathic pain, nociceptive pain, cancer pain, lower back pain, eye pain) in a mammal (including human) in need of such treatment. The methods comprise administering to the mammal therapeutically effective amount of one or more compounds as described herein, or pharmaceutically acceptable salts, solvates, or salts of solvates thereof, alone or in combination with one or more pharmaceutically acceptable carrier(s). The method further comprises administration of the present compounds as a single dose. The method also comprises repeated or chronic administration of compounds described herein over a period of days, weeks, months, or longer. In certain embodiments, the methods comprise administering to the mammal therapeutically effective amount(s) of one or more of the compounds as described herein, or pharmaceutically acceptable salts, solvates, or salts of solvates thereof, in combination with one or more nonsteroidal anti-inflammatory drug (NSAID), or other analgesics (for example, acetaminophen, opioids), or combinations thereof, alone or in combination with one or more pharmaceutically acceptable carrier(s).

Another embodiment provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount(s) of one or more compounds described herein or pharmaceutically acceptable salts, solvates, or salts of solvates thereof, alone or in combination with one or more pharmaceutically acceptable carrier(s).

Yet another embodiment relates to methods for providing neuroprotection in a mammal in need of such treatment. These methods comprise administering to the mammal therapeutically effective amount(s) of one or more compounds described herein or pharmaceutically acceptable salts, solvates, or salts of solvates thereof, alone or in combination with one or more pharmaceutically acceptable carrier(s).

Another embodiment provides methods for increasing the therapeutic effectiveness or potency of compounds described herein by repeated or chronic administration of the compounds or pharmaceutically acceptable salts, solvates, or salts of solvates thereof, or pharmaceutical composition(s) thereof, over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds described herein may be required to achieve the desired therapeutic response. "Repeated or chronic administration" refers to the administration of the present compounds daily (i.e., every day) or intermittently (i.e., not every day) over a period of days, weeks, months, or longer. In particular, the treatment of chronic painful conditions may require such repeated or chronic administration of the present compounds. The present compounds may become more effective upon repeated or chronic administration such that the therapeutically effective doses on repeated or chronic administration may be lower than the therapeutically effective dose from a single administration.

Compounds described herein can also be administered as a pharmaceutical composition comprising the compounds of interest in combination with one or more pharmaceutically acceptable carriers. The phrase "therapeutically effective amount" means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds may be administered alone, or in combination with one or more other compounds described herein, or in combination (i.e. co-administered) with one or more additional pharmaceutical agents. For example, one or more compounds, or pharmaceutically acceptable salts, solvates, or salts of solvates thereof, may be administered in combination with one or more analgesic (e.g. acetaminophen, opioid such as morphine), or with one or more nonsteroidal anti-inflammatory drug (NSAID), or combinations thereof. Non limiting examples of NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds described herein and one or more additional pharmaceutical agents, as well as administration of the compounds described herein and each additional pharmaceutical agent, in its own separate pharmaceutical dosage formulation. For example, a compound and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds described herein and one or or more additional pharmaceutical agents may be administered at essentially the same time (e.g., concurrently) or at separately staggered times (e.g., sequentially).

The total daily dose of the compounds administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

g. Pharmaceutical Compositions

Further provided herein are pharmaceutical compositions that comprise compounds described herein or pharmaceutically acceptable salts, solvates, or salts of solvates thereof.

Another aspect provides pharmaceutical compositions comprising one or more compounds described herein, or pharmaceutically acceptable salts, solvates, or salts of solvates thereof, and one or more pharmaceutically acceptable carriers, alone or in combination with one or more analgesics (e.g. acetaminophen), or in combination with one or more nonsteroidal anti-inflammatory drug (NSAID), or a combination thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to one or more compounds of interest, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated herein are compounds formed by synthetic means or formed by in vivo biotransformation of a prodrug.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

We claim:

1. A compound selected from the group consisting of:
   neopentyl (5Z)-4-butyl-2-tert-butylisothiazol-5(2H)-ylidenecarbamate;
   2,2,2-trichloroethyl (5Z)-4-butyl-2-tert-butylisothiazol-5(2H)-ylidenecarbamate;
   1-adamantyl (5Z)-4-butyl-2-tert-butylisothiazol-5(2H)-ylidenecarbamate;
   $N^2$-({[(5Z)-4-butyl-2-tert-butylisothiazol-5(2H)-ylidene]amino}carbonyl)-$N^1$-3-dimethyl-L-valinamide; and
   N-[(5Z)-4-butyl-2-tert-butylisothiazol-5(2H)-ylidene]-N'-(4-methylcyclohexyl)urea;
   or a pharmaceutically acceptable salt thereof.

2. A pharmaceutical composition comprising a therapeutically effective amount of a compound of claim 1 or a pharmaceutically acceptable salt thereof, in combination with a pharmaceutically acceptable carrier.

3. A method for treating pain in a mammal in need of such treatment comprising administering to the mammal a therapeutically effective amount of a compound of claim 1, or a pharmaceutically acceptable salt thereof.

4. A method for treating an inflammatory disorder in a mammal in need of such treatment, comprising administering to the mammal a therapeutically effective amount of a compound of claim 1, or a pharmaceutically acceptable salt thereof.

5. A compound selected from the group consisting of:
   (1R,3S)-$N^1$-[(5Z)-4-butyl-2-tert-butylisothiazol-5 (2H)-ylidene]-$N^3$-(2-hydroxyethyl)- 1,2,2-trimethylcyclopentane-1,3-dicarboxamide;
   (1 S,3R)-$N^3$-[(5Z)-4-butyl-2-tert-butylisothiazol-5 (2H)-ylidene]-$N^1$ -(2-hydroxyethyl)- 1,2,2-trimethylcyclopentane- 1,3 -dicarboxamide;
   (1R,3S)-$N^1$-[(5Z)-4-butyl-2-tert-butylisothiazol-5 (2H)-ylidene]-$N^3$-(3-hydroxyp ropyl)- 1,2,2-trimethylcyclopentane- 1,3 -dicarboxamide;
   (1 S,3R)-$N^1$-[(5Z)-4-butyl-2-tert-butylisothiazol-5 (2H)-ylidene]-$N^3$-(2-methoxyethyl)-1,2,2-trimethylcyclopentane-1,3-dicarboxamide;, (1 S,3R)-$N^1$-[(5Z)-4-butyl-2-tert-butylisothiazol-5 (2H)-ylidene]-$N^3$-(3-hydroxypropyl)-1,2,2-trimethylcyclopentane-1,3-dicarboxamide; (1 S,3R)-$N^1$-[(5Z)-4-butyl-2-tert-butylisothiazol-5 (2H)-ylidene]-$N^3$-(2-hydroxyethyl)-1,2,2-trimethylcyclopentane-1,3-dicarboxamide; (1R, 3S)-$N^3$-[(5Z)-4-butyl-2-tert-butylisothiazol-5 (2H)-ylidene]-$N^1$ -(2-hydroxyethyl)-1,2,2-trimethylcyclopentane- 1,3-dicarboxamide ;
   (1R,3S)-$N^1$-[(5Z)-4-butyl-2-tert-butylisothiazol- 5 (2H)-ylidene]- 1,2,2- trimethyl-$N^3$-prop-2-ynylcyclopentane- 1,3 -dicarboxamide:
   (1 S,3R)-$N^1$-[(5Z)-4-butyl-2-tert-butylisothiazol- 5 (2H)-ylidene]- 1,2,2-trimethyl-$N^3$-prop-2-ynylcyclopentane-1,3-dicarboxamide: and (1 R,3S)-$N^1$ -[(5Z)-4-butyl-2-tert-butylisothiazol-5 (2H)-ylidene]-$N^3$-methoxy-$N^3$,1,2,2-tetramethylcyclopentane- 1,3 -dicarboxamide ;
   or a pharmaceutically acceptable salt thereof.

6. A compound selected from the group consisting of:
   N-[(5Z)-2-tert-butyl-4-(1-hydroxyethyl)isothiazol-5(2H)-ylidene]-5-chloro-2-methoxybenzamide;
   N-[(5Z)-2-tert-butyl-4-(1 -ethoxyethyl)isothiazol-5 (2H)-ylidene]-5-chloro-2-methoxybenzamide;
   N-[(5Z)-2-tert-butyl-4-(1 -methoxyethyl)isothiazol-5 (2H)-ylidene]-5-chloro-2-methoxybenzamide;
   N-[(5Z)-2-tert-butyl-4-[1 -(2,2,2-trifluoro ethoxy)ethyl] isothiazol-5 (2H)-ylidene]-5-chloro-2-methoxybenzamide;
   N-[(5 Z)-2-tert-butyl-4-vinylisothiazol-5 (2H)-ylidene]-5-chloro-2-methoxybenzamide;
   (1R,3S)-3-({[(5Z)-4-butyl-2-tert-butylisothiazol-5 (2H)-ylidene]amino}carbonyl)-3-hydroxy -1,2,2-trimethylcyclopentanecarboxylic acid;
   (1 S,3R)-3- ({[(5Z)-4-butyl-2-tert-butylisothiazol-5 (2H)-ylidene]amino}carbonyl)-3-hydroxy-1,2,2-trimethylcyclopentanecarboxylic acid;
   methyl (1R,3S)-3-({[(5Z)-4-butyl-2-tert-butylis othiazol-5 (2H)-ylidene]amino}carbonyl)-1,2,2-trimethylcyclopentanecarboxylate;
   (1 R,3S)-$N^3$-[(5Z)-4-butyl-2-tert-butylisothiazol-5 (2H)-ylidene]-1,2,2-trimethylcyclopentane -1,3-dicarboxamide;
   (1 S,3R)-N-[(5Z)-4-butyl-2-tert-butylisothiazol-5 (2H)-ylidene]-1,2,2-trimethyl-3-(pyrrolidin-1 -ylcarbonyl) cyclopentanecarboxamide;
   (1 S,3R)-3-({[(5Z)-4-butyl-2-tert-butylisothiazol-5 (2H)-ylidene]amino}carbonyl)-2,2,3-trimethylcyclopentanecarboxylic acid;

(1R,3S)-3-({[(5Z)-4-butyl-2-tert-butylisothiazol-5 (2H)-ylidene]amino}carbonyl)-2,2,3-trimethylcyclopentanecarboxylic acid;
ethyl (1S,3R)-3-({[(5Z)-4-butyl 1-2-tert-butylisothiazol-5 (2H)-ylidene]amino}carbonyl)-2,2,3-trimethylcyclopentanecarboxylate;
ethyl (1R,3S)-3-({[(5Z)-4-butyl-2-tert-butylisothiazol-5 (2H)-ylidene]amino}carbonyl) -2,2,3-trimethylcyclopentanecarboxylate;
methyl (1 S,3R)-3-({[(5Z)-4-butyl-2-tert-butylis othiazol-5 (2H)-ylidene]amino}carbonyl) -2,2,3-trimethylcyclopentanecarboxylate;
(1R,3S)-3-(azetidin-1 -ylcarbonyl)-N-[(5Z)-4-butyl-2-tert-butylisothiazol-5 (2H)-ylidene]-1,2,2-trimethylcyclopentanecarboxamide;
(1R,3S)-N$^1$-[(5Z)-4-butyl-2-tert-butylisothiazol-5 (2H)-ylidene]-N$^3$,N$^3$,1,2,2-pentamethylcyclopentane-1,3-dicarboxamide;
(1 R,3S)-N-[(5Z)-4-butyl-2-tert-butylisothiazol-5 (2H)-ylidene]-3-[(3-hydroxyazetidin-1 -yl) carbonyl]-1,2,2-trimethylcyclopentanecarboxamide;
(1R,3S)-3-({[(5Z)-4-butyl-2-tert-butylisothiazol-5 (2H)-ylidene]amino}carbonyl)-1,2,2-trimethylcyclopentanecarboxylic acid;
(1R,3S)-N$^3$-[(5Z)-4-butyl-2-tert-butylisothiazol-5 (2H)-ylidene]-N$^1$,1,2,2-tetramethylcyclopentane-1,3-dicarboxamide;
(1R,3S)-N$^3$-[(5Z) -4-butyl-2-tert-butylisothiazol-5 (2H)-ylidene]-N$^1$,N$^1$,1,2,2-pentamethylcyclopentane-1,3-dicarboxamide;
(1R,3S)-N$^1$-[(5Z)-4-butyl-2-tert-butylisothiazol-5 (2H)-ylidene]tetramethylcyclopentane-1,3-dicarboxamide;
(1R,3S)-N-[(5Z)-4-butyl-2-tert-butylisothiazol-5 (2H)-ylidene]-3-[(3,3-difluoroazetidin-1 -yl)carbonyl]-1,2,2-trimethylcyclopentanecarboxamide;
methyl (1R,3S)-3-({[(5Z)-4-butyl-2-tert-butylis othiazol-5 (2H)-ylidene]amino}carbonyl)-2,2,3-trimethylcyclopentanecarboxylate;
neopentyl (5Z)-4-butyl-2-tert-butylisothiazol-5 (2H)-ylidenecarbamate;
2,2,2-trichloroethyl(5 Z)-4-butyl-2-tert-butylisothiazol-5 (2H)-ylidenecarbamate;
1 -adamantyl(5 Z)-4-butyl-2-tert-butylisothiazol-5 (2H)-ylidenecarbamate;
N$^2$-({[(5Z)-4-butyl-2-tert-butylisothiazol-5 (2H) -ylidene] amino}carbonyl)-N$^1$-3-dimethyl-L -valinamide;
N-[(5Z)-4-butyl-2-tert-butylisothiazol-5 (2H)-ylidene](4-methylcyclohexyl)urea;
N-[(5Z)-4-butyl-2-tert-butylisothiazol-5 (2H)-ylidene]-2-{[(2S)-1 -methylpyrrolidin-2-yl]methoxy}-5-(trifluoromethyl)benzamide;
N-[(5Z)-4-butyl-2-tert-butylisothiazol-5 (2H)-ylidene]-N'-cyano-2-{[(2S)-1-methylpyrrolidin -2-yl]methoxy}-5-(trifluoromethyl)benzenecarboximidamide;
N-[(5 Z)-4-butyl-2-tert-butylisothiazol-5 (2H)-ylidene]-2-{[(2S)-5-oxopyrrolidin-2-yl]methoxy}-5-(trifluoromethyl)benzamide;
N-[(5Z)-4-butyl-2-tert-butylisothiazol-5 (2H)-ylidene]-2-{[(4R)-2-oxo-1,3-oxazolidin-4-yl]methoxy}-5- (trifluoromethyl)benzamide;
N-[(5Z)-4-butyl-2-tert-butylisothiazol-5 (2H)-ylidene]-2-[(1-methylpiperidin-2-yl)methoxy]-5-(trifluoromethyl)benzamide;
N-[(5 Z)-2-tert-butyl-4-isobutylisothiazol-5 (2H)-ylidene]-2-{[(2S) 1 -methylpyrrolidin-2-yl]methoxy}-5-(trifluoromethyl)benzamide;
N-[(5Z)-4-butyl-2-tert-butylisothiazol-5 (2H)-ylidene]-2-(pyrazin-2-ylmethoxy) -5-(trifluoromethyl)benzamide;
N-[(5Z)-2-tert-butyl-4-isobutylisothiazol-5 (2H)-ylidene]-2- (pyrazin-2-ylmethoxy)-5-(trifluoromethyl)benzamide;
N-[(5Z)-2-tert-butyl-4-isobutylisothiazol-5 (2H)-ylidene]-2- (pyridin-2-ylmethoxy)-5-(trifluoromethyl)benzamide;
(1R,3S)-N$^1$-[(5Z)-4-butyl-2-tert-butylisothiazol-5 (2H)-ylidene]-N$^3$-ethyl-1,2,2-trimethylcyclopentane-1,3-dicarboxamide;
(1R,3S)-N$^1$-[(5Z)-4-butyl-2-tert-butylisothiazol-5 (2H) -ylidene]-1,2,2-trimethyl-N$^3$-propylcyclopentane-1,3-dicarboxamide;
(1R,3S)-N$^1$-[(5Z)-4-butyl-2-tert-butylisothiazol-5 (2H)-ylidene]-N$^3$-(2-hydroxyethyl)-1,2,2-trimethylcyclopentane-1,3-dicarboxamide;
methyl (1 S,3R)-3-({[(5Z)-4-butyl-2-tert-butylisothiazol-5 (2H)-ylidene]amino}carbonyl)-1,2,2-trimethylcyclopentanecarboxylate;
(1 S,3R)-3-({[(5Z)-4-butyl-2-tert-butylisothiazol-5 (2H)-ylidene]amino}carbonyl)-1,2,2-trimethylcyclopentanecarboxylic acid;
(1R,3S)-N$^1$-[(5Z) -4-butyl-2-tert-butylisothiazol-5 (2H)-ylidene]-N$^3$-isopropyl-1,2,2-trimethylcyclopentane-1,3-dicarboxamide;
(1R,3S)-N$^1$-[(5Z)-4-butyl-2-tert-butylisothiazol-5 (2H)-ylidene]-N$^3$-cyclobutyl-1,2,2-trimethylcyclopentane-1,3-dicarboxamide;
(1R,3S)-N$^1$-[(5Z)-4-butyl-2-tert-butylisothiazol-5 (2H)-ylidene]-N$^3$-cyclopropyl-1,2,2-trimethylcyclopentane-1,3-dicarboxamide;
(1 S,3R)-N$^3$-[(5Z)-4-butyl-2-tert-butylisothiazol-5 (2H)-ylidene]-N$^1$,1,2,2-tetramethylcyclop entane-1,3-dicarboxamide;
(1 S,3R)-N$^3$-[(5Z)-4-butyl-2-tert-butylisothiazol-5 (2H)-ylidene]-N$^1$-ethyl-1,2,2-trimethylcyclopentane-1,3-dicarboxamide;
(1 S,3R)-N$^3$-[(5Z)-4-butyl-2-tert-butylisothiazol-5 (2H)-ylidene]-1,2,2-trimethyl-N$^1$-propylcyclopentane-1,3-dicarboxamide;
(1 S,3R)-N$^3$-[(5Z) -4-butyl-2-tert-butylisothiazol-5 (2H)-ylidene]-N$^1$-(2-hydroxyethyl)-1,2,2-trimethylcyclopentane-1,3-dicarboxamide;
(1R,3S)-N$^1$-[(5Z) -4-butyl-2-tert-butylisothiazol-5 (2H)-ylidene]-N$^3$-(3-hydroxypropyl)-1,2,2-trimethylcyclopentane-1,3-dicarboxamide; and
(1R,3S)-N$^1$-[(5Z)-4-butyl-2-tert-butylisothiazol-5(2H)-ylidene]-1,2,2-trimethyl-N$^3$-[(2R)- tetrahydrofuran-2-ylmethyl]cyclopentane-1,3-dicarboxamide;
or a pharmaceutically acceptable salt thereof.

7. A compound selected from the group consisting of:
methyl (1 S,3R)-3-({[(5Z) -4-butyl-2-tert-butylisothiazol-5 (2H)-ylidene]amino}carbonyl)-2,2,3-trimethylcyclopentylcarbamate;
ethyl (1 S,3R) -3-({[(5Z) -4-butyl-2-tert-butylisothiazol-5 (2H)-ylidene]amino}carbonyl)-2,2,3-trimethylcyclopentylcarbamate;
(1R,3S)-N-[(5Z)-4-butyl-2-tert-butylisothiazol-5(2H)-ylidene]-3-(4,5-dihydro-1,3-oxazol-2-y1)-1,2,2-trimethylcyclopentanecarboxamide;
(1S,3R)-N$^1$-[(5Z)-4-butyl-2-tert-butylisothiazol-5(2H)-ylidene]-N$^3$-1,2,2- tetramethylcyclopentane-1,3-dicarboxamide;
(1S,3R)-N$^1$-[(5Z)-4-butyl-2-tert-butylisothiazol-5(2H)-ylidene]-1,2,2-trimethyl-N$^3$-propylcyclopentane-1,3-dicarboxamide;

(1S,3R)-N$^1$-[(5Z)-4-butyl-2-tert-butylisothiazol-5(2H)-ylidene]-N$^3$-(2-methoxyethyl)-1, 2,2-trimethylcyclopentane-1,3-dicarboxamide;

(1S,3R)-N$^1$-[(5Z)-4-butyl-2-tert-butylisothiazol-5(2H)-ylidene]-N$^3$-(3-hydroxypropyl)-1,2,2-trimethylcyclopentane-1,3-dicarboxamide;

(1S,3R)-3-(azetidin-1-ylcarbonyl)-N-[(5Z)-4-bu 1-2-tert-butylisothiazol-5(2H)-ylidene]-1,2,2-trimethylcyclopentanecarboxamide;

(1S,3R)-N$^1$-[(5Z)-4-bu 1-2-tert-butylisothiazol-5(2H)-ylidene]-N$^3$, N$^3$,1,2,2-pentamethylcyclopentane-1,3-dicarboxamide;

(1R,3S)-N-[(5Z)-4-butyl-2-tert-butylisothiazol-5(2H)-ylidene]-3-(4,5-dihydro-1,3-oxazol-2-y1)-2,2,3-trimethylcyclopentanecarboxamide;

(1S,3R)-N$^1$-[(5Z)-4-butyl-2-tert-butylisothiazol-5(2H)-ylidene]-N$^3$-cyclobutyl-1,2,2-trimethylcyclopentane-1,3-dicarboxamide;

(1R,3S)-N$^1$-[(5Z)-4-butyl-2-tert-butylisothiazol-5(2H)-ylidene]-1,2,2-trimethyl-N$^3$-[(2S) -tetrahydrofuran-2-yl-methyl]cyclopentane-1,3-dicarboxamide;

(1S,3R)-N$^3$-[(5Z)-4-butyl-2-tert-butylisothiazol-5(2H)-ylidene]-1,2,2-trimethyl-N$^1$-[(2S) -tetrahydrofuran-2-ylmethyl]cyclopentane-1,3-dicarboxamide;

(1S,3R)-N$^1$-[(5Z)-4-butyl-2-tert-butylisothiazol-5(2H)-ylidene]-N$^3$-(2-hydroxyethyl)-1,2,2-trimethylcyclopentane-1,3-dicarboxamide;

(1R,3S)-N$^3$-[(5Z)-4-butyl-2-tert-butylisothiazol-5(2H)-ylidene]-N$^1$-ethyl-1,2,2-trimethylcyclopentane-1,3-dicarboxamide;

(1R,3S)-N$^3$-[(5Z)-4-butyl-2-tert-butylisothiazol-5(2H)-ylidene]-N$^1$-(2-hydroxyethyl)-1,2,2-trimethylcyclopentane-1,3-dicarboxamide;

(1S,3R)-N-[(5Z)-4-butyl-2-tert-butylisothiazol-5(2H)-ylidene]-3-(4,5-dihydro-1,3-oxazol-2-y1)-1,2,2-trimethylcyclopentanecarboxamide;

(1S,3R)-N-[(5Z)-4-butyl-2-tert-butylisothiazol-5(2H)-ylidene]-3-(4,5-dihydro-1,3-oxazol-2-y1)-2,2,3-trimethylcyclopentanecarboxamide;

(1R,3S)-N$^3$-benzyl-N$^1$-[(5Z)-4-butyl-2-tert-butylisothiazol-5(2H)-ylidene]-1,2,2-trimethylcyclopentane-1,3-dicarboxamide;

(1R,3S)-N$^1$-[(5Z)-4-butyl-2-tert-butylisothiazol-5(2H)-ylidene]-1,2,2-trimethyl-N$^3$-(pyridin-2-ylmethyl)cyclopentane-1,3-dicarboxamide;

(1R,3S)-N$^1$-[(5Z)-4-butyl-2-tert-butylisothiazol-5(2H)-ylidene]-1,2,2-trimethyl-N$^3$-(pyridin-3-ylmethyl)cyclopentane-1,3-dicarboxamide;

(1R,3S)-N$^1$-[(5Z)-4-butyl-2-tert-butylisothiazol-5(2H)-ylidene]-1,2,2-trimethyl-N$^3$-(pyridin-4-ylmethyl)cyclopentane-1,3-dicarboxamide;

(1R,3S)-N$^1$-[(5Z)-4-butyl-2-tert-butylisothiazol-5(2H)-ylidene]-1,2,2-trimethyl-N$^3$-prop-2-ynylcyclopentane-1,3-dicarboxamide;

(1R,3S)-N$^1$-[(5Z)-4-butyl-2-tert-butylisothiazol-5(2H)-ylidene]-1,2,2-trimethyl-N$^3$-(2,2,2-trifluoroethyl)cyclopentane-1,3-dicarboxamide;

(1S,3R)-N$^1$-[(5Z)-4-butyl-2-tert-butylisothiazol-5(2H)-ylidene]-1,2,2-trimethyl-N$^3$-prop-2-ynylcyclopentane-1,3-dicarboxamide;

(1S,3R)-N$^1$-[(5Z)-4-butyl-2-tert-butylisothiazol-5(2H)-ylidene]-1,2,2-trimethyl-N$^3$-(2,2,2-trifluoroethyl)cyclopentane-1,3-dicarboxamide;

(1R,3S)-N$^1$-[(5Z)-4-butyl-2-tert-butylisothiazol-5(2H)-ylidene]-N$^3$-methoxy-N$^3$,1,2,2-tetramethylcyclopentane-1,3-dicarboxamide;

(1 S,3R)-N-[(5Z)-4-bu 1-2-tert-butylisothiazol-5(2H)-ylidene]-3-(5,6-dihydro-4H-1,3-oxazin -2-yl)-1,2,2-trimethylcyclopentanecarboxamide;

(1R,3S)-N-[(5Z)-4-butyl-2-tert-butylisothiazol-5(2H)-ylidene]-3-(5,6-dihydro-4H-1,3-oxazin -2-yl)-1,2,2-trimethylcyclopentanecarboxamide;

N-[(1 S,3R) -3- ({[(5Z)-4-butyl-2-tert-butylisothiazol-5 (2H)-ylidene]amino}carbonyl) -2,2,3-trimethylcyclopentyl]pyrrolidine-1-carboxamide;

(1 R,3S)-3-[(aminocarbonyl) amino]-N-[(5Z)-4-butyl-2-tert-butylisothiazol-5 (2H) -ylidene]-1,2,2-trimethylcyclopentanecarboxamide;

(1 R,3S)-3-[(aminocarbonyl) amino]-N-[(5Z)-4-butyl-2-tert-butylisothiazol-5 (2H) -ylidene]-2,2,3-trimethylcyclopentanecarboxamide;

(1R,3S)-N-[(5Z)-4-butyl-2-tert-butylisothiazol-5 (2H)-ylidene]-2,2,3-trimethyl-3-{[(methylamino) carbonyl] amino }cyclopentanecarboxamide;

(1R,3S)-N-[(5Z)-4-butyl-2-tert-butylisothiazol-5 (2H)-ylidene]-1,2,2-trimethyl-3-(morpholin -4-ylcarbonyl) cyclopentanecarboxamide;

(1 R,3S)-N$^1$-[(5Z) -4-bu 1-2-tert-butylisothiazol-5 (2H) -ylidene]-1,2,2-trimethyl-N$^3$-pyrrolidin -1 -ylcyclopentane-1,3-dicarboxamide;

N-[(1 S,3R) -3-({[(5Z)-4-butyl-2-tert-butylisothiazol-5 (2H)-ylidene]amino}carbonyl) -2,2,3-trimethylcyclopentyl]morpholine-4-carboxamide;

N-[(1 S,3R) -3-({[(5Z)-4-butyl-2-tert-butylisothiazol-5 (2H)-ylidene]amino}carbonyl) -2,2,3-trimethylcyclopentyl]benzamide;

(1R,3S)-N-[(5Z)-4-butyl-2-tert-butylisothiazol-5 (2H)-ylidene]-1,2,2-trimethyl-3-{[(methylamino)carbonyl] amino }cyclopentanecarboxamide;

(1 S,3R)-3-[(aminocarbonyl) amino]-N-[(5Z)-4-butyl-2-tert-butylisothiazol-5 (2H) -ylidene]-1,2,2-trimethylcyclopentanecarboxamide;

(1 S,3R)-N-[(5Z)-4-butyl-2-tert-butylisothiazol-5 (2H)-ylidene]-1,2,2-trimethyl-3-{[(methylamino) carbonyl] amino }cyclopentanecarboxamide;

N-[(1R,3S) -3-({[(5Z)-4-butyl-2-tert-butylisothiazol-5 (2H)-ylidene]amino}carbonyl)-2,2,3-trimethylcyclopentyl]benzamide;

(1R,3S)-3-(acetylamino)-N-[(5Z)-4-butyl-2-tert-butylisothiazol-5 (2H)-ylidene]-1,2,2-trimethylcyclopentanecarboxamide;

(1R,3S)-N-[(5Z)-4-butyl-2-tert-butylisothiazol-5 (2H)-ylidene]-3-({[(2-hydroxyethyl)amino] carbonyl}amino) -1,2,2-trimethylcyclopentanecarboxamide;

(1 R,3S)-N- [(5Z)-4-butyl-2-tert-butylisothiazol-5 (2H)-ylidene]-3-[({[(2S) -2-hydroxypropyl] amino}carbonyl) amino]-1,2,2-trimethylcyclopentanecarboxamide;

(1 R,3S)-N-[(5Z)-4-butyl-2-tert-butylisothiazol-5 (2H)-ylidene]-3-[({[(2R)-2-hydroxypropyl] amino}carbonyl) amino]-1,2,2-trimethylcyclopentanecarboxamide;

N-[(1 S,3R) -3-({[(5Z)-4-butyl-2-tert-butylisothiazol-5 (2H)-ylidene]amino}carbonyl)-2,2,3-trimethylcyclopentyl]-3-hydroxyazetidine-1 -carboxamide;

N-[(1 S,3R) -3-({[(5Z)-4-butyl-2-tert-butylisothiazol-5 (2H)-ylidene]amino}carbonyl) -2,2,3-trimethylcyclopentyl]-3,3-difluoroazetidine-1 -carboxamide;

N-[(5Z)-4-butyl-2-tert-butylisothiazol-5 (2H)-ylidene]-2-(2-hydroxy-2-methylpropoxy)-5-(trifluoromethyl)benzamide;

N-[(1S,3R)-3-({[(5Z)-4-butyl-2-tert-butylisothiazol-5(2H)-ylidene]amino}carbonyl)-2,2,3-trimethylcyclopentyl]azetidine-1-carboxamide;

(1R,3S)-N-[(5Z)-4-butyl-2-tert-butylisothiazol-5(2H)-ylidene]-1,2,2-trimethyl-3-({[methyl(phenyl)amino]carbonyl}amino)cyclopentanecarboxamide;

methyl 3-({[(5Z)-4-butyl-2-tert-butylisothiazol-5(2H)-ylidene]amino}carbonyl)adamantane-1-carboxylate;

3-({[(5Z)-4-butyl-2-tert-butylisothiazol-5(2H)-ylidene]amino}carbonyl) adamantane-1-carboxylic acid; and 2-[(tert-butylamino)oxy]-N-[(5Z)-4-butyl-2-tert-butyl-isothiazol-5(2H)-ylidene]-5-(trifluoromethyl)benzamide;

or a pharmaceutically acceptable salt thereof.

* * * * *